US008859574B2

(12) United States Patent
Marsilje et al.

(10) Patent No.: US 8,859,574 B2
(45) Date of Patent: Oct. 14, 2014

(54) COMPOUNDS AND COMPOSITIONS AS KINASE INHIBITORS

(71) Applicants: Thomas H. Marsilje, San Diego, CA (US); Wenshuo Lu, San Diego, CA (US); Bei Chen, San Diego, CA (US); Xiaohui He, San Diego, CA (US); Christian Cho-Hua Lee, San Diego, CA (US); Songchun Jiang, San Diego, CA (US); Kunyong Yang, San Diego, CA (US)

(72) Inventors: Thomas H. Marsilje, San Diego, CA (US); Wenshuo Lu, San Diego, CA (US); Bei Chen, San Diego, CA (US); Xiaohui He, San Diego, CA (US); Christian Cho-Hua Lee, San Diego, CA (US); Songchun Jiang, San Diego, CA (US); Kunyong Yang, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 13/948,356

(22) Filed: Jul. 23, 2013

(65) Prior Publication Data
US 2013/0310361 A1 Nov. 21, 2013

Related U.S. Application Data

(63) Continuation of application No. 13/000,955, filed as application No. PCT/US2009/048428 on Jun. 24, 2009, now Pat. No. 8,519,129.

(60) Provisional application No. 61/075,583, filed on Jun. 25, 2008, provisional application No. 61/155,434, filed on Feb. 25, 2009.

(51) Int. Cl.
C07D 401/14 (2006.01)
C07D 403/12 (2006.01)
C07D 403/14 (2006.01)
C07D 413/14 (2006.01)
A61K 31/506 (2006.01)
A61P 35/00 (2006.01)
A61K 31/5377 (2006.01)
C07D 405/14 (2006.01)
C07D 409/14 (2006.01)
A61K 45/06 (2006.01)
A61K 31/55 (2006.01)

(52) U.S. Cl.
CPC .......... C07D 401/14 (2013.01); A61K 31/5377 (2013.01); C07D 403/14 (2013.01); C07D 405/14 (2013.01); C07D 403/12 (2013.01); C07D 409/14 (2013.01); A61K 45/06 (2013.01); A61K 31/55 (2013.01); C07D 413/14 (2013.01); A61K 31/506 (2013.01)
USPC .......... 514/275; 514/231.5; 544/323; 544/122

(58) Field of Classification Search
USPC .......... 544/323, 122; 514/275, 231.5
See application file for complete search history.

(56) References Cited

U.S. PATENT DOCUMENTS

| 8,519,129 B2 * | 8/2013 | Marsilje et al. ............... 544/323 |
| 2006/0270694 A1 | 11/2006 | Wong |
| 2008/0176881 A1 | 7/2008 | Michellys et al. |
| 2010/0298295 A1 | 11/2010 | Marsilje et al. |
| 2011/0112096 A1 | 5/2011 | Marsilje et al. |

FOREIGN PATENT DOCUMENTS

| WO | 00/12485 A1 | 3/2000 |
| WO | 01/07027 A2 | 2/2001 |
| WO | 0160816 A1 | 8/2001 |
| WO | 01/64655 A1 | 9/2001 |
| WO | 03/018021 A1 | 3/2003 |
| WO | 03/026664 A1 | 4/2003 |
| WO | 03/026666 A1 | 4/2003 |
| WO | 03/078404 A1 | 9/2003 |
| WO | 2004/080980 A1 | 9/2004 |
| WO | 2004087698 A2 | 10/2004 |
| WO | 2005/016893 A2 | 2/2005 |
| WO | 2005/016894 A1 | 2/2005 |
| WO | 2005/026130 A1 | 3/2005 |
| WO | 2005/026158 A1 | 3/2005 |
| WO | 2006/074057 A2 | 7/2006 |
| WO | 2006/137706 A1 | 12/2006 |
| WO | 2007/027238 A2 | 3/2007 |
| WO | 2007/031829 A2 | 3/2007 |
| WO | 2007053452 A1 | 5/2007 |
| WO | 2008/005538 A2 | 1/2008 |
| WO | 2008/015250 A1 | 2/2008 |
| WO | 2008/051547 A1 | 5/2008 |
| WO | 2008/073687 A2 | 6/2008 |
| WO | 2008/083465 A1 | 7/2008 |
| WO | 2008/127349 A2 | 10/2008 |
| WO | 2009/017838 A2 | 2/2009 |
| WO | 2009/067081 A1 | 5/2009 |
| WO | 2009/103652 A1 | 8/2009 |

OTHER PUBLICATIONS

USPTO Office Action dated Sep. 25, 2012, U.S. Appl. No. 12/675,379 (U.S. Patent Publication No. 20100298295).
USPTO Office Action dated Dec. 13, 2012, U.S. Appl. No. 12/675,379 (U.S. Patent Publication No. 20100298295).
USPTO Office Action dated Aug. 24, 2012, U.S. Appl. No. 13/000,999 (U.S. Patent Publication No. 20110112096).

(Continued)

Primary Examiner — Venkataraman Balasubramanian
(74) Attorney, Agent, or Firm — Emily Tongco Wu; Genomics Institute of the Novartis Research Foundation

(57) ABSTRACT

The invention provides novel pyrimidine derivatives and pharmaceutical compositions thereof, and methods for using such compounds. For example, the pyrimidine derivatives of the invention may be used to treat, ameliorate or prevent a condition which responds to inhibition of insulin-like growth factor (IGF-1R) or analplastic lymphoma kinase (ALK).

8 Claims, No Drawings

(56) References Cited

OTHER PUBLICATIONS

USPTO Office Action dated Nov. 29, 2012, U.S. Appl. No. 13/000,999 (U.S. Patent Publication No. 20110112096).
Snyder, et al., "Common bacteria whose susceptibility to antimicrobials is no longer predictable", J. Med. Liban, 2000, pp. 208-214, vol. 48, No. 4, Pubmed Abstract.
Mass, et al., The HER Receptor Family: A Rich Target for Therapeutic Development, Int. J. Radiation Oncology Biol. Phys., 2004, pp. 932-940, vol. 58, No. 3, Elsevier Inc.
Yee, et al., Insulin-like Growth Factor Receptor Inhibitors: Baby or the Bathwater?, J. Natl. Cancer Inst., 2012, pp. 975-981, vol. 104, No. 13, Oxford University Press.
Golub, et al., "Molecular Classification of Cancer: Class Discovery and Class Prediction by Gene Expression Monitoring", Science, 1999, pp. 531-537, vol. 286, American Association for the Advancement of Science.
Fabbro, et al., "Protein kinases as targets for anticancer agents: from inhibitors to useful drugs", Pharmacology & Therapeutics, 2002, pp. 79-98, vol. 93, Elsevier.
Freshney, et al., "Culture of Animal Cells, a Manual of Basic Technique", Alan R. Liss, Inc., 1983, pp. 1-6, New York.
Turner, et al., "Recent Advanced in the Medicinal Chemistry of Antifungal Agents", Current Pharmaceutical Design, 1996, pp. 209-224, vol. 2, No. 2, Bentham Science Publishers, B.V.
Cecil Textbook of Medicine, edited by Bennet, J.C., and Plum F., 20th edition, 1996, pp. 1004-1010, vol. 1.
Sugar, et al., "Comparison of Three Methods of Antifungal Susceptibility Testing with the Proposed NCCLS Standard Broth Macrodilution Assay: Lack of Effect of Phenol Red", Diagn. Microbiol. Infect. Dis., 1995, pp. 129-133, vol. 21, Elsevier.
Dermer, et al., "Another Anniversary for the War on Cancer", Bio/Technology, 1994, p. 320, vol. 12.
Cohen, et al.., "The development and therapeutic potential of protein kinase inhibitors", Current Opinion in Chemical Biology, 1999, pp. 459-465, vol. 3.

\* cited by examiner

COMPOUNDS AND COMPOSITIONS AS KINASE INHIBITORS

CROSS-REFERENCE TO RELATED APPLICATIONS

This application is a continuation of U.S. application Ser. No. 13/000,955, now U.S. Pat. No. 8,519,129, which is a 371 U.S. national phase application of international application number PCT/US2009/048428 filed 24 Jun. 2009 and claims the benefit of U.S. provisional application Ser. Nos. 61/075,583 filed 25 Jun. 2008, and 61/155,434 filed 25 Feb. 2009. Each of these applications is incorporated herein by reference in its entirety.

TECHNICAL FIELD

The invention relates to protein kinase inhibitors, more particularly novel pyrimidine derivatives and pharmaceutical compositions thereof, and their use as pharmaceuticals.

BACKGROUND ART

Insulin-like growth factor (IGF-1) signaling is highly implicated in cancer, with the IGF-1 receptor (IGF-1R) as the predominating factor. IGR-1R is important for tumor transformation and survival of malignant cells, but is only partially involved in normal cell growth. Targeting of IGF-1R has been suggested to be a promising option for cancer therapy. (Larsson et al., Br. J. Cancer 92:2097-2101 (2005)).

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life. Sci. 61:2939-2953 (2004)).

Because of the emerging disease-related roles of IGF-1R and ALK, there is a continuing need for compounds which may be useful for treating and preventing a disease which responds to inhibition of IGF-1R and ALK.

DISCLOSURE OF THE INVENTION

The invention relates to novel pyrimidine derivatives and pharmaceutical compositions thereof, and their use as pharmaceuticals.

In one aspect, the invention provides a compound of Formula (1):

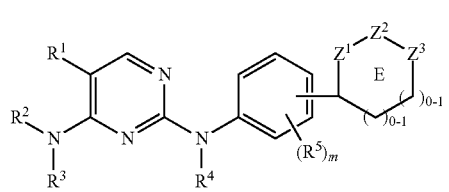

(1)

or a physiologically acceptable salt thereof;
wherein ring E may optionally contain a double bond; one of $Z^1$, $Z^2$ and $Z^3$ is $NR^6$, $N(R^6)^+$—$O^-$ or $S(O)_{1-2}$ and the others are $CR_2$;

$R^1$ is halo or an optionally halogenated $C_{1-6}$ alkyl;
$R^2$ is pyridine-2-onyl, azepan-2-onyl or a monocyclic 5-6 membered heteroaryl having 1-3 heteroatoms selected from N, O and S; each of which is optionally substituted with $R^9$ wherein $R^9$ is $C_{1-6}$ alkyl, $C_{1-6}$ haloalkyl or $C_{3-7}$ cycloalkyl;
$R^3$ and $R^4$ are each H;
$R^5$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or $C(O)O_{0-1}R^8$;
$R^6$ is H; $C_{1-6}$ alkyl, $C_{2-6}$ alkenyl or $C_{2-6}$ alkynyl, each of which may be optionally substituted with halo and/or hydroxyl groups; —$(CR_2)_p$—$OR^7$, —$(CR_2)_p$—$CH(OH)C_tF_{2t+1}$ wherein t is 1-3, $(CR_2)_p$—CN; $(CR_2)_p$—$NR(R^7)$, —$(CR_2)_p$—$C(O)OR^7$, $(CR_2)_p NR(CR_2)_p OR^7$, $(CR_2)_p NR$-L-$C(O)R^8$, $C(O)(CR_2)_q OR^8$, —$C(O)O$—$(CR_2)_p$—$NRR^7$, —$C(O)$—$(CR_2)_p$—$OR^7$, L-Y, -L-$C(O)R^7$, -L-$C(O)$—$NRR^7$, -L-$C(O)$—NR—$(CR_2)_p$—$NRR^7$, -L-$C(O)NR(CR_2)_p OR^7$, -L-$C(O)$—$(CR_2)_q$—NR—$C(O)$—$R^8$, -L-$C(O)NR(CR_2)_p SR^7$, -L-$C(O)NR(CR_2)_p S(O)_{1-2}R^8$, -L-$S(O)_2R^8$, -L-$S(O)_2$—$(CR_2)_q$—$NRR^7$, -L-$S(O)_2NR(CR_2)_p NR(R^7)$ or -L-$S(O)_2NR(CR_2)_p OR^7$;
alternatively, $R^6$ is a radical selected from formula (a), (b), (c) or (d):

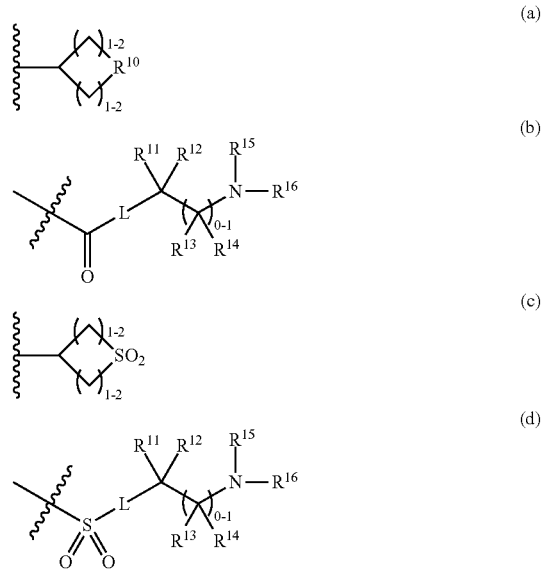

$R^{10}$ is O, S, $NR^{17}$ wherein $R^{17}$ is H, $C_{1-6}$ alkyl, $SO_2 R^{8a}$ or $CO_2 R^{8a}$;
$R^{11}$, $R^{12}$, $R^{13}$, $R^{14}$, $R^{15}$ and $R^{16}$ are independently selected from H; $C_{1-6}$ alkoxy; $C_{1-6}$ alkyl, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the atoms to which they are attached may form a 3-7 membered saturated, unsaturated or partially unsaturated ring containing 1-3 heteroatoms selected from N, O and S, and optionally substituted with oxo and 1-3 $R^5$ groups;
L is $(CR_2)_{1-4}$ or a bond;
Y is $C_{3-7}$ carbocyclic ring, $C_{6-10}$ aryl, or a 5-10 membered heteroaryl or 4-10 membered heterocyclic ring, each of which is optionally substituted with 1-3 $R^5$ groups;

$R^7$, $R^8$ and $R^{8a}$ are independently $C_{1-6}$ alkyl, $C_{2-6}$ alkenyl or $C_{2-6}$ alkynyl, each of which may be optionally substituted with halo, amino, hydroxyl or cyano; $(CR_2)_qY$ or $C_{1-6}$ alkoxy; or $R^7$ is H;

each R is independently H or $C_{1-6}$ alkyl;

R and $R^7$ together with N in each $NRR^7$ may form a 5-6 membered ring containing 1-3 heteroatoms selected from N, O and S, and optionally substituted with oxo and 1-3 $R^5$ groups;

m is 2-4;

n is 1-3;

p is 1-4; and q is 0-4.

In one embodiment, the invention provides a compound is of Formula (2):

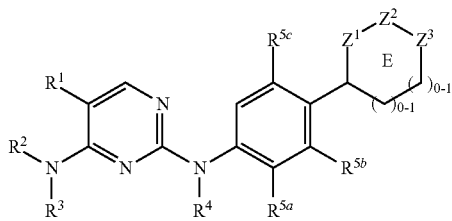

(2)

wherein one of $R^{5a}$, $R^{5b}$ and $R^{8c}$ is H and the others are independently halo, $C_{1-6}$ alkyl, $C_{1-6}$ alkoxy, halo-substituted $C_{1-6}$ alkyl, cyano or $C(O)O_{0-1}R^8$ wherein $R^8$ is $C_{1-6}$ alkyl; and $R^1$, $R^2$, $R^3$, $R^4$, E, $Z^1$, $Z^2$ and $Z^3$ are as defined in Formula (1).

In some examples, $Z^3$ in the above Formula (2) is $NR^6$ or $N(R^6)^+$—$O^-$; and $Z^1$ and $Z^2$ are $CH_2$. In other examples, $R^6$ is H, $C_{1-6}$ alkyl optionally substituted with halo and/or hydroxyl groups; —$(CR_2)_p$—$OR^7$, —$(CR_2)_p$—$CH(OH)C_tF_{2t+1}$ wherein t is 1-3, L-Y, $(CR_2)_p$—CN; $(CR_2)_p$—$NR(R^7)$, —$(CR_2)$—$C(O)OR^7$, $C(O)(CR_2)_qOR^8$, —$C(O)O$—$(CR_2)_p$—$NRR^7$, -L-C(O)$R^7$, -L-C(O)—$NRR^7$, -L-C(O)—NR—$(CR_2)_p$—$NRR^7$, -L-C(O)—$(CR_2)_q$—NR—C(O)—$R^8$, -L-S(O)$_2R^8$, -L-S(O)$_2$—$(CR_2)_q$—$NRR^7$, or a radical selected from formula (a), (b), (c) or (d):

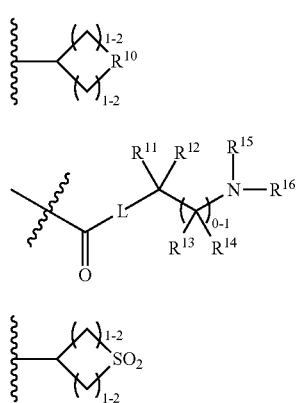

(a)

(b)

(c)

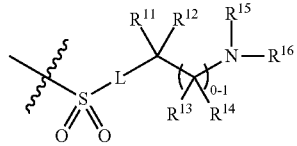

(d)

$R^{10}$ is O, S, $NR^{17}$ wherein $R^{17}$ is H, $C_{1-6}$ alkyl, $SO_2R^{8a}$ or $CO_2R^{8a}$;

$R^{8a}$ is $C_{1-6}$ alkyl; and $R^7$, $R^8$, $R^{10}$, $R^{11}$, $R^{12}$, $R^{13}$, $R^{14}$, $R^{15}$, $R^{16}$, R, L, Y, p and q are as defined in Formula (1).

In the above Formula (1) and (2), $R^2$ may be pyrazolyl, isoxazolyl, pyridine-2-onyl or azepan-2-onyl, each of which is substituted with $C_{1-6}$ alkyl, $C_{1-6}$ haloalkyl or $C_{3-7}$ cycloalkyl.

In another embodiment, the invention provides a compound of Formula (3):

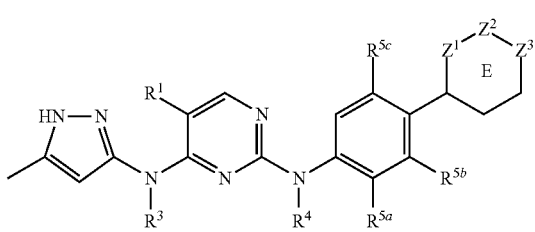

(3)

or a tautomer thereof;

wherein $R^{5b}$ is H; and $R^{5a}$ and $R^{5c}$ are independently halo, $C_{1-6}$ alkyl, $C_{1-6}$ alkoxy, halo-substituted $C_{1-6}$ alkyl, cyano or $C(O)O_{0-1}R^8$ wherein $R^8$ is $C_{1-6}$ alkyl;

$Z^1$ and $Z^2$ are $CH^2$;

$Z^3$ is $NR^6$ or $N(R^6)^+$—$O^-$;

$R^6$ is H, $C_{1-6}$ alkyl optionally substituted with halo and/or hydroxyl groups; —$(CR_2)_p$—$OR^7$, —$(CR_2)_p$—CH(OH)$C_tF_{2t+1}$ wherein t is 1-3, $(CR_2)_p$—CN; $(CR_2)_p$—$NR(R^7)$, —$(CR_2)_p$—$C(O)OR^7$, $C(O)(CR_2)_qOR^8$, —$C(O)O$—$(CR_2)_p$—$NRR^7$, L-Y, -L-C(O)$R^7$, -L-C(O)—$NRR^7$, -L-C(O)—NR—$(CR_2)$—$NRR^7$, -L-C(O)—$(CR_2)_q$—NR—C(O)—$R^8$, -L-S(O)$_2R^8$, -L-S(O)$_2$—$(CR_2)$—$NRR^7$, or a radical selected from formula (a), (b), (c) or (d):

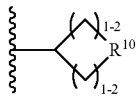

(a)

(b)

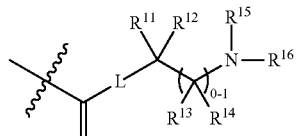

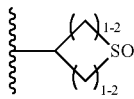

(c)

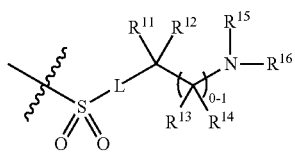
(d)

$R^{10}$ is O, S, $NR^{17}$ wherein $R^{17}$ is H, $C_{1-6}$ alkyl, $SO_2R^{8a}$ or $CO_2R^{8a}$;

$R^{8a}$ is $C_{1-6}$ alkyl; and $R^1$, $R^3$, $R^4$, $R^7$, $R^8$, $R^{10}$, $R^{11}$, $R^{12}$, $R^{13}$, $R^{14}$, $R^{15}$, $R^{16}$, R, L, Y, p, q and E are as defined in Formula (1).

In the above Formula (3), $R^{5a}$ may be halo and $R^{5c}$ is $C_{1-6}$ alkyl. In some examples, $R^6$ is $C_{1-6}$ alkyl or a radical of formula (a) or (c); and $R^{10}$ is O.

In the above Formula (1), (2) and (3), $R^1$ may be halo. In particular examples, $R^1$ is chloro. In other examples, $R^3$ and $R^4$ are H.

In another aspect, the present invention provides a compound of Formula (4):

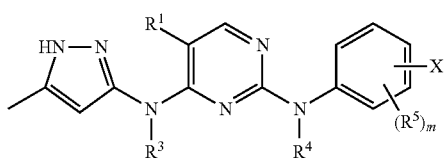
(4)

or a physiologically acceptable salt thereof;

wherein X is a monocyclic 5-6 membered heterocyclic ring containing 1-3 heteroatoms selected from N, O and S, and optionally substituted on a substitutable ring carbon with oxo and at any substitutable ring nitrogen by $R^6$;

$R^1$ is halo;

$R^3$ and $R^4$ are each H;

$R^5$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or $C(O)O_{0-1}R^8$;

$R^6$ is H; $C_{1-6}$ alkyl, $C_{2-6}$ alkenyl or $C_{2-6}$ alkynyl, each of which may be optionally substituted with halo and/or hydroxyl groups; —(CR$_2$)$_p$—OR$^7$, —(CR$_2$)$_p$—CH(OH)C$_t$F$_{2t+1}$ wherein t is 1-3, (CR$_2$)$_p$—CN; (CR$_2$)$_p$—NR(R$^7$), —(CR$_2$)$_p$—C(O)OR$^7$, (CR$_2$)$_p$NR(CR$_2$)$_p$OR$^7$, (CR$_2$)$_p$NR-L-C(O)R$^8$, C(O)(CR$_2$)$_q$OR$^8$, —C(O)O—(CR$_2$)$_p$—NRR$^7$, —C(O)—(CR$_2$)—OR$^7$, L-Y, -L-C(O)R$^7$, -L-C(O)—NRR$^7$, -L-C(O)—NR—(CR$_2$)$_p$—NRR$^7$, -L-C(O)NR(CR$_2$)$_p$OR$^7$, -L-C(O)—(CR$_2$)$_q$—NR—C(O)—R$^8$, -L-C(O)NR(CR$_2$)$_p$SR$^7$, -L-C(O)NR(CR$_2$)$_p$S(O)$_{1-2}$R$^8$, -L-S(O)$_2$R$^8$, -L-S(O)$_2$—(CR$_2$)$_q$—NRR$^7$, -L-S(O)$_2$NR(CR$_2$)$_p$NR(R$^7$) or -L-S(O)$_2$NR(CR$_2$)$_p$OR$^7$;

alternatively, $R^6$ is a radical selected from formula (a), (b), (c) or (d):

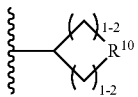
(a)

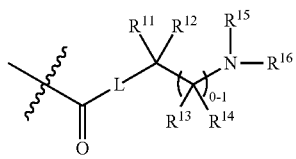
(b)

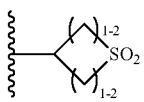
(c)

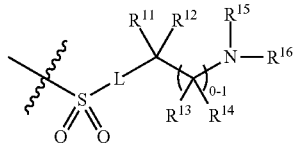
(d)

$R^{10}$ is O, S, $NR^{17}$ wherein $R^{17}$ is H, $C_{1-6}$ alkyl, $SO_2R^{8a}$ or $CO_2R^{8a}$;

$R^{11}$, $R^{12}$, $R^{13}$, $R^{14}$, $R^{15}$ and $R^{16}$ are independently selected from H; $C_{1-6}$ alkoxy; $C_{1-6}$ alkyl, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the atoms to which they are attached may form a 3-7 membered saturated, unsaturated or partially unsaturated ring containing 1-3 heteroatoms selected from N, O and S, and optionally substituted with oxo and 1-3 $R^5$ groups;

L is (CR$_2$)$_{1-4}$ or a bond;

Y is $C_{3-7}$ carbocyclic ring, $C_{6-10}$ aryl, or a 5-10 membered heteroaryl or 4-10 membered heterocyclic ring, each of which is optionally substituted with 1-3 $R^5$ groups;

$R^7$, $R^8$ and $R^{8a}$ are independently $C_{1-6}$ alkyl, $C_{2-6}$ alkenyl or $C_{2-6}$ alkynyl, each of which may be optionally substituted with halo, amino, hydroxyl or cyano; (CR$_2$)$_q$Y or $C_{1-6}$ alkoxy; or $R^7$ is H;

each R is independently H or $C_{1-6}$ alkyl;

R and $R^7$ together with N in each NRR$^7$ may form a 5-6 membered ring containing 1-3 heteroatoms selected from N, O and S, and optionally substituted with oxo and 1-3 $R^5$ groups;

m is 2-4;

n is 1-3;

p is 1-4; and q is 0-4.

In the above Formula (4), X may be morpholinyl, piperazinyl, piperazin-2-onyl, oxazolidin-2-onyl or piperidin-2-onyl each of which is substituted at any substitutable ring nitrogen by $C_{1-6}$ alkyl; or X is tetrahydro-2H-pyran-2-onyl; and $R^1$ is chloro.

In another aspect, the present invention provides pharmaceutical compositions comprising a compound having Formula (1), (2), (3) and (4), and a physiologically acceptable excipient.

In yet another aspect, the invention provides methods for inhibiting IGF-1R in a cell, comprising contacting the cell with an effective amount of a compound having Formula (1), (2), (3) and (4) or a pharmaceutical composition thereof.

The invention also provides methods to treat, ameliorate or prevent a condition which responds to inhibition of IGF-1R or anaplastic lymphoma kinase (ALK) in a mammal suffering from said condition, comprising administering to the mammal a therapeutically effective amount of a compound having Formula (1), (2), (3) and (4) or a pharmaceutical composition thereof, and optionally in combination with a second therapeutic agent. Alternatively, the present invention provides for the use of a compound having Formula (1), (2), (3) and (4), and optionally in combination with a second therapeutic agent, in the manufacture of a medicament for treating a condition mediated by IGF-1R or ALK. The compounds of the invention may be administered, for example, to a mammal suffering from an autoimmune disease, a transplantation disease, an infectious disease or a cell proliferative disorder. In particular examples, the compounds of the invention may be used alone or in combination with a chemotherapeutic agent to treat a cell proliferative disorder, including but not limited to, multiple myeloma, neuroblastoma, synovial, hepatocellular, Ewing's Sarcoma or a solid tumor selected from a osteosarcoma, melanoma, and tumor of breast, renal, prostate, colorectal, thyroid, ovarian, pancreatic, lung, uterine or gastrointestinal tumor.

Definitions

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. "Arylene" means a divalent radical derived from an aryl group. For example, an aryl group may be phenyl, indenyl, indanyl, naphthyl, or 1,2,3,4-tetrahydronaphthalenyl, which may be optionally substituted in the ortho, meta or para position.

"Heteroaryl" as used herein is as defined for aryl above, where one or more of the ring members is a heteroatom. For example, a heteroaryl substituent for use in the compounds of the invention may be a monocyclic or bicyclic 5-10 membered heteroaryl containing 1-4 heteroatoms selected from N, O, and S. Examples of heteroaryls include but are not limited to pyridyl, pyrazinyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, benzotriazolyl, tetrazolyl, pyrazolyl, thienyl, pyrrolyl, isoquinolinyl, purinyl, thiazolyl, tetrazinyl, benzothiazolyl, oxadiazolyl, benzoxadiazolyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring for use in the compounds of the invention may be a 4-7 membered heterocyclic ring containing 1-3 heteroatoms selected from N, O and S, or a combination thereof such as —S(O)— or —$S(O)_2$—. Examples of heterocyclic rings include but are not limited to azetidinyl, morpholino, pyrrolidinyl, pyrrolidinyl-2-one, piperazinyl, piperidinyl, piperidinylone, 1,4-dioxa-8-aza-spiro[4.5]dec-8-yl, 1,2,3,4-tetrahydroquinolinyl, etc. Heterocyclic rings as used herein may encompass bicyclic amines and bicyclic diamines.

As used herein, an H atom in any substituent groups (e.g., $CH_2$) encompasses all suitable isotopic variations, e.g., H, $^2H$ and $^3H$.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

"Mammal" refers to any animal classified as a mammal, including humans, domestic and farm animals, and zoo, sports, or pet animals, such as dogs, cats, cattle, horses, sheep, pigs, goats, rabbits, etc. In particular examples, the mammal is human.

The term "administration" or "administering" of the subject compound means providing a compound of the invention and prodrugs thereof to a subject in need of treatment. Administration "in combination with" one or more further therapeutic agents includes simultaneous (concurrent) and consecutive administration in any order, and in any route of administration.

An "effective amount" of a compound is an amount sufficient to carry out a specifically stated purpose. An "effective amount" may be determined empirically and in a routine manner, in relation to the stated purpose.

The term "therapeutically effective amount" refers to an amount of a compound (e.g., an IGF-1R antagonist) effective to "treat" an IGF-1R-mediated disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The term "cancer" refers to the physiological condition in mammals that is typically characterized by unregulated cell growth/proliferation. Examples of cancer include, but are not limited to: carcinoma, lymphoma, blastoma, and leukemia. More particular examples of cancers include, but are not limited to: chronic lymphocytic leukemia (CLL), lung, including non small cell (NSCLC), breast, ovarian, cervical, endometrial, prostate, colorectal, intestinal carcinoid, bladder, gastric, pancreatic, hepatic (hepatocellular), hepatoblastoma, esophageal, pulmonary adenocarcinoma, mesothelioma, synovial sarcoma, osteosarcoma, head and neck squamous cell carcinoma, juvenile nasopharyngeal angiofibromas, liposarcoma, thyroid, melanoma, basal cell carcinoma (BCC), medulloblastoma and desmoid.

"Treating" or "treatment" or "alleviation" refers to both therapeutic treatment and prophylactic or preventative measures, wherein the object is to prevent or slow down (lessen) the targeted pathologic disease or condition or disorder. Those in need of treatment include those already with the disorder as well as those prone to having the disorder or those in whom the disorder is to be prevented (prophylaxis). When the IGF-1R-mediated disorder is cancer, a subject or mammal is successfully "treated" or shows a reduced tumor burden if, after receiving a therapeutic amount of an IGF-1R antagonist according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the IGF-1R antagonist may prevent growth and/or kill existing cancer cells, it may be cytostatic and/or cytotoxic. Reduction of these signs or symptoms may also be felt by the patient.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Furthermore, a "chemotherapeutic agent" may include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; antiprogesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Modes of Carrying out the Invention

The invention provides novel pyrimidine derivatives and pharmaceutical compositions thereof, and methods for using such compounds.

In one aspect, the invention provides a compound of Formula (1):

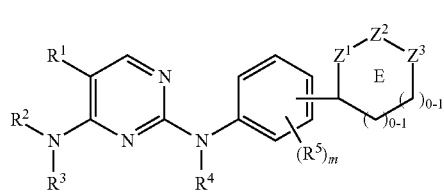

(1)

or a physiologically acceptable salt thereof;
wherein ring E may optionally contain a double bond;
one of $Z^1$, $Z^2$ and $Z^3$ is $NR^6$, $N(R^6)^+$—$O^-$ or $S(O)_{1-2}$ and the others are $CR_2$;
$R^1$ is halo or an optionally halogenated $C_{1-6}$ alkyl;
$R^2$ is pyridine-2-onyl, azepan-2-onyl or a monocyclic 5-6 membered heteroaryl having 1-3 heteroatoms selected from N, O and S; each of which is optionally substituted with $R^9$ wherein $R^9$ is $C_{1-6}$ alkyl, $C_{1-6}$ haloalkyl or $C_{3-7}$ cycloalkyl;
$R^3$ and $R^4$ are each H;
$R^5$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or $C(O)O_{0-1}R^8$;
$R^6$ is H; $C_{1-6}$ alkyl, $C_{2-6}$ alkenyl or $C_{2-6}$ alkynyl, each of which may be optionally substituted with halo and/or hydroxyl groups; —$(CR_2)_p$—$OR^7$, —$(CR_2)_p$—CH (OH)$C_tF_{2t+1}$ wherein t is 1-3, $(CR_2)_p$—CN; $(CR_2)_p$—NR($R^7$), —$(CR_2)_p$—C(O)$OR^7$, $(CR_2)_p$NR$(CR_2)_p$OR$^7$, $(CR_2)_p$NR-L-C(O)$R^8$, C(O)$(CR_2)_q$OR$^8$, —C(O)O—$(CR_2)_p$—NRR$^7$, —C(O)—$(CR_2)_p$—OR$^7$, L-Y, -L-C(O)R$^7$, -L-C(O)—NRR$^7$, -L-C(O)—NR—$(CR_2)_p$—NRR$^7$, -L-C(O)NR$(CR_2)_p$OR$^7$, -L-C(O)—$(CR_2)_q$—NR—C(O)—R$^8$, -L-C(O)NR$(CR_2)_p$SR$^7$, -L-C(O)NR$(CR_2)_p$S(O)$_{1-2}$R$^8$, -L-S(O)$_2$R$^8$, -L-S(O)$_2$—$(CR_2)_q$—NRR$^7$, -L-S(O)$_2$NR$(CR_2)_p$NR($R^7$) or -L-S(O)$_2$NR$(CR_2)_p$OR$^7$;

alternatively, $R^6$ is a radical selected from formula (a), (b), (c) or (d):

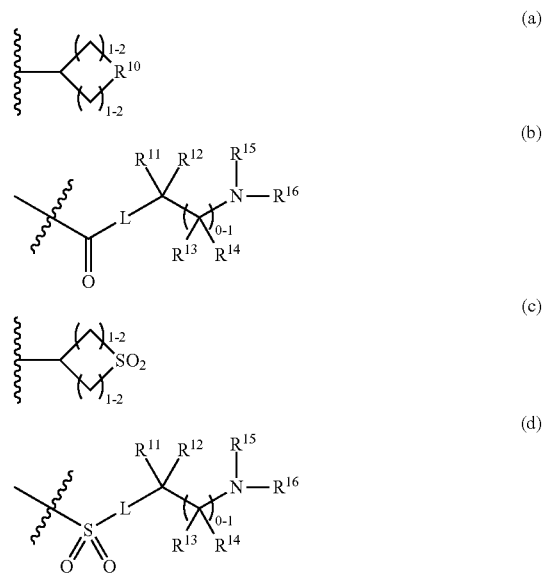

$R^{10}$ is O, S, $NR^{17}$ wherein $R^{17}$ is H, $C_{1-6}$ alkyl, $SO_2R^{8a}$ or $CO_2R^{8a}$;
$R^{11}$, $R^{12}$, $R^{13}$, $R^{14}$, $R^{15}$ and $R^{16}$ are independently selected from H; $C_{1-6}$ alkoxy; $C_{1-6}$ alkyl, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the atoms to which they are attached may form a 3-7 membered saturated, unsaturated or partially unsaturated ring containing 1-3 heteroatoms selected from N, O and S, and optionally substituted with oxo and 1-3 $R^5$ groups;
L is $(CR_2)_{1-4}$ or a bond;
Y is $C_{3-7}$ carbocyclic ring, $C_{6-10}$ aryl, or a 5-10 membered heteroaryl or 4-10 membered heterocyclic ring, each of which is optionally substituted with 1-3 $R^5$ groups;
$R^7$, $R^8$ and $R^{8a}$ are independently $C_{1-6}$ alkyl, $C_{2-6}$ alkenyl or $C_{2-6}$ alkynyl, each of which may be optionally substituted with halo, amino, hydroxyl or cyano; $(CR_2)_qY$ or $C_{1-6}$ alkoxy; or $R^7$ is H;
each R is independently H or $C_{1-6}$ alkyl;
R and $R^7$ together with N in each NRR$^7$ may form a 5-6 membered ring containing 1-3 heteroatoms selected from N, O and S, and optionally substituted with oxo and 1-3 $R^5$ groups;
m is 2-4;
n is 1-3;
p is 1-4; and
q is 0-4.

In one embodiment, the invention provides a compound is of Formula (2):

(2)

wherein one of $R^{5a}$, $R^{5b}$ and $R^{5c}$ is H and the others are independently halo, $C_{1-6}$ alkyl, $C_{1-6}$ alkoxy, halo-substituted $C_{1-6}$ alkyl, cyano or $C(O)O_{0-1}R^8$ wherein $R^8$ is $C_{1-6}$ alkyl; and $R^1$, $R^2$, $R^3$, $R^4$, E, $Z^1$, $Z^2$ and $Z^3$ are as defined in Formula (1).

In another embodiment, the invention provides a compound of Formula (3):

(3)

or a tautomer thereof;

wherein $R^{5b}$ is H; and $R^{5a}$ and $R^{5c}$ are independently halo, $C_{1-6}$ alkyl, $C_{1-6}$ alkoxy, halo-substituted $C_{1-6}$ alkyl, cyano or $C(O)O_{0-1}R^8$ wherein $R^8$ is $C_{1-6}$ alkyl;

$Z^1$ and $Z^2$ are $CH^2$;

$Z^3$ is $NR^6$ or $N(R^6)^+$—$O^-$;

$R^6$ is H, $C_{1-6}$ alkyl optionally substituted with halo and/or hydroxyl groups; —$(CR_2)_p$—$OR^7$, —$(CR_2)_p$—CH(OH)$C_tF_{2t+1}$ wherein t is 1-3, $(CR_2)_p$—CN; $(CR_2)_p$—NR(R$^7$), —$(CR_2)_p$—C(O)OR$^7$, C(O)$(CR_2)_q$OR$^8$, —C(O)O—$(CR_2)_p$—NRR$^7$, L-Y, -L-C(O)R$^7$, -L-C(O)—NRR$^7$, -L-C(O)—NR—$(CR_2)_p$—NRR$^7$, -L-C(O)—$(CR_2)_q$—NR—C(O)—R$^8$, -L-S(O)$_2$R$^8$, -L-S(O)$_2$—$(CR_2)_q$—NRR$^7$, or a radical selected from formula (a), (b), (c) or (d):

(a)

(b)

(c)

(d)

$R^{10}$ is O, S, $NR^{17}$ wherein $R^{17}$ is H, $C_{1-6}$ alkyl, $SO_2R^{8a}$ or $CO_2R^{8a}$;

$R^{8a}$ is $C_{1-6}$ alkyl; and $R^1$, $R^3$, $R^4$, $R^7$, $R^8$, $R^{10}$, $R^{11}$, $R^{12}$, $R^{13}$, $R^{14}$, $R^{15}$, $R^{16}$, R, L, Y, p, q and E are as defined in Formula (1).

In another aspect, the present invention provides a compound of Formula (4):

(4)

or a physiologically acceptable salt thereof;

wherein X is a monocyclic 5-6 membered heterocyclic ring containing 1-3 heteroatoms selected from N, O and S, and optionally substituted on a substitutable ring carbon with oxo and at any substitutable ring nitrogen by $R^6$;

$R^1$ is halo;

$R^3$ and $R^4$ are each H;

$R^5$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or $C(O)O_{0-1}R^8$;

$R^6$ is H; $C_{1-6}$ alkyl, $C_{2-6}$ alkenyl or $C_{2-6}$ alkynyl, each of which may be optionally substituted with halo and/or hydroxyl groups; —$(CR_2)_p$—$OR^7$, —$(CR_2)_p$—CH(OH)$C_tF_{2t+1}$ wherein t is 1-3, $(CR_2)_p$—CN; $(CR_2)_p$—NR(R$^7$), —$(CR_2)_p$—C(O)OR$^7$, $(CR_2)_p$NR$(CR_2)_p$OR$^7$, $(CR_2)_p$NR-L-C(O)R$^8$, C(O)$(CR_2)_q$OR$^8$, —C(O)O—$(CR_2)_p$—NRR$^7$, —C(O)—$(CR_2)_p$—OR$^7$, L-Y, -L-C(O)R$^7$, -L-C(O)—NRR$^7$, -L-C(O)—NR—$(CR_2)_p$—NRR$^7$, -L-C(O)NR$(CR_2)_p$OR$^7$, -L-C(O)—$(CR_2)_q$—NR—C(O)—R$^8$, -L-C(O)NR$(CR_2)_p$SR$^7$, -L-C(O)NR$(CR_2)_p$S(O)$_{1-2}$R$^8$, -L-S(O)$_2$R$^8$, -L-S(O)$_2$—$(CR_2)_q$—NRR$^7$, -L-S(O)$_2$NR$(CR_2)_p$NR(R$^7$) or -L-S(O)$_2$NR$(CR_2)_p$OR$^7$;

alternatively, $R^6$ is a radical selected from formula (a), (b), (c) or (d):

(a)

-continued

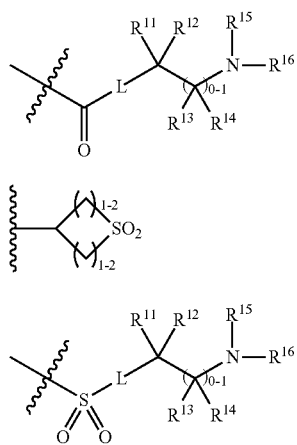

$R^{10}$ is O, S, $NR^{17}$ wherein $R^{17}$ is H, $C_{1-6}$ alkyl, $SO_2R^{8a}$ or $CO_2R^{8a}$;

$R^{11}$, $R^{12}$, $R^{13}$, $R^{14}$, $R^{15}$ and $R^{16}$ are independently selected from H; $C_{1-6}$ alkoxy; $C_{1-6}$ alkyl, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the atoms to which they are attached may form a 3-7 membered saturated, unsaturated or partially unsaturated ring containing 1-3 heteroatoms selected from N, O and S, and optionally substituted with oxo and 1-3 $R^5$ groups;

L is $(CR_2)_{1-4}$ or a bond;

Y is $C_{3-7}$ carbocyclic ring, $C_{6-10}$ aryl, or a 5-10 membered heteroaryl or 4-10 membered heterocyclic ring, each of which is optionally substituted with 1-3 $R^5$ groups;

$R^7$, $R^8$ and $R^{8a}$ are independently $C_{1-6}$ alkyl, $C_{2-6}$ alkenyl or $C_{2-6}$ alkynyl, each of which may be optionally substituted with halo, amino, hydroxyl or cyano; $(CR_2)_qY$ or $C_{1-6}$ alkoxy; or $R^7$ is H;

each R is independently H or $C_{1-6}$ alkyl;

R and $R^7$ together with N in each $NRR^7$ may form a 5-6 membered ring containing 1-3 heteroatoms selected from N, O and S, and optionally substituted with oxo and 1-3 $R^5$ groups;

m is 2-4;

n is 1-3;

p is 1-4; and q is 0-4.

In yet another aspect, the invention provides compounds of Formula (5):

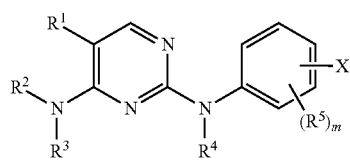

or physiologically acceptable salts thereof;

wherein X is a 4-7 membered heterocyclic ring containing $NR^6$,  $-N^+R^6\overset{O^-}{|}$, O or S, and optionally substituted with 1-3 $R^5$ groups;

wherein $R^1$ is halo, $C_{1-6}$ alkyl, or a halo-substituted $C_{1-6}$ alkyl;

$R^2$ is an optionally substituted 5-6 membered heteroaryl or 5-7 membered heterocyclic ring, each having 1-3 heteroatoms selected from N, O and S and optionally substituted with 1-3 $R^9$ groups;

$R^3$ and $R^4$ are independently H, $C(O)R^8$, $C_{1-6}$ alkyl or halo-substituted $C_{1-6}$ alkyl;

$R^5$ and $R^9$ are independently $C_{1-6}$ alkyl, $C_{2-6}$ alkenyl or $C_{2-6}$ alkynyl, each of which may be optionally substituted with halo, amino or hydroxyl groups; or $R^5$ and $R^9$ are independently $C_{1-6}$ alkoxy, halo-substituted $C_{1-6}$ alkoxy, halo, nitro, cyano, $CR(OR^7)R^7$, $OR^7$, $O(CR_2)_p$—$OR^7$, $NR(R^7)$, $CR(R^7)NRR^7$, $(CR_2)_{1-6}NR(CR_2)OR^7$, $(CR_2)_{1-6}NR(CR_2)_qC(O)R^8$, —$C(O)$—$(CR_2)_q$—NR—C(O)—$R^8$, $(CR_2)_qY$, $C(O)O_{0-1}R^7$, $C(O)NR(R^7)$, $C(O)CRR^7$—$NR(R^7)$, $C(O)NR(CR_2)_pNR(R^7)$, $C(O)NR(CR_2)_pOR^7$, $C(O)NR(CR_2)_pSR^7$, $C(O)NR(CR_2)_pS(O)_{1-2}R^8$, $S(O)_{0-2}R^8$, $S(O)_2NRR^7$, $S(O)_2NR(CR_2)_pNR(R^7)$, or $S(O)_2NR(CR_2)_pOR^7$;

$R^6$ is H; $C_{1-6}$ alkyl, $C_{2-6}$ alkenyl or $C_{2-6}$ alkynyl, each of which may be optionally substituted with halo, amino, hydroxyl or alkoxy; —$(CR_2)_p$—CN; C(O)H, $CR(OR^7)R^7$, $(CR_2)_p$—$OR^7$, $(CR_2)_p$—$NR(R^7)$, $CR(R^7)NRR^7$, -L-Y, -L-C(O)$O_{0-1}$—$(CR_2)_q$—$R^8$, —$(CR_2)_p$—$C(O)O_{0-1}$—$R^7$, -L-C(O)—$NRR^7$, -L-C(O)$O_{0-1}$—CR($R^7$)—$NRR^7$, -L-C(O)—NR—$(CR_2)_p$—$NRR^7$, -L-C(O)NR($CR_2)_pOR^7$, -L-C(O)—$(CR_2)_q$—NR—C(O)—$R^8$, -L-C(O)NR($CR_2)_pSR^7$, -L-C(O)NR($CR_2)_pS(O)_{1-2}R^8$, -L-S(O)$_2R^8$, $(CR_2)_pNR(CR_2)_pOR^7$, $(CR_2)_pNR$-L-C(O)$R^8$, -L-S(O)$_2NRR^7$, -L-S(O)$_2NR(CR_2)_pNR(R^7)$ or -L-S(O)$_2NR(CR^2)_pOR^7$;

alternatively, $R^6$ is a radical selected from formula (a), (b), (c) or (d):

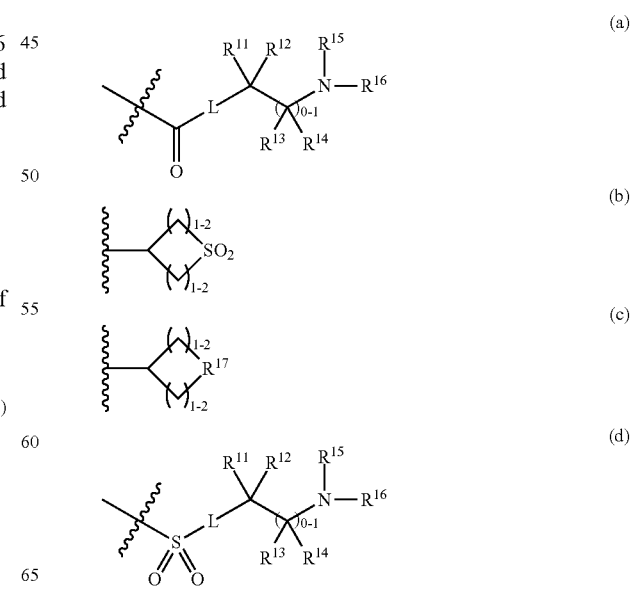

wherein $R^{11}$, $R^{12}$, $R^{13}$, $R^{14}$, $R^{15}$ and $R^{16}$ are independently selected from H or $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the carbon and/or nitrogen atoms to which they are attached may form a 3-7 membered saturated, unsaturated or partially unsaturated ring optionally containing up to 3 atoms or groups selected from C(O), N, O and $S(O)O_{0-2}$;

$R^{17}$ is O or $SO_2R^8$;

L is $(CR_2)_{1-4}$ or a bond;

Y is $C_{3-7}$ carbocyclic ring, $C_{6-10}$ aryl, or a 5-10 membered heteroaryl or 4-10 membered heterocyclic ring, each of which is optionally substituted with 1-3 $R^5$ groups;

$R^7$ and $R^8$ are independently $C_{1-6}$ alkyl, $C_{2-6}$ alkenyl or $C_{2-6}$ alkynyl, each of which may be optionally substituted with halo, amino, hydroxyl or cyano; $(CR_2)_qY$ or $C_{1-6}$ alkoxy; or $R^7$ is H;

each R is H or $C_{1-6}$ alkyl;

m is 2-4;

n is 1-3;

p is 1-4; and q is 0-4.

In the above Formula (5), examples of 5-6 membered heteroaryl or 5-7 membered heterocyclic ring $R^2$ groups include but are not limited to pyrazolyl, pyrrolyl, thiophenyl, pyrimidinyl, isoxazolyl, pyridyl, azepan-2-onyl, 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5, 6-dihydro-4H-thiazine, 4H-1, 4-thiazine, tetrahydro-1, 4-thiazine, 2H-1, 2-oxazine, 4H-1, 2-oxazine, 6H-1, 2-oxazine, 2H-1,3-oxazine, 4H-1,3-oxazine, 4H-1, 4-oxazine, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidinone, pyrazoline, pyrazolidine, imidazoline, imidazolidine, 1,2-dioxole, 1,2-dioxolane, 1,3-dioxole, 1,3-dioxolane, 3H-1,2-dithiole, 1, 2-dithiolane, 1,3-dithiole, 1,3-dithiolane, isoxazoline, isoxazolidine, oxazoline, oxazolidine, thiazoline, thiozolidine, 3H-1, 2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2, 3-trioxolane, 1,2, 4-trioxolane, 1,2, 3-triazoline and 1,2, 3-triazolidine.

In each of the above formula, any asymmetric carbon atoms may be present in the (R)—, (S)— or (R,S)-configuration. The compounds may thus be present as mixtures of isomers or as pure isomers, for example, as pure enantiomers or diastereomers. The invention further encompasses possible tautomers of the inventive compounds.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively.

The invention includes various isotopically labeled compounds as defined herein, for example, those into which radioactive isotopes such as $^3H$, $^{13}C$, and $^{14}C$, are present. Such isotopically labelled compounds are useful in metabolic studies (with, for example, $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In other examples, an $^{18}F$ or labeled compound may be used for PET or SPECT studies. Isotopic variations of the compounds have the potential to change a compound's metabolic fate and/or create small changes in physical properties such as hydrophobicity, and the like. Isotopic variations also have the potential to enhance efficacy and safety, enhance bioavailability and half-life, alter protein binding, change biodistribution, increase the proportion of active metabolites and/or decrease the formation of reactive or toxic metabolites. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl$C_1$-$C_8$alkyl, $C_1$-$C_8$alkoxy$C_1$-$C_8$alkyl); halo, amino, amidino, $C_{1-6}$ alkoxy; hydroxyl, methylenedioxy, carboxy; $C_{1-8}$ alkylcarbonyl, $C_{1-8}$ alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Pharmacology and Utility

The compounds of the invention and their pharmaceutically acceptable salts exhibit valuable pharmacological properties when tested in vitro in cell-free kinase assays and in cellular assays, and are therefore useful as pharmaceuticals.

In one aspect, the compounds of the invention may inhibit insulin like growth-factor receptor 1 (IGF-1R), and may be useful in the treatment of IGF-1 R mediated diseases. Examples of IGF-1R mediated diseases include but are not limited to proliferative diseases, such as tumors, for example breast, renal, prostate, colorectal, thyroid, ovarian, pancreas, neuronal, lung, uterine and gastro intestinal tumors, as well as osteosarcomas and melanomas. The efficacy of the compounds of the invention as inhibitors of IGF-1R tyrosine kinase activity may be demonstrated using a cellular capture ELISA. In this assay, the activity of the compounds of the invention against (IGF-1)-induced autophosphorylation of the IGF-1R is determined.

In another aspect, the compounds of the invention may inhibit the tyrosine kinase activity of anaplastic lymphoma kinase (ALK) and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 μCi/assay (=30 μl) [γ-$^{33}$P]-ATP, 2 μM ATP, 3 μg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 μl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition.

The compounds of the invention may potently inhibit the growth of human NPM-ALK overexpressing murine BaF3 cells (DSMZ Deutsche Sammiung von Mikroorganismen und Zellkulturen GmbH, Germany). The expression of NPM-ALK may be achieved by transfecting the BaF3 cell line with an expression vector pCIneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 μl of lysis buffer comprising 20 mM sodium citrate, pH 4.0, 26.8 mM sodium chloride, 0.4% NP40 and 20 mM EDTA is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

The compounds of the invention may also be useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitis, seborrhoeic dermatitis), inflammatory eye diseases, e.g. Sjoegren's syndrome, keratoconjunctivitis or uveitis, inflammatory bowel disease, Crohn's disease or ulcerative colitis.

In accordance with the foregoing, the present invention provides:

(1) a compound of the invention for use as a pharmaceutical;

(2) a compound of the invention for use as an IGF-1R inhibitor, for example for use in any of the particular indications hereinbefore set forth;

(3) a pharmaceutical composition, e.g. for use in any of the indications herein before set forth, comprising a compound of the invention as active ingredient together with one or more pharmaceutically acceptable diluents or carriers;

(4) a method for the treatment of any particular indication set forth hereinbefore in a subject in need thereof which comprises administering an effective amount of a compound of the invention or a pharmaceutical composition comprising same;

(5) the use of a compound of the invention for the manufacture of a medicament for the treatment or prevention of a disease or condition in which IGF-1R activation plays a role or is implicated;

(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;

(7) a combination comprising a therapeutically effective amount of a compound of the invention and one or more further drug substances, said further drug substance being useful in any of the particular indications set forth hereinbefore;

(8) use of a compound of the invention for the manufacture of a medicament for the treatment or prevention of a disease which responds to inhibition of the anaplastic lymphoma kinase;

(9) the use according to (8), wherein the disease to be treated is selected from anaplastic large cell lymphoma, non-Hodgkin's lymphomas, inflammatory myofibroblastic tumors, neuroblastomas and neoplastic diseases;

(10) the use according to (8) or (9), wherein the compound is any one of the examples, or a pharmaceutically acceptable salt thereof;

(11) a method for the treatment of a disease which responds to inhibition of the anaplastic lymphoma kinase, especially a disease selected from anaplastic large-cell lymphoma, non Hodgkin's lymphomas, inflammatory myofibroblastic tumors, neuroblastomas and neoplastic diseases, comprising administering an effective amount of a compound of the invention or a pharmaceutically acceptable salt thereof.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.01 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the invention may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length $C_8$ to $C_{12}$ from Hüls A G, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the invention may be administered as the sole active ingredient, or together with other drugs useful against neoplastic diseases or useful in immunomodulating regimens. For example, the compounds of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991).

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. A compound of the invention in a base addition salt form may be converted to the corresponding free acid by treating with a suitable acid (e.g., hydrochloric acid, etc.). In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the inventive compounds with a salt-forming group may be prepared in a manner known per se. Acid addition salts of compounds of Formula (1), (2), (3) and (4), may thus be obtained by treatment with an acid or with a suitable anion exchange reagent. Pharmaceutically acceptable salts of the compounds of the invention may be formed, for example, as acid addition salts, with organic or inorganic acids, from compounds of Formula (1), (2), (3) and (4), with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid. For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", $3^{rd}$ edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process as described in the Examples; and
(a) optionally converting a compound of the invention into a pharmaceutically acceptable salt;
(b) optionally converting a salt form of a compound of the invention to a non-salt form;
(c) optionally converting an unoxidized form of a compound of the invention into a pharmaceutically acceptable N-oxide;
(d) optionally converting an N-oxide form of a compound of the invention to its unoxidized form;
(e) optionally resolving an individual isomer of a compound of the invention from a mixture of isomers;
(f) optionally converting a non-derivatized compound of the invention into a pharmaceutically acceptable prodrug derivative; and
(g) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

Intermediate 1

2,5-dichloro-N-(5-methyl-1H-pyrazol-3-yl)pyrimidin-4-amine

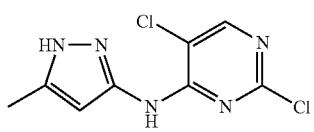

A mixture of 5-methyl-1H-pyrazol-3-amine (3.00 g, 30.9 mmol), 2,4,5-trichloropyrimidine (5.67 g, 30.9 mmol, 1 equiv.) and $Na_2CO_3$ (3.60 g, 34.0 mmol, 1.1 equiv.) in EtOH (100 mL) was heated at 40° C. for 24 h. The solvent was removed in vacuo. The resulting residue was partitioned between EtOAc (350 mL) and water (100 mL). The EtOAc layer was washed with water (3×), saturated aqueous NaCl (1×) and dried over $Na_2SO_4$. The resulting EtOAc solution was concentrated in vacuo, providing the product 2,5-dichloro-N-(5-methyl-1H-pyrazol-3-yl)pyrimidin-4-amine; ESMS m/z 244.0 (M+H$^+$).

Intermediate 2

2-chloro-N-(5-methyl-1H-pyrazol-3-yl)-5-(trifluoromethyl)pyrimidin-4-amine

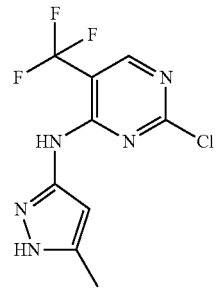 [SMILES: Cc1cc(Nc2nc(Cl)ncc2C(F)(F)F)n[nH]1]

A mixture of 2,4-dichloro-5-(trifluoromethyl)pyrimidine (1.06 g, 4.86 mmol), 5-methyl-1H-pyrazol-3-amine (472.2 mg, 4.86 mmol) and sodium carbonate (2.06 g, 19.4 mmol) in 100 mL of EtOH was stirred at room temperature overnight. The reaction mixture was concentrated in vacuo. The crude solid was partitioned between EtOAc and water. The combined organic extracts were dried ($Na_2SO_4$), concentrated in vacuo, and purified by silica chromatography (EtOAc/hexanes: 1/1) to afford 2-chloro-N-(5-methyl-1H-pyrazol-3-yl)-5-(trifluoromethyl)pyrimidin-4-amine; ESMS m/z 278.0 (M+H$^+$).

Intermediate 3

2-chloro-5-methyl-N-(5-methyl-1H-pyrazol-3-yl)pyrimidin-4-amine

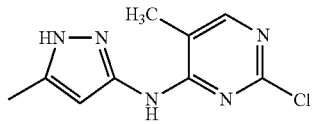

A mixture of 5-methyl-1H-pyrazol-3-amine (3.00 g, 30.9 mmol), 2,4-dichloro-5-methylpyrimidine (5.03 g, 30.9 mmol, 1 equiv.) and $Na_2CO_3$ (3.60 g, 34.0 mmol, 1.1 equiv.) in EtOH (100 mL) was heated at 40° C. for 24 h. The solvent was removed in vacuo. The resulting residue was partitioned between EtOAc (350 mL) and water (100 mL). The EtOAc layer was washed with water (3×), saturated aqueous NaCl (1×), dried over $Na_2SO_4$, and concentrated in vacuo. The resulting crude product was sonicated in $Et_2O$ (200 mL) and the resulting precipitate collected by filtration. This powder was further washed with $Et_2O$, providing the product 2-chloro-5-methyl-N-(5-methyl-1H-pyrazol-3-yl)pyrimidin-4-amine; ESMS m/z 224.1 (M+H$^+$).

Intermediate 4

N-(2,5-dichloropyrimidin-4-yl)-5-methylisoxazol-3-amine

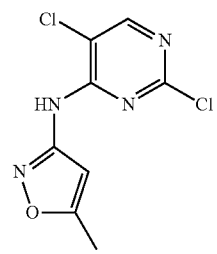

The mixture 5-methylisoxazol-3-amine (98 mg, 1.0 mmol), 2,4,5-trichloropyrimidine (344 µL, 3.0 mmol), and sodium carbonate (106 mg, 1.0 mmol) in 3 mL of EtOH was heated at 60° C. overnight. The reaction mixture was concentrated and then partitioned between EtOAc and brine. The collected organic extracts were dried ($Na_2SO_4$), concentrated in vacuo, and purified with silica gel chromatography (MeOH/DCM: 1/9) to afford N-(2,5-dichloropyrimidin-4-yl)-5-methylisoxazol-3-amine; ESMS m/z 245.0 (M+H$^+$).

Intermediate 5

2,5-dichloro-N-(5-cyclopropyl-1H-pyrazol-3-yl)pyrimidin-4-amine

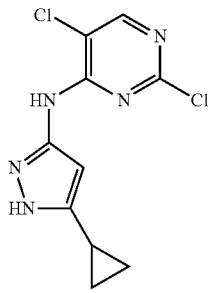 [SMILES: Clc1ncc(Cl)c(Nc2cc(C3CC3)[nH]n2)n1]

A mixture of 5-cyclopropyl-1H-pyrazol-3-amine (246 mg, 2.00 mmol), 2,4,5-trichloropyrimidine (367 mg, 2.00 mmol, 1 equiv.) and $Na_2CO_3$ (233 mg, 2.20 mmol, 1.1 equiv.) in EtOH (10 mL) was heated at 40° C. for 16 h. The crude reaction mixture was diluted with EtOAc and sequentially washed with: water (3×) and saturated aqueous NaCl (1×). The resulting EtOAc layer was dried over $Na_2SO_4$ and then concentrated in vacuo, providing 2,5-dichloro-N-(5-cyclopropyl-1H-pyrazol-3-yl)pyrimidin-4-amine; ESMS m/z 270.0 (M+H$^+$).

Intermediate 6

3-(2,5-dichloropyrimidin-4-ylamino)azepan-2-one

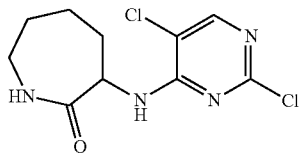 [SMILES: O=C1NCCCCC1Nc1nc(Cl)ncc1Cl]

A mixture of (±)-α-amino-ε-caprolactam (256 mg, 2.0 mmol), 2,4,5-trichloropyrimidine (366 mg, 2.0 mmol, 1 equiv.) and NaHCO$_3$ (168 mg, 2 mmol, 1 equiv.) in a mixture of MeOH (12 mL) and H$_2$O (6 mL) was stirred at room temperature for 15 h. The resulting precipitate was collected by vacuum filtration and washed with small amounts of MeOH and water, providing the product 3-(2,5-dichloropyrimidin-4-ylamino)azepan-2-one; ESMS m/z 275.0 (M+H$^+$).

Intermediate 7

3-(2,5-dichloropyrimidin-4-ylamino)pyridin-2(1H)-one

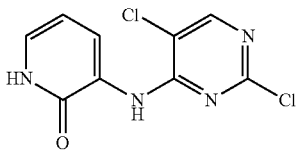 [SMILES: O=c1[nH]cccc1Nc1nc(Cl)ncc1Cl]

A mixture of 3-aminopyridin-2(1H)-one (99 mg, 0.90 mmol), 2,4,5-trichloropyrimidine (165 mg, 0.90 mmol, 1 equiv.) and NaHCO$_3$ (76 mg, 0.90 mmol, 1 equiv.) in a mixture of MeOH (6 mL) and H$_2$O (3 mL) was stirred at room temperature for 24 h. The resulting precipitate was collected by vacuum filtration and washed with small amounts of MeOH and water, providing the product 3-(2,5-dichloropyrimidin-4-ylamino)pyridin-2(1H)-one; ESMS m/z 257.0 (M+H$^+$).

Intermediate 8

2,5-Dichloro-N-(5-methyl-1-(tetrahydro-2H-pyran-2-yl)-1H-pyrazol-3-yl)pyrimidin-4-amine

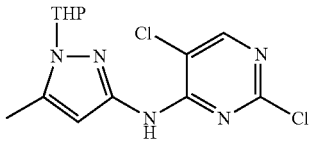

To a mixture of 2,5-dichloro-N-(5-methyl-1H-pyrazol-3-yl)pyrimidin-4-amine (2.44 g, 10 mmol) and 4-toluenesulfonic acid monohydrate (1.9 g, 10 mmol) in THF (200 mL), was added DHP (4.25 g, 50 mmol). After stirring overnight, the reaction turned clear. After concentration, the residue was dissolved in ethyl acetate and washed with Na$_2$CO$_3$ saturated aqueous solution. The organic layer was then washed with brine, dried over sodium sulfate and concentrated in vacuo to afford 2,5-Dichloro-N-(5-methyl-1-(tetrahydro-2H-pyran-2-yl)-1H-pyrazol-3-yl)pyrimidin-4-amine as light yellow solid, which was used in subsequent reactions without further purification; ESMS m/z 244 (M−THP+H$^+$); TLC Rf=0.6 (Silica; 1:1 ethyl acetate/hexanes; starting material Rf=0.2).

Intermediate 9

2,5-Dichloro-N-(5-(trifluoromethyl)-1H-pyrazol-3-yl)pyrimidin-4-amine

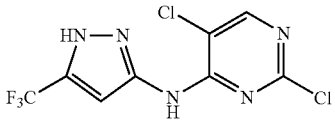 [SMILES: FC(F)(F)c1cc(Nc2nc(Cl)ncc2Cl)n[nH]1]

Step 1: 5-(Trifluoromethyl)-1H-pyrazol-3-amine

A mixture of (E)-4-amino-4-ethoxy-1,1,1-trifluorobut-3-en-2-one (5.00 g, 27 mmol) and hydrazine (1.05 g) in anhydrous EtOH (20 mL) was stirred at 80° C. in a sealed vial overnight. The reaction was quenched with water (50 mL), and extracted with EtOAc (100 ml, then 2×50 mL). The EtOAc layers were combined and sequentially washed with water (25 mL), brine (25 mL), dried over $Na_2SO_4$ and evaporated to give a light brown oily residue. The crude product was purified by silica chromatography (30-100% EtOAc in hexanes gradient) to give 5-(trifluoromethyl)-1H-pyrazol-3-amine as an off white solid; ESMS m/z 152.0 (M+H$^+$).

Step 2: 2,5-Dichloro-N-(5-(trifluoromethyl)-1H-pyrazol-3-yl)pyrimidin-4-amine A mixture of 5-(trifluoromethyl)-1H-pyrazol-3-amine (500 mg, 3.3 mmol), 2,4,5-trichloropyrimidine (607 mg, 3.3 mmol) and sodium carbonate (525 mg, 5 mmol) in anhydrous EtOH (10 mL) was stirred at rt. After one day, LCMS showed the reaction was not complete. Additional 2,4,5-trichloropyrimidine (0.15 mL) and sodium carbonate (525 mg) were added and the reaction continued for two more days. The solvent was evaporated, and the residue was extracted with DCM (3×20 mL). The combined DCM layers were washed with brine (10 mL), dried over $Na_2SO_4$ and evaporated. The crude product was purified by silica chromatography (0-50% EtOAc in hexanes gradient) to give 2,5-Dichloro-N-(5-(trifluoromethyl)-1H-pyrazol-3-yl)pyrimidin-4-amine as a light tan colored solid; ESMS m/z 297.9 (M+H$^+$).

Intermediate 10

2,5-Dichloro-N-(5-ethyl-1H-pyrazol-3-yl)pyrimidin-4-amine

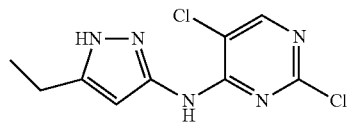 [SMILES: CCc1cc(Nc2nc(Cl)ncc2Cl)n[nH]1]

A mixture of 5-ethyl-1H-pyrazol-3-amine (1.00 g, 6.77 mmol), 2,4,5-trichloropyrimidine (1.24 g, 6.77 mmol) and $Na_2CO_3$ (1.79 g, 16.9 mmol) in iso-propanol (15 mL) was stirred in a sealed vial at rt for two days. Water (10 mL) was added. The solid was collected by filtration, washed with water (10 mL) and dried to give 2,5-Dichloro-N-(5-ethyl-1H-pyrazol-3-yl)pyrimidin-4-amine as a light yellow solid; ESMS m/z 258.0 (M+H$^+$).

Intermediate 11

1-chloro-5-methyl-4-nitro-2-(trifluoromethyl)benzene

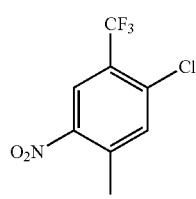

To a solution of 2-chloro-4-methyl-1-(trifluoromethyl) benzene (6.65 g, 34.1 mmol) in conc. sulfuric acid (25 mL) at 0° C. was added potassium nitrate (3.46 g, 34.1 mmol) in sulfuric acid (15 mL). After stirring at 0° C. for 1.5 h, the reaction mixture was poured into 500 mL of ice water. The precipitate was collected by filtration and washed with copious amounts of water, yielding 1-chloro-5-fluoro-4-nitro-2-(trifluoromethyl)benzene as an orange solid; $^1$H NMR (400 MHz, chloroform-d) δ 8.356 (s, 1H), 7.543 (s, 1H), 2.660 (s, 3H).

Intermediate 12

2-Bromo-4-methyl-5-nitrobenzonitrile

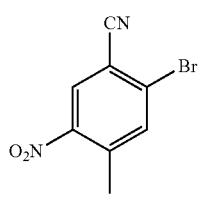

Following the same procedure as described in Intermediate 11 starting with 2-bromo-4-methylbenzonitrile, 2-bromo-4-methyl-5-nitrobenzonitrile was obtained as a yellow solid; $^1$H NMR (400 MHz, chloroform-d) δ 8.290 (s, 1H), 7.742 (s, 1H), 2.683 (s, 3H).

Intermediate 13

5-Amino-2-bromo-4-methylbenzonitrile

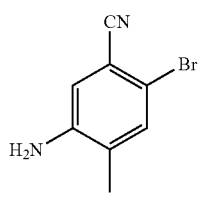

To a solution of 2-bromo-4-methyl-5-nitrobenzonitrile (500 mg, 2.07 mmol) in ethanol (20 mL) was added tin chloride (785 mg, 4.14 mmol). The mixture was refluxed for 5 h. After cooling to room temperature, triethylamine (1.01 g, 10 mmol) was added. The mixture was concentrated and purified by silica chromatography (30-50% ethyl acetate in hexanes gradient) to afford 5-Amino-2-bromo-4-methylbenzonitrile a as beige solid; ESMS m/z 211 (M+H$^+$).

Intermediate 14

Methyl 2-bromo-4-methyl-5-nitrobenzoate

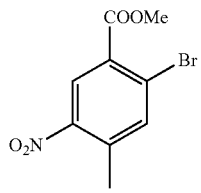

Following the same procedure as described in Intermediate 11 starting with methyl 2-bromo-4-methylbenzoate, the title compound was obtained as a white solid; $^1$H NMR (400 MHz, chloroform-d) δ 8.505 (s, 1H), 7.711 (s, 1H), 3.967 (s, 3H), 2.640 (s, 3H).

Intermediate 15

Methyl 5-amino-2-bromo-4-methylbenzoate

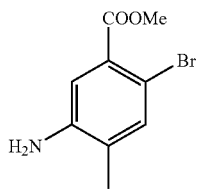

Following the same procedure as described in Intermediate 13, the title compound was obtained as a beige solid; ESMS m/z 244 (M+H$^+$).

Intermediate 16

4-Bromo-5-methoxy-2-methylaniline

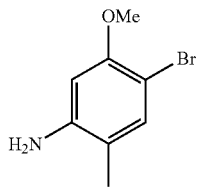

Step 1: N-(5-methoxy-2-methylphenyl)acetamide

To a solution of triethylamine (2.9 g, 14.4 mmol) and 5-methoxy-2-methylaniline (1.0 g, 7.2 mmol) in DCM (30 mL) at 0° C., was added acetyl chloride (0.57 g, 7.2 mmol) dropwise. The mixture was stirred at room temperature for 1 hour. The reaction was quenched with saturated ammonium chloride aqueous solution, and extracted with DCM. The organic layer was dried over Na$_2$SO$_4$ and concentrated to give N-(5-methoxy-2-methylphenyl)acetamide as needle-shaped crystals. The crude product was used in the next step without further purification.

Step 2:
N-(4-bromo-5-methoxy-2-methylphenyl)acetamide

To a solution of N-(5-methoxy-2-methylphenyl)acetamide in acetic acid (40 mL) was added Br$_2$ (3 g, 19 mmol) slowly. The mixture was capped and stirred at 50° C. for 5 hours. The reaction was cooled to room temperature, then quenched with sodium sulfite aqueous solution, and extracted with ethyl acetate (3×50 mL). The combined organic layer was dried over Na$_2$SO$_4$ and concentrated to give crude N-(4-bromo-5-methoxy-2-methylphenyl)acetamide as a brown oil, which was used in the next step without further purification.

Step 3: 4-bromo-5-methoxy-2-methylaniline

N-(4-bromo-5-methoxy-2-methylphenyl)acetamide was dissolved in methanol (15 mL) and concentrated HCl (30 mL). The mixture was refluxed at 95° C. overnight. After cooling to room temperature, the mixture was poured into ice water, and basified to pH=12 with conc. NaOH aqueous solution. The mixture was then extracted with ethyl acetate (3×50 mL). The combined organic layer was dried over Na$_2$SO$_4$ and concentrated. The crude product was purified by silica chromatography (15% ethyl acetate in hexanes) to give 4-bromo-5-methoxy-2-methylaniline as a beige solid; $^1$H NMR (400 mHz, CDCl$_3$) 7.20 (s, 1H), 6.37 (s, 1H), 4.6 (br, 2H), 3.82 (s, 3H), 2.12 (s, 3H).

Intermediate 17

2-Fluoro-5-methyl-4-(4,4,5,5-tetramethyl-1,3,2-di-oxaborolan-2-yl)aniline

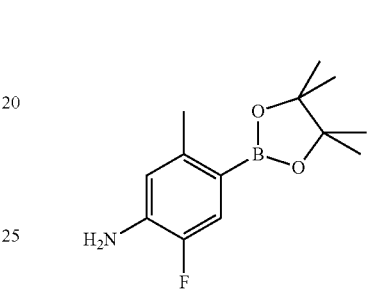

A mixture of 4-bromo-2-fluoro-5-methylaniline (2.0 g, 9.8 mmol), bis(pinacolato)diboron (2.74 g, 10.8 mmol), tricyclohexylphosphine (274.8 mg, 0.98 mmol), Pd$_2$(dba)$_3$ (448.9 mg, 0.49 mmol), and potassium acetate (1.92 g, 19.6 mmol) in 60 mL of 1,4-dioxane was degassed and purged with nitrogen. The reaction mixture was heated at 80° C. overnight and then cooled to room temperature. The mixture was partitioned between EtOAc and water and the collected organic extracts were dried (Na$_2$SO$_4$), concentrated in vacuo, and purified by silica chromatography (EtOAc/Hexanes: 20/80) to afford 2-fluoro-5-methyl-4-(4,4,5,5-tetramethyl-1,3,2-di-oxaborolan-2-yl)aniline; ESMS m/z 252.2 (M+H$^+$).

Intermediate 18

2-Isopropoxy-5-methyl-4-(1-methyl-piperidin-4-yl)-phenylamine

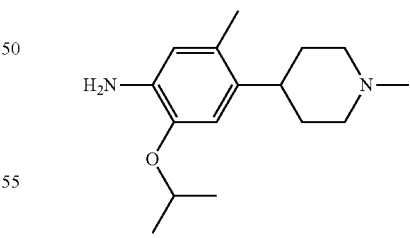

Step 1: 1-bromo-5-fluoro-2-methyl-4-nitrobenzene

To a solution of 2-bromo-4-fluoro-1-methylbenzene (5 g, 26.4 mmol) dissolved in conc. sulfuric acid (20 mL) was added potassium nitrate (2.67 g, 26.4 mmol) in sulfuric acid (5 mL) at 0° C. After stirring at 0° C. for 1 hr, the reaction was diluted with water, extracted with ethyl acetate (3×40 mL). The combined organic phases were washed with saturated sodium bicarbonate solution and brine sequentially, and then dried over Na$_2$SO$_4$. The crude product obtained after concentration was purified by silica gel column chromatography with mixed solvent hexanes/EtOAc (95/5) to afford 1-bromo-5-fluoro-2-methyl-4-nitrobenzene as an orange solid. $^1$H NMR (400 MHz, chloroform-d) δ 7.93 (d, 1H, J=7.6 Hz), 7.50 (d, 1H, J=10 Hz), 2.43 (s, 3H).

Step 2:
1-bromo-5-isopropoxy-2-methyl-4-nitrobenzene

To a solution of 1-bromo-5-fluoro-2-methyl-4-nitrobenzene (Step 1, 1.5 g, 6.4 mmol) in 2-propanol (30 mL) was added cesium carbonate (5.3 g, 16 mmol). The mixture was heated at 50° C. overnight. The mixture was concentrated and partitioned between ethyl acetate and water. The organic layer was concentrated and the residue was purified with silica gel column chromatography with 5% ethyl acetate in hexanes to afford 1-bromo-5-isopropoxy-2-methyl-4-nitrobenzene as a yellow solid.

Step 3:
4-(5-Isopropoxy-2-methyl-4-nitrophenyl)pyridine

To a mixture of 1-bromo-5-isopropoxy-2-methyl-4-nitrobenzene (Step 2, Ig, 3.65 mmol), pyridine-4-boronic acid (490 mg, 4 mmol), 2-dicyclohexylphosphino-2',6'-dimethoxybiphenyl (300 mg, 0.73 mmol) and potassium phosphate (1.55 g, 7.3 mmol) in mixed solvent of dioxane (15 mL) and water (7.5 mL) was added tris(dibenzylidene-acetone)dipalladium (0) (334 mg, 0.36 mmol). This mixture was sealed and purged with nitrogen for 3 minutes and then heated at 120° C. for 5 hours. The mixture was cooled to room temperature, filtered, and the filtrate was concentrated. After concentration, the crude product was purified with silica gel flash column chromatography (60% ethyl acetate in hexanes) to afford 4-(5-isopropoxy-2-methyl-4-nitrophenyl)pyridine a as yellow solid: ESMS m/z 273.2 (M+H$^+$).

Step 4: 4-(5-Isopropoxy-2-methyl-4-nitro-phenyl)-1-methyl-pyridinium iodide 4-(5-Isopropoxy-2-methyl-4-nitro-phenyl)-pyridine (Step 3, 217 mg, 0.797 mmol) was dissolved in anhydrous THF (9 mL). Iodomethane (0.10 mL, 1.61 mmol, 2 equiv.) was added, and the reaction was stirred at 40° C. in a sealed tube for 2 days. The volatiles were removed under vacuum, generating 4-(5-Isopropoxy-2-methyl-4-nitro-phenyl)-1-methyl-pyridinium iodide as a brown solid: ESMS m/z 287.1 (M+).

Steps 5 and 6: 2-Isopropoxy-5-methyl-4-(1-methyl-piperidin-4-yl)-phenylamine 4-(5-Isopropoxy-2-methyl-4-nitro-phenyl)-1-methyl-pyridinium iodide (Step 4, 0.697 mmol) was dissolved in CH$_3$OH (20 mL) and cooled to 0° C. NaBH$_4$ (264 mg, 6.97 mmol, 10 equiv.) was slowly added. After this addition was complete, the cooling bath was removed and the reaction was stirred at room temperature for 1 h. The reaction was quenched by the slow addition of 1N aqueous HCl (14 mL). The CH$_3$OH was partially removed by vacuum. The resulting residue was partitioned between EtOAc and 1 N aqueous NaOH. Additional 50% aqueous NaOH was added until the aqueous layer had a pH>12. The EtOAc layer was washed with 1 N aqueous NaOH (2×), the organic layer was then dried over sodium sulfate, filtered, and concentrated under vacuum. After concentration, the crude product (175 mg) was dissolved in acetic acid (10 mL). TFA (0.15 mL, 3 equiv.) and PtO$_2$ (53 mg, 30% w/w) were added and the reaction was placed under 50 psi H$_2$ gas in a Parr Shaker for 14 h. The reaction mixture was filtered and the filtrate was concentrated under vacuum. The resulting residue was partitioned between EtOAc and 1 N aqueous NaOH. Additional 50% aqueous NaOH was added until the aqueous layer has a pH>12. The EtOAc layer was washed with 1 N aqueous NaOH (2×), the organic layer was then dried over sodium sulfate, filtered, and concentrated under vacuum to give 2-isopropoxy-5-methyl-4-(1-methyl-piperidin-4-yl)-phenylamine, which was used in subsequent steps without further purification: ESMS m/z 263.2 (M+H+).

Intermediate 19 tert-butyl 4-(4-amino-5-fluoro-2-methylphenyl)piperidine-1-carboxylate

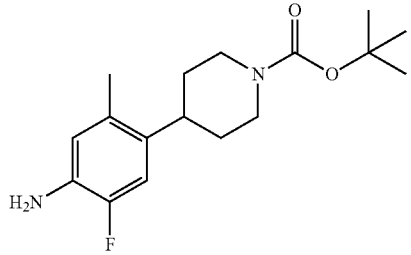 [SMILES: Cc1cc(N)c(F)cc1C1CCN(C(=O)OC(C)(C)C)CC1]

Step 1: 4-Trifluoromethanesulfonyloxy-3,6-dihydro-2H-pyridine-1-carboxylic acid tert-butyl ester A solution of N-tert-Butoxycarbonyl-4-piperidone (10.17 g, 0.05 mol) in THF (100 mL) was added dropwise into a cooled (−78° C.), vigorously stirring solution of LDA (40 mL of 1.5 M solution in cyclohexanes, 0.06 mol) in THF (100 mL), under N$_2$. The reaction mixture was left at −78° C. for 30 min before adding a solution of phenyl trifluorosulfonimide (19.85 g, 0.055 mol) in THF (50 mL). Then the reaction mixture was warmed to room temperature and stirred for 3 h. The reaction was quenched at 0° C. with 100 mL of saturated aqueous NH$_4$Cl and filtered through Celite. The filtrate was added to 100 mL of EtOAc, and the layers were separated. The organic layer was washed with H$_2$O, dried over MgSO$_4$ and concentrated. The crude product was purified by silica gel chromatography (0-30% EtOAc in Hexanes as eluent and checked by TLC stained with 2% of KMnO4 in EtOH) to afford 4-Trifluoromethanesulfonyloxy-3,6-dihydro-2H-pyridine-1-carboxylic acid tert-butyl ester as a yellow oil.

Step 2: Tert-butyl 4-(4,4,5,5-tetramethyl-1,3,2-dioxaborolan-2-yl)-5,6-dihydropyridine-1(2H)-carboxylate A solution of tert-butyl 4-(trifluoromethylsulfonyloxy)-5,6-dihydropyridine-1(2H)-carboxylate (16.0 g, 48.2 mmol) in DMSO (200 mL) was treated with bis(pinacolato)diboron (12.6 g, 49.6 mmol), potassium acetate (14.65 g, 149 mmol) and Pd(dppf)Cl$_2$ (790 mg, 0.96 mmol). The solution was purged with N$_2$ (g) for 5 minutes, and then sealed and heated at 80° C. for 15 h. The reaction was cooled to room temperature and poured into ice water. The mixture was extracted with ethyl acetate (3×100 mL). The combined organic phase was washed with brine, dried over sodium sulfate, and concentrated in vacuo. The crude product was purified with silica gel chromatography (15% ethyl acetate in hexanes) to afford tert-butyl 4-(4,4,5,5-tetramethyl-1,3,2-dioxaborolan-2-yl)-5,6-dihydropyridine-1(2H)-carboxylate as a white solid.

Steps 3 and 4: Tert-butyl 4-(4-amino-5-fluoro-2-methylphenyl)piperidine-1-carboxylate To a mixture of 5'-chloro-N,2'-dimethyl-4'-nitrobiphenyl-4-carboxamide (204 mg, 1 mmol), tert-butyl 4-(4,4,5,5-tetramethyl-1,3,2-dioxaborolan-2-yl)-5,6-dihydropyridine-1(2H)-carboxylate (370 mg, 1.2 mmol) and sodium carbonate (742 mg, 7 mmol) in DMF/H$_2$O (12/3 mL) was added tetrakis(triphenylphosphine) palladium (0) (58 mg, 5% mmol). The reaction tube was sealed, the mixture was purged with N$_2$ for 3 min and then heated at 90° C. under N$_2$ for overnight. The reaction was cooled to room temperature, and poured into saturated aqueous ammonia chloride solution. The crude reaction mixture was extracted with ethyl acetate (3×15 mL). The organic extracts were combined, washed with brine and concentrated. The crude product was purified with silica gel chromatography (20% ethyl acetate in hexanes) to afford tert-butyl 4-(4-amino-5-fluoro-2-methylphenyl)-5,6-dihydropyridine-1(2H)-carboxylate as a yellow oil. The obtained oil was dissolved in methanol (20 mL). To the solution was added Pd/C (10%). The reaction mixture was degassed and purged with H$_2$ for several times and stirred under H$_2$ (1 atm) overnight. The mixture was filtered and concentrated to afford the tert-butyl 4-(4-amino-5-fluoro-2-methylphenyl)piperidine-1-carboxylate as a white solid. ESMS m/z 207 (M−Boc+H$^+$).

Intermediate 20

2,5-Dimethyl-4-(piperidin-2-yl)aniline

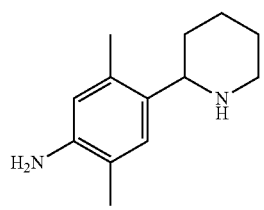

To a mixture of 1-bromo-2,5-dimethyl-4-nitrobenzene (185 mg, 1 mmol) and 2-(tributylstannyl)pyridine (202 mg, 1.1 mmol) in DMF (4 mL) was added tetrakis(triphenylphosphine) palladium (0) (58 mg, 5% mmol). The reaction tube was sealed, the mixture was purged with N$_2$ for 3 min and then heated at 120° C. under N$_2$ for overnight. The reaction was cooled to room temperature and poured into saturated aqueous ammonia chloride solution. The crude reaction mixture was extracted with ethyl acetate (3×15 mL). The organic extracts were combined, washed with brine and concentrated. The crude product was purified with silica gel column chromatography (60% ethyl acetate in hexanes) to afford 2-(2,5-dimethyl-4-nitrophenyl)pyridine as a white solid. The obtained solid was dissolved in acetic acid/TFA (15 mL/200 uL). To this solution was added PtO$_2$ (10% w/w). The reaction mixture was degassed and purged with H$_2$ for several times and stirred under 1 atm. hydrogen gas overnight. The mixture was filtered and concentrated to afford 2,5-Dimethyl-4-(piperidin-2-yl)aniline as a yellow oil. ESMS m/z 205 (M+H$^+$).

Intermediate 21 tert-butyl 3-(4-amino-2,5-dimethylphenyl)azetidine-1-carboxylate

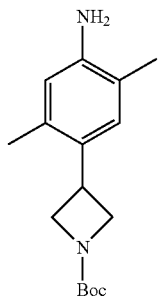

Step 1: tert-Butyl 3-(2,5-dimethyl-4-nitrophenyl)azetidine-1-carboxylate

Prepared from tert-butyl 3-iodoazetidine-1-carboxylate and 1-bromo-2,5-dimethyl-4-nitrobenzene by following the general protocol as described in Billotte, S. *Synlett* 1998, 379.

Step 2: tert-butyl 3-(4-amino-2,5-dimethylphenyl)azetidine-1-carboxylate tert-Butyl 3-(2,5-dimethyl-4-nitrophenyl)azetidine-1-carboxylate was reduced to tert-butyl 3-(4-amino-2,5-dimethylphenyl)azetidine-1-carboxylate by standard Raney Ni hydrogenation at room temperature using MeOH as the solvent.

Intermediate 22

5-Ethyl-2-methyl-4-(piperidin-4-yl)aniline

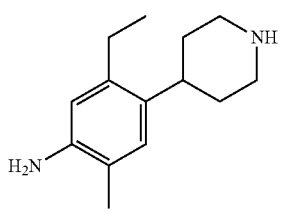 [SMILES: CCc1cc(N)c(C)cc1C1CCNCC1]

Step 1: tert-butyl 4-(4-amino-5-methyl-2-vinylphenyl)-5,6-dihydropyridine-1(2H)-carboxylate To a mixture of 4-bromo-5-chloro-2-methylaniline (500 mg, 2.27 mmol), tert-butyl 4-(4,4,5,5-tetramethyl-1,3,2-dioxaborolan-2-yl)-5,6-dihydropyridine-1(2H)-carboxylate (840 mg, 3.73 mmol) and sodium carbonate (2.52 g, 15.9 mmol) in DMF/H$_2$O (20/5 mL) was added tetrakis(triphenylphosphine) palladium (0) (131 mg, 5 mol %). The reaction tube was sealed, the mixture was purged with N$_2$ for 3 min and then heated at 100° C. under N$_2$ for overnight. The reaction was cooled to room temperature and poured into saturated aqueous ammonia chloride solution. The crude reaction mixture was extracted with ethyl acetate (3×15 mL). The organic extracts were combined, washed with brine and concentrated. The crude product was purified with silica chromatography (80% ethyl acetate in hexanes) to afford tert-butyl 4-(4-amino-2-chloro-5-methylphenyl)-5,6-dihydropyridine-1(2H)-carboxylate as a yellow solid. This obtained product (322 mg, 1 mmol) was dissolved in dioxane/NMP (anhydrous, 4 mL, 3/1). To this solution was added tributyl(vinyl)stannane (380 mg, 1.2 mmol), cesium fluoride (304 mg, 2 mmol) and palladium bis(tri-tert-butyl-phosphine) (51 mg, 10 mol %). This mixture was purged with $N_2$ for 3 minutes and then heated in a sealed tube at 120° C. for overnight. The mixture was cooled to room temperature and diluted with ethyl acetate. The resulting mixture was sequentially washed with saturated aqueous ammonium chloride and brine, and finally dried over sodium sulfate. After concentration, the crude product was purified via silica chromatography (10% ethyl acetate in hexanes) to afford tert-butyl 4-(4-amino-5-methyl-2-vinylphenyl)-5,6-dihydropyridine-1 (2H)-carboxylate as a light yellow oil;

ESMS m/z 215.2 (M−Boc+H$^+$).

Step 2: 5-Ethyl-2-methyl-4-(piperidin-4-yl)aniline

The product obtained from the previous step was dissolved in methanol (20 mL). To this solution was added conc. aqueous HCl (200 uL) and platinum oxide (23 mg, 0.1 mmol). The reaction mixture was degassed and purged with $H_2$ for several times and vigorously stirred under 1 atm. $H_2$ for 3 h. The mixture was filtered and concentrated to afford 5-Ethyl-2-methyl-4-(piperidin-4-yl)aniline as a yellow solid. ESMS m/z 219.2 (M+H$^+$).

Intermediate 23

2,5-Dimethyl-4-(piperidin-3-yl)aniline

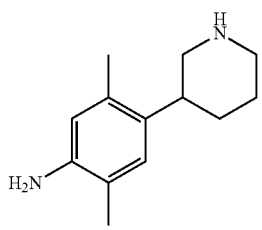

Step 1: 2,5-Dimethyl-4-(pyridin-3-yl)aniline

A suspension of 4-bromo-2,5-dimethylaniline (4.00 g, 20 mmol), pyridin-3-ylboronic acid (2.70 g, 11 mmol), $Pd_2$(dba)$_3$ (0.55 g, 0.6 mmol), 2-dicyclohexylphosphino-2',6'-dimethoxybiphenyl (0.98 g, 1.2 mmol) and $Na_2CO_3$ (10.6 g, 100 mmol) in n-BuOH (50 mL) was degassed by a stream of argon gas for 15 min. The reaction flask was sealed and placed in a pre-heated oil bath (115° C.). After stirring overnight, the reaction was cooled and filtered. The filter cake was washed with DCM and the filtrate was concentrated in vacuo. The resulting residue was dissolved in EtOAc (150 mL). EtOAC was sequentially washed with water (20 mL), brine (20 mL), dried over $Na_2SO_4$ and evaporated. The crude product was purified by silica chromatography (0-50% EtOAC in hexanes gradient) to give 2,5-dimethyl-4-(pyridin-3-yl)aniline as a yellow solid; ESMS m/z 199.1 (M+H$^+$).

Step 2: 2,5-Dimethyl-4-(piperidin-3-yl)aniline 2,5-Dimethyl-4-(pyridin-3-yl)aniline (403 mg, 2.03 mmol) was dissolved in MeOH (5 mL) and conc. aqueous HCl (1 mL), followed by addition of $PtO_2$ (40 mg). The flask was purged with $H_2$ and the reaction was vigorously stirred at rt under $H_2$ (1 atm). After two days, LCMS shows the completion of the reaction. The catalyst was removed by filtration and the remaining solution was concentrated in vacuo to give 2,5-Dimethyl-4-(piperidin-3-yl)aniline as a white solid, which can be used in subsequent reactions without further purification; ESMS m/z 205.2 (M+H$^+$).

Intermediate 24

1-(tert-butoxycarbonyl(methyl)amino)cyclopropanecarboxylic acid

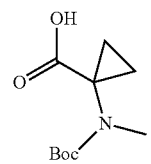

To a solution of 1-(tert-butoxycarbonylamino)cyclopropanecarboxylic acid (201 mg, 1.0 mmol) in DMF (2 mL) was added NaH (120 mg, 3.0 mmol) at 0° C. The resulting mixture was stirred at 0° C. for 10 min. before the addition of MeI (568 mg, 4.0 mmol). The mixture was then warmed up to room temperature and stirred for 2 hr. Saturated NH$_4$Cl aqueous solution (20 mL) was added into the mixture, and the solution was extracted with EtOAc (3×10 mL). The combined organic layers were concentrated and the residue was dissolved in MeOH (3 ml) with NaOH (3 N, 1 mL). This mixture was stirred at 80° C. for 1 hr and cooled down to room temperature. The clear solution was purified directly on preparative RP-HPLC to provide 1-(tert-butoxycarbonyl(methyl)amino) cyclopropanecarboxylic acid. ESMS m/z 238.2 (M+Na$^+$).

Intermediate 25

(R)-2-bromopropanamide

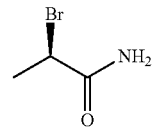

Step 1: (R)-2-bromopropanoyl chloride

Under nitrogen, to the solution of (R)-2-bromopropanoic acid (5.0 g, 32.68 mmol) in 100 mL of DCM was added thionyl chloride (7.1 mL, 98.04 mmol) and 1 mL of DMF sequentially at 0° C. The reaction was stirred at room temperature overnight, and concentrated in vacuo. The resulting crude product was directly used in next step without further purification.

Step 2: (R)-2-bromopropanamide (R)-2-bromopropanoyl chloride was slowly added to a 37% ammonia hydroxide water solution cooled to 0° C. The reaction was allowed to warm to room temperature and was stirred for 2 h. The product was extracted with EtOAc and the collected organic extracts were dried (Na₂SO₄) and concentrated in vacuo to afford (R)-2-bromopropanamide.

Intermediate 26

(R)-2-bromo-N-methylpropanamide

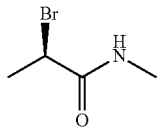

(R)-2-bromopropanoyl chloride was slowly added to a methylamine water solution cooled to 0° C. The reaction was allowed to warm to room temperature and was stirred for 2 h. The product was extracted with EtOAc and the collected organic extracts were dried (Na₂SO₄) and concentrated in vacuo to afford (R)-2-bromo-N-methylpropanamide.

Intermediate 27

1-(tert-butoxycarbonyl(ethyl)amino)cyclopropanecarboxylic acid

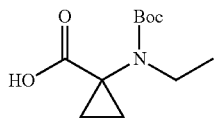

Step 1: Ethyl 1-(tert butoxycarbonyl(ethyl)amino)cyclopropanecarboxylate

Under nitrogen, to the solution of 1-(tert-butoxycarbonylamino)cyclopropanecarboxylic acid (201.2 mg, 1.0 mmol) in 4 mL of DMF was added NaH (120.0 mg, 3.0 mmol) at 0° C. After 30 min stirring, iodoethane (0.4 mL, 5.0 mmol) was added to the reaction. The reaction was warmed gradually to room temperature and stirred overnight. The reaction mixture was partitioned between EtOAc and water. The combined organic extracts were dried (Na₂SO₄), and concentrated in vacuo to afford crude ethyl 1-(tert butoxycarbonyl(ethyl)amino) cyclopropanecarboxylate, which was used in the next step without further purification.

Step 2: 1-(tert-butoxycarbonyl(ethyl)amino)cyclopropanecarboxylic acid

The crude product from Step 1 was dissolved in a mixture of EtOH (4.0 mL) and water (1.0 mL). LiOH (82.0 mg, 2.0 mmol) was added to the reaction. The reaction was heated at 120° C. in a microwave reactor for 10 min. The reaction was concentrated in vacuo, and the crude product was partitioned between EtOAc and water. The water layer was neutralized with 4N aq. HCl to pH 4 and then extracted with EtOAc. The combined organic extracts were dried (Na₂SO₄), and concentrated in vacuo to afford 1-(tert butoxycarbonyl(ethyl)amino) cyclopropanecarboxylic acid.

Intermediate 28

1-(tert-butoxycarbonyl(ethyl)amino)cyclobutanecarboxylic acid

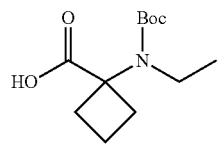

Step 1: Ethyl 1-(tert-butoxycarbonyl(ethyl)amino)cyclobutanecarboxylate

Under nitrogen, to the solution of 1-(tert-butoxycarbonylamino)cyclobutanecarboxylic acid (430.0 mg, 2.0 mmol) in 4 mL of DMF was added NaH (240.0 mg, 6.0 mmol) at 0° C. After stirring for 30 min., iodoethane (0.8 mL, 10.0 mmol) was added to the reaction. The reaction was warmed to room temperature gradually and stirred overnight. The reaction mixture was partitioned between EtOAc and water. The combined organic extracts were dried (Na₂SO₄), and concentrated in vacuo to afford crude ethyl 1-(tert-butoxycarbonyl(ethyl)amino) cyclobutanecarboxylate.

Step 2: 1-(tert-butoxycarbonyl(ethyl)amino)cyclobutanecarboxylic acid

The crude product from Step 1 was dissolved in EtOH (4.0 mL) and water (1.0 mL). LiOH (164.0 mg, 4.0 mmol) was added to the reaction. The reaction was heated at 120° C. in a microwave reactor for 10 min. The reaction was concentrated in vacuo, and the crude was partitioned between EtOAc and water. The water layer was neutralized with 4N aq. HCl to pH 4 and then extracted with EtOAc. The combined organic extracts were dried (Na₂SO₄), and concentrated in vacuo to afford 1-(tert-butoxycarbonyl(ethyl)amino) cyclobutanecarboxylic acid.

Intermediate 29

1-(tert-butoxycarbonyl(methyl)amino)cyclobutanecarboxylic acid

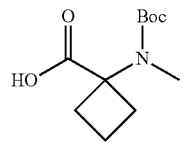

Step 1: Methyl 1-(tert-butoxycarbonyl(ethyl)amino)cyclobutanecarboxylate

Under nitrogen, to the solution of 1-(tert-butoxycarbonylamino) cyclobutanecarboxylic acid (430.0 mg, 2.0 mmol) in 4 mL of DMF was added NaH (240.0 mg, 6.0 mmol) at 0° C.

After stirring for 30 min., iodomethane (0.62 mL, 10.0 mmol) was added to the reaction. The reaction was warmed to room temperature gradually and stirred overnight. The reaction mixture was partitioned between EtOAc and water. The combined organic extracts were dried (Na₂SO₄), and concentrated in vacuo to afford crude methyl 1-(tert-butoxycarbonyl(ethyl)amino) cyclobutanecarboxylate.

Step 2: 1-(tert-butoxycarbonyl(methyl)amino)cyclobutanecarboxylic acid

The crude product from Step 1 was dissolved in MeOH (4.0 mL) and water (1.0 mL). LiOH (164.0 mg, 4.0 mmol) was added to the reaction. The reaction was heated at 120° C. in a microwave reactor for 10 min. The reaction was concentrated in vacuo, and the crude was partitioned between EtOAc and water. The water layer was neutralized with 4N aq. HCl to pH 4, and then extracted with EtOAc. The combined organic extracts were dried (Na₂SO₄), and concentrated in vacuo to afford 1-(tert-butoxycarbonyl(methyl)amino) cyclobutanecarboxylic acid.

Intermediate 30

2-bromobutanamide

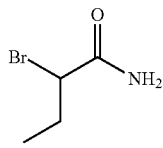

Under nitrogen, to a solution of 2-bromobutanoic acid (2.0 g, 12.0 mmol) in DCM (50 mL) at 0° C. were sequentially added thionyl chloride (2.6 mL, 35.9 mmol) and 0.5 mL of DMF. The reaction was allowed to warm to room temperature and was stirred overnight. The reaction mixture was concentrated in vacuo and then cooled to 0° C. Thirty (30) mL of 37% aqueous ammonia hydroxide was added slowly. The reaction was allowed to warm to room temperature and was stirred for 2 h followed by extraction with EtOAc. The combined organic extracts were dried (Na₂SO₄), and concentrated in vacuo to afford 2-bromobutanamide.

Intermediate 31

2-bromo-N-methylbutanamide

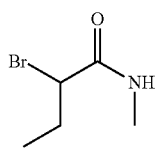

Under nitrogen, to a solution of 2-bromobutanoic acid (2.0 g, 12.0 mmol) in DCM (50 mL) at 0° C. were sequentially added thionyl chloride (2.6 mL, 35.9 mmol) and 0.5 mL of DMF. The reaction was allowed to warm to room temperature and was stirred overnight. The reaction mixture was concentrated in vacuo and then cooled to 0° C. Thirty (30) mL of 40% methylamine water solution was added slowly. The reaction was allowed to warm to room temperature and was stirred for 2 h followed by extraction with EtOAc. The combined organic extracts were dried (Na₂SO₄), and concentrated in vacuo to afford 2-bromo-N-methylbutanamide.

Intermediate 32

2-bromo-N-ethylbutanamide

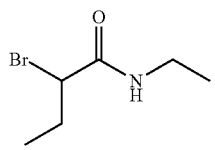

Under nitrogen, to a solution of 2-bromobutanoic acid (2.0 g, 12.0 mmol) in DCM (50 mL) at 0° C. were sequentially added thionyl chloride (2.6 mL, 35.9 mmol) and 0.5 mL of DMF. The reaction was allowed to warm to room temperature and was stirred overnight. The reaction mixture was concentrated in vacuo and then cooled to 0° C. Thirty (30) mL of 40% ethylamine water solution was added slowly. The reaction was allowed to warm to room temperature and was stirred for 2 h, followed by extraction with EtOAc. The combined organic extracts were dried (Na₂SO₄), and concentrated in vacuo to afford 2-bromo-N-ethylbutanamide.

Intermediate 33

1-(Methylsulfonyl)azetidin-3-one

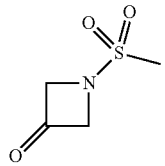

To a mixture of 3-azetidinone hydrochloride (471 mg, 3.28 mmol) and K₂CO₃ (1.50 g, 11 mmol) in CHCl₃/H₂O (5/5 mL) was added methanesulfonic anhydride (1.14 g, 6.57 mmol) in one portion at 0° C. After stirring for 2 h, the reaction was diluted with saturated aqueous NaHCO₃ (5 mL) and extracted with DCM (3×25 mL). The combined DCM layers were washed with brine (5 mL), dried over Na₂SO₄ and evaporated to afford 1-(Methylsulfonyl)azetidin-3-one as an off white solid, which was used without further purification; ¹H NMR (400 MHz, CDCl₃) δ 4.82 (s, 4H), 3.05 (s, 3H).

EXAMPLE 1

5-Chloro-N2-(2-fluoro-5-methyl-4-(1-methylpiperidin-4-yl)phenyl)-N4-(5-methyl-1H-pyrazol-3-yl)pyrimidine-2,4-diamine (1)

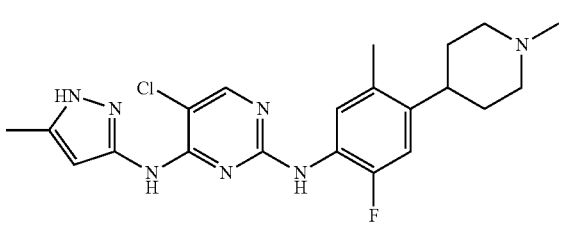

Step 1: A mixture of 2,5-dichloro-N-(5-methyl-1H-pyrazol-3-yl)pyrimidin-4-amine (Intermediate 1, 132 mg, 0.54 mmol) and tert-butyl 4-(4-amino-5-fluoro-2-methylphenyl)piperidine-1-carboxylate (Intermediate 19, 166 mg, 0.54 mmol) in 2-propanol (15 mL) was treated with conc. aqueous HCl (14 drops). The mixture was sealed and heated in a microwave at 130° C. for 60 min. The mixture was concentrated to afford 5-chloro-N2-(2-fluoro-5-methyl-4-(piperidin-4-yl)phenyl)-N4-(5-methyl-1H-pyrazol-3-yl)pyrimidine-2,4-diamine as a yellow solid. A portion of the crude product was purified with preparative RP-HPLC to afford 5-chloro-N2-(2-fluoro-5-methyl-4-(piperidin-4-yl)phenyl)-N4-(5-methyl-1H-pyrazol-3-yl)pyrimidine-2,4-diamine as a white solid; ESMS m/z 416.1 (M+H$^+$). The remainder of the crude product was used directly for the next step without further purification.

Step 2: To a solution of the crude product from previous step in THF (5 mL) and methanol (5 mL) was added formaldehyde (100 uL, 1.3 mmol) and 10 drops of AcOH sequentially. The reaction mixture was stirred at room temperature for 1 h, then sodium cyanoborohydride (175 mg, 2.78 mmol) was added in one portion, and the reaction was stirred for an additional 30 min. The reaction was quenched by saturated aqueous NH$_4$Cl and concentrated in vacuo to give an oily residue. The residue was purified with preparative RP-HPLC to afford 5-Chloro-N2-(2-fluoro-5-methyl-4-(1-methylpiperidin-4-yl)phenyl)-N4-(5-methyl-1H-pyrazol-3-yl)pyrimidine-2,4-diamine as a white solid. $^1$H NMR (400 MHz, DMSO-d$_6$) δ 10.33 (br, 1H), 9.90 (br, 1H0, 9.60 (br, 1H), 8.22 (s, 1H), 7.56 (d, 1H), 7.00 (d, 1H), 6.20 (s, 1H), 3.53-3.50 (m, 2H), 3.16-3.10 (m, 2H), 2.97-2.92 (m, 1H), 2.81 (d, 3H), 2.26 (s, 3H), 2.16 (s, 3H), 1.94-1.91 (m, 2H), 1.83-1.73 (m, 2H); ESMS m/z 430.1 (M+H$^+$).

EXAMPLE 2

5-chloro-N2-(2-fluoro-5-methyl-4-(piperidin-4-yl)phenyl)-N4-(5-methyl-1H-pyrazol-3-yl)pyrimidine-2,4-diamine (2)

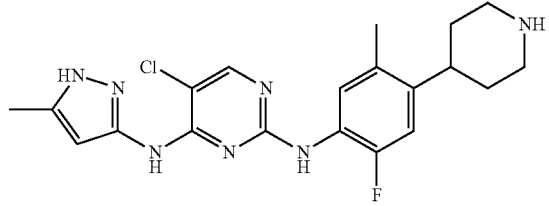 [SMILES: Cc1cc(Nc2nc(Nc3cc(C)c(C4CCNCC4)cc3F)ncc2Cl)n[nH]1]

A mixture of 2,5-dichloro-N-(5-methyl-1H-pyrazol-3-yl)pyrimidin-4-amine (Intermediate 1, 132 mg, 0.54 mmol) and tert-butyl 4-(4-amino-5-fluoro-2-methylphenyl)piperidine-1-carboxylate (Intermediate 19, 166 mg, 0.54 mmol) in 2-propanol (15 mL) was treated with conc. aqueous HCl (14 drops). The mixture was sealed and heated in a microwave at 130° C. for 60 min. The mixture was concentrated to afford 5-chloro-N2-(2-fluoro-5-methyl-4-(piperidin-4-yl)phenyl)-N4-(5-methyl-1H-pyrazol-3-yl)pyrimidine-2,4-diamine as yellow solid. A portion of the crude product was purified with preparative RP-HPLC to afford 5-chloro-N2-(2-fluoro-5-methyl-4-(piperidin-4-yl)phenyl)-N4-(5-methyl-1H-pyrazol-3-yl)pyrimidine-2,4-diamine as a white solid; ESMS m/z 416.1 (M+H$^+$).

EXAMPLES 3 AND 4

(S)-3-(5-chloro-2-(2-fluoro-5-methyl-4-(1-methylpiperidin-4-yl)phenylamino) pyrimidin-4-ylamino) azepan-2-one (10)

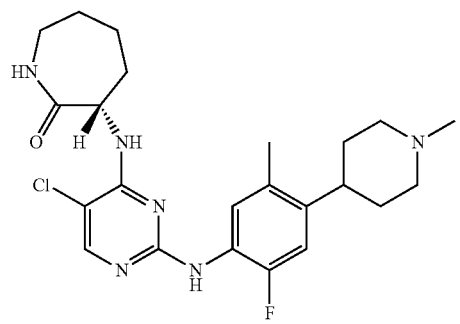 [SMILES: Cc1cc(Nc2ncc(Cl)c(N[C@H]3CCCCNC3=O)n2)c(F)cc1C1CCN(C)CC1]

(R)-3-(5-chloro-2-(2-fluoro-5-methyl-4-(1-methylpiperidin-4-yl)phenylamino) pyrimidin-4-ylamino) azepan-2-one (11)

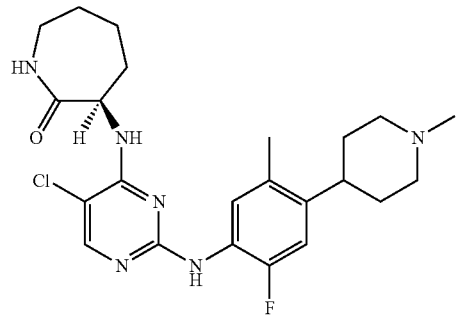 [SMILES: Cc1cc(Nc2ncc(Cl)c(N[C@@H]3CCCCNC3=O)n2)c(F)cc1C1CCN(C)CC1]

(±)-3-(5-chloro-2-(2-fluoro-5-methyl-4-(1-methylpiperidin-4-yl)phenylamino)pyrimidin-4-ylamino)azepan-2-one was synthesized by the same series of procedures as described in Example 1, utilizing Intermediate 6 and Intermediate 19. Chiral separation of the racemic mixture was conducted with normal phase HPLC using ChiralPaK AD column using the following solvent system: hexanes (80%) and iPrOH (20%) modified with 0.1% Diethylamine. The two purified enantiomer peaks were collected separately: (S)-3-(5-chloro-2-(2-fluoro-5-methyl-4-(1-methylpiperidin-4-yl)phenylamino) pyrimidin-4-ylamino)azepan-2-one and (R)-3-(5-chloro-2-(2-fluoro-5-methyl-4-(1-methylpiperidin-4-yl)phenylamino)pyrimidin-4-ylamino)azepan-2-one; both peaks: ESMS m/z 461.2 (M+H$^+$). The earlier eluting peak (RT=7.26 min.) and the later eluting peak (RT=10.17 min.) were arbitrarily assigned as the (S) and (R) enantiomer, respectively.

EXAMPLE 5

5-Chloro-N2-(4-(1-((3,5-dimethylisoxazol-4-yl)methyl)piperidin-4-yl)-2-fluoro-5-methylphenyl)-N4-(5-methyl-1H-pyrazol-3-yl)pyrimidine-2,4-diamine (19)

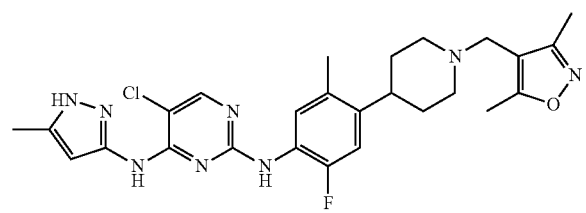 [SMILES: Cc1cc(Nc2nc(Nc3cc(C)c(C4CCN(Cc5c(C)noc5C)CC4)cc3F)ncc2Cl)n[nH]1]

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (83 uL, 0.6 mmol) in DMF (1.5 mL), was added 4-(chloromethyl)-3,5-dimethylisoxazole (35 mg, 0.24 mmol). The mixture was stirred at room temperature for 3 hours. The reaction was filtered and the filtrate was purified by preparative RP-HPLC to afford 5-Chloro-N2-(4-(1-((3,5-dimethylisoxazol-4-yl)methyl)piperidin-4-yl)-2-fluoro-5-methylphenyl)-N4-(5-methyl-1H-pyrazol-3-yl)pyrimidine-2,4-diamine as a white solid. $^1$H NMR (400 MHz, MeOD-d4) 8.12 (s, 1H), 7.75 (d, 1H), 7.03 (s, 1H), 6.27 (s, 1H), 4.25 (s, 2H), 3.69-3.67 (m, 2H), 3.27-3.20 (m, 3H), 2.54 (s, 3H), 2.37 (s, 3H), 2.34 (s, 3H), 2.30 (s, 3H), 2.10-1.95 (m, 4H); ESMS m/z 525.1 (M+H+).

EXAMPLE 6

2-(4-(4-(5-chloro-4-(5-methyl-1H-pyrazol-3-ylamino)pyrimidin-2-ylamino)-5-fluoro-2-methylphenyl)piperidin-1-yl)ethanol (22)

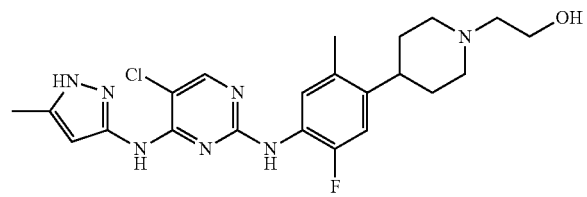 [SMILES: Cc1cc(Nc2nc(Nc3cc(C)c(C4CCN(CCO)CC4)cc3F)ncc2Cl)n[nH]1]

5-chloro-N2-(2-fluoro-5-methyl-4-(piperidin-4-yl)phenyl)-N4-(5-methyl-1H-pyrazol-3-yl)pyrimidine-2,4-diamine (0.12 mmol) was dissolved in anhydrous DMF (1 mL). TEA (50 uL, 0.36 mmol, 3 equiv.) was added followed by 2-bromo-ethanol (0.018 mL, 0.24 mmol, 2 equiv.) dissolved in anhydrous DMF (0.7 mL). The reaction vessel was sealed and heated in a microwave at 100° C. for 20 min. After cooling to room temperature, the reaction was concentrated and the crude product was purified using preparative RP-HPLC to give 2-(4-(4-(5-chloro-4-(5-methyl-1H-pyrazol-3-ylamino)pyrimidin-2-ylamino)-5-fluoro-2-methylphenyl)piperidin-1-yl)ethanol as a white solid: ESMS m/z 460.2 (M+H+).

EXAMPLE 7

5-chloro-N$^2$-(2-fluoro-5-methyl-4-(1-(3,3,3-trifluoropropyl)piperidin-4-yl)phenyl)-N$^4$-(5-methyl-1H-pyrazol-3-yl)pyrimidine-2,4-diamine (24)

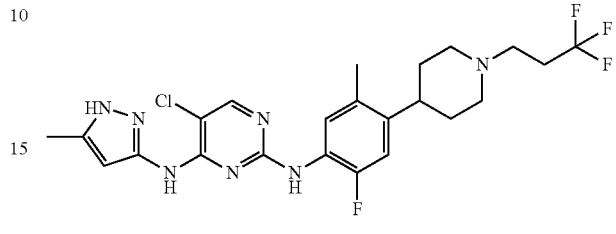

The mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol), 3-bromo-1,1,1-trifluoropropane (85.0 uL, 0.60 mmol) and triethylamine (102.0 uL, 0.60 mmol) in 2 mL of DMF was stirred overnight. The reaction mixture was purified by preparative RP-HPLC to afford 5-chloro-N2-(2-fluoro-5-methyl-4-(1-(3,3,3-trifluoropropyl)piperidin-4-yl)phenyl)-N4-(5-methyl-1H-pyrazol-3-yl) pyrimidine-2,4-diamine. ESMS m/z 512.2 (M+H$^+$).

EXAMPLE 8

3-(4-(4-(5-chloro-4-(5-methyl-1H-pyrazol-3-ylamino)pyrimidin-2-ylamino)-5-fluoro-2-methylphenyl)piperidin-1-yl)-1,1,1-trifluoropropan-2-ol (30)

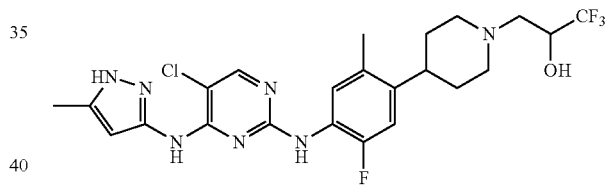

The mixture of 5-chloro-N2-(2-fluoro-5-methyl-4-(piperidin-4-yl)phenyl)-N4-(5-methyl-1H-pyrazol-3-yl)pyrimidine-2,4-diamine (50.0 mg, 0.12 mmol) and 2-(trifluoromethyl)oxirane (67.8 mg, 0.60 mmol) in 2 mL of DMF was stirred overnight. The reaction mixture was purified by preparative RP-HPLC to afford 3-(4-(4-(5-chloro-4-(5-methyl-1H-pyrazol-3-ylamino)pyrimidin-2-ylamino)-5-fluoro-2-methylphenyl)piperidin-1-yl)-1,1,1-trifluoropropan-2-ol. ESMS m/z 528.2 (M+H$^+$).

EXAMPLE 9

2-(4-(4-(5-Chloro-4-(5-methyl-1H-pyrazol-3-ylamino)pyrimidin-2-ylamino)-5-fluoro-2-methylphenyl)piperidin-1-yl)acetamide (39)

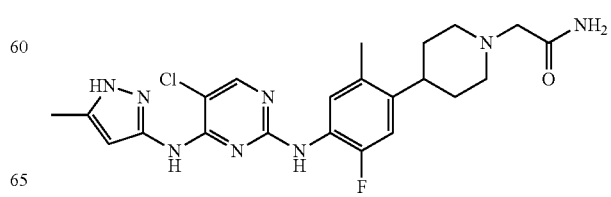

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (50 uL, 0.36 mmol) in DMF (1.5 mL), was added 2-bromoacetamide (33 mg, 0.24 mmol). The mixture was stirred at room temperature for 2 hours. The reaction was filtered and the filtrate was purified by preparative RP-HPLC to give 2-(4-(4-(5-chloro-4-(5-methyl-1H-pyrazol-3-ylamino)pyrimidin-2-ylamino)-5-fluoro-2-methylphenyl)piperidin-1-yl)acetamide as a white solid: $^1$H NMR (400 MHz, MeOD-d$_4$) δ 8.11 (s, 1H), 7.76 (d 1H), 7.09 (d, 1H), 6.27 (s, 1H), 4.0 (s, 2H), 3.75-3.73 (m, 2H), 3.22-3.13 (m, 3H), 2.34 (s, 3H), 2.30 (s, 3H), 2.04-2.00 (m, 4H); ESMS m/z 473.2 (M+H$^+$).

EXAMPLE 10

5-Chloro-N2-(2-fluoro-5-methyl-4-(1-(2-(methylsulfonyl)ethyl)piperidin-4-yl)phenyl)-N4-(5-methyl-1H-pyrazol-3-yl)pyrimidine-2,4-diamine (55)

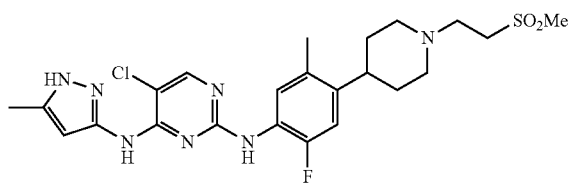 [SMILES: Cc1cc(Nc2nc(Nc3cc(C)c(C4CCN(CCS(C)(=O)=O)CC4)cc3F)ncc2Cl)n[nH]1]

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (83 uL, 0.6 mmol) in DMF (1.5 mL), was added methyl vinyl sulfone (38 mg, 0.36 mmol). The mixture was stirred at room temperature for 1 hour. The reaction was filtered and the filtrate was purified by preparative RP-HPLC to afford 5-Chloro-N2-(2-fluoro-5-methyl-4-(1-(2-(methylsulfonyl)ethyl)piperidin-4-yl)phenyl)-N4-(5-methyl-1H-pyrazol-3-yl)pyrimidine-2,4-diamine as a white solid.
ESMS m/z 522.1 (M+H+).

EXAMPLE 11

5-Chloro-N2-(2-fluoro-5-methyl-4-(1-(methylsulfonyl)piperidin-4-yl)phenyl)-N4-(5-methyl-1H-pyrazol-3-yl)pyrimidine-2,4-diamine (62)

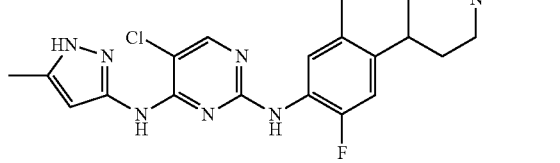

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (50 uL, 0.36 mmol) in DMF (1.5 mL) was added methanesulfonyl chloride (18 uL, 0.24 mmol). The mixture was stirred at room temperature for 2 hours. The reaction was filtered and the filtrate was purified by preparative RP-HPLC to give 5-Chloro-N2-(2-fluoro-5-methyl-4-(1-(methylsulfonyl)piperidin-4-yl)phenyl)-N4-(5-methyl-1H-pyrazol-3-yl)pyrimidine-2,4-diamine as a white solid: ESMS m/z 494.2 (M+H$^+$).

EXAMPLE 12

Ethyl 4-(4-(5-chloro-4-(5-methyl-1H-pyrazol-3-ylamino)pyrimidin-2-ylamino)-5-fluoro-2-methylphenyl)piperidine-1-carboxylate (66)

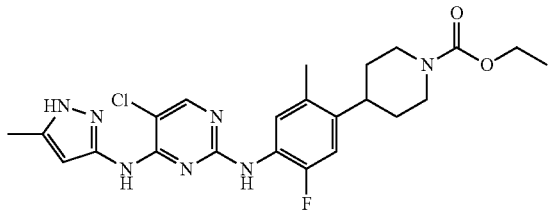 [SMILES: CCOC(=O)N1CCC(c2cc(F)c(Nc3ncc(Cl)c(Nc4cc(C)[nH]n4)n3)cc2C)CC1]

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (50 uL, 0.36 mmol) in DMF (1.5 mL) was added ethyl chloroformate (26 mg, 0.24 mmol). The mixture was stirred at room temperature for 2 hours. The reaction was filtered and the filtrate was purified by preparative RP-HPLC to give Ethyl 4-(4-(5-chloro-4-(5-methyl-1H-pyrazol-3-ylamino)pyrimidin-2-ylamino)-5-fluoro-2-methylphenyl)piperidine-1-carboxylate as a white solid: $^1$H NMR (400 MHz, MeOD-d$_4$) δ 8.13 (s, 1H), 7.54 (d, 1H), 7.10 (d, 1H), 6.28 (s, 1H), 4.30-4.26 (m, 2H), 4.14 (q, 2H), 2.99-2.96 (m, 3H), 2.33 (s, 3H), 2.29 (s, 3H), 1.8-1.77 (m, 2H), 1.64-1.55 (m, 2H), 1.28 (t, 3H); ESMS m/z 488.2 (M+H$^+$).

EXAMPLE 13

4-(4-(5-Chloro-4-(5-methyl-1H-pyrazol-3-ylamino)pyrimidin-2-ylamino)-5-fluoro-2-methylphenyl)-N,N-dimethylpiperidine-1-carboxamide (69)

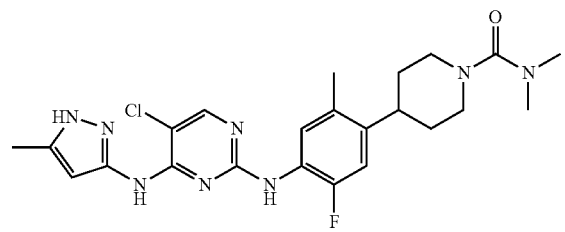

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (83 uL, 0.6 mmol) in DMF (1.5 mL) was added dimethylcarbamic chloride (39 mg, 0.36 mmol). The mixture was stirred at room temperature for 1 hour. The reaction was filtered and the filtrate was purified by preparative RP-HPLC to afford 4-(4-(5-chloro-4-(5-methyl-1H-pyrazol-3-ylamino)pyrimidin-2-ylamino)-5-fluoro-2-methylphenyl)-N,N-dimethylpiperidine-1-carboxamide as a white solid.
ESMS m/z 487.2 (M+H+).

EXAMPLE 14

1-(4-(4-(5-chloro-4-(5-methyl-1H-pyrazol-3-ylamino)pyrimidin-2-ylamino)-5-fluoro-2-methylphenyl)piperidin-1-yl)-2-(dimethylamino)ethanone (73)

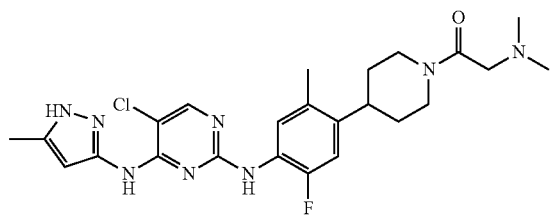

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol) and triethylamine (50 uL, 0.36 mmol) in DMF (1.5 mL) was added 2-(dimethylamino)acetyl chloride (38 mg, 0.24 mmol). The mixture was stirred at room temperature for 1 hour. The reaction was filtered and the filtrate was purified by preparative RP-HPLC to give 1-(4-(4-(5-chloro-4-(5-methyl-1H-pyrazol-3-ylamino)pyrimidin-2-ylamino)-5-fluoro-2-methylphenyl)piperidin-1-yl)-2-(dimethylamino)ethanone as a white solid: $^1$H NMR (400 MHz, MeOD-$d_4$) δ 8.08 (s, 1H), 7.71 (d, 1H), 7.03 (d, 1H), 6.26 (s, 1H), 4.71-4.67 (m, 2H), 3.81-3.77 (m, 2H), 3.14-3.12 (m, 2H), 2.98 (s, 3H), 2.96 (s, 3H), 2.90-2.83 (m, 1H), 2.34 (s, 3H), 2.28 (s, 3H), 1.87 (d, 2H), 1.76-1.55 (m, 2H); ESMS m/z 501.2 (M+H$^+$).

EXAMPLE 15

1-(4-(4-(5-chloro-4-(5-methyl-1H-pyrazol-3-ylamino)pyrimidin-2-ylamino)-5-fluoro-2-methylphenyl)piperidin-1-yl)-2-(4-methylpiperazin-1-yl)ethanone (105)

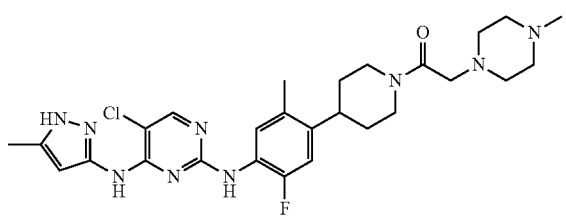

To the solution of 5-chloro-N2-(2-fluoro-5-methyl-4-(piperidin-4-yl)phenyl)-N4-(5-methyl-1H-pyrazol-3-yl)pyrimidine-2,4-diamine (100.0 mg, 0.24 mmol) in 4 mL of DCM was added 2-chloroacetylchloride (23.0 uL, 0.29 mmol) and triethylamine (67.0 uL, 0.48 mmol) sequentially. The reaction was stirred at room temperature for 1 h then washed by brine. The organic extract was dried over Na$_2$SO$_4$, followed by concentration in vacuo to afford a crude product. The crude product was mixed with 1-methylpiperazine (116.0 mg, 1.16 mmol) in 3 mL of DMF and the reaction was stirred overnight at room temperature. The reaction mixture was purified by preparative HPLC to afford 1-(4-(4-(5-chloro-4-(5-methyl-1H-pyrazol-3-ylamino)pyrimidin-2-ylamino)-5-fluoro-2-methylphenyl)piperidin-1-yl)-2-(4-methylpiperazin-1-yl)ethanone. ESMS m/z 556.3 (M+H$^+$).

EXAMPLE 16

Azetidin-3-yl(4-(4-(5-chloro-4-(5-methyl-1H-pyrazol-3-ylamino)pyrimidin-2-ylamino)-5-fluoro-2-methylphenyl)piperidin-1-yl)methanone (131)

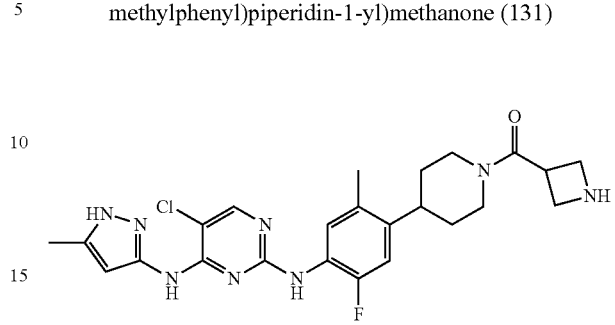

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.12 mmol), di-isopropylethylamine (50 uL, 0.36 mmol) and HATU (55 mg, 0.14 mmol) in DMF (1.5 mL) was added 1-(tert-butoxycarbonyl)azetidine-3-carboxylic acid (29 mg, 0.14 mmol). After stirring at room temperature for 4 hours, the mixture was diluted with methanol (1 mL) and conc. aqueous HCl (1 mL). The mixture was stirred at 50° C. for 30 min. The mixture was filtered and purified by preparative RP-HPLC to give azetidin-3-yl(4-(4-(5-chloro-4-(5-methyl-1H-pyrazol-3-ylamino)pyrimidin-2-ylamino)-5-fluoro-2-methylphenyl)piperidin-1-yl)methanone as white solid. $^1$H NMR (400 MHz, MeOD-$d_4$) δ 8.08 (s, 1H), 7.68 (d, 2H), 7.04 (d, 2H), 6.26 (s, 1H), 4.74-4.68 (m, 2H), 4.39-4.35 (m, 1H), 4.29-4.24 (m, 2H), 4.11-4.07 (m, 1H), 3.74-3.71 (m, 1H), 3.25-3.24 (m, 1H), 3.07-3.04 (m, 1H), 2.87-2.80 (m, 1H), 2.33 (s, 3H), 2.28 (s, 3H), 1.87-1.84 (m, 2H), 1.66-1.56 (m, 2H); ESMS m/z 499.2 (M+H$^+$).

EXAMPLE 17

5-chloro-N$^2$-(2-fluoro-5-methyl-4-(1-(tetrahydro-1,1-dioxido-3-thienyl)piperidin-4-yl)phenyl)-N$^4$-(5-methyl-1H-pyrazol-3-yl)pyrimidine-2,4-diamine (145)

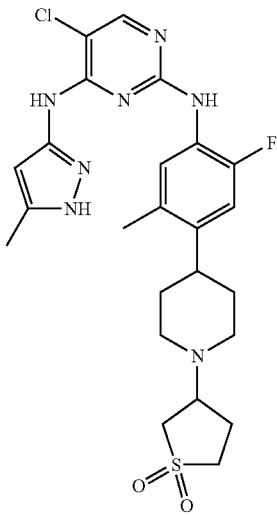 [SMILES: Cc1cc(Nc2nc(Nc3cc(C)c(C4CCN(C5CCS(=O)(=O)C5)CC4)cc3F)ncc2Cl)n[nH]1]

To 5-chloro-N2-(2-fluoro-5-methyl-4-(piperidin-4-yl)phenyl)-N4-(5-methyl-1H-pyrazol-3-yl)pyrimidine-2,4-diamine (30 mg, 0.072 mml) in EtOH (0.5 mL) was added thiophene-2,3-dihydro-, 1,1-dioxide (17 mg, 0.144 mmol). The resulting mixture was then heated to 130° C. for 2 hr. After cooling down to room temperature, the mixture was concentrated and purified by preparative RP-HPLC to provide 5-chloro-N2-(2-fluoro-5-methyl-4-(1-(tetrahydro-1,1-dioxido-3-thienyl)piperidin-4-yl)phenyl)-N4-(5-methyl-1H-pyrazol-3-yl)pyrimidine-2,4-diamine. ESMS m/z 534.2 (M+H$^+$).

EXAMPLE 18

5-chloro-N$^2$-(2,5-dimethyl-4-(1-(tetrahydro-1,1-dioxido-2H-thiopyran-4-yl))piperidin-4-yl)phenyl)-N$^4$-(5-methyl-1H-pyrazol-3-yl)pyrimidine-2,4-diamine (146)

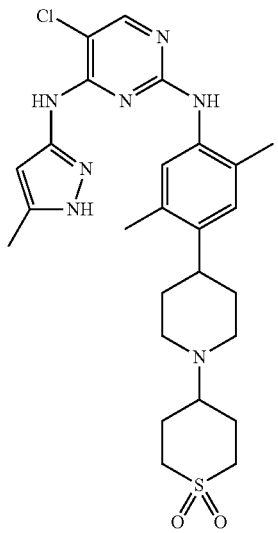

Step 1: To a solution of 5-chloro-N2-(2,5-dimethyl-4-(piperidin-4-yl)phenyl)-N4-(5-methyl-1H-pyrazol-3-yl)pyrimidine-2,4-diamine (30 mg, 0.073 mmol) in acetonitrile (1 mL) was added Cs$_2$CO$_3$ (47 mg, 0.15 mmol) and 4-iodotetrahydro-2H-thiopyran (48 mg, 0.22 mmol). This mixture was then stirred at 80° C. for 16 hr. After cooling down to room temperature, the mixture was treated with saturated aqueous NH$_4$Cl solution (3 mL) and extracted with EtOAc (3×3 mL). The organic layers were combined and concentrated. The residue was purified by silica gel chromatography (Gradient 0~8% MeOH/CH$_2$Cl$_2$ with NH$_3$) to provide 5-chloro-N2-(2,5-dimethyl-4-(1-(tetrahydro-2H-thiopyran-4-yl)piperidin-4-yl)phenyl)-N4-(5-methyl-1H-pyrazol-3-yl)pyrimidine-2,4-diamine as a white solid. ESMS m/z 512.2 (M+H$^+$).

Step 2: To 5-chloro-N2-(2,5-dimethyl-4-(1-(tetrahydro-2H-thiopyran-4-yl)piperidin-4-yl)phenyl)-N4-(5-methyl-1H-pyrazol-3-yl)pyrimidine-2,4-diamine (18 mg, 0.035 mmol) in CH$_2$Cl$_2$ (1 mL) was added m-CPBA (16 mg, 0.71 mmol) at 0° C. The mixture was then warmed up to room temperature and stirred for 30 min; saturated aqueous NaHCO$_3$ solution (3 mL) was then added and the crude product extracted with CH$_2$Cl$_2$ (3×3 mL). The combined organic layers were concentrated and purified by preparative thin layer chromatography (silica gel, 12% MeOH/CH$_2$Cl$_2$ with NH$_3$) to provide 5-chloro-N2-(2,5-dimethyl-4-(1-(tetrahydro-1,1-dioxido-2H-thiopyran-4-yl))piperidin-4-yl)phenyl)-N4-(5-methyl-1H-pyrazol-3-yl)pyrimidine-2,4-diamine. ESMS m/z 544.2 (M+H$^+$).

EXAMPLE 19

5-chloro-N$^2$-(2-fluoro-5-methyl-4-(1-(1,1-dioxido-3-thietanyl)piperidin-4-yl)phenyl)-N$^4$-(5-methyl-1H-pyrazol-3-yl)pyrimidine-2,4-diamine (148)

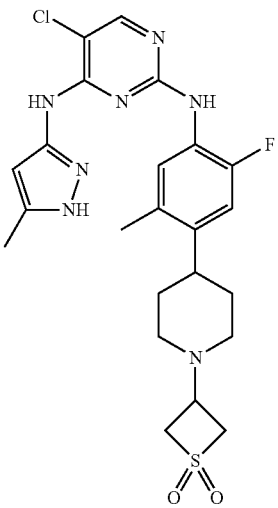 [SMILES: Cc1cc(Nc2nc(Nc3cc(C)c(C4CCN(C5CS(=O)(=O)C5)CC4)cc3F)ncc2Cl)n[nH]1]

To 5-chloro-N2-(2-fluoro-5-methyl-4-(piperidin-4-yl)phenyl)-N4-(5-methyl-1H-pyrazol-3-yl)pyrimidine-2,4-diamine (30 mg, 0.072 mmol) in MeOH (1 mL) was added 3-bromothietane 1,1-dioxide (15 mg, 0.079 mmol) followed by TEA (15 mg). The resulting mixture was stirred at room temperature for 5 hr and then concentrated. The resulting residue was purified by preparative RP-HPLC to provide 5-chloro-N2-(2-fluoro-5-methyl-4-(1-(1,1-dioxido-3-thietanyl)piperidin-4-yl)phenyl)-N4-(5-methyl-1H-pyrazol-3-yl)pyrimidine-2,4-diamine. $^1$H NMR (400 MHz, DMSO-d6+1 drop D2O) δ 8.02 (s, 1H), 7.37 (s, 1H), 7.02 (s, 1H), 6.23 (s, 1H), 4.28-4.22 (m, 2H), 4.12-4.07 (m, 2H), 3.22-3.18 (m, 1H), 2.95-2.92 (m, 2H), 2.68-2.62 (m, 1H), 2.22 (s, 3H), 2.13 (s, 3H), 2.07-2.01 (m, 2H), 1.71-1.55 (m, 4H). ESMS m/z 520.2 (M+H$^+$).

EXAMPLE 20

5-Chloro-N2-(4-(1-(5-ethylpyrimidin-2-yl)piperidin-4-yl)-2-fluoro-5-methylphenyl)-N4-(5-methyl-1H-pyrazol-3-yl)pyrimidine-2,4-diamine (149)

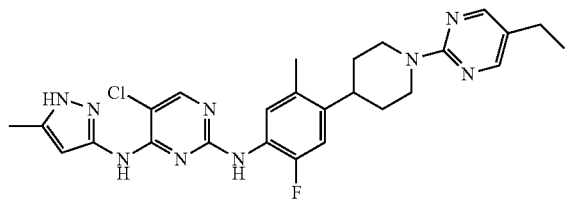 [SMILES: CCc1cnc(N2CCC(c3cc(F)c(Nc4ncc(Cl)c(Nc5cc(C)[nH]n5)n4)cc3C)CC2)nc1]

To a mixture of 5-chloro-N2-(2-fluoro-5-methyl-4-(piperidin-4-yl)phenyl)-N4-(5-methyl-1H-pyrazol-3-yl)pyrimidine-2,4-diamine (0.10 mmol) and triethylamine (83 uL, 0.6 mmol) in DMF (1.5 mL), was added 2-chloro-5-ethylpyrimidine (27 mg, 0.20 mmol). The mixture was heated in a microwave at 120° C. for 10 min. The reaction was filtered and the filtrate was purified by preparative RP-HPLC to afford 5-chloro-N2-(4-(1-(5-ethylpyrimidin-2-yl)piperidin-4-yl)-2-fluoro-5-methylphenyl)-N4-(5-methyl-1H-pyrazol-3-yl)pyrimidine-2,4-diamine as a white solid. ESMS m/z 522.2 (M+H+).

EXAMPLE 21

4-(4-(5-chloro-4-(5-methyl-1H-pyrazol-3-ylamino)pyrimidin-2-ylamino)-2,5-dimethylphenyl)piperidin-2-one (151)

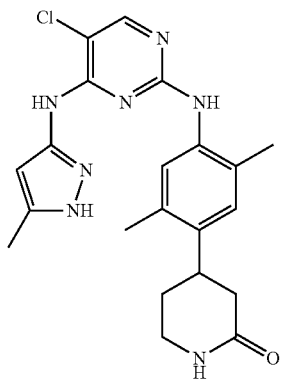 [SMILES: Cc1cc(Nc2nc(Nc3cc(C)c(C4CCNC(=O)C4)cc3C)ncc2Cl)n[nH]1]

Step 1: In a 5 mL microwave reaction tube was added 2-(2,5-dimethyl-4-nitrophenyl)-4,4,5,5-tetramethyl-1,3,2-dioxaborolane (143 mg, 0.516 mmol, prepared from 1-bromo-2,5-dimethyl-4-nitrobenzene by standard protocol), 1-(4-methoxybenzyl)-5,6-dihydropyridin-2(1H)-one (56 mg, 0.26 mmol, prepared by following a similar procedure as reported by Lerchner etc. in Chem. Eur. J. 2006, 12, 8208), chloro(1,5-cyclooctadiene)rhodium (I) dimer (13 mg, 0.026 mmol), KOH (0.13 mL 1N aqueous solution) and dioxane (1.2 mL). The tube was degassed, filled with $N_2$ and sealed. The reaction tube was then heated to 100° C. in a microwave reactor for 10 min. After the reaction tube was opened, the mixture was treated with saturated $NH_4Cl$ aqueous solution (3 mL) and extracted with EtOAc (3×4 mL). The organic layers were combined and concentrated. The residue was purified by flash column chromatography (silica gel, gradient 0%~70% EtOAc/hexane), to provide 4-(2,5-dimethyl-4-nitrophenyl)-1-(4-methoxybenzyl)piperidin-2-one. ESMS m/z 369.2 (M+H+).

Step 2: To 4-(2,5-dimethyl-4-nitrophenyl)-1-(4-methoxybenzyl)piperidin-2-one (63 mg, 0.17 mmol) in MeOH (10 mL) was added 10% w/w Pd/C (6 mg), the mixture was degassed and stirred under $H_2$ at room temperature for 14 hr. After removing the catalyst by filtration, the filtrate was concentrated to provide 4-(4-amino-2,5-dimethylphenyl)-1-(4-methoxybenzyl)piperidin-2-one as a pale yellowish oil. ESMS m/z 339.2 (M+H+).

Step 3: To a mixture of 4-(4-amino-2,5-dimethylphenyl)-1-(4-methoxybenzyl)piperidin-2-one (23 mg, 0.094 mmol) and 2,5-dichloro-N-(5-methyl-1H-pyrazol-3-yl)pyrimidin-4-amine (29 mg, 0.086 mmol) in iPrOH (1 mL) was added HCl (60 uL, 4N in dioxane). The reaction vessel was then sealed and heated to 130° C. for 4 hr. After cooling to room temperature, the mixture was treated with saturated $NaHCO_3$ aqueous solution (3 mL) and extracted with EtOAc (3×4 mL). The organic layers were combined and concentrated. The residue was purified by flash column chromatography (silica gel, gradient 0~10% $MeOH/CH_2Cl_2$) to provide 4-(4-(5-chloro-4-(5-methyl-1H-pyrazol-3-ylamino)pyrimidin-2-ylamino)-2,5-dimethylphenyl)-1-(4-methoxybenzyl)piperidin-2-one. ESMS m/z 546.2 (M+H+).

Step 4: A solution of 4-(4-(5-chloro-4-(5-methyl-1H-pyrazol-3-ylamino)pyrimidin-2-ylamino)-2,5-dimethylphenyl)-1-(4-methoxybenzyl)piperidin-2-one (45 mg) in TFA (0.5 mL) was heated to 100° C. for 24 hr. After cooling down to room temperature, the mixture was concentrated and purified by preparative RP-HPLC to provide 4-(4-(5-chloro-4-(5-methyl-1H-pyrazol-3-ylamino)pyrimidin-2-ylamino)-2,5-dimethylphenyl)piperidin-2-one. ESMS m/z 426.2 (M+H+).

EXAMPLE 22

5-chloro-$N^2$-(2-fluoro-4-(4-methylpiperazin-1-yl)-5-(trifluoromethyl)phenyl)-$N^4$-(5-methyl-1H-pyrazol-3-yl)pyrimidine-2,4-diamine (157)

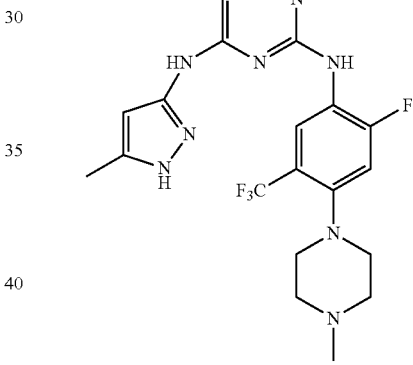

Step 1: To a microwave reaction tube was added 4-bromo-2-fluoro-5-(trifluoromethyl)aniline (256 mg, 1.0 mmol), 1-methylpiperazine (300 mg, 3 mmol) $Pd_2(dba)_3$ (91.5 mg, 0.1 mmol), di-tert-butyl(2',4',6'-triisopropylbiphenyl-2-yl)phosphine (60 mg, 0.2 mmol), NaOtBu (144 mg, 1.5 mmol) and THF (3 mL). After the reaction tube was degassed and filled with $N_2$, the tube was heated to 120° C. in a microwave reactor for 40 min. The mixture was then poured into saturated $NH_4Cl$ aqueous solution (10 mL) and extracted with EtOAc (3×10 mL). The organic layers were combined and concentrated. The residue was purified by flash column chromatography (silica gel, gradient $MeOH/CH_2Cl_2$, 0~10%) to provide 2-fluoro-4-(4-methylpiperazin-1-yl)-5-(trifluoromethyl)aniline as a white solid. ESMS m/z 278.1 (M+H+).

Step 2: To a mixture of 2-fluoro-4-(4-methylpiperazin-1-yl)-5-(trifluoromethyl)aniline (37 mg, 0.133 mmol) and 2,5-dichloro-N-(5-methyl-1H-pyrazol-3-yl)pyrimidin-4-amine (36 mg, 0.147 mmol) in iPrOH (1 mL) was added HCl (100 uL, 4N in dioxane). The reaction vessel was then sealed and heated to 130° C. for 4 hr. After cooling to room temperature, the mixture was treated with saturated $NaHCO_3$ aqueous solution (5 mL) and extracted with EtOAc (3×5 mL). The organic layers were combined and concentrated. The residue was purified by preparative thin layer chromatography (silica gel, 8% MeOH/CH$_2$Cl$_2$), to provide 5-chloro-N2-(2-fluoro-4-(4-methylpiperazin-1-yl)-5-(trifluoromethyl)phenyl)-N4-(5-methyl-1H-pyrazol-3-yl)pyrimidine-2,4-diamine. ESMS m/z 485.2 (M+H$^+$).

EXAMPLE 23

(S)-2-(4-(4-(5-methyl-1H-pyrazol-3-ylamino)pyrimidin-2-ylamino)-5-fluoro-2-methylphenyl)piperidin-1-yl)propanamide (163)

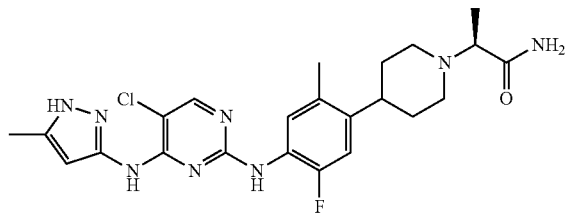 [SMILES: Cc1cc(Nc2nc(Nc3cc(C)c(C4CCN([C@@H](C)C(N)=O)CC4)cc3F)ncc2Cl)n[nH]1]

A mixture of 5-chloro-N$^2$-(2-fluoro-5-methyl-4-(piperidin-4-yl)phenyl)-N$^4$-(5-methyl-1H-pyrazol-3-yl)pyrimidine-2,4-diamine (50.0 mg, 0.12 mmol), (R)-2-bromopropanamide (90.6 mg, 0.60 mmol), and triethylamine (102.0 μL, 0.60 mmol) in 2 mL of DMF was heated at 150° C. in a microwave reactor for 30 min. The reaction mixture was directly purified by preparative RP-HPLC to afford (S)-2-(4-(4-(5-methyl-1H-pyrazol-3-ylamino)pyrimidin-2-ylamino)-5-fluoro-2-methylphenyl)piperidin-1-yl)propanamide; ESMS m/z 487.2 (M+H$^+$).

EXAMPLE 24

(S)-2-(4-(4-(5-chloro-4-(5-methyl-1H-pyrazol-3-ylamino)pyrimidin-2-ylamino)-5-fluoro-2-methylphenyl)piperidin-1-yl)-N-methylpropanamide (164)

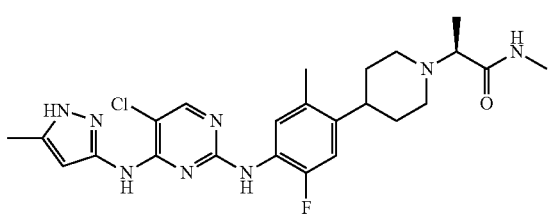

A mixture of 5-chloro-N$^2$-(2-fluoro-5-methyl-4-(piperidin-4-yl)phenyl)-N$^4$-(5-methyl-1H-pyrazol-3-yl)pyrimidine-2,4-diamine (50.0 mg, 0.12 mmol), (R)-2-bromo-N-methylpropanamide (100.0 mg, 0.60 mmol), and triethylamine (102.0 μL, 0.60 mmol) in 2 mL of DMF was heated at 150° C. in a microwave reactor for 30 min. The reaction mixture was directly purified by preparative RP-HPLC to afford (S)-2-(4-(4-(5-chloro-4-(5-methyl-1H-pyrazol-3-ylamino)pyrimidin-2-ylamino)-5-fluoro-2-methylphenyl)piperidin-1-yl)-N-methylpropanamide; ESMS m/z 501.2 (M+H$^+$).

EXAMPLE 25

(S)-2-(4-(4-(5-chloro-4-(5-methyl-1H-pyrazol-3-ylamino)pyrimidin-2-ylamino)-2,5-dimethylphenyl)piperidin-1-yl)propanamide (166)

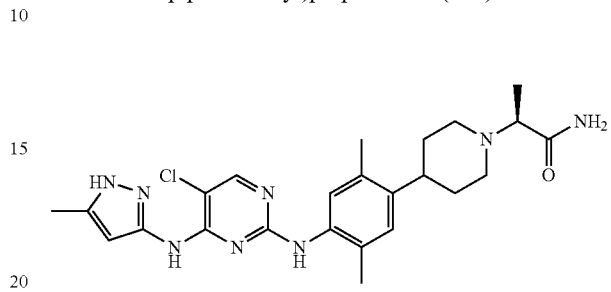

A mixture of 5-chloro-N$^2$-(2,5-dimethyl-4-(piperidin-4-yl)phenyl)-N$^4$-(5-methyl-1H-pyrazol-3-yl)pyrimidine-2,4-diamine (50.0 mg, 0.12 mmol), (R)-2-bromopropanamide (90.6 mg, 0.60 mmol), and triethylamine (102.0 μL, 0.60 mmol) in 2 mL of DMF was heated at 150° C. in a microwave reactor for 30 min. The reaction mixture was directly purified by preparative RP-HPLC to afford (S)-2-(4-(4-(5-chloro-1H-pyrazol-3-ylamino)pyrimidin-2-ylamino)-2,5-dimethylphenyl)piperidin-1-yl)propanamide; ESMS m/z 483.2 (M+H$^+$).

EXAMPLE 26

(4-(4-(5-chloro-4-(5-methyl-1H-pyrazol-3-ylamino)pyrimidin-2-ylamino)-5-fluoro-2-methylphenyl)piperidin-1-yl)(1-(ethylamino)cyclopropyl)methanone (169)

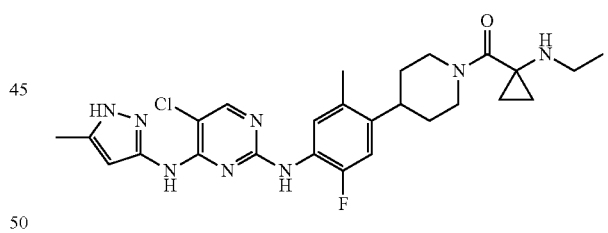

A mixture of 5-chloro-N$^2$-(2-fluoro-5-methyl-4-(piperidin-4-yl)phenyl)-N$^4$-(5-methyl-1H-pyrazol-3-yl)pyrimidine-2,4-diamine (67.3 mg, 0.17 mmol), 1-(tert-butoxycarbonyl(ethyl)amino)cyclopropanecarboxylic acid (38.0 mg, 0.17 mmol), HATU (63.0 mg, 0.17 mmol) and diisopropylethylamine (57 μL, 0.34 mmol) in 1 mL of DMF was stirred at room temperature overnight. The reaction mixture was partitioned between EtOAc and water, the combined organic extracts were dried (Na$_2$SO$_4$) and then concentrated in vacuo. The resulting crude mixture was dissolved in 5 mL of DCM and 4 mL of TFA and was then stirred for 2 h followed by concentration in vacuo. The crude product was purified by RP-HPLC to afford (4-(4-(5-chloro-4-(5-methyl-1H-pyrazol-3-ylamino)pyrimidin-2-ylamino)-5-fluoro-2-methylphenyl)piperidin-1-yl)(1-(ethylamino)cyclopropyl)methanone; ESMS m/z 527.2 (M+H$^+$).

EXAMPLE 27

1-(4-(4-(5-chloro-4-(5-methyl-1H-pyrazol-3-ylamino)pyrimidin-2-ylamino)-2,5-dimethylphenyl)piperidin-1-yl)-2-(ethylamino)-2-methylpropan-1-one (175)

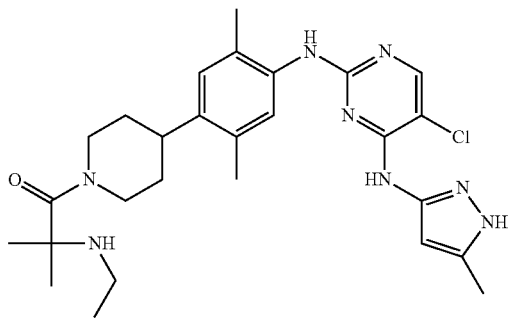 [SMILES: CCNC(C)(C)C(=O)N1CCC(c2cc(C)c(Nc3ncc(Cl)c(Nc4cc(C)[nH]n4)n3)cc2C)CC1]

To a solution of 2-amino-1-(4-(4-(5-chloro-4-(5-methyl-1H-pyrazol-3-ylamino)pyrimidin-2-ylamino)-2,5-dimethylphenyl)piperidin-1-yl)-2-methylpropan-1-one (6 mg, 0.012 mmol) in acetone (0.5 mL) was added $K_2CO_3$ (11 mg, 0.079 mmol). The mixture was stirred at room temperature for 10 min. before the addition of EtI (6 mg, 0.038 mmol). The resulting mixture was then stirred at room temperature for 14 h before it was treated with saturated aqueous $NH_4Cl$ (1 mL) and extracted with EtOAc (3×2 mL). The organic layers were combined, concentrated, and the residue was purified by preparative thin layer chromatography (silica gel, 8% MeOH/DCM/$NH_3$) followed by further purification with preparative RP-HPLC to provide 1-(4-(4-(5-chloro-4-(5-methyl-1H-pyrazol-3-ylamino)pyrimidin-2-ylamino)-2,5-dimethylphenyl)piperidin-1-yl)-2-(ethylamino)-2-methylpropan-1-one; ESMS m/z 525.3 (M+H$^+$).

EXAMPLE 28

(4-(4-(5-chloro-4-(5-methyl-1H-pyrazol-3-ylamino)pyrimidin-2-ylamino)-5-fluoro-2-methylphenyl)piperidin-1-yl)(1-(ethylamino)cyclobutyl)methanone (176)

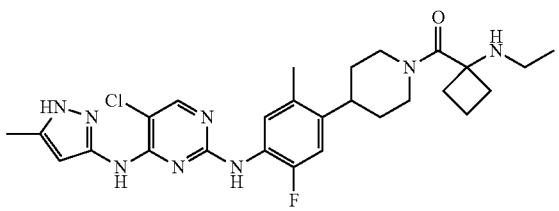 [SMILES: CCNC1(C(=O)N2CCC(c3cc(F)c(Nc4ncc(Cl)c(Nc5cc(C)[nH]n5)n4)cc3C)CC2)CCC1]

A mixture of 5-chloro-$N^2$-(2-fluoro-5-methyl-4-(piperidin-4-yl)phenyl)-$N^4$-(5-methyl-1H-pyrazol-3-yl)pyrimidine-2,4-diamine (50.0 mg, 0.12 mmol), 1-(tert-butoxycarbonyl(ethyl)amino)cyclobutanecarboxylic acid (29.2 mg, 0.12 mmol), HATU (45.8 mg, 0.12 mmol) and di-isopropylethylamine (20 µL, 0.12 mmol) in 1 mL of DMF was stirred at room temperature overnight. The reaction mixture was partitioned between EtOAc and water. The combined organic extracts were dried ($Na_2SO_4$), and concentrated in vacuo. The resulting crude mixture was dissolved in 5 mL of DCM and 4 mL of TFA and was then stirred for 2 h followed by concentration in vacuo. The crude product was purified by RP-HPLC to afford (4-(4-(5-chloro-4-(5-methyl-1H-pyrazol-3-ylamino)pyrimidin-2-ylamino)-5-fluoro-2-methylphenyl)piperidin-1-yl)(1-(ethylamino)cyclobutyl)methanone; ESMS m/z 541.3 (M+H$^+$).

EXAMPLE 29

(4-(4-(5-chloro-4-(5-methyl-1H-pyrazol-3-ylamino)pyrimidin-2-ylamino)-5-fluoro-2-methylphenyl)piperidin-1-yl)(1-(methylamino)cyclobutyl)methanone (177)

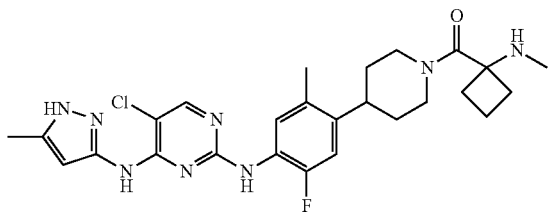

A mixture of 5-chloro-$N^2$-(2-fluoro-5-methyl-4-(piperidin-4-yl)phenyl)-$N^4$-(5-methyl-1H-pyrazol-3-yl)pyrimidine-2,4-diamine (50.0 mg, 0.12 mmol), 1-(tert-butoxycarbonyl(methyl)amino)cyclobutanecarboxylic acid (27.5 0.12 mmol), HATU (45.8 mg, 0.12 mmol) and di-isopropylethylamine (20 µL, 0.12 mmol) in 1 mL of DMF was stirred at room temperature overnight. The reaction mixture was partitioned between EtOAc and water. The combined organic extracts were dried ($Na_2SO_4$), and concentrated in vacuo. The resulting crude mixture was dissolved in 5 mL of DCM and 4 mL of TFA, and was stirred for 2 h followed by concentration in vacuo. The crude product was purified by RP-HPLC to afford (4-(4-(5-chloro-4-(5-methyl-1H-pyrazol-3-ylamino)pyrimidin-2-ylamino)-5-fluoro-2-methylphenyl)piperidin-1-yl)(1-(methylamino)cyclobutyl)methanone; ESMS m/z 527.2 (M+H$^+$).

EXAMPLE 30

(S)-3-(4-(2,5-dimethyl-4-(5-methyl-4-(5-methyl-1H-pyrazol-3-ylamino)pyrimidin-2-ylamino)phenyl)piperidin-1-yl)-1,1,1-trifluoropropan-2-ol (179)

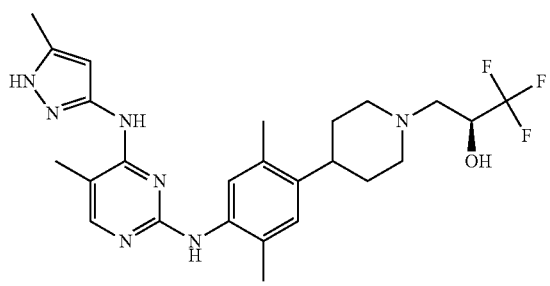 [SMILES: Cc1cc(Nc2nc(Nc3cc(C)c(C4CCN(C[C@H](O)C(F)(F)F)CC4)cc3C)ncc2C)n[nH]1]

To a solution of N²-(2,5-dimethyl-4-(piperidin-4-yl)phenyl)-5-methyl-N⁴-(5-methyl-1H-pyrazol-3-yl)pyrimidine-2,4-diamine hydrochloride (36.0 mg, 0.084 mmol) in DMF (0.5 mL) were added TEA (23.4 µL, 0.168 mmol) and (S)-2-(trifluoromethyl)oxirane (72.8 µL, 0.84 mmol). The reaction mixture was stirred at room temperature overnight, and purified by preparative RP-HPLC to provide (S)-3-(4-(2,5-dimethyl-4-(5-methyl-4-(5-methyl-1H-pyrazol-3-ylamino)pyrimidin-2-ylamino)phenyl)piperidin-1-yl)-1,1,1-trifluoropropan-2-ol; ESMS m/z 504.3 (M+H⁺).

EXAMPLE 31

2-(2-(4-(5-Chloro-4-(5-methyl-1H-pyrazol-3-ylamino)pyrimidin-2-ylamino)-2,5-dimethylphenyl)piperidin-1-yl)acetamide (181)

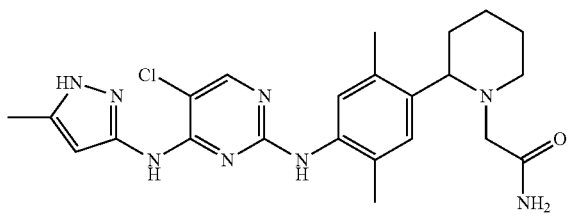 [SMILES: Cc1cc(Nc2nc(Nc3cc(C)c(C4CCCCN4CC(N)=O)cc3C)ncc2Cl)n[nH]1]

To a mixture of 5-Chloro-N2-(2,5-dimethyl-4-(piperidin-2-yl)phenyl)-N4-(5-methyl-1H-pyrazol-3-yl)pyrimidine-2,4-diamine (0.12 mmol) and triethylamine (83 uL, 0.6 mmol) in DMF (1.5 mL), was added 2-bromoacetamide (35 mg, 0.24 mmol). The mixture was stirred at room temperature for 3 h. The reaction was filtered and the filtrate was purified by RP-HPLC to afford 2-(2-(4-(5-chloro-4-(5-methyl-1H-pyrazol-3-ylamino)pyrimidin-2-ylamino)-2,5-dimethylphenyl)piperidin-1-yl)acetamide as a white solid; ¹H NMR (400 MHz, MeOD-d4) 8.09 (s, 1H), 7.65 (d, 1H), 7.43 (s, 1H), 6.41 (s, 1H), 4.79-4.74 (m, 2H), 3.83-3.48 (m, 2H), 2.71 (s, 3H), 2.42 (s, 3H), 2.34 (s, 6H), 2.15-1.84 (m, 7H); ESMS m/z 469.2 (M+H⁺).

EXAMPLES 32 AND 33

(S) 5-Chloro-N2-(2,5-dimethyl-4-(1-methylpiperidin-2-yl)phenyl)-N4-(5-methyl-1H-pyrazol-3-yl)pyrimidine-2,4-diamine (183)

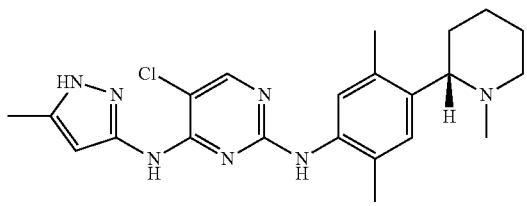 [SMILES: Cc1cc(Nc2nc(Nc3cc(C)c([C@@H]4CCCCN4C)cc3C)ncc2Cl)n[nH]1]

(R) 5-Chloro-N2-(2,5-dimethyl-4-(1-methylpiperidin-2-yl)phenyl)-N4-(5-methyl-1H-pyrazol-3-yl)pyrimidine-2,4-diamine (184)

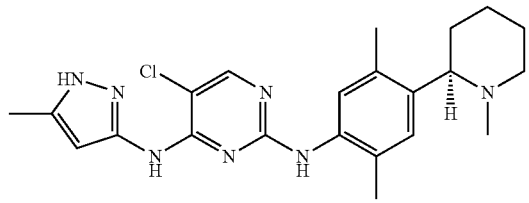 [SMILES: Cc1cc(Nc2nc(Nc3cc(C)c([C@H]4CCCCN4C)cc3C)ncc2Cl)n[nH]1]

Step 1: To a mixture of 1-bromo-2,5-dimethyl-4-nitrobenzene (185 mg, 1 mmol) and 2-(tributylstannyl)pyridine (202 mg, 1.1 mmol) in DMF (4 mL) was added tetrakis(triphenylphosphine) palladium (0) (58 mg, 0.05 mmol). The reaction tube was sealed, the mixture was purged with N₂ for 3 min and then heated at 120° C. under N₂ for overnight. The reaction was cooled to room temperature and poured into saturated aqueous ammonia chloride solution. The crude reaction mixture was extracted with ethyl acetate (3×15 mL). The organic extracts were combined, washed with brine and concentrated. The crude product was purified with silica chromatography (60% ethyl acetate in hexanes) to afford 2-(2,5-dimethyl-4-nitrophenyl)pyridine as a white solid. The obtained solid was dissolved in acetic acid/TFA (15 mL/200 uL). To this solution was added PtO₂ (10% w/w). The reaction mixture was degassed and purged with H₂ for several times and then vigorously stirred under 1 atm. H₂ overnight. The mixture was filtered and the filtrate concentrated to afford 2,5-Dimethyl-4-(piperidin-2-yl)aniline as a yellow oil; ESMS m/z 205 (M+H⁺).

Step 2: A mixture of 2,5-dichloro-N-(5-methyl-1H-pyrazol-3-yl)pyrimidin-4-amine (120 mg, 0.49 mmol) and 2,5-dimethyl-4-(piperidin-2-yl)aniline (100 mg, 0.49 mmol) in 2-propanol (10 mL) was treated with conc. aqueous HCl (7 drops). The mixture was sealed and heated in a microwave at 130° C. for 45 min. The mixture was concentrated to afford 5-Chloro-N2-(2,5-dimethyl-4-(piperidin-2-yl)phenyl)-N4-(5-methyl-1H-pyrazol-3-yl)pyrimidine-2,4-diamine; ESMS m/z 412.1 (M+H⁺). The crude product was used directly for the next step without further purification.

Step 3: To a solution of the crude product from the previous step in THF (1 mL) and methanol (1 mL) was sequentially added formaldehyde (100 uL, 1.3 mmol) and 5 drops of AcOH. The reaction mixture was stirred at room temperature for 1 h, then sodium cyanoborohydride (160 mg, 2.45 mmol) was added in one portion, and the reaction was stirred for an additional 30 min. The reaction was quenched by saturated aqueous NH₄Cl and concentrated in vacuo to give an oily residue. The residue was purified with RP-HPLC to afford (±)-5-Chloro-N2-(2,5-dimethyl-4-(1-methylpiperidin-2-yl)phenyl)-N4-(5-methyl-1H-pyrazol-3-yl)pyrimidine-2,4-diamine as a white solid; ESMS m/z 426.2 (M+H⁺).

Step 4: Chiral separation of the racemic mixture was conducted with normal phase HPLC using ChiralPaK AD-H column using the following solvent system: hexanes (95%), EtOH (2.5%), MeOH (2.5%). The two purified enantiomer peaks were collected separately: (R)-5-Chloro-N2-(2,5-dimethyl-4-(1-methylpiperidin-2-yl)phenyl)-N4-(5-methyl-1H-pyrazol-3-yl)pyrimidine-2,4-diamine and (S)-5-Chloro-N2-(2,5-dimethyl-4-(1-methylpiperidin-2-yl)phenyl)-N4-(5-methyl-1H-pyrazol-3-yl)pyrimidine-2,4-diamine; both peaks: ESMS m/z 426.2 (M+H⁺). The earlier eluting peak has been arbitrarily assigned as the (R) enantiomer.

EXAMPLE 34

5-Chloro-N²-(2,5-dimethyl-4-(1-(3-morpholinopropylsulfonyl)piperidin-4-yl)phenyl)-N⁴-(5-methyl-1H-pyrazol-3-yl)pyrimidine-2,4-diamine (194)

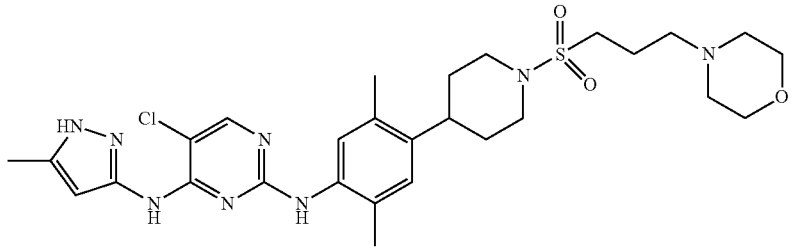 [SMILES: Cc1cc(Nc2nc(Nc3cc(C)c(C4CCN(S(=O)(=O)CCCN5CCOCC5)CC4)cc3C)ncc2Cl)n[nH]1]

Step 1: To a solution of 5-chloro-N²-(2,5-dimethyl-4-(piperidin-4-yl)phenyl)-N⁴-(5-methyl-1H-pyrazol-3-yl)pyrimidine-2,4-diamine (78 mg, 0.19 mmol) and TEA (0.52 mL, 3.78 mmol) in DCM (10 mL) was added 3-chloropropane-1-sulfonyl chloride (63 mg, 0.36 mmol, in 1 mL DCM). After stirring at rt for one hour, EtOAc (100 mL) was added. The mixture was sequentially washed with water (10 mL), brine (10 mL), dried over Na$_2$SO$_4$ and concentrated in vacuo. The crude product was purified by silica chromatography (0-100% EtOAc in hexanes gradient) to give 5-chloro-N2-(4-(1-(3-chloropropylsulfonyl)piperidin-4-yl)-2,5-dimethylphenyl)-N4-(5-methyl-1H-pyrazol-3-yl)pyrimidine-2,4-diamine as an off white solid; ESMS m/z 552.2 (M+H⁺).

Step 2: The product from Step 1 was stirred in neat morpholine (0.5 mL) at 100° C. in a sealed vial for one hour. The reaction was purified by RP-HPLC to give 5-Chloro-N2-(2,5-dimethyl-4-(1-(3-morpholinopropylsulfonyl)piperidin-4-yl)phenyl)-N4-(5-methyl-1H-pyrazol-3-yl)pyrimidine-2,4-diamine as a white powder; ESMS m/z 603.2 (M+H⁺).

EXAMPLE 35

1-((4-(4-(5-chloro-4-(5-methyl-1H-pyrazol-3-ylamino)pyrimidin-2-ylamino)-2,5-dimethylphenyl)piperidin-1-yl)methyl)cyclopropanecarbonitrile (198)

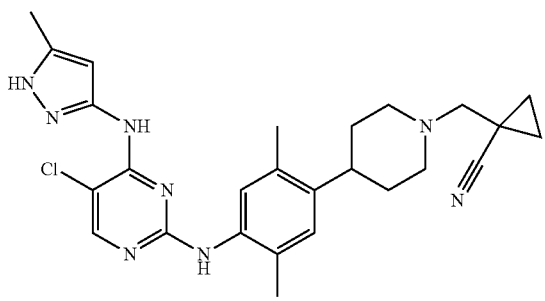 [SMILES: Cc1cc(Nc2nc(Nc3cc(C)c(C4CCN(CC5(C#N)CC5)CC4)cc3C)ncc2Cl)n[nH]1]

To a solution of 5-chloro-N²-(2,5-dimethyl-4-(piperidin-4-yl)phenyl)-N⁴ (5-methyl-1H-pyrazol-3-yl)pyrimidine-2,4-diamine (30 mg, 0.078 mmol) in acetonitrile (1.0 mL) was added (1-cyanocyclopropyl)methyl 4-methylbenzenesulfonate (16 mg, 0.10 mmol, prepared according to the procedure described in patent WO2005063247) followed by DIEA (30 mg, 0.23 mmol) and KI (catalytic amount). The resulting mixture was heated to 70° C. for 14 h and then cooled down to room temperature. The resulting mixture was directly purified by preparative RP-HPLC to provide 1-((4-(4-(5-chloro-4-(5-methyl-1H-pyrazol-3-ylamino)pyrimidin-2-ylamino)-2,5-dimethylphenyl)-piperidin-1-yl)methyl)cyclopropanecarbonitrile; ESMS m/z 491.2 (M+H⁺).

EXAMPLE 36

2-(4-(4-(5-chloro-4-(5-methyl-1H-pyrazol-3-ylamino)pyrimidin-2-ylamino)-5-fluoro-2-methylphenyl)piperidin-1-yl)acetonitrile (199)

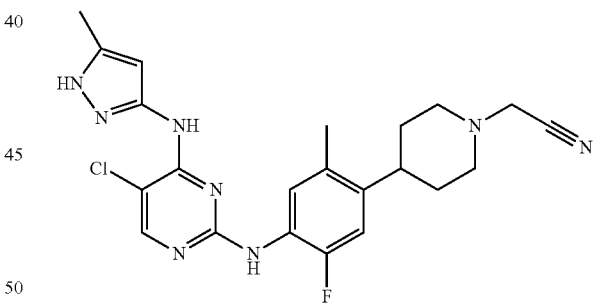

To a solution of 5-chloro-N²-(2-fluoro-5-methyl-4-(piperidin-4-yl)phenyl)-N⁴-(5-methyl-1H-pyrazol-3-yl)pyrimidine-2,4-diamine (20 mg, 0.048 mmol) in acetonitrile (0.5 mL) was added Cs$_2$CO$_3$ (31 mg, 0.096 mmol) and chloroacetonitrile (7 mg, 0.096 mmol). The resulting mixture was stirred at room temperature for 14 h before it was treated with saturated aqueous NH$_4$Cl (1 mL) and extracted with EtOAc (3×2 mL). The organic layers were combined, concentrated, and the residue was purified by preparative RP-HPLC to provide 2-(4-(4-(5-chloro-4-(5-methyl-1H-pyrazol-3-ylamino)pyrimidin-2-ylamino)-5-fluoro-2-methylphenyl)piperidin-1-yl)acetonitrile; ESMS m/z 455.2 (M+H⁺).

EXAMPLE 37

3-(4-(4-(5-chloro-4-(5-methyl-1H-pyrazol-3-ylamino)pyrimidin-2-ylamino)-5-fluoro-2-methylphenyl)piperidin-1-yl)propanenitrile (200)

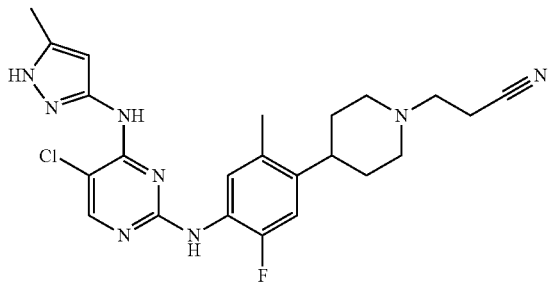 [SMILES: Cc1cc(Nc2nc(Nc3cc(C)c(C4CCN(CCC#N)CC4)cc3F)ncc2Cl)n[nH]1]

To a solution of 5-chloro-$N^2$-(2-fluoro-5-methyl-4-(piperidin-4-yl)phenyl)-$N^4$-(5-methyl-1H-pyrazol-3-yl)pyrimidine-2,4-diamine (20 mg, 0.048 mmol) in MeOH (0.5 mL) was added acrylonitrile (5 mg, 0.096 mmol). The resulting mixture was stirred at room temperature for 14 h and then purified directly by preparative RP-HPLC to provide 3-(4-(4-(5-chloro-4-(5-methyl-1H-pyrazol-3-ylamino)pyrimidin-2-ylamino)-5-fluoro-2-methylphenyl)piperidin-1-yl)propanenitrile; ESMS m/z 469.2 (M+H$^+$).

EXAMPLES 38 AND 39

(R)-2-(3-(4-(5-chloro-4-(5-methyl-1H-pyrazol-3-ylamino)pyrimidin-2-ylamino)-2,5-dimethylphenyl)piperidin-1-yl)-N-methylacetamide (207)

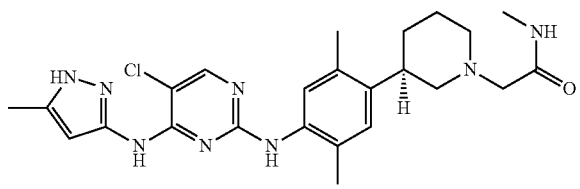 [SMILES: CNC(=O)CN1CCC[C@H](c2cc(C)c(Nc3ncc(Cl)c(Nc4cc(C)[nH]n4)n3)cc2C)C1]

(S)-2-(3-(4-(5-chloro-4-(5-methyl-1H-pyrazol-3-ylamino)pyrimidin-2-ylamino)-2,5-dimethylphenyl)piperidin-1-yl)-N-methylacetamide (208)

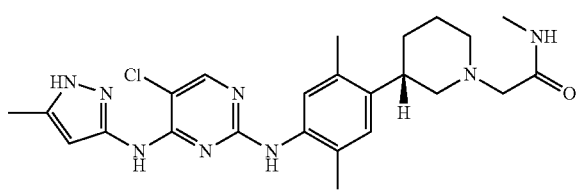 [SMILES: CNC(=O)CN1CCC[C@@H](c2cc(C)c(Nc3ncc(Cl)c(Nc4cc(C)[nH]n4)n3)cc2C)C1]

A solution of 5-chloro-$N^2$-(2,5-dimethyl-4-(piperidin-3-yl)phenyl)-$N^4$-(5-methyl-1H-pyrazol-3-yl)pyrimidine-2,4-diamine (700 mg, 1.70 mmol), 2-bromo-N-methylacetamide (258 mg, 1.70 mmol) and TEA (1.2 mL, 8.5 mmol) in DMF (4 mL) was stirred at rt for 30 min. The reaction was purified by RP-HPLC to give the product as a racemate; ESMS m/z 483.2 (M+1). Chiral separation of the racemic mixture was conducted with chiral HPLC (ChiralCel OD-H, Hex:EtOH: MeOH/80:10:10, 15 min run time, 1 mL/min). The two purified enantiomer peaks were collected separately, both as white solids: (R)-2-(3-(4-(5-chloro-4-(5-methyl-1H-pyrazol-3-ylamino)pyrimidin-2-ylamino)-2,5-dimethylphenyl)piperidin-1-yl)-N-methylacetamide and (S)-2-(3-(4-(5-chloro-4-(5-methyl-1H-pyrazol-3-ylamino)pyrimidin-2-ylamino)-2,5-dimethylphenyl)piperidin-1-yl)-N-methylacetamide; both peaks: ESMS m/z 483.2 (M+H$^+$). The earlier eluting peak (rt=5.63 min. vs. rt=7.62 min.) was arbitrarily assigned as the (R) enantiomer.

EXAMPLE 40

5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (209)

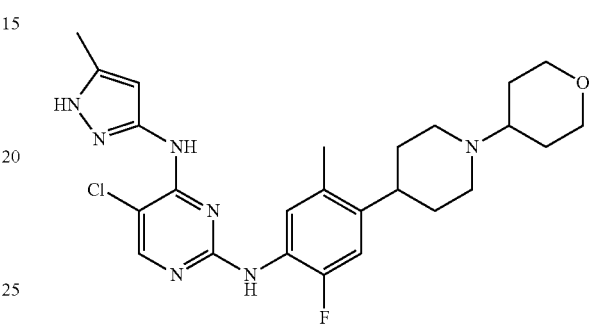

To a suspension of 5-chloro-$N^2$-(2-fluoro-5-methyl-4-(piperidin-4-yl)phenyl)-$N^4$-(5-methyl-1H-pyrazol-3-yl)pyrimidine-2,4-diamine (2.50 g, 6.0 mmol) in a mixed solvent of MeOH (42 mL) and DCM (10 mL) was added dihydro-2H-pyran-4(3H)-one (3.33 mL, 36.0 mmol) and TEA (8.36 mL, 60.0 mmol). The reaction mixture was heated at 60° C. for 1 h before NaCNBH$_3$ (1.66 g, 26.4 mmol) was added. The mixture was heated at 60° C. for another 2 h, cooled down to room temperature, diluted with DCM (60 mL), dry loaded onto silica gel (12.5 g), and purified by silica gel chromatography (DCM with 1% NH$_3$ to 10% MeOH in DCM with 1% NH$_3$ gradient) to provide 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine as a white solid; $^1$H NMR (DMSO-d$_6$, 400 MHz) δ 12.08 (br, 1H), 9.58 (br, 1H), 8.65 (d, J=28.4 Hz, 1H), 8.02 (s, 1H), 7.36 (d, J=8.4 Hz, 1H), 7.03 (d, J=12.4 Hz, 1H), 6.08 (br, 1H), 3.89 (dd, J=10.8, 3.6 Hz, 2H), 3.28 (t, J=10.4 Hz, 2H), 2.99 (d, J=10.8 Hz, 2H), 2.64-2.43 (m, 2H), 2.24-2.15 (m, 8H), 1.71-1.40 (m, 8H); ESMS m/z 500.2 (M+H$^+$).

EXAMPLE 41

5-chloro-$N^2$-(4-(1-cyclopropylpiperidin-4-yl)-2-fluoro-5-methylphenyl)-$N^4$-(5-methyl-1H-pyrazol-3-yl)pyrimidine-2,4-diamine (210)

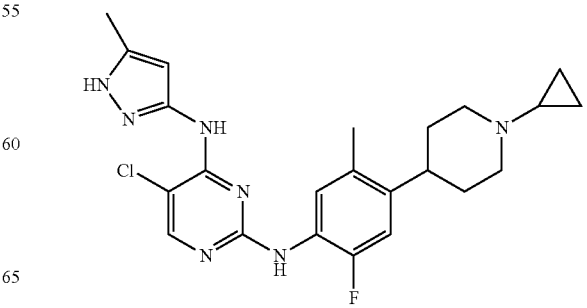

To a solution of 5-chloro-$N^2$-(2-fluoro-5-methyl-4-(piperidin-4-yl)phenyl)-$N^4$-(5-methyl-1H-pyrazol-3-yl)pyrimidine-2,4-diamine (30 mg, 0.072 mmol) in MeOH (0.7 mL) was added AcOH (35 mg, 0.58 mmol), (1-ethoxycyclopropoxy)trimethylsilane (37 mg, 0.216 mmol) and a small amount of 4 Å molecular sieves. The mixture was stirred at room temperature for 1 h before the addition of Na(CN)BH$_3$ (14 mg, 0.216 mmol). The resulting mixture was then stirred at 60° C. for 14 h and cooled to room temperature. Saturated aqueous NH$_4$Cl (2 mL) was added and the mixture was extracted with EtOAc (3×3 mL). The combined organic layers were concentrated and purified by preparative RP-HPLC to provide 5-chloro-$N^2$-(4-(1-cyclopropylpiperidin-4-yl)-2-fluoro-5-methylphenyl)-$N^4$-(5-methyl-1H-pyrazol-3-yl)pyrimidine-2,4-diamine; $^1$H NMR (400 MHz, MeOD-d4) δ 7.97 (s, 1H), 7.84 (d, 1H), 7.50 (s, 1H), 6.93 (d, 1H), 6.29 (s, 1H), 5.33 (s, 1H), 2.80 (m, 1H), 2.58 (s, 2H), 2.28 (s, 3H), 2.24 (s, 3H), 1.96 (m, 1H), 1.80-1.85 (m, 2H), 1.65-1.75 (m, 2H), 0.2-0.7 (m, 6H); ESMS m/z 456.2 (M+H$^+$).

EXAMPLE 42

$N^2$-(4-(1-(3-(azetidin-1-ylsulfonyl)propyl)piperidin-4-yl)-2,5-dimethylphenyl)-5-chloro-$N^4$-(5-methyl-1H-pyrazol-3-yl)pyrimidine-2,4-diamine (214)

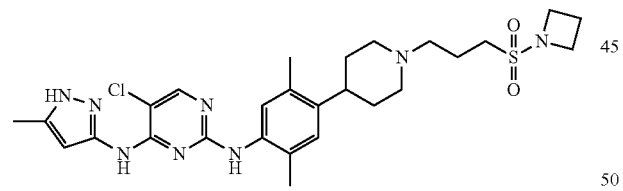

Step 1: To a solution of azetidine (12 mg, 0.21 mmol) and TEA (0.1 mL, 0.71 mmol) in DCM (5 mL) was slowly added a solution of 3-chloropropane-1-sulfonyl chloride (34 mg, 0.19 mmol) in DCM (1 mL). After stirring at rt overnight, the solvent was removed in vacuo. The resulting 1-(3-chloropropylsulfonyl)azetidine crude product was dissolved in NMP (1.9 mL, 0.1 mmol/mL) and used in the next step without further purification; ESMS m/z 198.0 (M+H$^+$).

Step 2: A mixture of 5-chloro-$N^2$-(2,5-dimethyl-4-(piperidin-4-yl)phenyl)-$N^4$-(5-methyl-1H-pyrazol-3-yl)pyrimidine-2,4-diamine (42 mg, 0.1 mmol), 1-(3-chloropropylsulfonyl)azetidine (Step 1, 0.1 mmol), TEA (70 μL) and sodium iodide (150 mg) in NMP (1 mL) was placed in a sealed vial which was heated in a microwave for 30 min at 150° C. The reaction was purified by RP-HPLC to give N2-(4-(1-(3-(azetidin-1-ylsulfonyl)propyl)piperidin-4-yl)-2,5-dimethylphenyl)-5-chloro-N4-(5-methyl-1H-pyrazol-3-yl)pyrimidine-2,4-diamine as a white powder; ESMS m/z 573.3 (M+H$^+$).

EXAMPLE 43

1-(4-(4-(5-Chloro-4-(5-methyl-1H-pyrazol-3-ylamino)pyrimidin-2-ylamino)-2,5-dimethylphenyl)piperidin-1-yl)-4-morpholinobutan-1-one (224)

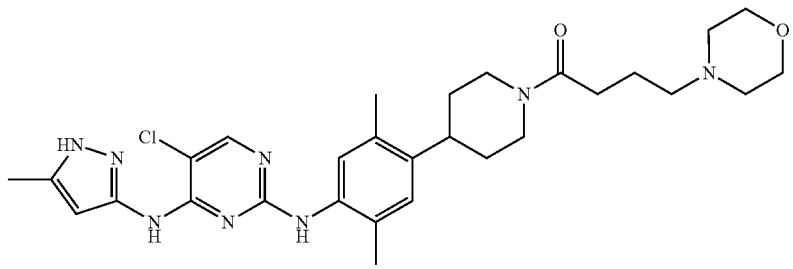 [SMILES: Cc1cc(Nc2nc(Nc3cc(C)c(C4CCN(C(=O)CCCN5CCOCC5)CC4)cc3C)ncc2Cl)n[nH]1]

Step 1: To a solution of HATU (95 mg, 0.255 mmol) and 4-chlorobutanoic acid (36 mg, 0.25 mmol) in DMF (1 mL) was added DIEA (0.1 mL). After stirring at rt for 3 min, 5-chloro-$N^2$-(2,5-dimethyl-4-(piperidin-4-yl)phenyl)-$N^4$-(5-methyl-1H-pyrazol-3-yl)pyrimidine-2,4-diamine (100 mg, 0.24 mmol) in DMF (2 mL) was added. The reaction was stirred at rt for 90 min. at which point LCMS indicates the reaction was complete and that 4-chloro-1-(4-(4-(5-chloro-4-(5-methyl-1H-pyrazol-3-ylamino)pyrimidin-2-ylamino)-2,5-dimethylphenyl)piperidin-1-yl)butan-1-one has been generated; ESMS m/z 516.1 (M+H$^+$).

Step 2: Morpholine (0.5 mL) was added directly to the crude reaction mixture from Step 1 (1 mL). The resulting solution was stirred at 100° C. in a sealed vial for 1.5 h. The crude product was purified by RP-HPLC to give 1-(4-(4-(5-Chloro-4-(5-methyl-1H-pyrazol-3-ylamino)pyrimidin-2-ylamino)-2,5-dimethylphenyl)piperidin-1-yl)-4-morpholinobutan-1-one as a white powder; ESMS m/z 567.3 (M+H$^+$).

EXAMPLE 44

1-(4-(4-(5-Chloro-4-(5-methyl-1H-pyrazol-3-ylamino)pyrimidin-2-ylamino)-2,5-dimethylphenyl)piperidin-1-yl)-3-morpholinopropan-1-one (225)

Step 1: A solution of HATU (108 mg, 0.28 mmol), 3-chloropropanoic acid (30 mg, 0.28 mmol) and DIEA (0.1 mL) in DMF (1 mL) was stirred at rt. After 3 min, this solution was transferred to a solution of 5-chloro-N-(2,5-dimethyl-4-(piperidin-4-yl)phenyl)-$N^4$-(5-methyl-1H-pyrazol-3-yl)pyrimidine-2,4-diamine solution (111 mg, 0.27 mmol) in DMF (10 mL). The resulting mixture was stirred at rt overnight. The reaction was quenched with water (20 mL) and extracted with EtOAc (3×30 mL). The combined EtOAc layers were washed with brine (10 mL), dried over Na$_2$SO$_4$ and concentrated in vacuo. The crude product was purified by silica chromatography (0-10% MeOH in DCM gradient with 1% NH$_3$ additive) to give 1-(4-(4-(5-chloro-4-(5-methyl-1H-pyrazol-3-ylamino)pyrimidin-2-ylamino)-2,5-dimethylphenyl)piperidin-1-yl)prop-2-en-1-one as a light brown oil; ESMS m/z 466.1 (M+H$^+$).

Step 2: A solution of 1-(4-(4-(5-chloro-4-(5-methyl-1H-pyrazol-3-ylamino)pyrimidin-2-ylamino)-2,5-dimethylphenyl)piperidin-1-yl)prop-2-en-1-one (41 mg, 0.88 mmol) and morpholine (0.1 mL) in DMF (1 mL) was stirred at rt overnight. The crude product was purified by RP-HPLC to give 1-(4-(4-(5-Chloro-4-(5-methyl-1H-pyrazol-3-ylamino)pyrimidin-2-ylamino)-2,5-dimethylphenyl)piperidin-1-yl)-3-morpholinopropan-1-one as a white powder; ESMS m/z 553.2 (M+H$^+$).

EXAMPLE 45

(S)-4-(4-(5-chloro-4-(5-methyl-1H-pyrazol-3-ylamino)pyrimidin-2-ylamino)-2,5-dimethylphenyl)oxazolidin-2-one (230)

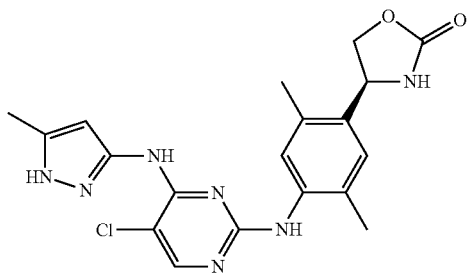 [SMILES: Cc1cc(Nc2nc(Nc3cc(C)c([C@H]4COC(=O)N4)cc3C)ncc2Cl)n[nH]1]

Step 1: To a microwave reaction vessel was added a mixture of 1-bromo-2,5-dimethyl-4-nitrobenzene (1.15 g, 5.0 mmol), dibutyl vinylboronate (1.16 g, 6.3 mmol), Pd(PPh$_3$)$_4$ (289 mg, 0.25 mmol), CsF (2.28 g, 15 mmol) and a mixed solvent (1,2-dimethoxyethane/MeOH=2:1, 15 mL). The mixture was degassed and sealed with N$_2$. The reaction vessel was then heated to 130° C. in a microwave reactor for 15 min. After opening the reaction vessel, the mixture was poured into saturated NH$_4$Cl aqueous solution (30 mL) and extracted with EtOAc (3×50 mL). The combined organic layers were washed with brine and dried (MgSO$_4$). After removing the drying agent by filtration, the filtrate was concentrated and purified by flash column chromatography (silica gel, 0-30% EtOAc in hexanes gradient) to provide 1,4-dimethyl-2-nitro-5-vinylbenzene as needlelike crystals; ESMS m/z 178.1 (M+H$^+$).

Step 2: 1,4-dimethyl-2-nitro-5-vinylbenzene was reacted via the asymmetric synthetic method reported by N. Barta et al. (*Org. Lett.* 2000, 2, 2821) followed by purification with preparative RP-HPLC to provide (S)-4-(2,5-dimethyl-4-nitrophenyl)oxazolidin-2-one; ESMS m/z 237.1 (M+H$^+$).

Step 3: To a solution of (S)-4-(2,5-dimethyl-4-nitrophenyl)oxazolidin-2-one (55 mg, 0.23 mmol) in MeOH (5 mL) was added Pd/C (5 mg, 10% w/w). The mixture was degassed and stirred at room temperature under 1 atm. H$_2$ for 14 h. The Pd/C was removed by filtering through Celite. The filtrate was concentrated to provide (S)-4-(4-amino-2,5-dimethylphenyl)-oxazolidin-2-one which was used in the next step without further purification; ESMS m/z 207.1 (M+H$^+$).

Step 4: To a reaction tube was added (S)-4-(4-amino-2,5-dimethylphenyl)oxazolidin-2-one (48 mg, 0.23 mmol), 2,5-dichloro-N-(5-methyl-1H-pyrazol-3-yl)pyrimidin-4-amine (77 mg, 0.32 mmol), $^i$PrOH (2 mL) and HCl (0.13 mL, 0.52 mmol, 4N in dioxane). The tube was then sealed and heated at 130° C. for 6 h. After cooling down to room temperature, the mixture was concentrated and purified by preparative RP-HPLC to provide (S)-4-(4-(5-chloro-4-(5-methyl-1H-pyrazol-3-ylamino)pyrimidin-2-ylamino)-2,5-dimethyl-phenyl)oxazolidin-2-one; ESMS m/z 414.1 (M+H$^+$).

EXAMPLE 46

5-chloro-N$^2$-(4-(1-ethylpiperidin-4-yl)-2-fluoro-5-methylphenyl)-N$^4$-(5-methyl-1H-pyrazol-3-yl)pyrimidine-2,4-diamine (232)

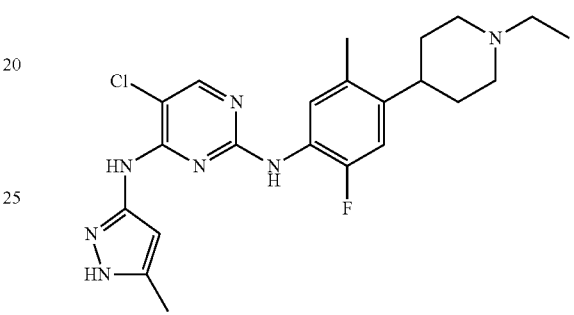

A mixture of 5-chloro-N$^2$-(2-fluoro-5-methyl-4-(piperidin-4-yl)phenyl)-N$^4$-(5-methyl-1H-pyrazol-3-yl)pyrimidine-2,4-diamine (400 mg, 0.96 mmol), iodoethane (92.5 µL, 1.2 mmol) and triethylamine (201.5 µL, 1.4 mmol) in 4 mL of DMF was heated at 60° C. for 2 h. The reaction mixture was partitioned between EtOAc and water. The combined organic extracts were dried (Na$_2$SO$_4$) and concentrated in vacuo. The crude product was purified by silica gel chromatography (MeOH/DCM: 1/9) to afford 5-chloro-N$^2$-(4-(1-ethylpiperidin-4-yl)-2-fluoro-5-methylphenyl)-N$^4$-(5-methyl-1H-pyrazol-3-yl)pyrimidine-2,4-diamine; $^1$HNMR (DMSO-d$_6$) δ 8.01 (s, 1H), 7.35 (m, 1H), 7.02 (d, 1H), 6.22 (s, 1H), 2.97 (d, 2H), 2.62 (m, 1H), 2.34 (q, 2H), 2.21 (s, 3H), 2.13 (s, 3H), 1.98 (t, 2H), 1.64 (m, 4H), 1.01 (t, 3H); ESMS m/z 444.2 (M+H$^+$).

EXAMPLE 47

5-chloro-N-(4-(1-((2,2-difluorocyclopropyl)methyl)piperidin-4-yl)-2-fluoro-5-methylphenyl)-N$^4$-(5-methyl-1H-pyrazol-3-yl)pyrimidine-2,4-diamine (235)

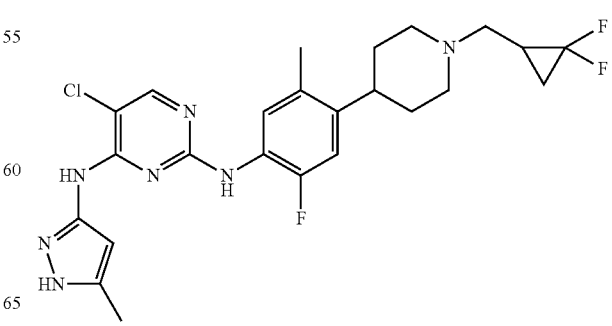

A mixture of 5-chloro-$N^2$-(2-fluoro-5-methyl-4-(piperidin-4-yl)phenyl)-$N^4$-(5-methyl-1H-pyrazol-3-yl)pyrimidine-2,4-diamine (40 mg, 0.096 mmol), 2-(bromomethyl)-1,1-difluorocyclopropane (32.8 mg, 0.19 mmol) and triethylamine (20.2 μL, 0.14 mmol) in 1 mL of DMF was heated at 150° C. in a microwave reactor for 30 min. The crude product was purified by RP-HPLC to afford 5-chloro-$N^2$-(4-(1-((2,2-difluorocyclopropyl)methyl)piperidin-4-yl)-2-fluoro-5-methylphenyl)-$N^4$-(5-methyl-1H-pyrazol-3-yl)pyrimidine-2,4-diamine; ESMS m/z 506.2 (M+H$^+$).

EXAMPLE 48

3-(4-(4-(5-Chloro-4-(5-methyl-1H-pyrazol-3-ylamino)pyrimidin-2-ylamino)-2,5-dimethylphenyl)piperidin-1-yl)propanamide (236)

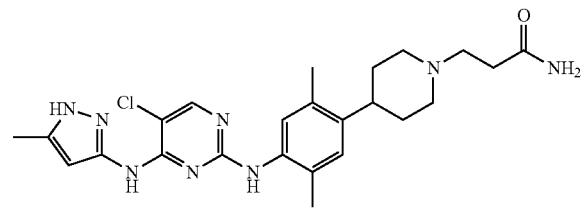 [SMILES: Cc1cc(Nc2nc(Nc3cc(C)c(C4CCN(CCC(N)=O)CC4)cc3C)ncc2Cl)n[nH]1]

A solution of 5-chloro-$N^2$-(2,5-dimethyl-4-(piperidin-4-yl)phenyl)-$N^4$-(5-methyl-1H-pyrazol-3-yl)pyrimidine-2,4-diamine (41 mg, 0.1 mmol), acrylamide (24 mg, 0.33 mmol) and DIEA (87 μL, 0.5 mmol) in NMP (1 mL) was stirred at 80° C. for 10 h. LCMS at this point shows the reaction was not complete, so additional acrylamide (2×36 mg) was added and the reaction continued until LCMS shows the reaction was complete. The crude product was purified by RP-HPLC to give 3-(4-(4-(5-Chloro-4-(5-methyl-1H-pyrazol-3-ylamino)pyrimidin-2-ylamino)-2,5-dimethylphenyl)piperidin-1-yl)propanamide as a white powder; ESMS m/z 483.2 (M+1).

EXAMPLE 49

4-(4-(4-(5-Chloro-4-(5-methyl-1H-pyrazol-3-ylamino)pyrimidin-2-ylamino)-5-fluoro-2-methylphenyl)piperidin-1-yl)-1-morpholinobutan-1-one (246)

A mixture of 5-chloro-$N^2$-(2-fluoro-5-methyl-4-(piperidin-4-yl)phenyl)-$N^4$-(5-methyl-1H-pyrazol-3-yl)pyrimidine-2,4-diamine (41 mg, 0.1 mmol), 4-chloro-1-morpholinobutan-1-one (29 mg, 0.15 mmol) and DIEA (0.1 mL, 0.58 mmol) in NMP (1 mL) was stirred at 80° C. After 10 h, additional 4-chloro-1-morpholinobutan-1-one (51 mg) was added, and the reaction continued overnight. The crude product was purified by RP-HPLC to give 4-(4-(4-(5-Chloro-4-(5-methyl-1H-pyrazol-3-ylamino)pyrimidin-2-ylamino)-5-fluoro-2-methylphenyl)piperidin-1-yl)-1-morpholinobutan-1-one as a white powder; ESMS m/z 571.3.3 (M+H$^+$).

EXAMPLE 50

$N^2$-(4-(1-((2,2-difluorocyclopropyl)methyl)piperidin-4-yl)-2-fluoro-5-methylphenyl)-$N^4$-(5-methyl-1H-pyrazol-3-yl)-5-(trifluoromethyl)pyrimidine-2,4-diamine (251)

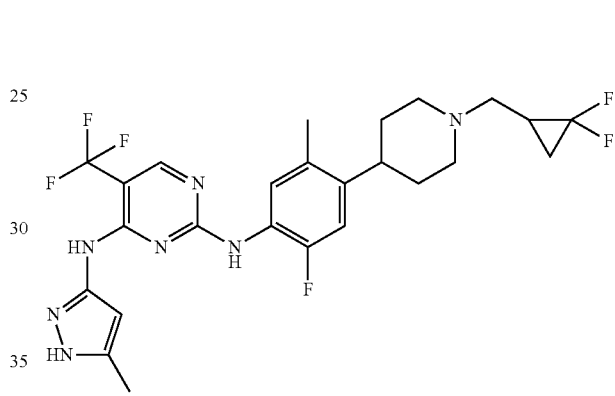

A mixture of N2-(2-fluoro-5-methyl-4-(piperidin-4-yl)phenyl)-N4-(5-methyl-1H-pyrazol-3-yl)-5-(trifluoromethyl)pyrimidine-2,4-diamine (100 mg, 0.22 mmol), 2-(bromomethyl)-1,1-difluorocyclopropane (76.4 mg, 0.45 mmol) and triethylamine (60.6 μL, 0.42 mmol) in 1 mL of DMF was heated at 60° C. in a microwave reactor for 2 h. The crude product was purified by RP-HPLC to afford $N^2$-(4-(1-((2,2-difluorocyclopropyl)methyl)piperidin-4-yl)-2-fluoro-5-methylphenyl)-$N^4$-(5-methyl-1H-pyrazol-3-yl)-5-(trifluoromethyl)pyrimidine-2,4-diamine; ESMS m/z 540.2 (M+H$^+$).

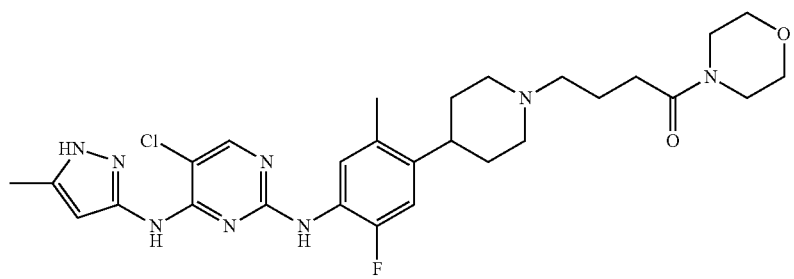 [SMILES: Cc1cc(Nc2nc(Nc3cc(C)c(C4CCN(CCCC(=O)N5CCOCC5)CC4)cc3F)ncc2Cl)n[nH]1]

EXAMPLE 51

N²-(2,5-dimethyl-4-(piperidin-4-yl)phenyl)-N⁴-(5-methyl-1H-pyrazol-3-yl)-5-(trifluoromethyl)pyrimidine-2,4-diamine (257)

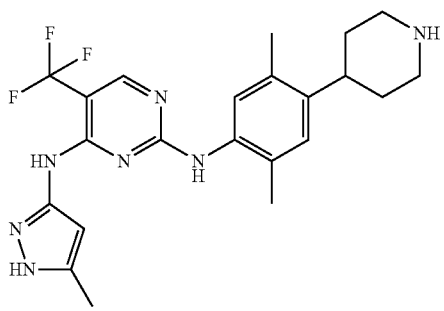 [SMILES: Cc1cc(Nc2nc(Nc3cc(C)c(C4CCNCC4)cc3C)ncc2C(F)(F)F)n[nH]1]

A mixture of 2-chloro-N-(5-methyl-1H-pyrazol-3-yl)-5-(trifluoromethyl)pyrimidin-4-amine (513.0 mg, 0.9 mmol), tert-butyl-4-(4-amino-2,5-dimethylphenyl)piperidine-1-carboxylate (282.7 mg, 0.9 mmol), and concentrated aqueous HCl (10 drops) in i-PrOH (12 mL) was heated at 150° C. in a microwave reactor for 30 min. The crude product was purified by RP-HPLC to afford N²-(2,5-dimethyl-4-(piperidin-4-yl)phenyl)-N⁴-(5-methyl-1H-pyrazol-3-yl)-5-(trifluoromethyl)pyrimidine-2,4-diamine; ESMS m/z 446.2 (M+H⁺).

EXAMPLE 52

5-Chloro-N²-(2-fluoro-4-(1-((3-isopropyl-1,2,4-oxadiazol-5-yl)methyl)piperidin-4-yl)-5-methylphenyl)-N-(5-methyl-1H-pyrazol-3-yl)pyrimidine-2,4-diamine (259)

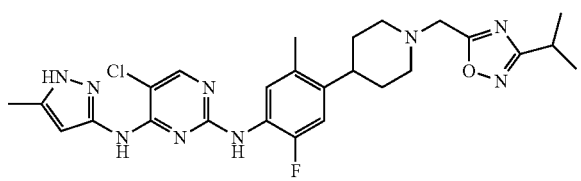 [SMILES: Cc1cc(Nc2nc(Nc3cc(C)c(C4CCN(Cc5nc(C(C)C)no5)CC4)cc3F)ncc2Cl)n[nH]1]

A mixture of 5-chloro-N²-(2-fluoro-5-methyl-4-(piperidin-4-yl)phenyl)-N⁴-(5-methyl-1H-pyrazol-3-yl)pyrimidine-2,4-diamine (42 mg, 0.1 mmol), 5-(chloromethyl)-3-isopropyl-1,2,4-oxadiazole (17 mg, 0.10 mmol) and DIEA (86 μL, 0.5 mmol) in DMF (1 mL) was stirred at rt overnight. The reaction was diluted with EtOAc (50 mL) and washed with water (2×5 mL). The EtOAc layer was dried over Na₂SO₄ and concentrated in vacuo. The crude product was purified by silica chromatography (50-100% EtOAc in hexanes gradient) to give 5-Chloro-N2-(2-fluoro-4-(1-((3-isopropyl-1,2,4-oxadiazol-5-yl)methyl)piperidin-4-yl)-5-methylphenyl)-N4-(5-methyl-1H-pyrazol-3-yl)pyrimidine-2,4-diamine as a white solid; ESMS m/z 540.2 (M+H⁺).

EXAMPLE 53

(4-(4-(5-Chloro-4-(5-methyl-1H-pyrazol-3-ylamino)pyrimidin-2-ylamino)-5-fluoro-2-methylphenyl)piperidin-1-yl)(3-isopropyl-1,2,4-oxadiazol-5-yl)methanone (265)

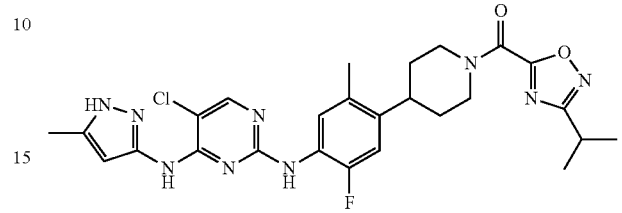

Step 1: A solution of isobutyronitrile (4.49 mL, 50 mmol) and hydroxylamine (12.3 mL, 200 mmol) in anhydrous ethanol (20 mL) was stirred at 60° C. for two days. The solvent was evaporated. The residue was coevaporated repeatedly with toluene to give (E)-N'-hydroxyisobutyrimidamide as a light yellow liquid; ¹H NMR (400 MHz, CDCl₃) δ 7.50 (br s, 1H), 4.52 (br s, 2H), 2.43 (septet, J=6.8 Hz, 1H), 1.15 (d, J=6.8 Hz, 6H).

Step 2: A solution of (E)-N'-hydroxyisobutyrimidamide (0.51 g, 5 mmol) and trichloroacetic anhydride (2.31 g, 7.5 mmol) in toluene (20 mL) was stirred at 80° C. After 4 h, the reaction was diluted with EtOAc (50 mL), washed with saturated aqueous NaHCO₃ (2×10 mL), dried over Na₂SO₄ and evaporated to give 3-Isopropyl-5-(trichloromethyl)-1,2,4-oxadiazole as a clear liquid which was used without further purification; ¹H NMR (400 MHz, CDCl₃) δ 3.16 (septet, J=7.2 Hz, 1H), 1.39 (d, J=6.8 Hz, 6H).

Step 3: A mixture of 5-chloro-N²-(2-fluoro-5-methyl-4-(piperidin-4-yl)phenyl)-N⁴-(5-methyl-1H-pyrazol-3-yl)pyrimidine-2,4-diamine (42 mg, 0.1 mmol), 3-isopropyl-5-(trichloromethyl)-1,2,4-oxadiazole (46 mg, 0.2 mmol) and DIEA (40 μL, 0.23 mmol) in MeOH (1 mL) was stirred at 70° C. overnight. The crude reaction mixture was purified by RP-HPLC to give (4-(4-(5-Chloro-4-(5-methyl-1H-pyrazol-3-ylamino)pyrimidin-2-ylamino)-5-fluoro-2-methylphenyl)piperidin-1-yl)(3-isopropyl-1,2,4-oxadiazol-5-yl)methanone as a white solid; ¹H NMR (400 MHz, CDCl₃) δ 9.67 (br s, 2H), 8.50 (s, 1H), 8.07 (s, 1H), 7.57 (d, J=8.4 Hz, 1H), 7.05 (d, J=12.4 Hz, 1H), 6.16 (s, 1H), 5.53 (s, 1H), 3.98 (d, J=13.2 Hz, 1H), 3.34 (dt, J=2.0, 2.8 Hz, 1H), 3.15 (m, 1H), 2.82 (m, 2H), 2.62 (t, J=4.8 Hz, 2H), 2.34 (s, 3H), 2.25 9s, 3H), 1.90 (m, 2H), 1.76 (2H); ESMS m/z 554.2 (M+H⁺).

EXAMPLE 54

5-Chloro-N₂-(4-(1-(2-(3-isopropyl-1,2,4-oxadiazol-5-yl)ethyl)piperidin-4-yl)-2,5-dimethylphenyl)-N₄-(5-methyl-1H-pyrazol-3-yl)pyrimidine-2,4-diamine (269)

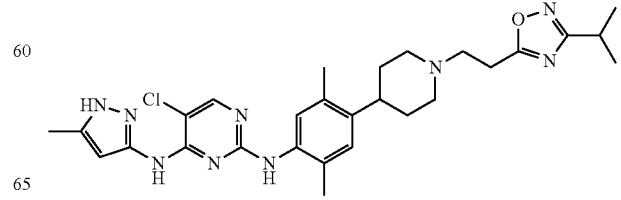

Step 1: A mixture of (E)-N'-hydroxyisobutyrimidamide (510 mg, 5 mmol), 3-chloropropanoic acid (542 mg, 5 mmol) and dicyclohexylcarbodiimide (1.24 g, 6 mmol) in anhydrous dioxane (20 mL) was stirred at 0° C. for 1 h and then at room temperature for an additional 1 h. The reaction was then heated at 80° C. for an additional 18 h. The reaction was filtered and the filtrate was evaporated. The resulting residue was purified by silica chromatography (0-100% EtOAc in hexanes gradient) to give 5-(2-chloroethyl)-3-isopropyl-1,2,4-oxadiazole; $^1$H NMR (400 MHz, CDCl$_3$) δ 3.85 (t, J=7.2 Hz, 2H), 3.27 (t, J=7.2 Hz, 2H), 3.03 (septet, J=7.2 Hz, 1H), 1.13 (d, J=7.2 Hz, 6H); ESMS m/z 175.1 (M+H$^+$).

Step 2: A mixture of 5-chloro-N$_2$-(2,5-dimethyl-4-(piperidin-4-yl)phenyl)-N$_4$-(5-methyl-1H-pyrazol-3-yl)pyrimidine-2,4-diamine (14 mg, 0.033 mmol), 5-(2-chloroethyl)-3-isopropyl-1,2,4-oxadiazole (9 mg, 0.053 mmol) and DIEA (29 uL, 0.17 mmol) in NMP (1 mL) was stirred at 50° C. for 3 days. The crude reaction mixture was purified by RP-HPLC to give 5-Chloro-N2-(4-(1-(2-(3-isopropyl-1,2,4-oxadiazol-5-yl)ethyl)piperidin-4-yl)-2,5-dimethylphenyl)-N4-(5-methyl-1H-pyrazol-3-yl)pyrimidine-2,4-diamine as a white solid; ESMS m/z 550.3 (M+H$^+$).

EXAMPLE 55

5-Chloro-N$_2$-(2-fluoro-5-methyl-4-(1-(6-methylpyridazin-3-yl)piperidin-4-yl)phenyl)-N$_4$-(5-methyl-1H-pyrazol-3-yl)pyrimidine-2,4-diamine (277)

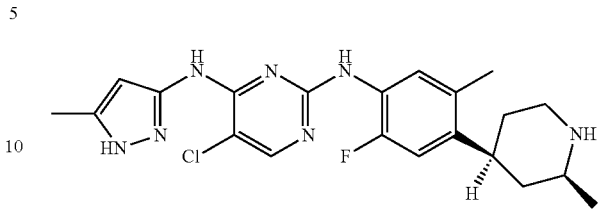

A suspension of 5-chloro-N$^2$-(2-fluoro-5-methyl-4-(piperidin-4-yl)phenyl)-N$^4$-(5-methyl-1H-pyrazol-3-yl)pyrimidine-2,4-diamine (20 mg, 0.05 mmol), 3-chloro-6-methylpyridazine (13 mg, 0.1 mmol) and Cs$_2$CO$_3$ (33 mg, 0.1 mmol) in dioxane (1 mL) was stirred at 150° C. in a sealed vial. After 15 h, additional 3-chloro-6-methylpyridazine (26 mg) and Cs$_2$CO$_3$ (66 mg) were added. The reaction was continued for an additional 3 h. The crude reaction mixture was purified by RP-HPLC to give 5-Chloro-N2-(2-fluoro-5-methyl-4-(1-(6-methylpyridazin-3-yl)piperidin-4-yl)phenyl)-N4-(5-methyl-1H-pyrazol-3-yl)pyrimidine-2,4-diamine as a white solid; ESMS m/z 508.2 (M+H$^+$).

EXAMPLES 56 AND 57

5-chloro-N2-(2-fluoro-5-methyl-4-((trans)-2-methylpiperidin-4-yl)phenyl)-N4-(5-methyl-1H-pyrazol-3-yl)pyrimidine-2,4-diamine (279)

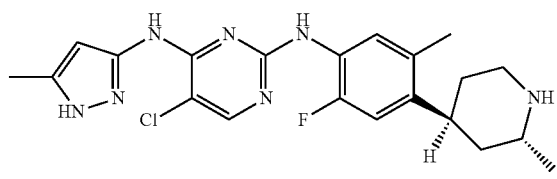

5-chloro-N2-(2-fluoro-5-methyl-4-((cis)-2-methylpiperidin-4-yl)phenyl)-N4-(5-methyl-1H-pyrazol-3-yl)pyrimidine-2,4-diamine (280)

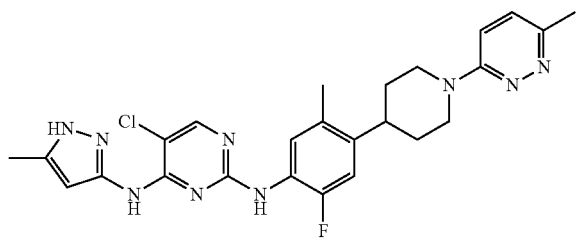

Step 1: A solution of tert-butyl-2-methyl-4-oxopiperidine-1-carboxylate (1 g, 4.69 mmol) in THF (20 mL) was added dropwise into a cooled (−78° C.), vigorously stirring solution of LDA (3.75 mL of 1.5 M solution in cyclohexanes, 5.63 mmol) in THF (20 mL), under N$_2$. The reaction mixture was stirred at −78° C. for 30 min before adding a solution of phenyl trifluorosulfonimide (1.84 g, 5.16 mmol) in THF (20 mL). Following this addition, the reaction mixture was warmed to room temperature and stirred for 3 h. The reaction was cooled to 0° C. and quenched with 100 mL of saturated aqueous NH$_4$Cl, followed by filtration through Celite. The filtrate was added to 100 mL of EtOAc and the layers were separated. The organic layer was washed with water, dried over MgSO$_4$ and concentrated. The crude product was purified by silica chromatography (0-30% EtOAc in hexanes gradient and checked by TLC stained with 2% of KMnO$_4$ in EtOH) to afford tert-butyl 2-methyl-4-(trifluoromethylsulfonyloxy)-5,6-dihydropyridine-1(2H)-carboxylate as a yellow solid.

Step 2: To a mixture of 2-fluoro-5-methyl-4-(4,4,5,5-tetramethyl-1,3,2-dioxaborolan-2-yl)aniline (587 mg, 2.33 mmol), tert-butyl 2-methyl-4-(trifluoromethylsulfonyloxy)-5,6-dihydropyridine-1(2H)-carboxylate (968 mg, 2.80 mmol) and sodium carbonate (1.73 g, 16.35 mmol) in DMF/H$_2$O (20/5 mL) was added tetrakis(triphenylphosphine) palladium (0) (135 mg, 5% mmol). The reaction tube was sealed, the mixture was purged with N$_2$ for 3 min and then heated at 100° C. under N$_2$ for 8 h. The reaction was cooled to room temperature and poured into saturated aqueous ammonia chloride solution. The crude reaction mixture was extracted with ethyl acetate (3×15 mL). The organic extracts were combined, washed with brine and concentrated. The crude product was purified with silica chromatography (50% ethyl acetate in hexanes) to afford tert-butyl 4-(4-amino-5-fluoro-2-methylphenyl)-6-methyl-5,6-dihydropyridine-1(2H)-carboxylate as a yellow oil. The obtained oil was dissolved in methanol (20 mL). To the solution was added Pd/C (10%). The reaction mixture was degassed and purged with H$_2$ for several times and stirred vigorously under 1 atm. H$_2$ overnight. The mixture was filtered and the filtrate concentrated to afford tert-butyl 4-(4-amino-5-fluoro-2-methylphenyl)-2-methylpiperidine-1-carboxylate as a white solid. ESMS m/z 267 (M−56+H$^+$).

Step 3: A mixture of 2,5-dichloro-N-(5-methyl-1H-pyrazol-3-yl)pyrimidin-4-amine (346 mg, 1.42 mmol) and tert-butyl 4-(4-amino-5-fluoro-2-methylphenyl)-2-methylpiperidine-1-carboxylate (352 mg, 1.09 mmol) in 2-propanol (10 mL) was treated with conc. HCl (12N, 0.43 mL). The mixture was sealed and heated in a microwave at 130° C. for 45 min. The mixture was concentrated. The residue was purified by RP-HPLC to afford 5-Chloro-N2-(2-fluoro-5-methyl-4-(2-methylpiperidin-4-yl)phenyl)-N4-(5-methyl-1H-pyrazol-3-yl)pyrimidine-2,4-diamine as a white solid. ESMS m/z 430.1 (M+H$^+$).

Step 4: 5-Chloro-N2-(2-fluoro-5-methyl-4-(2-methylpiperidin-4-yl)phenyl)-N4-(5-methyl-1H-pyrazol-3-yl)pyrimidine-2,4-diamine (20 mg, 0.046 mmol) was dissolved in a solvent mixture of DCM and methanol (0.5 mL, 10/1 v/v+ 0.175N NH$_3$). The mixture was applied to preparative TLC in order to separate the cis and trans stereoisomers (eluent: 6% MeOH in DCM with 0.1N NH$_3$) of 5-Chloro-N2-(2-fluoro-5-methyl-4-(2-methylpiperidin-4-yl)phenyl)-N4-(5-methyl-1H-pyrazol-3-yl)pyrimidine-2,4-diamine as white solids. The trans isomer was the preparative TLC top band and the cis isomer was the preparative TLC bottom band; ESMS m/z 430.1 (M+H$^+$); cis stereoisomer $^1$H NMR (400 MHz, MeOD-d4): δ 8.03 (s, 1H), 7.84 (d, 1H), 7.02 (d, 1H), 6.24 (d, 1H), 3.90-3.85 (m, 1H), 2.32 (s, 3H), 2.27 (s, 3H), 2.03-1.84 (m, 2H), 1.65-1.54 (m, 1H), 1.55 (d, 3H), 1.38-1.19 (m, 4H).

EXAMPLE 58

3-(4-(4-(5-Chloro-4-(5-methyl-1H-pyrazol-3-ylamino)pyrimidin-2-ylamino)-5-fluoro-2-methylphenyl)piperidin-1-yl)cyclopent-2-en-one (282)

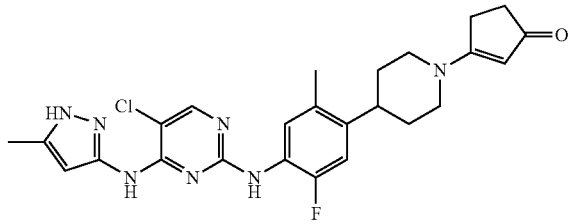 [SMILES: Cc1cc(Nc2nc(Nc3cc(C)c(C4CCN(C5=CC(=O)CC5)CC4)cc3F)ncc2Cl)n[nH]1]

A mixture of 5-chloro-N$^2$-(2-fluoro-5-methyl-4-(piperidin-4-yl)phenyl)-N$^4$-(5-methyl-1H-pyrazol-3-yl)pyrimidine-2,4-diamine (43 mg, 0.1 mmol), cyclopentane-1,3-dione (89 mg, 9.1 mmol), sodium cyanoborohydride (19 mg, 0.3 mmol) and DIEA (0.2 mL, 11 mmol) in MeOH (1 mL) was stirred in a sealed vial at 60° C. After 2.5 h, additional sodium cyanoborohydride (19 mg, 0.3 mmol) was added and the reaction continued to stir at 60° C. overnight. The mixture was purified by RP-HPLC to give 3-(4-(4-(5-Chloro-4-(5-methyl-1H-pyrazol-3-ylamino)pyrimidin-2-ylamino)-5-fluoro-2-methylphenyl)piperidin-1-yl)cyclopent-2-en-one as an off white solid; $^1$H NMR (400 MHz, DMSO-d$_6$) δ 9.97 (br s, 1H), 9.83 (br s, 1H), 8.90 (s, 1H), 8.32 (d, J=6.8 Hz, 1H), 7.88 (d, J=12.8 Hz, 1H), 6.97 (s, 1H), 6.04 (s, 1H), 5.30 (br s, 1H), 4.71 (d, J=12.0 Hz, 2H), 4.04 (t, J=12.4 Hz, 2H), 3.84 (m, 1H), 3.53 (m, 2H), 3.13 (m, 2H), 3.08 (s, 3H), 2.96 (s, 3H), 2.59-2.40 (m, 4H); ESMS m/z 496.2 (M+H$^+$).

EXAMPLE 59

4-(4-(5-chloro-4-(5-methyl-1H-pyrazol-3-ylamino)pyrimidin-2-ylamino)-5-fluoro-2-methylphenyl)-1-ethylpiperidine-1-oxide (289)

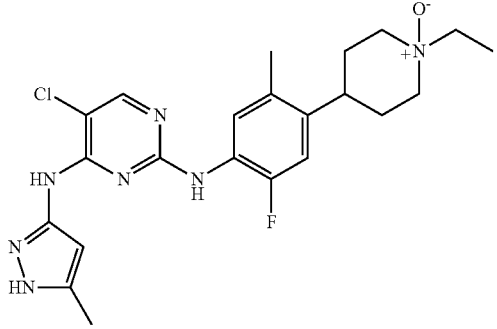

To a solution of 5-chloro-N$^2$-(4-(1-ethylpiperidin-4-yl)-2-fluoro-5-methylphenyl)-N$^4$-(5-methyl-1H-pyrazol-3-yl)pyrimidine-2,4-diamine (22.2 mg, 0.05 mmol) in DCM (10 mL) and MeOH (1 mL) was added MCPBA (11.2 mg, 0.07 mmol). The reaction was stirred at room temperature overnight. The reaction mixture was partitioned between DCM and saturated aqueous NaHCO$_3$, the combined organic extracts were dried (Na$_2$SO$_4$), and concentrated in vacuo. The crude product was purified by RP-HPLC to afford 4-(4-(5-chloro-4-(5-methyl-1H-pyrazol-3-ylamino)pyrimidin-2-ylamino)-5-fluoro-2-methylphenyl)-1-ethylpiperidine-1-oxide;

$^1$HNMR (MeOD-d$_4$) δ7.91 (s, 1H), 7.69 (d, 1H), 7.00 (d, 1H), 6.15 (s, 1H), 3.28 (m, 4H), 2.91 (m, 1H), 2.32 (m, 2H), 2.20 (s, 3H), 2.16 (s, 3H), 1.83 (s, 2H), 1.64 (d, 2H), 1.31 (t, 3H); ESMS m/z 460.2 (M+H$^+$).

EXAMPLE 60

5-Chloro-N$^2$-(2-fluoro-5-methyl-4-(1-(pyrimidin-5-ylmethyl)piperidin-4-yl)phenyl)-N$^4$-(5-methyl-1H-pyrazol-3-yl)pyrimidine-2,4-diamine (314)

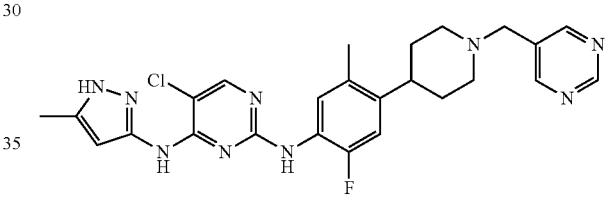

To a solution of 5-chloro-N$^2$-(2-fluoro-5-methyl-4-(piperidin-4-yl)phenyl)-N$^4$-(5-methyl-1H-pyrazol-3-yl)pyrimidine-2,4-diamine (45 mg, 0.1 mmol) and pyrimidine-5-carbaldehyde (32 mg, 0.3 mmol) in DCM (1.5 mL) was added NaBH(OAc)$_3$ (64 mg, 0.3 mmol), followed by addition of AcOH (12 uL). After stirring at room temperature in a sealed vial for 16 h, the reaction was quenched with EtOAc (50 mL). The reaction mixture was sequentially washed with water (10 mL), brine (5 mL), dried over Na$_2$SO$_4$ and concentrated in vacuo. The resulting residue was purified by silica chromatography (0-10% MeOH in EtOAc gradient with 1% NH$_3$ in MeOH additive) to give 5-Chloro-N2-(2-fluoro-5-methyl-4-(1-(pyrimidin-5-ylmethyl)piperidin-4-yl)phenyl)-N4-(5-methyl-1H-pyrazol-3-yl)pyrimidine-2,4-diamine as an off white solid; $^1$H NMR (400 MHz, CD$_3$OD) δ 9.09 (s, 1H), 8.81 (s, 2H), 8.00 (s, 1H), 7.73 (d, J=8.4 Hz, 1H), 6.99 (d, J=13.2 Hz, 1H), 6.23 (br s, 1H), 3.65 (s, 2H), 3.03 (m, 2H), 2.76 (m, 1H), 2.27 (s, 3H), 2.25 (s, 3H), 2.25 (m, 2H), 1.80-1.68 (m, 4H); ESMS m/z 508.2 (M+H$^+$).

The following compounds in Table 1 are obtained by repeating the procedures described in examples above and using appropriate starting materials.

TABLE 1

| | STRUCTURE | NMR or ESMS | IGF-1R Ba/F3 IC50 (uM) |
|---|---|---|---|
| 1 | 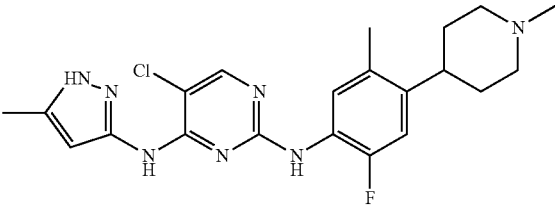<br>5-chloro-N2-(2-fluoro-5-methyl-4-(1-methylpiperidin-4-yl)phenyl)-N4-(5-methyl-1H-pyrazol-3-yl)pyrimidine-2,4-diamine | $^1$H NMR (400 MHz, DMSO-d6) δ 10.33 (br, 1H), 9.90 (br, 1H0, 9.60 (br, 1H), 8.22 (s, 1H), 7.56 (d, 1H), 7.00 (d, 1H), 6.20 (s, 1H), 3.53-3.50 (m, 2H), 3.16-3.10 (m, 2H), 2.97-2.92 (m, 1H), 2.81 (d, 3H), 2.26 (s, 3H), 2.16 (s, 3H), 1.94-1.91 (m, 2H), 1.83-1.73 (m, 2H); ESMS m/z 430.1 (M + H$^+$). | 0.011 |
| 2 | 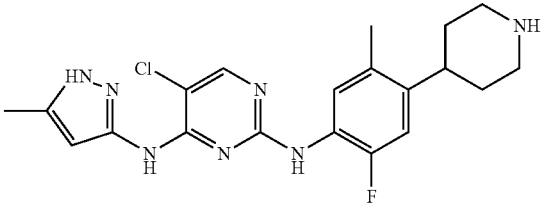 [SMILES: Cc1cc(Nc2nc(Nc3cc(C)c(C4CCNCC4)cc3F)ncc2Cl)n[nH]1]<br>5-chloro-N2-(2-fluoro-5-methyl-4-(piperidin-4-yl)phenyl)-N4-(5-methyl-1H-pyrazol-3-yl)pyrimidine-2,4-diamine | ESMS m/z 416.1 (M + H$^+$). | 0.050 |
| 3 | 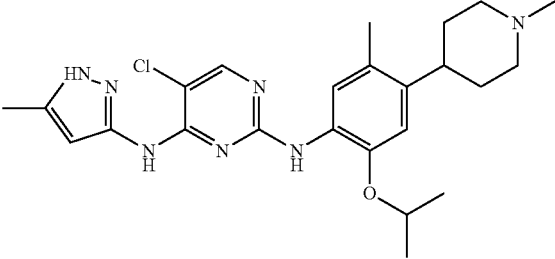<br>5-chloro-N2-(2-isopropoxy-5-methyl-4-(1-methylpiperidin-4-yl)phenyl)-N4-(5-methyl-1H-pyrazol-3-yl)pyrimidine-2,4-diamine | ESMS m/z 470.2 (M + H$^+$). | 0.104 |
| 4 | 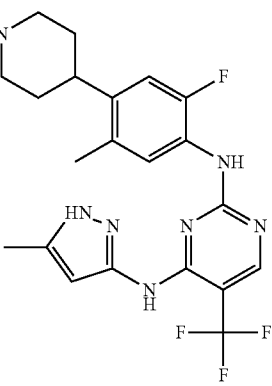<br>N2-(2-fluoro-5-methyl-4-(piperidin-4-yl)phenyl)-N4-(5-methyl-1H-pyrazol-3-yl)-5-(trifluoromethyl)pyrimidine-2,4-diamine | ESMS m/z 450.2 (M + H$^+$). | 0.150 |

TABLE 1-continued

| | STRUCTURE | NMR or ESMS | IGF-1R Ba/F3 IC50 (uM) |
|---|---|---|---|
| 5 | N2-(2-isopropoxy-5-methyl-4-(1-methylpiperidin-4-yl)phenyl)-5-methyl-N4-(5-methyl-1H-pyrazol-3-yl)pyrimidine-2,4-diamine | ESMS m/z 450.3 (M + H+). | 0.805 |
| 6 | 5-chloro-N2-(2,5-dimethyl-4-(1-methylpiperidin-4-yl)phenyl)-N4-(5-methyl-1H-pyrazol-3-yl)pyrimidine-2,4-diamine | ESMS m/z 426.2 (M + H+). | 0.015 |
| 7 | 5-chloro-N2-(5-chloro-2-methyl-4-(1-methylpiperidin-4-yl)phenyl)-N4-(5-methyl-1H-pyrazol-3-yl)pyrimidine-2,4-diamine | ESMS m/z 446.1 (M + H+). | 0.015 |
| 8 | 5-chloro-N2-(4-fluoro-2-methyl-5-(piperidin-4-yl)phenyl)-N4-(5-methyl-1H-pyrazol-3-yl)pyrimidine-2,4-diamine | ESMS m/z 461.2 (M + H+). | 1.93 |
| 9 | 3-(5-chloro-2-(2-fluoro-5-methyl-4-(1-methylpiperidin-4-yl)phenylamino)pyrimidin-4-ylamino)azepan-2-one | ESMS m/z 461.2 (M + H+). | 0.087 |

TABLE 1-continued

| | STRUCTURE | NMR or ESMS | IGF-1R Ba/F3 IC50 (uM) |
|---|---|---|---|
| 10 | (S)-3-(5-chloro-2-(2-fluoro-5-methyl-4-(1-methylpiperidin-4-yl)phenylamino)pyrimidin-4-ylamino)azepan-2-one | ESMS m/z 461.2 (M + H⁺). | 0.869 |
| 11 | (R)-3-(5-chloro-2-(2-fluoro-5-methyl-4-(1-methylpiperidin-4-yl)phenylamino)pyrimidin-4-ylamino)azepan-2-one | ESMS m/z 461.2 (M + H⁺). | 0.065 |
| 12 | 5-chloro-N2-(4-(1-isopropylpiperidin-4-yl)-2,5-dimethylphenyl)-N4-(5-methyl-1H-pyrazol-3-yl)pyrimidine-2,4-diamine | ESMS m/z 454.2 (M + H⁺). | 0.010 |
| 13 | 5-chloro-N2-(4-fluoro-5-(1-isopropylpiperidin-4-yl)-2-methylphenyl)-N4-(5-methyl-1H-pyrazol-3-yl)pyrimidine-2,4-diamine | ESMS m/z 458.2 (M + H⁺). | |

TABLE 1-continued

| | STRUCTURE | NMR or ESMS | IGF-1R Ba/F3 IC50 (uM) |
|---|---|---|---|
| 14 | 5-chloro-N2-(2,5-dimethyl-4-(piperidin-2-yl)phenyl)-N4-(5-methyl-1H-pyrazol-3-yl)pyrimidine-2,4-diamine | ESMS m/z 412.2 (M + H+). | 0.016 |
| 15 | 5-chloro-N2-(2,5-dimethyl-4-(piperidin-3-yl)phenyl)-N4-(5-methyl-1H-pyrazol-3-yl)pyrimidine-2,4-diamine | ESMS m/z 412.2 (M + H$^+$). | 0.050 |
| 16 | 5-chloro-N2-(2,5-dimethyl-4-(1-methylpiperidin-2-yl)phenyl)-N4-(5-methyl-1H-pyrazol-3-yl)pyrimidine-2,4-diamine | ESMS m/z 426.2 (M + H$^+$). | 0.019 |
| 17 | 5-chloro-N4-(5-cyclopropyl-1H-pyrazol-3-yl)-N2-(2-fluoro-5-methyl-4-(piperidin-4-yl)phenyl)pyrimidine-2,4-diamine | ESMS m/z 442.2 (M + H$^+$). | 0.160 |

TABLE 1-continued

| | STRUCTURE | NMR or ESMS | IGF-1R Ba/F3 IC50 (uM) |
|---|---|---|---|
| 18 | 5-chloro-N4-(5-cyclopropyl-1H-pyrazol-3-yl)-N2-(2,5-dimethyl-4-(piperidin-4-yl)phenyl)pyrimidine-2,4-diamine | ESMS m/z 438.2 (M + H+). | 0.095 |
| 19 | 5-Chloro-N2-(4-(1-((3,5-dimethylisoxazol-4-yl)methyl)piperidin-4-yl)-2-fluoro-5-methylphenyl)-N4-(5-methyl-1H-pyrazol-3-yl)pyrimidine-2,4-diamine | 1H NMR (400 MHz, MeOD-d4) 8.12 (s, 1H), 7.75 (d, 1H), 7.03 (s, 1H), 6.27 (s, 1H), 4.25 (s, 2H), 3.69-3.67 (m, 2H), 3.27-3.20 (m, 3H), 2.54 (s, 3H), 2.37 (s, 3H), 2.34 (s, 3H), 2.30 (s, 3H), 2.10-1.95 (m, 4H); ESMS m/z 525.1 (M + H+). | 0.056 |
| 20 | 5-chloro-N2-(4-(1-((3,5-dimethylisoxazol-4-yl)methyl)piperidin-4-yl)-2,5-dimethylphenyl)-N4-(5-methyl-1H-pyrazol-3-yl)pyrimidine-2,4-diamine | ESMS m/z 521.2 (M + H+). | 0.011 |
| 21 | 5-chloro-N2-(2,5-dimethyl-4-(1-(pyridazin-4-ylmethyl)piperidin-4-yl)phenyl)-N4-(5-methyl-1H-pyrazol-3-yl)pyrimidine-2,4-diamine | ESMS m/z 504.2 (M + H+) | 0.002 |

TABLE 1-continued

| | STRUCTURE | NMR or ESMS | IGF-1R Ba/F3 IC50 (uM) |
|---|---|---|---|
| 22 | 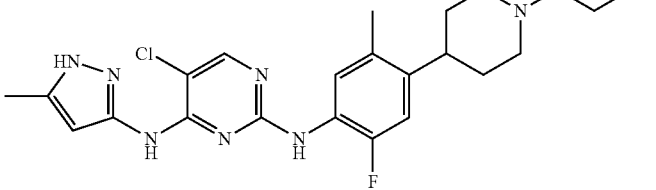<br>2-(4-(4-(5-chloro-4-(5-methyl-1H-pyrazol-3-ylamino)pyrimidin-2-ylamino)-5-fluoro-2-methylphenyl)piperidin-1-yl)ethanol | ESMS m/z 460.2 (M + H+). | 0.059 |
| 23 | 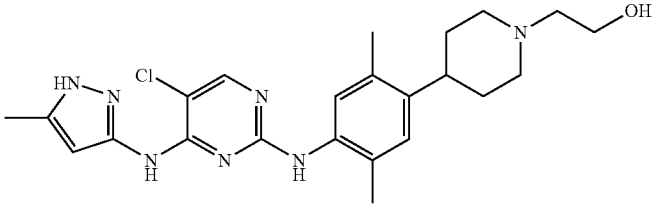 [SMILES: Cc1cc(Nc2nc(Nc3cc(C)c(C4CCN(CCO)CC4)cc3C)ncc2Cl)n[nH]1]<br>2-(4-(4-(5-chloro-4-(5-methyl-1H-pyrazol-3-ylamino)pyrimidin-2-ylamino)-2,5-dimethylphenyl)piperidin-1-yl)ethanol | ESMS m/z 456.21 (M + H$^+$). | 0.006 |
| 24 | 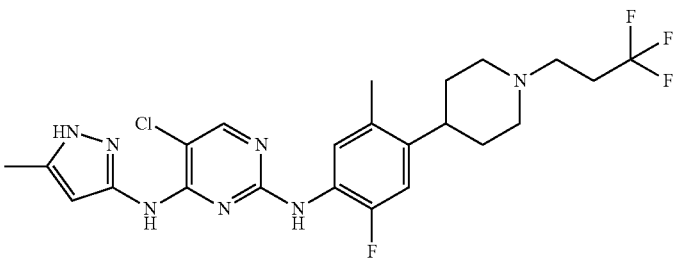 [SMILES: Cc1cc(Nc2nc(Nc3cc(C)c(C4CCN(CCC(F)(F)F)CC4)cc3F)ncc2Cl)n[nH]1]<br>5-chloro-N$^2$-(2-fluoro-5-methyl-4-(1-(3,3,3-trifluoropropyl)piperidin-4-yl)phenyl)-N$^4$-(5-methyl-1H-pyrazol-3-yl)pyrimidine-2,4-diamine | ESMS m/z 512.2 (M + H$^+$). | 0.085 |
| 25 | 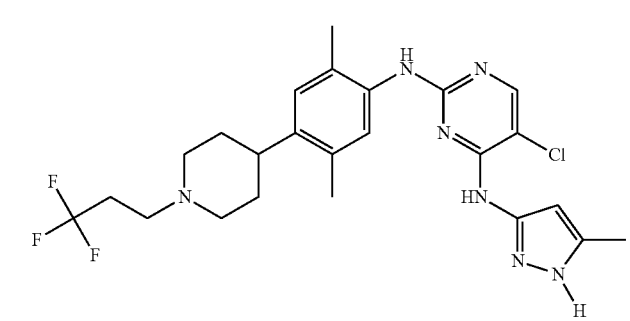 [SMILES: Cc1cc(Nc2nc(Nc3cc(C)c(C4CCN(CCC(F)(F)F)CC4)cc3C)ncc2Cl)n[nH]1]<br>5-chloro-N2-(2,5-dimethyl-4-(1-(3,3,3-trifluoropropyl)piperidin-4-yl)phenyl)-N4-(5-methyl-1H-pyrazol-3-yl)pyrimidine-2,4-diamine | ESMS m/z 508.2 (M + H+). | 0.031 |

TABLE 1-continued

| | STRUCTURE | NMR or ESMS | IGF-1R Ba/F3 IC50 (uM) |
|---|---|---|---|
| 26 | 5-chloro-N2-(2-fluoro-5-methyl-4-(1-(2,2,2-trifluoroethyl)piperidin-4-yl)phenyl)-N4-(5-methyl-1H-pyrazol-3-yl)pyrimidine-2,4-diamine | ESMS m/z 498.2 (M + H$^+$). | 0.142 |
| 27 | 5-chloro-N2-(5-chloro-2-methyl-4-(1-(3,3,3-trifluoropropyl)piperidin-4-yl)phenyl)-N4-(5-methyl-1H-pyrazol-3-yl)pyrimidine-2,4-diamine | ESMS m/z 528.2 (M + H$^+$). | 0.044 |
| 28 | 5-chloro-N2-(4-fluoro-2-methyl-5-(1-(3,3,3-trifluoropropyl)piperidin-4-yl)phenyl)-N4-(5-methyl-1H-pyrazol-3-yl)pyrimidine-2,4-diamine | ESMS m/z 512.2 (M + H$^+$). | 5.46 |
| 29 | 3-(4-(4-(5-chloro-4-(5-methyl-1H-pyrazol-3-ylamino)pyrimidin-2-ylamino)-2,5-dimethylphenyl) piperidin-1-yl)-1,1,1-trifluoropropan-2-ol | ESMS m/z 524.2 (M + H$^+$). | 0.023 |

TABLE 1-continued

| | STRUCTURE | NMR or ESMS | IGF-1R Ba/F3 IC50 (uM) |
|---|---|---|---|
| 30 | 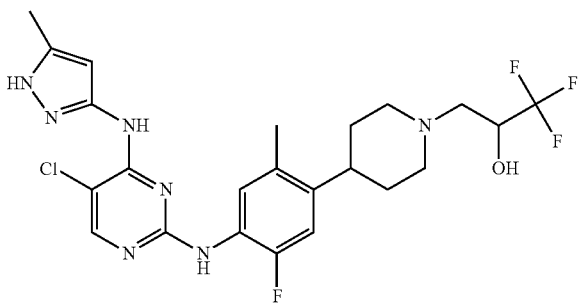 [SMILES: Cc1cc(Nc2nc(Nc3cc(C)c(C4CCN(CC(O)C(F)(F)F)CC4)cc3F)ncc2Cl)n[nH]1] 3-(4-(4-(5-chloro-4-(5-methyl-1H-pyrazol-3-ylamino) pyrimidin-2-ylamino)-5-fluoro-2-methylphenyl) piperidin-1-yl)-1,1,1-trifluoropropan-2-ol | ESMS m/z 528.2 (M + H$^+$). | 0.071 |
| 31 | 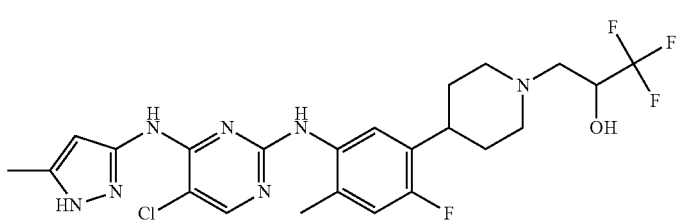 [SMILES: Cc1cc(Nc2nc(Nc3cc(C4CCN(CC(O)C(F)(F)F)CC4)c(F)cc3C)ncc2Cl)n[nH]1] 3-(4-(5-(5-chloro-4-(5-methyl-1H-pyrazol-3-ylamino)pyrimidin-2-ylamino)-2-fluoro-4-methylphenyl)piperidin-1-yl)-1,1,1-trifluoropropan-2-ol | ESMS m/z 528.2 (M + H+). | 6.47 |
| 32 | 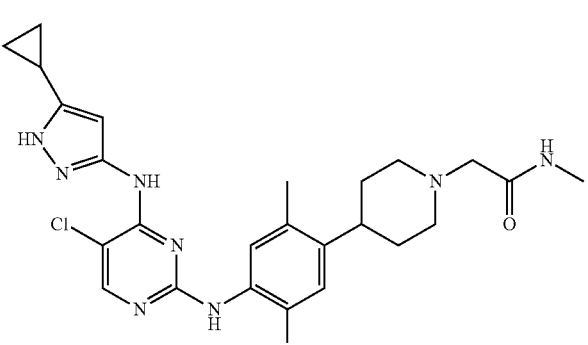 2-(4-(4-(5-chloro-4-(5-cyclopropyl-1H-pyrazol-3-ylamino)pyrimidin-2-ylamino)-5-fluoro-2-methylphenyl)piperidin-1-yl)-N-methylacetamide | ESMS m/z 513.2 (M + H$^+$). | 0.042 |

TABLE 1-continued

| | STRUCTURE | NMR or ESMS | IGF-1R Ba/F3 IC50 (uM) |
|---|---|---|---|
| 33 | 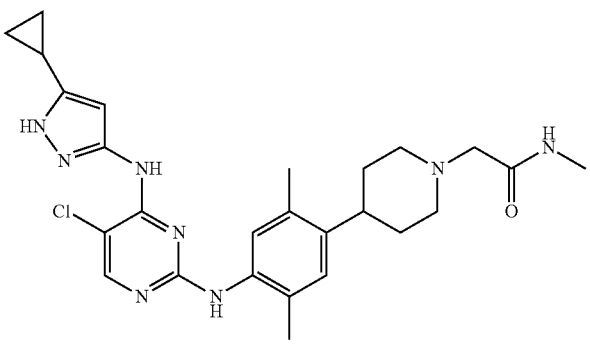 [SMILES: CNC(=O)CN1CCC(c2cc(C)c(Nc3ncc(Cl)c(Nc4cc(C5CC5)[nH]n4)n3)cc2C)CC1]<br>2-(4-(4-(5-chloro-4-(5-cyclopropyl-1H-pyrazol-3-ylamino)pyrimidin-2-ylamino)-2,5-dimethylphenyl)piperidin-1-yl)-N-methylacetamide | ESMS m/z 509.2 (M + H⁺). | 0.006 |
| 34 | 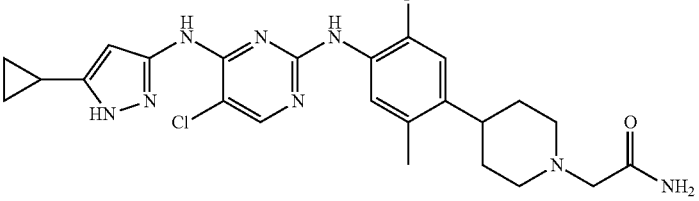<br>2-(4-(4-(5-chloro-4-(5-cyclopropyl-1H-pyrazol-3-ylamino)pyrimidin-2-ylamino)-5-fluoro-2-methylphenyl)piperidin-1-yl)acetamide | ESMS m/z 499.2 (M + H⁺). | 0.049 |
| 35 | 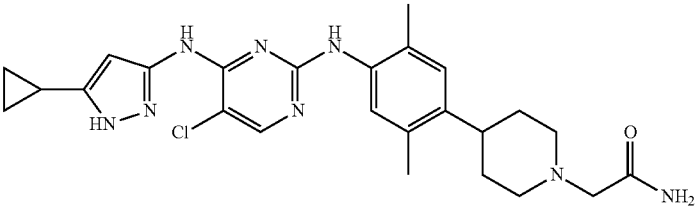 [SMILES: Cc1cc(C2CCN(CC(N)=O)CC2)c(C)cc1Nc1ncc(Cl)c(Nc2cc(C3CC3)[nH]n2)n1]<br>2-(4-(4-(5-chloro-4-(5-cyclopropyl-1H-pyrazol-3-ylamino)pyrimidin-2-ylamino)-2,5-dimethylphenyl)piperidin-1-yl)acetamide | ESMS m/z 495.2 (M + H⁺). | 0.011 |
| 36 | 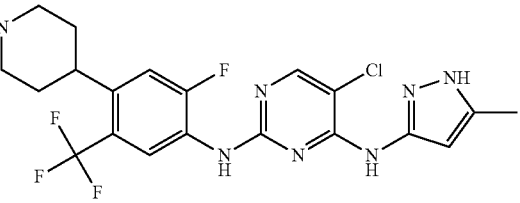<br>2-(4-(4-(5-chloro-4-(5-methyl-1H-pyrazol-3-ylamino)pyrimidin-2-ylamino)-5-fluoro-2-(trifluoromethyl)phenyl)piperidin-1-yl)acetamide | ESMS m/z 527.2 (M + H⁺). | 0.019 |

TABLE 1-continued

| | STRUCTURE | NMR or ESMS | IGF-1R Ba/F3 IC50 (uM) |
|---|---|---|---|
| 37 | 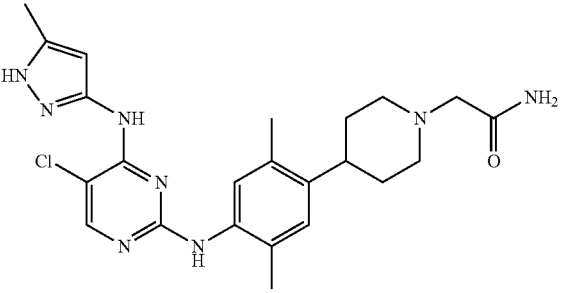 [SMILES: Cc1cc(Nc2nc(Nc3cc(C)c(C4CCN(CC(N)=O)CC4)cc3C)ncc2Cl)n[nH]1] 2-(4-(4-(5-chloro-4-(5-methyl-1H-pyrazol-3-ylamino)pyrimidin-2-ylamino)-2,5-dimethylphenyl)piperidin-1-yl)acetamide | ESMS m/z 469.2 (M + H$^+$). | 0.013 |
| 38 | 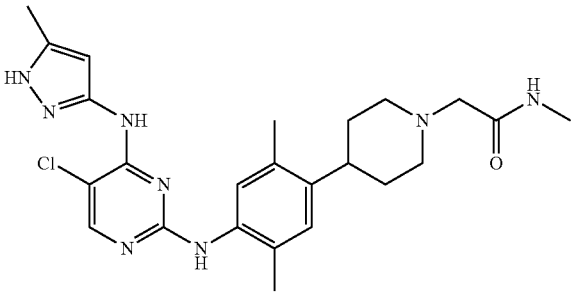 [SMILES: CNC(=O)CN1CCC(c2cc(C)c(Nc3ncc(Cl)c(Nc4cc(C)[nH]n4)n3)cc2C)CC1] 2-(4-(4-(5-chloro-4-(5-methyl-1H-pyrazol-3-ylamino)pyrimidin-2-ylamino)-2,5-dimethylphenyl)piperidin-1-yl)-N-methylacetamide | ESMS m/z 483.2 (M + H$^+$). | 0.010 |
| 39 | 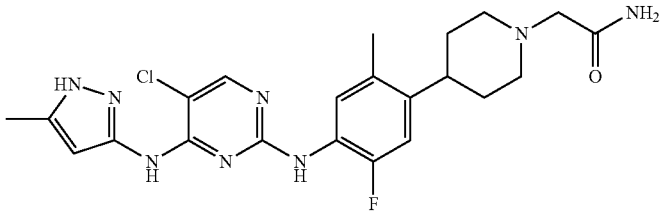 [SMILES: Cc1cc(Nc2nc(Nc3cc(C)c(C4CCN(CC(N)=O)CC4)cc3F)ncc2Cl)n[nH]1] 2-(4-(4-(5-Chloro-4-(5-methyl-1H-pyrazol-3-ylamino)pyrimidin-2-ylamino)-5-fluoro-2-methylphenyl)piperidin-1-yl)acetamide | $^1$H NMR (400 MHz, MeOD-d$_4$) δ 8.11 (s, 1H), 7.76 (d 1H), 7.09 (d, 1H), 6.27 (s, 1H), 4.0 (s, 2H), 3.75-3.73 (m, 2H), 3.22-3.13 (m, 3H), 2.34 (s, 3H), 2.30 (s, 3H), 2.04-2.00 (m, 4H); ESMS m/z 473.2 (M + H$^+$). | 0.019 |
| 40 | 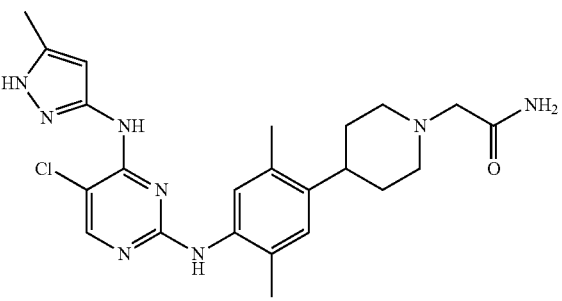 [SMILES: Cc1cc(Nc2nc(Nc3cc(C)c(C4CCN(CC(N)=O)CC4)cc3C)ncc2Cl)n[nH]1] 2-(4-(4-(5-chloro-4-(5-methyl-1H-pyrazol-3-ylamino)pyrimidin-2-ylamino)-2,5-dimethylphenyl)piperidin-1-yl)acetamide | ESMS m/z 469.2 (M + H$^+$). | |

TABLE 1-continued

| | STRUCTURE | NMR or ESMS | IGF-1R Ba/F3 IC50 (uM) |
|---|---|---|---|
| 41 | 2-(3-(4-(5-chloro-4-(5-methyl-1H-pyrazol-3-ylamino)pyrimidin-2-ylamino)-2,5-dimethylphenyl)piperidin-1-yl)acetamide | ESMS m/z 469.2 (M + H$^+$). | 0.026 |
| 42 | 2-(4-(4-(5-chloro-4-(5-methyl-1H-pyrazol-3-ylamino)pyrimidin-2-ylamino)-5-fluoro-2-methylphenyl)piperidin-1-yl)-N-methylacetamide | ESMS m/z 487.2 (M + H$^+$). | 0.019 |
| 43 | 2-(4-(4-(5-chloro-4-(5-methyl-1H-pyrazol-3-ylamino)pyrimidin-2-ylamino)-2,5-dimethylphenyl)piperidin-1-yl)-N-methylacetamide | ESMS m/z 483.2 (M + H$^+$). | |

TABLE 1-continued

| | STRUCTURE | NMR or ESMS | IGF-1R Ba/F3 IC50 (uM) |
|---|---|---|---|
| 44 | 2-(3-(4-(5-chloro-4-(5-methyl-1H-pyrazol-3-ylamino)pyrimidin-2-ylamino)-2,5-dimethylphenyl)piperidin-1-yl)-N-methylacetamide | ESMS m/z 483.2 (M + H+). | 0.015 |
| 45 | 2-(4-(2-chloro-4-(5-chloro-4-(5-methyl-1H-pyrazol-3-ylamino)pyrimidin-2-ylamino)-5-methylphenyl)piperidin-1-yl)-N-methylacetamide | ESMS m/z 503.2 (M + H+). | 0.018 |
| 46 | 2-(4-(4-(5-chloro-4-(5-methyl-1H-pyrazol-3-ylamino)pyrimidin-2-ylamino)-2-methoxy-5-methylphenyl)piperidin-1-yl)-N-methylacetamide | ESMS m/z 499.2 (M + H+). | 0.013 |
| 47 | 2-(4-(4-(5-chloro-4-(5-methyl-1H-pyrazol-3-ylamino)pyrimidin-2-ylamino)-5-methyl-2-(trifluoromethyl)phenyl)piperidin-1-yl)acetamide | ESMS m/z 523.2 (M + H+). | 0.022 |

TABLE 1-continued

| | STRUCTURE | NMR or ESMS | IGF-1R Ba/F3 IC50 (uM) |
|---|---|---|---|
| 48 | 2-(4-(5-(5-chloro-4-(5-methyl-1H-pyrazol-3-ylamino)pyrimidin-2-ylamino)-2-fluoro-4-methylphenyl)piperidin-1-yl)propanamide | ESMS m/z 487.2 (M + H+). | 3.68 |
| 49 | 2-(4-(4-(5-chloro-4-(5-methyl-1H-pyrazol-3-ylamino)pyrimidin-2-ylamino)-5-fluoro-2-methylphenyl)piperidin-1-yl)propanamide | ESMS m/z 487.2 (M + H+). | 0.015 |
| 50 | 2-(4-(4-(5-chloro-4-(5-methyl-1H-pyrazol-3-ylamino)pyrimidin-2-ylamino)-5-fluoro-2-methylphenyl)piperidin-1-yl)-N-methylpropanamide | ESMS m/z 501.2 (M + H+). | 0.022 |
| 51 | 2-(4-(4-(5-chloro-4-(5-methyl-1H-pyrazol-3-ylamino)pyrimidin-2-ylamino)-2,5-dimethylphenyl)piperidin-1-yl)propanamide | ESMS m/z 483.2 (M + H+). | 0.009 |

TABLE 1-continued

| | STRUCTURE | NMR or ESMS | IGF-1R Ba/F3 IC50 (uM) |
|---|---|---|---|
| 52 | 2-(4-(4-(5-chloro-4-(5-methyl-1H-pyrazol-3-ylamino)pyrimidin-2-ylamino)-2,5-dimethylphenyl)piperidin-1-yl)-N-methylpropanamide | ESMS m/z 497.2 (M + H+). | 0.006 |
| 53 | 2-(4-(5-fluoro-2-methyl-4-(4-(5-methyl-1H-pyrazol-3-ylamino)-5-(trifluoromethyl)pyrimidin-2-ylamino)phenyl)piperidin-1-yl)propanamide | ESMS m/z 521.2 (M + H+). | 0.078 |
| 54 | 2-(4-(4-(5-chloro-4-(5-methyl-1H-pyrazol-3-ylamino)pyrimidin-2-ylamino)-5-fluoro-2-methylphenyl)piperidin-1-yl)propanoic acid | ESMS m/z 488.2 (M + H+). | 1.53 |
| 55 | 5-Chloro-N2-(2-fluoro-5-methyl-4-(1-(2-(methylsulfonyl)ethyl)piperidin-4-yl)phenyl)-N4-(5-methyl-1H-pyrazol-3-yl)pyrimidine-2,4-diamine | ESMS m/z 522.1 (M + H+). | 0.024 |

TABLE 1-continued

| | STRUCTURE | NMR or ESMS | IGF-1R Ba/F3 IC50 (uM) |
|---|---|---|---|
| 56 | 5-chloro-N2-(2,5-dimethyl-4-(1-(2-(methylsulfonyl)ethyl)piperidin-4-yl)phenyl)-N4-(5-methyl-1H-pyrazol-3-yl)pyrimidine-2,4-diamine | ESMS m/z 518.2 (M + H$^+$). | 0.006 |
| 57 | 5-chloro-N2-(4-(1-(2-(ethylsulfonyl)ethyl)piperidin-4-yl)-2-fluoro-5-methylphenyl)-N4-(5-methyl-1H-pyrazol-3-yl)pyrimidine-2,4-diamine | ESMS m/z 536.2 (M + H$^+$). | 0.021 |
| 58 | 2-(4-(4-(5-chloro-4-(5-methyl-1H-pyrazol-3-ylamino)pyrimidin-2-ylamino)-5-fluoro-2-methylphenyl)piperidin-1-yl)-N,N-dimethylethanesulfonamide | ESMS m/z 551.2 (M + H$^+$). | 0.036 |

TABLE 1-continued

| | STRUCTURE | NMR or ESMS | IGF-1R Ba/F3 IC50 (uM) |
|---|---|---|---|
| 59 | 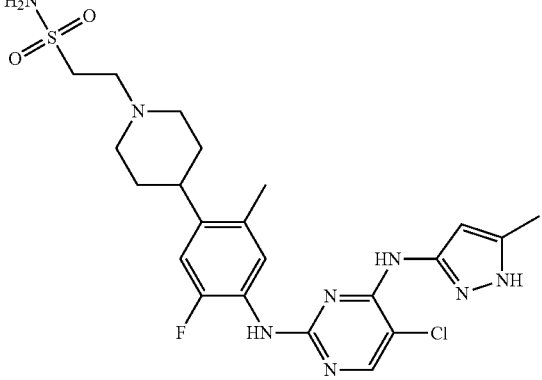<br>2-(4-(4-(5-chloro-4-(5-methyl-1H-pyrazol-3-ylamino)pyrimidin-2-ylamino)-5-fluoro-2-methylphenyl)piperidin-1-yl)ethanesulfonamide | ESMS m/z 523.2 (M + H$^+$). | 0.038 |
| 60 | 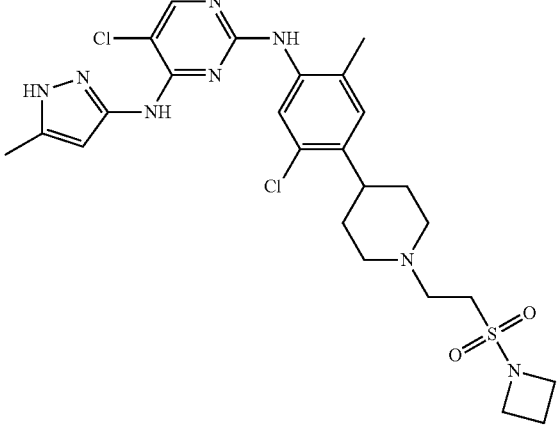<br>N2-(4-(1-(2-(azetidin-1-ylsulfonyl)ethyl)piperidin-4-yl)-5-chloro-2-methylphenyl)-5-chloro-N4-(5-methyl-1H-pyrazol-3-yl)pyrimidine-2,4-diamine | ESMS m/z 579.2 (M + H$^+$). | 0.011 |
| 61 | 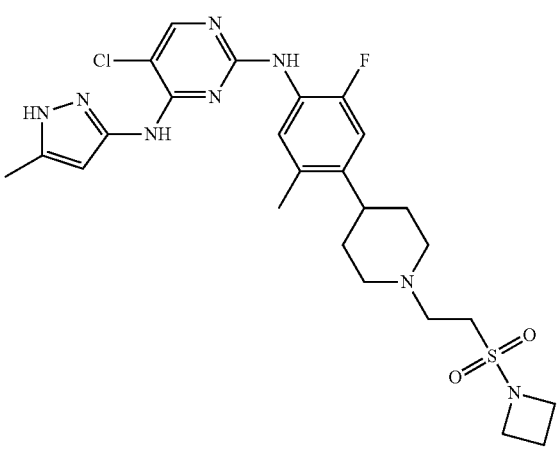 [SMILES: Cc1cc(Nc2nc(Nc3cc(C)c(C4CCN(CCS(=O)(=O)N5CCC5)CC4)cc3F)ncc2Cl)n[nH]1]<br>N2-(4-(1-(2-(azetidin-1-ylsulfonyl)ethyl)piperidin-4-yl)-2-fluoro-5-methylphenyl)-5-chloro-N4-(5-methyl-1H-pyrazol-3-yl)pyrimidine-2,4-diamine | ESMS m/z 563.2 (M + H$^+$). | 0.056 |

TABLE 1-continued

| | STRUCTURE | NMR or ESMS | IGF-1R Ba/F3 IC50 (uM) |
|---|---|---|---|
| 62 | 5-Chloro-N2-(2-fluoro-5-methyl-4-(1-(methylsulfonyl)piperidin-4-yl)phenyl)-N4-(5-methyl-1H-pyrazol-3-yl)pyrimidine-2,4-diamine | ESMS m/z 494.2 (M + H$^+$). | 0.005 |
| 63 | 5-chloro-N2-(2,5-dimethyl-4-(1-(methylsulfonyl)piperidin-4-yl)phenyl)-N4-(5-methyl-1H-pyrazol-3-yl)pyrimidine-2,4-diamine | ESMS m/z 490.2 (M + H$^+$). | 0.002 |
| 64 | 5-chloro-N2-(4-(1-(cyclopropylsulfonyl)piperidin-4-yl)-2-fluoro-5-methylphenyl)-N4-(5-methyl-1H-pyrazol-3-yl)pyrimidine-2,4-diamine | ESMS m/z 520.2 (M + H$^+$). | 0.059 |
| 65 | 5-chloro-N2-(2-fluoro-5-methyl-4-(1-(pyridin-3-ylsulfonyl)piperidin-4-yl)phenyl)-N4-(5-methyl-1H-pyrazol-3-yl)pyrimidine-2,4-diamine | ESMS m/z 557.2 (M + H$^+$). | 0.076 |

TABLE 1-continued

| | STRUCTURE | NMR or ESMS | IGF-1R Ba/F3 IC50 (uM) |
|---|---|---|---|
| 66 | 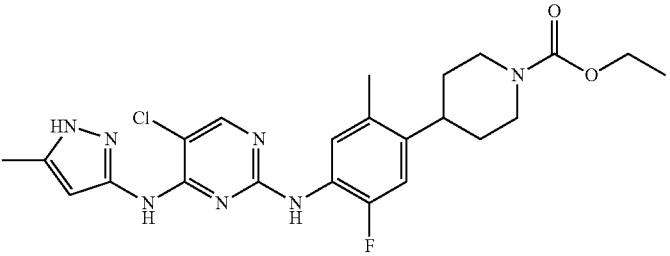 [SMILES: CCOC(=O)N1CCC(c2cc(F)c(Nc3ncc(Cl)c(Nc4cc(C)[nH]n4)n3)cc2C)CC1]<br>Ethyl 4-(4-(5-chloro-4-(5-methyl-1H-pyrazol-3-ylamino)pyrimidin-2-ylamino)-5-fluoro-2-methylphenyl)piperidine-1-carboxylate | $^1$H NMR (400 MHz, MeOD-d$_4$) δ 8.13 (s, 1H), 7.54 (d, 1H), 7.10 (d, 1H), 6.28 (s, 1H), 4.30-4.26 (m, 2H), 4.14 (q, 2H), 2.99-2.96 (m, 3H), 2.33 (s, 3H), 2.29 (s, 3H), 1.8-1.77 (m, 2H), 1.64-1.55 (m, 2H), 1.28 (t, 3H); ESMS m/z 488.2 (M + H$^+$). | 0.064 |
| 67 | 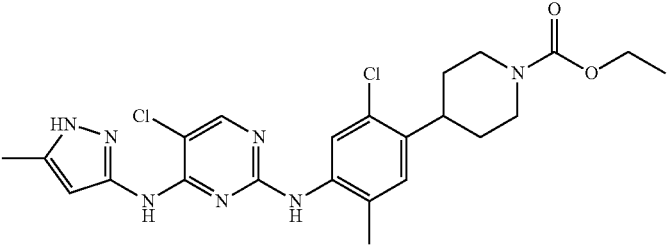 [SMILES: CCOC(=O)N1CCC(c2cc(C)c(Nc3ncc(Cl)c(Nc4cc(C)[nH]n4)n3)cc2Cl)CC1]<br>ethyl 4-(2-chloro-4-(5-chloro-4-(5-methyl-1H-pyrazol-3-ylamino)pyrimidin-2-ylamino)-5-methylphenyl)piperidine-1-carboxylate | ESMS m/z 504.2 (M + H$^+$). | 0.182 |
| 68 | 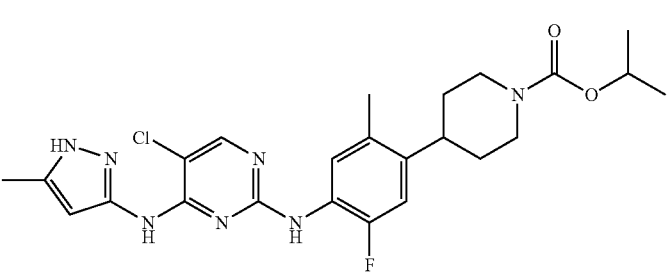 [SMILES: Cc1cc(Nc2nc(Nc3cc(C)c(C4CCN(C(=O)OC(C)C)CC4)cc3F)ncc2Cl)n[nH]1]<br>isopropyl 4-(4-(5-chloro-4-(5-methyl-1H-pyrazol-3-ylamino)pyrimidin-2-ylamino)-5-fluoro-2-methylphenyl)piperidine-1-carboxylate | ESMS m/z 502.2 (M + H$^+$). | 0.080 |
| 69 | 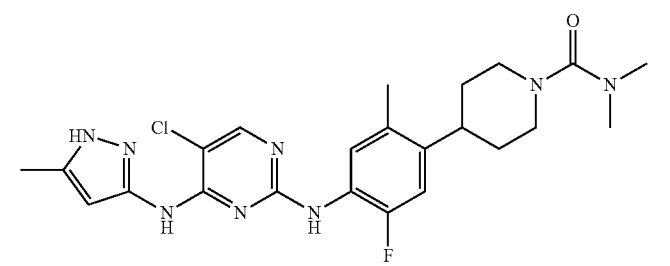<br>4-(4-(5-chloro-4-(5-methyl-1H-pyrazol-3-ylamino)pyrimidin-2-ylamino)-5-fluoro-2-methylphenyl)-N,N-dimethylpiperidine-1-carboxamide | ESMS m/z 487.2 (M + H+). | 0.011 |

TABLE 1-continued

| | STRUCTURE | NMR or ESMS | IGF-1R Ba/F3 IC50 (uM) |
|---|---|---|---|
| 70 | 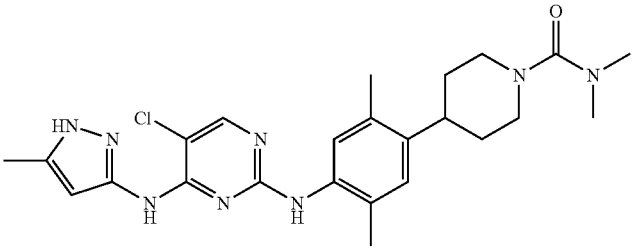<br>4-(4-(5-chloro-4-(5-methyl-1H-pyrazol-3-ylamino)pyrimidin-2-ylamino)-2,5-dimethylphenyl)-N,N-dimethylpiperidine-1-carboxamide | ESMS m/z 483.2 (M + H$^+$). | 0.006 |
| 71 | 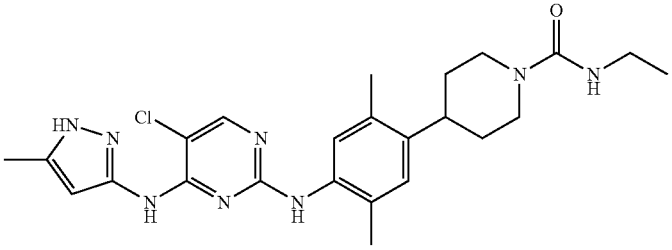 [SMILES: CCNC(=O)N1CCC(c2cc(C)c(Nc3ncc(Cl)c(Nc4cc(C)[nH]n4)n3)cc2C)CC1]<br>4-(4-(5-chloro-4-(5-methyl-1H-pyrazol-3-ylamino)pyrimidin-2-ylamino)-2,5-dimethylphenyl)-N-ethylpiperidine-1-carboxamide | ESMS m/z 483.2 (M + H$^+$). | 0.002 |
| 72 | 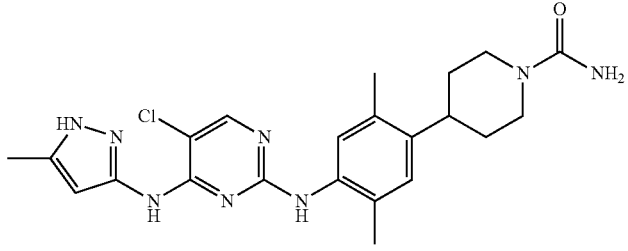 [SMILES: Cc1cc(Nc2nc(Nc3cc(C)c(C4CCN(C(N)=O)CC4)cc3C)ncc2Cl)n[nH]1]<br>4-(4-(5-chloro-4-(5-methyl-1H-pyrazol-3-ylamino)pyrimidin-2-ylamino)-2,5-dimethylphenyl)piperidine-1-carboxamide | ESMS m/z 455.2 (M + H$^+$). | 0.006 |
| 73 | 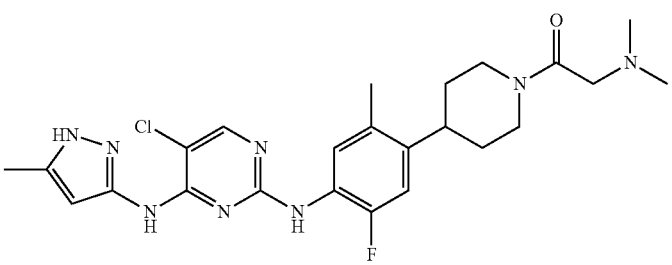<br>1-(4-(4-(5-chloro-4-(5-methyl-1H-pyrazol-3-ylamino)pyrimidin-2-ylamino)-5-fluoro-2-methylphenyl)piperidin-1-yl)-2-(dimethylamino)ethanone | $^1$H NMR (400 MHz, MeOD-d$_4$) δ 8.08 (s, 1H), 7.71 (d, 1H), 7.03 (d, 1H), 6.26 (s, 1H), 4.71-4.67 (m, 2H), 3.81-3.77 (m, 2H), 3.14-3.12 (m, 2H), 2.98 (s, 3H), 2.96 (s, 3H), 2.90-2.83 (m, 1H), 2.34 (s, 3H), 2.28 (s, 3H), 1.87 (d, 2H), 1.76-1.55 (m, 2H); ESMS m/z 501.2 (M + H$^+$). | 0.019 |

TABLE 1-continued

| | STRUCTURE | NMR or ESMS | IGF-1R Ba/F3 IC50 (uM) |
|---|---|---|---|
| 74 | 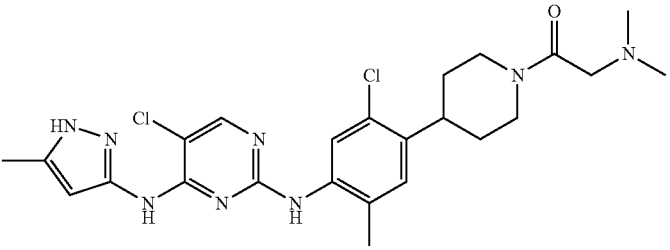<br>1-(4-(2-chloro-4-(5-chloro-4-(5-methyl-1H-pyrazol-3-ylamino)pyrimidin-2-ylamino)-5-methylphenyl)piperidin-1-yl)-2-(dimethylamino)ethanone | ESMS m/z 517.2 (M + H$^+$). | 0.007 |
| 75 | 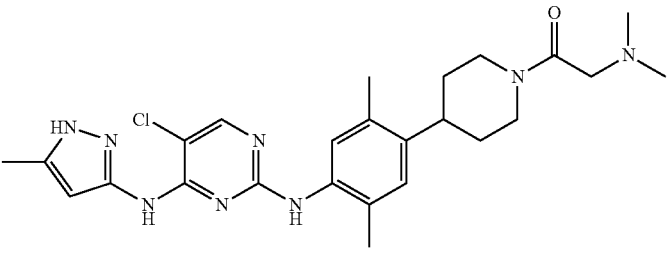<br>1-(4-(4-(5-chloro-4-(5-methyl-1H-pyrazol-3-ylamino)pyrimidin-2-ylamino)-2,5-dimethylphenyl)piperidin-1-yl)-2-(dimethylamino)ethanone | ESMS m/z 497.2 (M + H$^+$). | 0.011 |
| 76 | 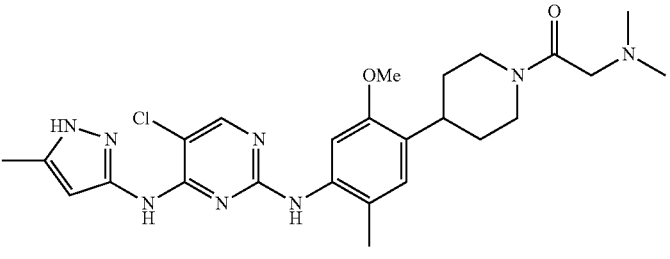<br>1-(4-(4-(5-chloro-4-(5-methyl-1H-pyrazol-3-ylamino)pyrimidin-2-ylamino)-2-methoxy-5-methylphenyl)piperidin-1-yl)-2-(dimethylamino)ethanone | ESMS m/z 513.2 (M + H$^+$). | 0.009 |
| 77 | 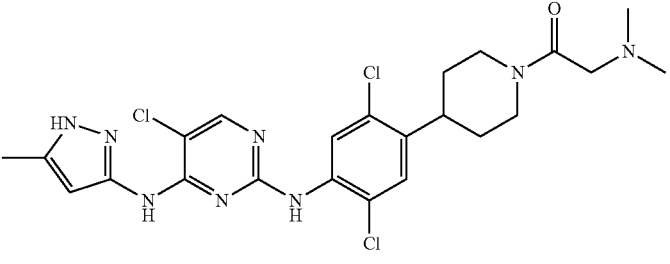<br>1-(4-(2,5-dichloro-4-(5-chloro-4-(5-methyl-1H-pyrazol-3-ylamino)pyrimidin-2-ylamino)phenyl)piperidin-1-yl)-2-(dimethylamino)ethanone | ESMS m/z 537.1 (M + H$^+$). | 0.007 |

TABLE 1-continued

| | STRUCTURE | NMR or ESMS | IGF-1R Ba/F3 IC50 (uM) |
|---|---|---|---|
| 78 | 1-(4-(4-(5-chloro-4-(5-methyl-1H-pyrazol-3-ylamino)pyrimidin-2-ylamino)-5-fluoro-2-methylphenyl)piperidin-1-yl)-3-(dimethylamino)propan-1-one | ESMS m/z 515.2(M + H+). | 0.138 |
| 79 | 2-amino-1-(4-(4-(5-chloro-4-(5-methyl-1H-pyrazol-3-ylamino)pyrimidin-2-ylamino)-5-fluoro-2-methylphenyl)piperidin-1-yl)ethanone | ESMS m/z 473.2 (M + H+). | 0.075 |
| 80 | 1-(4-(4-(5-chloro-4-(5-methyl-1H-pyrazol-3-ylamino)pyrimidin-2-ylamino)-5-fluoro-2-methylphenyl)piperidin-1-yl)-2-(methylamino)ethanone | ESMS m/z 487.2 (M + H+). | 0.103 |
| 81 | 1-(4-(4-(5-chloro-4-(5-methyl-1H-pyrazol-3-ylamino)pyrimidin-2-ylamino)-5-fluoro-2-methylphenyl)piperidin-1-yl)-2-(diethylamino)ethanone | ESMS m/z 529.3 (M + H+). | 0.030 |

TABLE 1-continued

| STRUCTURE | NMR or ESMS | IGF-1R Ba/F3 IC50 (uM) |
|---|---|---|
| 82 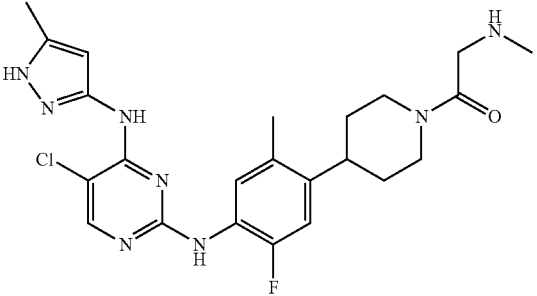 [SMILES: CNCC(=O)N1CCC(c2cc(F)c(Nc3ncc(Cl)c(Nc4cc(C)[nH]n4)n3)cc2C)CC1] 1-(4-(4-(5-chloro-4-(5-methyl-1H-pyrazol-3-ylamino)pyrimidin-2-ylamino)-5-fluoro-2-methylphenyl)piperidin-1-yl)-2-(methylamino)ethanone | ESMS m/z 487.2 (M + H$^+$). | |
| 83 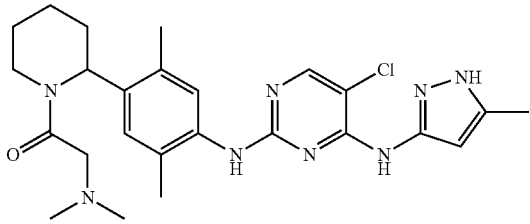 [SMILES: Cc1cc(Nc2nc(Nc3cc(C)c(C4CCCCN4C(=O)CN(C)C)cc3C)ncc2Cl)n[nH]1] 1-(2-(4-(5-chloro-4-(5-methyl-1H-pyrazol-3-ylamino)pyrimidin-2-ylamino)-2,5-dimethylphenyl)piperidin-1-yl)-2-(dimethylamino)ethanone | ESMS m/z 497.2 (M + H$^+$). | 0.013 |
| 84 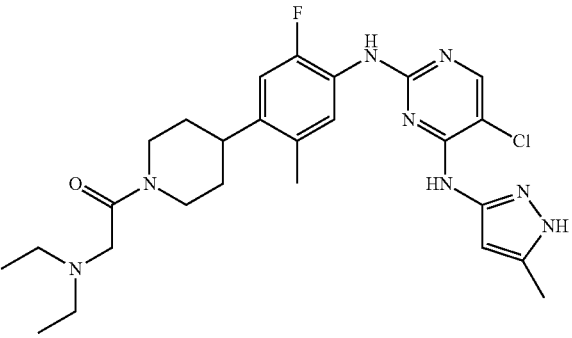 [SMILES: CCN(CC)CC(=O)N1CCC(c2cc(F)c(Nc3ncc(Cl)c(Nc4cc(C)[nH]n4)n3)cc2C)CC1] 1-(4-(4-(5-chloro-4-(5-methyl-1H-pyrazol-3-ylamino)pyrimidin-2-ylamino)-5-fluoro-2-methylphenyl)piperidin-1-yl)-2-(diethylamino)ethanone | ESMS m/z 529.3 (M + H$^+$). | |

| | STRUCTURE | NMR or ESMS | IGF-1R Ba/F3 IC50 (uM) |
|---|---|---|---|
| 85 | 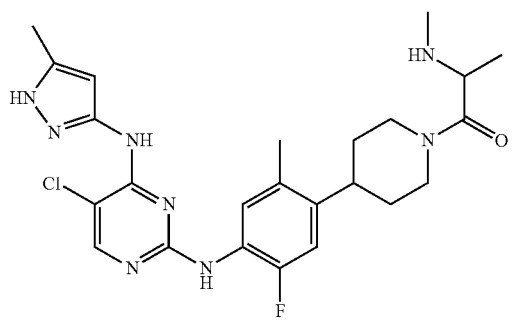 [SMILES: CNC(C)C(=O)N1CCC(c2cc(F)c(Nc3ncc(Cl)c(Nc4cc(C)[nH]n4)n3)cc2C)CC1]<br>1-(4-(4-(5-chloro-4-(5-methyl-1H-pyrazol-3-ylamino)pyrimidin-2-ylamino)-5-fluoro-2-methylphenyl)piperidin-1-yl)-2-(methylamino)propan-1-one | ESMS m/z 501.2 (M + H$^+$). | 0.042 |
| 86 | 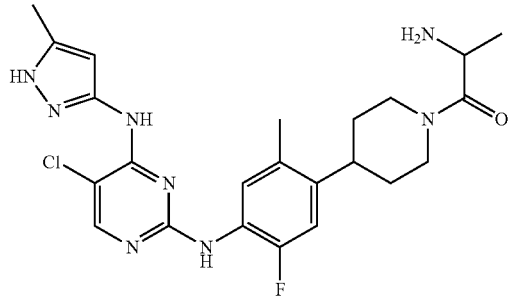<br>2-amino-1-(4-(4-(5-chloro-4-(5-methyl-1H-pyrazol-3-ylamino)pyrimidin-2-ylamino)-5-fluoro-2-methylphenyl)piperidin-1-yl)propan-1-one | ESMS m/z 487.2 (M + H$^+$). | 0.141 |
| 87 | 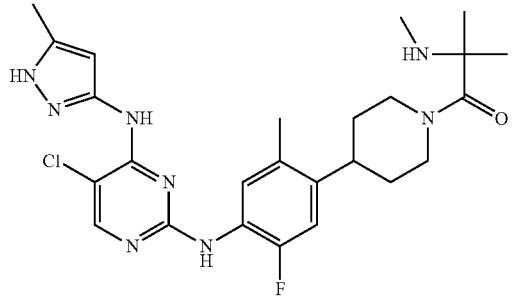 [SMILES: CNC(C)(C)C(=O)N1CCC(c2cc(F)c(Nc3ncc(Cl)c(Nc4cc(C)[nH]n4)n3)cc2C)CC1]<br>1-(4-(4-(5-chloro-4-(5-methyl-1H-pyrazol-3-ylamino)pyrimidin-2-ylamino)-5-fluoro-2-methylphenyl)piperidin-1-yl)-2-methyl-2-(methylamino)propan-1-one | ESMS m/z 515.2 (M + H$^+$). | 0.017 |

TABLE 1-continued

| | STRUCTURE | NMR or ESMS | IGF-1R Ba/F3 IC50 (uM) |
|---|---|---|---|
| 88 | 1-(4-(2-chloro-4-(5-chloro-4-(5-methyl-1H-pyrazol-3-ylamino)pyrimidin-2-ylamino)-5-methylphenyl)piperidin-1-yl)-2-methyl-2-(methylamino)propan-1-one | ESMS m/z 531.2 (M + H+). | 0.007 |
| 89 | 2-amino-1-(4-(4-(5-chloro-4-(5-methyl-1H-pyrazol-3-ylamino)pyrimidin-2-ylamino)-2,5-dimethylphenyl)piperidin-1-yl)-2-methylpropan-1-one | ESMS m/z 497.2 (M + H+). | 0.023 |
| 90 | (4-(4-(5-chloro-4-(5-methyl-1H-pyrazol-3-ylamino)pyrimidin-2-ylamino)-2,5-dimethylphenyl)piperidin-1-yl)(1-(methylamino)cyclopropyl)methanone | ESMS m/z 509.2 (M + H+). | 0.005 |

TABLE 1-continued

| | STRUCTURE | NMR or ESMS | IGF-1R Ba/F3 IC50 (uM) |
|---|---|---|---|
| 91 | (1-aminocyclobutyl)(4-(4-(5-chloro-4-(5-methyl-1H-pyrazol-3-ylamino)pyrimidin-2-ylamino)-2,5-dimethylphenyl)piperidin-1-yl)methanone | ESMS m/z 509.2 (M + H⁺). | 0.052 |
| 92 | (4-(4-(5-chloro-4-(5-methyl-1H-pyrazol-3-ylamino)pyrimidin-2-ylamino)-2,5-dimethylphenyl)piperidin-1-yl)(1-(dimethylamino)cyclobutyl)methanone | ESMS m/z 537.3 (M + H⁺). | 0.015 |
| 93 | (1-aminocyclopropyl)(4-(4-(5-chloro-4-(5-methyl-1H-pyrazol-3-ylamino)pyrimidin-2-ylamino)-5-fluoro-2-methylphenyl)piperidin-1-yl)methanone | ESMS m/z 499.2 (M + H⁺). | 0.033 |

127
128

TABLE 1-continued

| | STRUCTURE | NMR or ESMS | IGF-1R Ba/F3 IC50 (uM) |
|---|---|---|---|
| 94 | 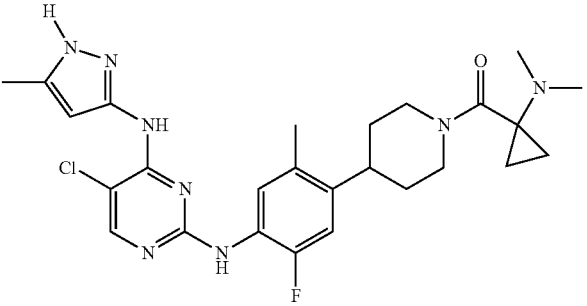<br>(4-(4-(5-chloro-4-(5-methyl-1H-pyrazol-3-ylamino)pyrimidin-2-ylamino)-5-fluoro-2-methylphenyl)piperidin-1-yl)(1-(dimethylamino)cyclopropyl)methanone | ESMS m/z 527.2 (M + H$^+$). | 0.013 |
| 95 | 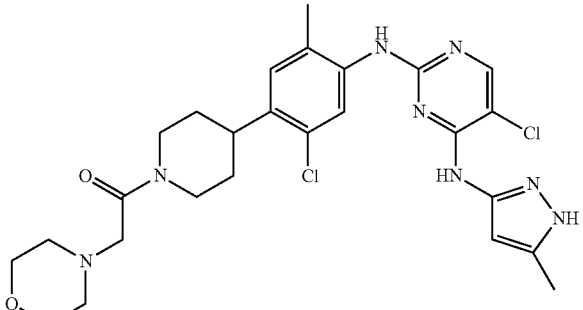<br>1-(4-(2-chloro-4-(5-chloro-4-(5-methyl-1H-pyrazol-3-ylamino)pyrimidin-2-ylamino)-5-methylphenyl)piperidin-1-yl)-2-morpholinoethanone | ESMS m/z 559.2 (M + H$^+$). | 0.006 |
| 96 | 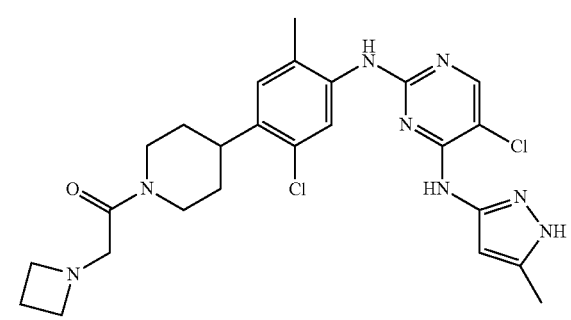 [SMILES: Cc1cc(Nc2nc(Nc3cc(Cl)c(C4CCN(C(=O)CN5CCC5)CC4)cc3C)ncc2Cl)n[nH]1]<br>2-(azetidin-1-yl)-1-(4-(2-chloro-4-(5-chloro-4-(5-methyl-1H-pyrazol-3-ylamino)pyrimidin-2-ylamino)-5-methylphenyl)piperidin-1-yl)ethanone | ESMS m/z 529.2 (M + H$^+$). | 0.024 |

TABLE 1-continued

| | STRUCTURE | NMR or ESMS | IGF-1R Ba/F3 IC50 (uM) |
|---|---|---|---|
| 97 | 1-(4-(4-(5-chloro-4-(5-methyl-1H-pyrazol-3-ylamino)pyrimidin-2-ylamino)-5-fluoro-2-methylphenyl)piperidin-1-yl)-2-morpholinoethanone | ESMS m/z 543.2 (M + H$^+$). | 0.020 |
| 98 | 2-(azetidin-1-yl)-1-(4-(4-(5-chloro-4-(5-methyl-1H-pyrazol-3-ylamino)pyrimidin-2-ylamino)-5-fluoro-2-methylphenyl)piperidin-1-yl)ethanone | ESMS m/z 513.2 (M + H$^+$). | 0.064 |
| 99 | 1-(4-(4-(5-chloro-4-(5-methyl-1H-pyrazol-3-ylamino)pyrimidin-2-ylamino)-5-fluoro-2-methylphenyl)piperidin-1-yl)-2-(pyrrolidin-1-yl)ethanone | ESMS m/z 527.2 (M + H$^+$). | 0.038 |

TABLE 1-continued

| | STRUCTURE | NMR or ESMS | IGF-1R Ba/F3 IC50 (uM) |
|---|---|---|---|
| 100 | 1-(4-(4-(5-chloro-4-(5-methyl-1H-pyrazol-3-ylamino)pyrimidin-2-ylamino)-5-fluoro-2-methylphenyl)piperidin-1-yl)-2-(1H-pyrrol-1-yl)ethanone | ESMS m/z 523.2 (M + H$^+$). | 0.025 |
| 101 | 1-(4-(4-(5-chloro-4-(5-methyl-1H-pyrazol-3-ylamino)pyrimidin-2-ylamino)-2,5-dimethylphenyl)piperidin-1-yl)-2-(piperidin-1-yl)ethanone | ESMS m/z 537.3 (M + H$^+$). | 0.007 |
| 102 | 1-(4-(4-(5-chloro-4-(5-methyl-1H-pyrazol-3-ylamino)pyrimidin-2-ylamino)-2,5-dimethylphenyl)piperidin-1-yl)-2-morpholinoethanone | ESMS m/z 539.3 (M + H$^+$). | 0.009 |

TABLE 1-continued

| | STRUCTURE | NMR or ESMS | IGF-1R Ba/F3 IC50 (uM) |
|---|---|---|---|
| 103 | 1-(4-(4-(5-chloro-4-(5-methyl-1H-pyrazol-3-ylamino)pyrimidin-2-ylamino)-2,5-dimethylphenyl)piperidin-1-yl)-2-(2,6-dimethylpiperidin-1-yl)ethanone | ESMS m/z 565.3 (M + H+). | 0.009 |
| 104 | 1-(4-(4-(5-chloro-4-(5-methyl-1H-pyrazol-3-ylamino)pyrimidin-2-ylamino)-2,5-dimethylphenyl)piperidin-1-yl)-2-(2,2,6,6-tetramethylpiperidin-1-yl)ethanone | ESMS m/z 593.3 (M + H+). | 0.018 |
| 105 | 1-(4-(4-(5-chloro-4-(5-methyl-1H-pyrazol-3-ylamino)pyrimidin-2-ylamino)-5-fluoro-2-methylphenyl)piperidin-1-yl)-2-(4-methylpiperazin-1-yl)ethanone | ESMS m/z 556.3 (M + H+). | 0.051 |

TABLE 1-continued

| | STRUCTURE | NMR or ESMS | IGF-1R Ba/F3 IC50 (uM) |
|---|---|---|---|
| 106 | 1-(4-(4-(5-chloro-4-(5-methyl-1H-pyrazol-3-ylamino)pyrimidin-2-ylamino)-2,5-dimethylphenyl)piperidin-1-yl)-2-methoxyethanone | ESMS m/z 484.2 (M + H$^+$). | 0.002 |
| 107 | N-(2-(4-(4-(5-chloro-4-(5-methyl-1H-pyrazol-3-ylamino)pyrimidin-2-ylamino)-5-fluoro-2-methylphenyl)piperidin-1-yl)-2-oxoethyl)acetamide | ESMS m/z 515.2 (M + H$^+$). | 0.057 |
| 108 | (dimethylamino)ethyl 4-(4-(5-chloro-4-(5-methyl-1H-pyrazol-3-ylamino)pyrimidin-2-ylamino)-5-fluoro-2-methylphenyl)piperidine-1-carboxylate | ESMS m/z 531.2 (M + H$^+$). | 0.053 |
| 109 | 4-(4-(5-chloro-4-(5-methyl-1H-pyrazol-3-ylamino)pyrimidin-2-ylamino)-5-fluoro-2-methylphenyl)-N-(2-(dimethylamino)ethyl)piperidine-1-carboxamide | ESMS m/z 530.2 (M + H$^+$). | 0.060 |

TABLE 1-continued

| | STRUCTURE | NMR or ESMS | IGF-1R Ba/F3 IC50 (uM) |
|---|---|---|---|
| 110 | 1-(4-(4-(5-chloro-4-(5-methyl-1H-pyrazol-3-ylamino)pyrimidin-2-ylamino)-2,5-dimethylphenyl)piperidin-1-yl)ethanone | ESMS m/z 454.2 (M + H$^+$). | 0.013 |
| 111 | (4-(4-(5-chloro-4-(5-methyl-1H-pyrazol-3-ylamino)pyrimidin-2-ylamino)-5-fluoro-2-methylphenyl)piperidin-1-yl)(morpholino)methanone | ESMS m/z 529.2 (M + H$^+$). | 0.008 |
| 112 | (4-(4-(5-chloro-4-(5-methyl-1H-pyrazol-3-ylamino)pyrimidin-2-ylamino)-5-fluoro-2-methylphenyl)piperidin-1-yl)(4-methylpiperazin-1-yl)methanone | ESMS m/z 542.2 (M + H$^+$). | 0.021 |
| 113 | 1-(4-(4-(5-chloro-4-(5-methyl-1H-pyrazol-3-ylamino)pyrimidin-2-ylamino)-2,5-dimethylphenyl)piperidine-1-carbonyl)imidazolidin-2-one | ESMS m/z 524.2 (M + H$^+$). | 0.013 |

TABLE 1-continued

| | STRUCTURE | NMR or ESMS | IGF-1R Ba/F3 IC50 (uM) |
|---|---|---|---|
| 114 | 1-(4-(4-(5-chloro-4-(5-methyl-1H-pyrazol-3-ylamino)pyrimidin-2-ylamino)-2,5-dimethylphenyl)piperidin-1-yl)-2-methoxyethanone | ESMS m/z 569.2 (M + H$^+$). | 0.048 |
| 115 | (4-(4-(5-chloro-4-(5-methyl-1H-pyrazol-3-ylamino)pyrimidin-2-ylamino)-5-fluoro-2-methylphenyl)piperidin-1-yl)(piperidin-4-yl)methanone | ESMS m/z 527.2 (M + H$^+$). | 1.57 |
| 116 | (S)-(4-(4-(5-chloro-4-(5-methyl-1H-pyrazol-3-ylamino)pyrimidin-2-ylamino)-5-fluoro-2-methylphenyl)piperidin-1-yl)(pyrrolidin-2-yl)methanone | ESMS m/z 513.2 (M + H$^+$). | 0.137 |
| 117 | (4-(4-(5-chloro-4-(5-methyl-1H-pyrazol-3-ylamino)pyrimidin-2-ylamino)-5-fluoro-2-methylphenyl)piperidin-1-yl)(1-methylazetidin-3-yl)methanone | ESMS m/z 513.2(M + H$^+$). | 0.099 |

TABLE 1-continued

| STRUCTURE | NMR or ESMS | IGF-1R Ba/F3 IC50 (uM) |
|---|---|---|
| 118 (4-(4-(5-chloro-4-(5-methyl-1H-pyrazol-3-ylamino)pyrimidin-2-ylamino)-5-fluoro-2-methylphenyl)piperidin-1-yl)(1-methylpiperidin-4-yl)methanone | ESMS m/z 541.2 (M + H+). | 0.081 |
| 119 3-(4-(4-(5-chloro-4-(5-methyl-1H-pyrazol-3-ylamino)pyrimidin-2-ylamino)-5-fluoro-2-methylphenyl)piperidine-1-carbonyl)azetidin-2-one | ESMS m/z 513.2 (M + H+). | 2.99 |
| 120 (4-(4-(5-chloro-4-(5-methyl-1H-pyrazol-3-ylamino)pyrimidin-2-ylamino)-2,5-dimethylphenyl)piperidin-1-yl)(1-methylazetidin-3-yl)methanone | ESMS m/z 509.2 (M + H+). | 0.025 |
| 121 (S)-(4-(4-(5-chloro-4-(5-methyl-1H-pyrazol-3-ylamino)pyrimidin-2-ylamino)-2,5-dimethylphenyl)piperidin-1-yl)(1-methylpyrrolidin-2-yl)methanone | ESMS m/z 523.2 (M + H+). | 0.017 |

TABLE 1-continued

| | STRUCTURE | NMR or ESMS | IGF-1R Ba/F3 IC50 (uM) |
|---|---|---|---|
| 122 | 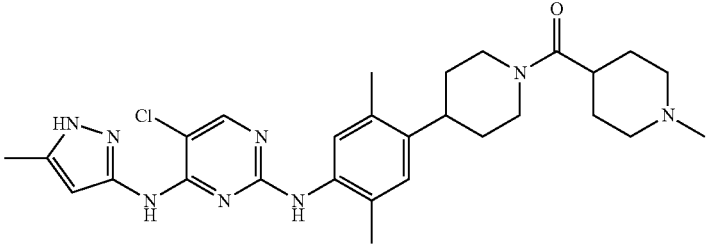<br>(4-(4-(5-chloro-4-(5-methyl-1H-pyrazol-3-ylamino)pyrimidin-2-ylamino)-2,5-dimethylphenyl)piperidin-1-yl)(1-methylpiperidin-4-yl)methanone | ESMS m/z 537.2 (M + H$^+$). | |
| 123 | 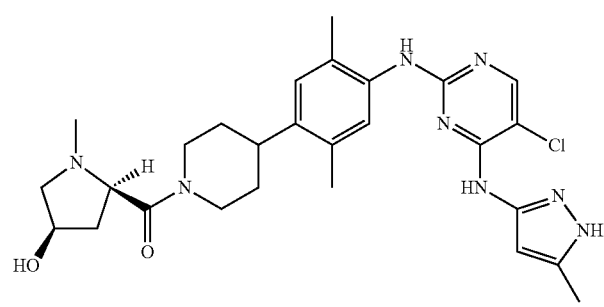 [SMILES: Cc1cc(Nc2nc(Nc3cc(C)c(C4CCN(C(=O)[C@H]5C[C@@H](O)CN5C)CC4)cc3C)ncc2Cl)n[nH]1]<br>(4-(4-(5-chloro-4-(5-methyl-1H-pyrazol-3-ylamino)pyrimidin-2-ylamino)-2,5-dimethylphenyl)piperidin-1-yl)((2R,4R)-4-hydroxy-1-methylpyrrolidin-2-yl)methanone | ESMS m/z 539.3 (M + H$^+$). | 0.048 |
| 124 | 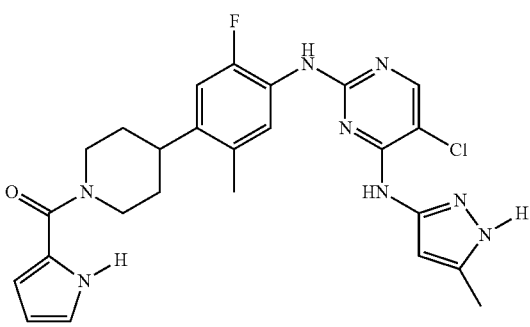 [SMILES: Cc1cc(Nc2nc(Nc3cc(C)c(C4CCN(C(=O)c5ccc[nH]5)CC4)cc3F)ncc2Cl)n[nH]1]<br>(4-(4-(5-chloro-4-(5-methyl-1H-pyrazol-3-ylamino)pyrimidin-2-ylamino)-5-fluoro-2-methylphenyl)piperidin-1-yl)(1H-pyrrol-2-yl)methanone | ESMS m/z 509.2 (M + H$^+$). | 0.145 |

TABLE 1-continued

| | STRUCTURE | NMR or ESMS | IGF-1R Ba/F3 IC50 (uM) |
|---|---|---|---|
| 125 | (S)-(4-(4-(5-chloro-4-(5-methyl-1H-pyrazol-3-ylamino)pyrimidin-2-ylamino)-5-fluoro-2-methylphenyl)piperidin-1-yl)(1-isopropylpiperidin-2-yl)methanone | ESMS m/z 569.3 (M + H$^+$). | 0.012 |
| 126 | (S)-(4-(4-(5-chloro-4-(5-methyl-1H-pyrazol-3-ylamino)pyrimidin-2-ylamino)-5-fluoro-2-methylphenyl)piperidin-1-yl)(4-isopropylmorpholin-3-yl)methanone | ESMS m/z 571.3 (M + H$^+$). | 0.029 |
| 127 | (4-(4-(5-chloro-4-(5-methyl-1H-pyrazol-3-ylamino)pyrimidin-2-ylamino)-5-fluoro-2-methylphenyl)piperidin-1-yl)(2,4-dimethyloxazol-5-yl)methanone | ESMS m/z 539.2 (M + H$^+$). | 0.027 |

TABLE 1-continued

| | STRUCTURE | NMR or ESMS | IGF-1R Ba/F3 IC50 (uM) |
|---|---|---|---|
| 128 | (4-(4-(5-chloro-4-(5-methyl-1H-pyrazol-3-ylamino)pyrimidin-2-ylamino)-5-fluoro-2-methylphenyl)piperidin-1-yl)((2S)-4-hydroxy-1-methylpyrrolidin-2-yl)methanone | ESMS m/z 543.2 (M + H+). | 0.175 |
| 129 | (4-(4-(5-chloro-4-(5-methyl-1H-pyrazol-3-ylamino)pyrimidin-2-ylamino)-5-fluoro-2-methylphenyl)piperidin-1-yl)(1,3,5-trimethyl-1H-pyrazol-4-yl)methanone | ESMS m/z 552.2 (M + H+). | 0.025 |
| 130 | (4-(4-(5-chloro-4-(5-methyl-1H-pyrazol-3-ylamino)pyrimidin-2-ylamino)-5-fluoro-2-methylphenyl)piperidin-1-yl)(1-methyl-5-(trifluoromethyl)-1H-pyrazol-4-yl)methanone | ESMS m/z 592.2 (M + H+). | 0.061 |
| 131 | azetidin-3-yl(4-(4-(5-chloro-4-(5-methyl-1H-pyrazol-3-ylamino)pyrimidin-2-ylamino)-5-fluoro-2-methylphenyl)piperidin-1-yl)methanone | $^1$H NMR (400 MHz, MeOD-d$_4$) δ 8.08 (s, 1H), 7.68 (d, 2H), 7.04 (d, 2H), 6.26 (s, 1H), 4.74-4.68 (m, 2H), 4.39-4.35 (m, 1H), 4.29-4.24 (m, 2H), 4.11-4.07 (m, 1H), 3.74-3.71 (m, 1H), 3.25-3.24 (m, 1H), 3.07-3.04 (m, 1H), 2.87-2.80 (m, 1H), 2.33 (s, 3H), 2.28 (s, 3H), 1.87-1.84 (m, 2H), 1.66-1.56 (m, 2H); ESMS m/z 499.2 (M + H+). | 1.25 |

TABLE 1-continued

| | STRUCTURE | NMR or ESMS | IGF-1R Ba/F3 IC50 (uM) |
|---|---|---|---|
| 132 | (S)-azetidin-2-yl(4-(4-(5-chloro-4-(5-methyl-1H-pyrazol-3-ylamino)pyrimidin-2-ylamino)-5-fluoro-2-methylphenyl)piperidin-1-yl)methanone | ESMS m/z 499.2 (M + H+). | 0.161 |
| 133 | (R)-(4-(4-(5-chloro-4-(5-methyl-1H-pyrazol-3-ylamino)pyrimidin-2-ylamino)-2,5-dimethylphenyl) piperidin-1-yl)(1-methylpyrrolidin-2-yl)methanone | ESMS m/z 523.3 (M + H+). | 0.013 |
| 134 | (R)-(4-(4-(5-chloro-4-(5-methyl-1H-pyrazol-3-ylamino)pyrimidin-2-ylamino)-5-fluoro-2-methylphenyl) piperidin-1-yl)(1-methylpyrrolidin-2-yl)methanone | ESMS m/z 527.2 (M + H+). | 0.021 |

TABLE 1-continued

| | STRUCTURE | NMR or ESMS | IGF-1R Ba/F3 IC50 (uM) |
|---|---|---|---|
| 135 | 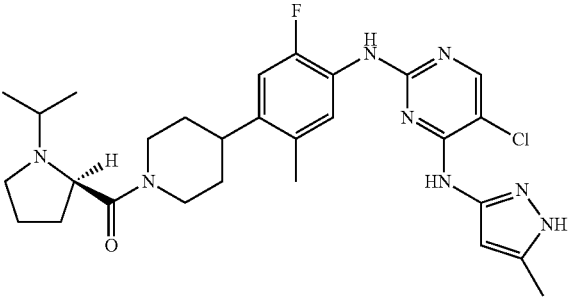 [SMILES: Cc1cc(Nc2nc(Nc3cc(C)c(C4CCN(C(=O)[C@H]5CCCN5C(C)C)CC4)cc3F)ncc2Cl)n[nH]1]<br>(R)-(4-(4-(5-chloro-4-(5-methyl-1H-pyrazol-3-ylamino)pyrimidin-2-ylamino)-5-fluoro-2-methylphenyl)piperidin-1-yl)(1-isopropylpyrrolidin-2-yl)methanone | ESMS m/z 555.3 (M + H⁺). | 0.048 |
| 136 | 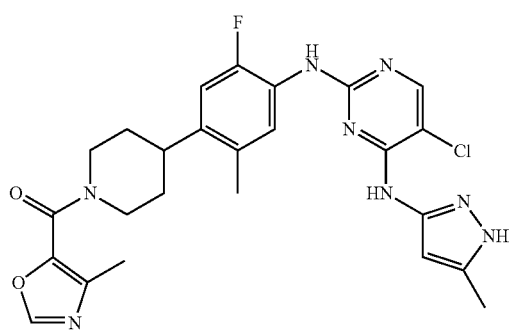 [SMILES: Cc1cc(Nc2nc(Nc3cc(C)c(C4CCN(C(=O)c5ocnc5C)CC4)cc3F)ncc2Cl)n[nH]1]<br>(4-(4-(5-chloro-4-(5-methyl-1H-pyrazol-3-ylamino)pyrimidin-2-ylamino)-5-fluoro-2-methylphenyl)piperidin-1-yl)(4-methyloxazol-5-yl)methanone | ESMS m/z 525.2 (M + H⁺). | 0.035 |
| 137 | 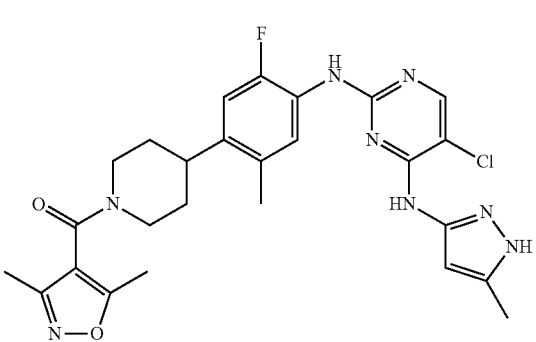 [SMILES: Cc1cc(Nc2nc(Nc3cc(C)c(C4CCN(C(=O)c5c(C)noc5C)CC4)cc3F)ncc2Cl)n[nH]1]<br>(4-(4-(5-chloro-4-(5-methyl-1H-pyrazol-3-ylamino)pyrimidin-2-ylamino)-5-fluoro-2-methylphenyl)piperidin-dimethylisoxazol-4-yl)methanone | ESMS m/z 539.2 (M + H⁺). | 0.018 |

TABLE 1-continued

| | STRUCTURE | NMR or ESMS | IGF-1R Ba/F3 IC50 (uM) |
|---|---|---|---|
| 138 | (S)-(4-(4-(5-chloro-4-(5-methyl-1H-pyrazol-3-ylamino)pyrimidin-2-ylamino)-5-fluoro-2-methylphenyl)piperidin-1-yl)(2-methylpyrrolidin-2-yl)methanone | ESMS m/z 527.2 (M + H$^+$). | 0.091 |
| 139 | (4-(4-(5-chloro-4-(5-methyl-1H-pyrazol-3-ylamino)pyrimidin-2-ylamino)-5-fluoro-2-methylphenyl)piperidin-1-yl)((2S,3R)-3-hydroxy-1-methylpyrrolidin-2-yl)methanone | ESMS m/z 543.2 (M + H$^+$). | 0.175 |
| 140 | (4-(4-(5-chloro-4-(5-methyl-1H-pyrazol-3-ylamino)pyrimidin-2-ylamino)-5-fluoro-2-methylphenyl)piperidin-1-yl)(1H-tetrazol-1-yl)methanone | ESMS m/z 512.2 (M + H$^+$). | 0.139 |

TABLE 1-continued

| | STRUCTURE | NMR or ESMS | IGF-1R Ba/F3 IC50 (uM) |
|---|---|---|---|
| 141 | 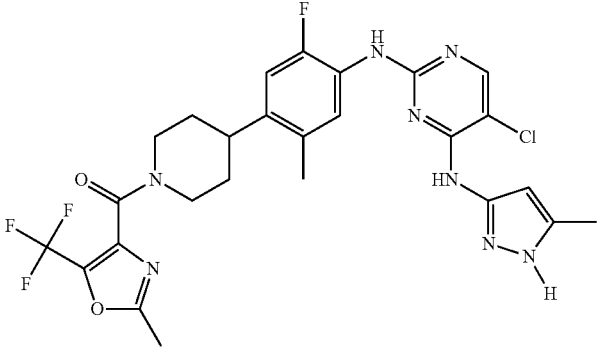 [SMILES: Cc1cc(Nc2nc(Nc3cc(C)c(C4CCN(C(=O)c5nc(C)oc5C(F)(F)F)CC4)cc3F)ncc2Cl)n[nH]1]<br>(4-(4-(5-chloro-4-(5-methyl-1H-pyrazol-3-ylamino)pyrimidin-2-ylamino)-5-fluoro-2-methylphenyl)piperidin-1-yl)(2-methyl-5-(trifluoromethyl)oxazol-4-yl)methanone | ESMS m/z 593.2 (M + H$^+$). | 0.069 |
| 142 | 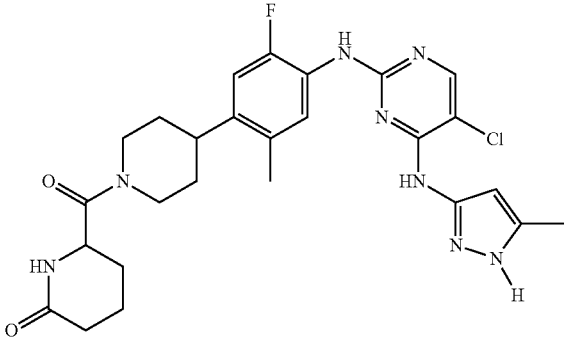 [SMILES: Cc1cc(Nc2nc(Nc3cc(C)c(C4CCN(C(=O)C5CCCC(=O)N5)CC4)cc3F)ncc2Cl)n[nH]1]<br>6-(4-(4-(5-chloro-4-(5-methyl-1H-pyrazol-3-ylamino)pyrimidin-2-ylamino)-5-fluoro-2-methylphenyl)piperidine-1-carbonyl)piperidin-2-one | ESMS m/z 541.2 (M + H$^+$). | 0.282 |
| 143 | 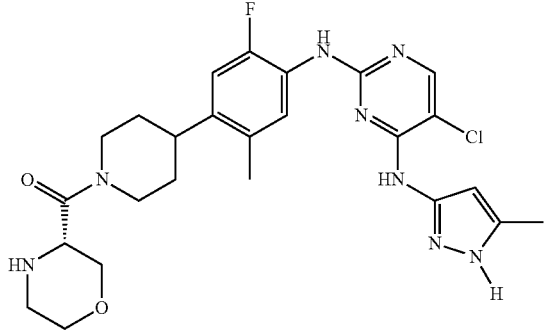 [SMILES: Cc1cc(Nc2nc(Nc3cc(C)c(C4CCN(C(=O)[C@@H]5COCCN5)CC4)cc3F)ncc2Cl)n[nH]1]<br>(S)-(4-(4-(5-chloro-4-(5-methyl-1H-pyrazol-3-ylamino)pyrimidin-2-ylamino)-5-fluoro-2-methylphenyl)piperidin-1-yl)(morpholin-3-yl)methanone | ESMS m/z 529.2 (M + H$^+$). | 0.071 |

TABLE 1-continued

| | STRUCTURE | NMR or ESMS | IGF-1R Ba/F3 IC50 (uM) |
|---|---|---|---|
| 144 | 5-chloro-N²-(2-methyl-5-chloro-4-(1-(tetrahydro-1,1-dioxido-3-thienyl)piperidin-4-yl)phenyl)-N⁴-(5-methyl-1H-pyrazol-3-yl)pyrimidine-2,4-diamine | ESMS m/z 550.1 (M + H⁺). | 0.007 |
| 145 | 5-chloro-N²-(2-fluoro-5-methyl-4-(1-(tetrahydro-1,1-dioxido-3-thienyl)piperidin-4-yl)phenyl)-N⁴-(5-methyl-1H-pyrazol-3-yl)pyrimidine-2,4-diamine | ESMS m/z 534.2 (M + H⁺). | 0.018 |
| 146 | 5-chloro-N2-(2,5-dimethyl-4-(1-(tetrahydro-1,1-dioxido-2H-thiopyran-4-yl))piperidin-4-yl)phenyl)-N4-(5-methyl-1H-pyrazol-3-yl)pyrimidine-2,4-diamine | ESMS m/z 544.2 (M + H⁺). | 0.258 |
| 147 | 5-chloro-N2-(2-chloro-5-methyl-4-(1-(1,1-dioxido-3-thietanyl)piperidin-4-yl)phenyl)-N4-(5-methyl-1H-pyrazol-3-yl)pyrimidine-2,4-diamine | ESMS m/z 536.1 (M + H⁺). | 0.016 |

TABLE 1-continued

| | STRUCTURE | NMR or ESMS | IGF-1R Ba/F3 IC50 (uM) |
|---|---|---|---|
| 148 | 5-chloro-N2-(2-fluoro-5-methyl-4-(1-(1,1-dioxido-3-thietanyl)piperidin-4-yl)phenyl)-N4-(5-methyl-1H-pyrazol-3-yl)pyrimidine-2,4-diamine | ESMS m/z 520.2 (M + H$^+$). $^1$H NMR (400 MHz, DMSO-d$_6$ + 1 drop D$_2$O) δ 8.02 (s, 1H), 7.37 (s, 1H). 7.02 (s, 1H), 6.23 (s, 1H), 4.28-4.22 (m, 2H), 4.12-4.07 (m, 2H), 3.22-3.18 (m, 1H), 2.95-2.92 (m, 2H), 2.68-2.62 (m, 1H), 2.22 (s, 3H), 2.13 (s, 3H), 2.07-2.01 (m, 2H), 1.71-1.55 (m, 4H). | 0.018 |
| 149 | 5-chloro-N2-(4-(1-(5-ethylpyrimidin-2-yl)piperidin-4-yl)-2-fluoro-5-methylphenyl)-N4-(5-methyl-1H-pyrazol-3-yl)pyrimidine-2,4-diamine | ESMS m/z 522.2 (M + H+). | 0.955 |
| 150 | 5-chloro-N2-(2-fluoro-5-methyl-4-(1,2,3,6-tetrahydropyridin-4-yl)phenyl)-N4-(5-methyl-1H-pyrazol-3-yl)pyrimidine-2,4-diamine | ESMS m/z 414.1 (M + H$^+$). | 0.025 |
| 151 | 4-(4-(5-chloro-4-(5-methyl-1H-pyrazol-3-ylamino)pyrimidin-2-ylamino)-2,5-dimethylphenyl)piperidin-2-one | ESMS m/z 426.2 (M + H$^+$). | 0.009 |

TABLE 1-continued

| | STRUCTURE | NMR or ESMS | IGF-1R Ba/F3 IC50 (uM) |
|---|---|---|---|
| 152 | 4-(4-(5-chloro-4-(5-methyl-1H-pyrazol-3-ylamino)pyrimidin-2-ylamino)-2,5-dimethylphenyl)tetrahydro-2H-pyran-2-one | ESMS m/z 427.2 (M + H$^+$). | 0.155 |
| 153 | 5-chloro-N2-(2-fluoro-4-morpholino-5-(trifluoromethyl)phenyl)-N4-(5-methyl-1H-pyrazol-3-yl)pyrimidine-2,4-diamine | ESMS m/z 472.1 (M + H+). | 0.091 |
| 154 | 5-Chloro-N$^2$-[4-(1,1-dioxo-tetrahydro-1$\lambda^6$-thiophen-3-yl)-2,5-dimethyl-phenyl]-N$^4$-(5-methyl-1H-pyrazol-3-yl)-pyrimidine-2,4-diamine | ESMS m/z 447.1 (M + H$^+$). | 0.012 |
| 155 | 1-(4-(5-chloro-4-(5-methyl-1H-pyrazol-3-ylamino)pyrimidin-2-ylamino)-2,5-dimethylphenyl)piperazin-2-one | ESMS m/z 427.2 (M + H$^+$). | 1.65 |

TABLE 1-continued

| | STRUCTURE | NMR or ESMS | IGF-1R Ba/F3 IC50 (uM) |
|---|---|---|---|
| 156 | 5-chloro-N4-(5-methyl-1H-pyrazol-3-yl)-N2-(2-methyl-4-(4-methylpiperazin-1-yl)-5-(trifluoromethyl)phenyl)pyrimidine-2,4-diamine | ESMS m/z 481.2 (M + H+) | 0.040 |
| 157 | 5-chloro-N2-(2-fluoro-4-(4-methylpiperazin-1-yl)-5-(trifluoromethyl)phenyl)-N4-(5-methyl-1H-pyrazol-3-yl)pyrimidine-2,4-diamine | ESMS m/z 485.2 (M + H+). | 0.075 |
| 158 | 3-(5-chloro-2-(2,5-dimethyl-4-(piperidin-4-yl)phenylamino)pyrimidin-4-ylamino)pyridin-2(1H)-one | ESMS m/z 425.2 (M + H+). | 0.062 |
| 159 | 5-chloro-N2-(2-fluoro-5-methyl-4-(1-methylpiperidin-4-yl)phenyl)-N4-(5-methylisoxazol-3-yl)pyrimidine-2,4-diamine | ESMS m/z 431.2 (M + H+). | 0.073 |

| | STRUCTURE | NMR or ESMS | IGF-1R Ba/F3 IC50 (uM) |
|---|---|---|---|
| 160 | 3-(5-chloro-2-(2,5-dimethyl-4-(piperidin-4-yl)phenylamino)pyrimidin-4-ylamino)pyridin-2(1H)-one | ESMS m/z 425.2 (M + H⁺). | |
| 161 | 5-chloro-N2-(2-isopropoxy-5-methyl-4-(1-methylpiperidin-4-yl)phenyl)-N4-(1H-pyrazol-3-yl)pyrimidine-2,4-diamine | ESMS m/z 456.2 (M + H⁺). | 0.332 |
| 162 | ethyl 4-(4-(5-chloro-4-(5-methyl-1H-pyrazol-3-ylamino)pyrimidin-2-ylamino)-2,5-dimethylphenyl)piperidine-1-carboxylate | ESMS m/z 438.9 (M + H⁺). | 0.013 |
| 163 | (S)-2-(4-(4-(5-chloro-4-(5-methyl-1H-pyrazol-3-ylamino)pyrimidin-2-ylamino)-5-fluoro-2-methylphenyl)piperidin-1-yl)propanamide | ESMS m/z 487.2 (M + H⁺) | 0.056 |

TABLE 1-continued

| | STRUCTURE | NMR or ESMS | IGF-1R Ba/F3 IC50 (uM) |
|---|---|---|---|
| 164 | 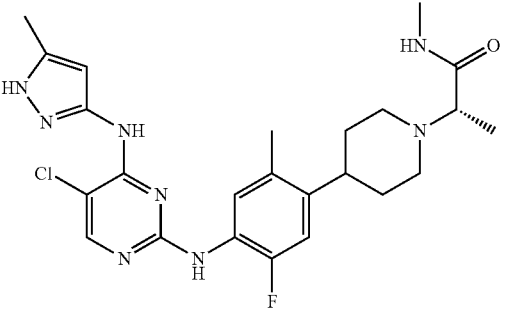 [SMILES: CNC(=O)[C@H](C)N1CCC(c2cc(F)c(Nc3ncc(Cl)c(Nc4cc(C)[nH]n4)n3)cc2C)CC1]<br>(S)-2-(4-(4-(5-chloro-4-(5-methyl-1H-pyrazol-3-ylamino)pyrimidin-2-ylamino)-5-fluoro-2-methylphenyl)piperidin-1-yl)-N-methylpropanamide | ESMS m/z 501.2 (M + H$^+$); $^1$HNMR (MeOD-d$_4$) δ 8.25 (s, 1H), 7.56 (m, 1H), 7.20 (d, 1H), 6.46 (s, 1H), 3.97 (m, 1H), 3.79 (m, 1H), 3.62 (m, 1H), 3.25 (m, 3H), 2.84 (s, 3H), 2.40 (d, 6H), 2.08 (m, 4H), 1.62 (m, 3H). | 0.033 |
| 165 | 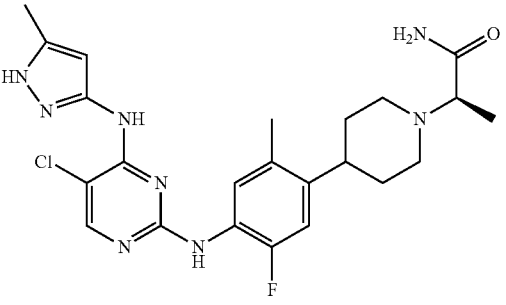 [SMILES: Cc1cc(Nc2nc(Nc3cc(C)c(C4CCN([C@H](C)C(N)=O)CC4)cc3F)ncc2Cl)n[nH]1]<br>(R)-2-(4-(4-(5-chloro-4-(5-methyl-1H-pyrazol-3-ylamino)pyrimidin-2-ylamino)-5-fluoro-2-methylphenyl)piperidin-1-yl)propanamide | ESMS m/z 487.2 (M + H$^+$); $^1$HNMR (MeOD-d$_4$) δ 8.22 (s, 1H), 7.61 (t, 1H), 7.18 (d, 1H), 6.40 (s, 1H), 3.79 (m, 1H), 3.65 (m, 1H), 3.54 (m, 1H), 3.22 (m, 3H), 2.39 (d, 6H), 2.08 (m, 4H), 1.66 (d, 3H) | 0.038 |
| 166 | 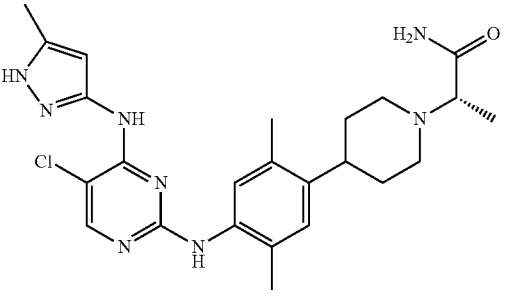 [SMILES: Cc1cc(Nc2nc(Nc3cc(C)c(C4CCN([C@@H](C)C(N)=O)CC4)cc3C)ncc2Cl)n[nH]1]<br>(S)-2-(4-(4-(5-chloro-4-(5-methyl-1H-pyrazol-3-ylamino)pyrimidin-2-ylamino)-2,5-dimethylphenyl)piperidin-1-yl)propanamide | ESMS m/z 483.2 (M + H$^+$) | 0.007 |

TABLE 1-continued

| | STRUCTURE | NMR or ESMS | IGF-1R Ba/F3 IC50 (uM) |
|---|---|---|---|
| 167 | (R)-2-(4-(4-(5-chloro-4-(5-methyl-1H-pyrazol-3-ylamino)pyrimidin-2-ylamino)-2,5-dimethylphenyl)piperidin-1-yl)propanamide | ESMS m/z 483.2 (M + H$^+$) | 0.006 |
| 168 | (S)-2-(4-(4-(5-chloro-4-(5-methyl-1H-pyrazol-3-ylamino)pyrimidin-2-ylamino)-2,5-dimethylphenyl)piperidin-1-yl)-N-methylpropanamide | ESMS m/z 497.2 (M + H$^+$) | 0.01 |
| 169 | (4-(4-(5-chloro-4-(5-methyl-1H-pyrazol-3-ylamino)pyrimidin-2-ylamino)-5-fluoro-2-methylphenyl)piperidin-1-yl)(1-(ethylamino)cyclopropyl)methanone | ESMS m/z 527.2 (M + H$^+$); $^1$HNMR (MeOD-d$_4$) δ 8.24 (s, 1H), 7.49 (d, 1H), 7.23 (d, 1H), 6.47 (s, 1H), 4.52 (d, 2H), 3.26 (q, 2H), 3.18 (m, 3H), 2.40 (s, 6H), 1.91(d, 2H), 1.71(m, 2H), 1.49 (m, 3H), 1.39 (t, 3H). | 0.004 |

TABLE 1-continued

| | STRUCTURE | NMR or ESMS | IGF-1R Ba/F3 IC50 (uM) |
|---|---|---|---|
| 170 | (4-(4-(5-chloro-4-(5-methyl-1H-pyrazol-3-ylamino)pyrimidin-2-ylamino)-2,5-dimethylphenyl)piperidin-1-yl)(1-(ethylamino)cyclopropyl)methanone | ESMS m/z 523.3 (M + H$^+$) | 0.003 |
| 171 | 5-chloro-N2-(2-fluoro-5-methyl-4-(piperidin-4-yl)phenyl)-N4-(5-(trifluoromethyl)-1H-pyrazol-3-yl)pyrimidine-2,4-diamine | ESMS m/z 470.1 (M + H$^+$) | 0.067 |
| 172 | 2-(4-(4-(5-chloro-4-(5-(trifluoromethyl)-1H-pyrazol-3-ylamino)pyrimidin-2-ylamino)-5-fluoro-2-methylphenyl)piperidin-1-yl)-N-methylacetamide | ESMS m/z 541.2 (M + H$^+$) | 0.069 |
| 173 | 2-(4-(4-(5-chloro-4-(5-(trifluoromethyl)-1H-pyrazol-3-ylamino)pyrimidin-2-ylamino)-5-fluoro-2-methylphenyl)piperidin-1-yl)acetamide | ESMS m/z 527.2 (M + H$^+$) | 0.049 |

TABLE 1-continued

| | STRUCTURE | NMR or ESMS | IGF-1R Ba/F3 IC50 (uM) |
|---|---|---|---|
| 174 | 5-chloro-N2-(2,5-dimethyl-4-(1-(tetrahydro-2H-thiopyran-4-yl)piperidin-4-yl)phenyl)-N4-(5-methyl-1H-pyrazol-3-yl )pyrimidine-2,4-diamine | ESMS m/z 512.2 (M + H$^+$) | 0.008 |
| 175 | 1-(4-(4-(5-chloro-4-(5-methyl-1H-pyrazol-3-ylamino)pyrimidin-2-ylamino)-2,5-dimethylphenyl)piperidin-1-yl)-2-(ethylamino)-2-methylpropan-1-one | ESMS m/z 525.3 (M + H$^+$) | 0.005 |
| 176 | (4-(4-(5-chloro-4-(5-methyl-1H-pyrazol-3-ylamino)pyrimidin-2-ylamino)-5-fluoro-2-methylphenyl)piperidin-1-yl)(1-(ethylamino)cyclobutyl)methanone | ESMS m/z 541.3 (M + H$^+$) | 0.084 |

TABLE 1-continued

| | STRUCTURE | NMR or ESMS | IGF-1R Ba/F3 IC50 (uM) |
|---|---|---|---|
| 177 | (4-(4-(5-chloro-4-(5-methyl-1H-pyrazol-3-ylamino)pyrimidin-2-ylamino)-5-fluoro-2-methylphenyl)piperidin-1-yl)(1-(methylamino)cyclobutyl)methanone | ESMS m/z 527.2 (M + H+) | 0.08 |
| 178 | N2-(2,5-dimethyl-4-(piperidin-4-yl)phenyl)-5-methyl-N4-(5-methyl-1H-pyrazol-3-yl)pyrimidine-2,4-diamine | ESMS m/z 392.2 (M + H+) | 3.229 |
| 179 | (S)-3-(4-(2,5-dimethyl-4-(5-methyl-4-(5-methyl-1H-pyrazol-3-ylamino)pyrimidin-2-ylamino)phenyl)piperidin-1-yl)-1,1,1-trifluoropropan-2-ol | ESMS m/z 504.3 (M + H+) | 0.12 |

TABLE 1-continued

| | STRUCTURE | NMR or ESMS | IGF-1R Ba/F3 IC50 (uM) |
|---|---|---|---|
| 180 | 1-(3-(4-(5-chloro-4-(5-methyl-1H-pyrazol-3-ylamino)pyrimidin-2-ylamino)-2,5-dimethylphenyl)piperidin-1-yl)-2-(dimethylamino)ethanone | ESMS m/z 497.2 (M + H$^+$) | 0.025 |
| 181 | 2-(2-(4-(5-chloro-4-(5-methyl-1H-pyrazol-3-ylamino)pyrimidin-2-ylamino)-2,5-dimethylphenyl)piperidin-1-yl)acetamide | ESMS m/z 469.2 (M + H$^+$) | 0.024 |
| 182 | 2-(2-(4-(5-chloro-4-(5-methyl-1H-pyrazol-3-ylamino)pyrimidin-2-ylamino)-2,5-dimethylphenyl)piperidin-1-yl)-N-methylacetamide | ESMS m/z 483.2 (M + H$^+$) | 0.019 |

TABLE 1-continued

| | STRUCTURE | NMR or ESMS | IGF-1R Ba/F3 IC50 (uM) |
|---|---|---|---|
| 183 | (S)-5-chloro-N2-(2,5-dimethyl-4-(1-methylpiperidin-2-yl)phenyl)-N4-(5-methyl-1H-pyrazol-3-yl)pyrimidine-2,4-diamine | ESMS m/z 426.2 (M + H⁺) | |
| 184 | (R)-5-chloro-N2-(2,5-dimethyl-4-(1-methylpiperidin-2-yl)phenyl)-N4-(5-methyl-1H-pyrazol-3-yl)pyrimidine-2,4-diamine | ESMS m/z 426.2 (M + H⁺) | |
| 185 | 2-(4-(4-(5-chloro-4-(5-methyl-1H-pyrazol-3-ylamino)pyrimidin-2-ylamino)-2,5-dimethylphenyl)piperidin-1-yl)butanamide | ESMS m/z 497.2 (M + H⁺) | 0.009 |
| 186 | 1-(4-(4-(5-chloro-4-(5-cyclopropyl-1H-pyrazol-3-ylamino)pyrimidin-2-ylamino)-2,5-dimethylphenyl)piperidin-1-yl)-2-(dimethylamino)ethanone | ESMS m/z 523.3 (M + H⁺) | 0.012 |

TABLE 1-continued

| STRUCTURE | NMR or ESMS | IGF-1R Ba/F3 IC50 (uM) |
|---|---|---|
| 187 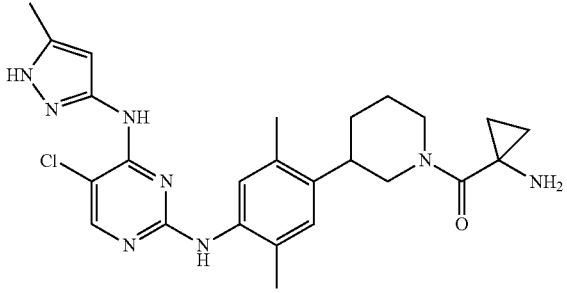 [SMILES: Cc1cc(Nc2nc(Nc3cc(C)c(C4CCCN(C(=O)C5(N)CC5)C4)cc3C)ncc2Cl)n[nH]1]<br>(1-aminocyclopropyl)(3-(4-(5-chloro-4-(5-methyl-1H-pyrazol-3-ylamino)pyrimidin-2-ylamino)-2,5-dimethylphenyl)piperidin-1-yl)methanone | ESMS m/z 495.2 (M + H$^+$) | 0.095 |
| 188 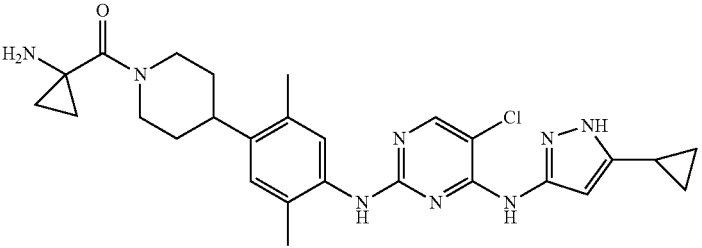 [SMILES: Cc1cc(C2CCN(C(=O)C3(N)CC3)CC2)c(C)cc1Nc1ncc(Cl)c(Nc2cc(C3CC3)[nH]n2)n1]<br>(1-aminocyclopropyl)(4-(4-(5-chloro-4-(5-cyclopropyl-1H-pyrazol-3-ylamino)pyrimidin-2-ylamino)-2,5-dimethylphenyl)piperidin-1-yl)methanone | ESMS m/z 521.2 (M + H$^+$) | 0.019 |
| 189 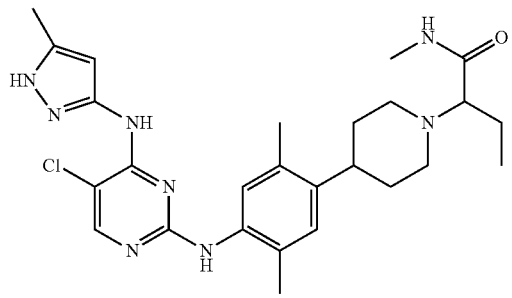 [SMILES: CCC(C(=O)NC)N1CCC(c2cc(C)c(Nc3ncc(Cl)c(Nc4cc(C)[nH]n4)n3)cc2C)CC1]<br>2-(4-(4-(5-chloro-4-(5-methyl-1H-pyrazol-3-ylamino)pyrimidin-2-ylamino)-2,5-dimethylphenyl)piperidin-1-yl)-N-methylbutanamide | ESMS m/z 511.3 (M + H$^+$) | 0.007 |

TABLE 1-continued

| | STRUCTURE | NMR or ESMS | IGF-1R Ba/F3 IC50 (uM) |
|---|---|---|---|
| 190 | 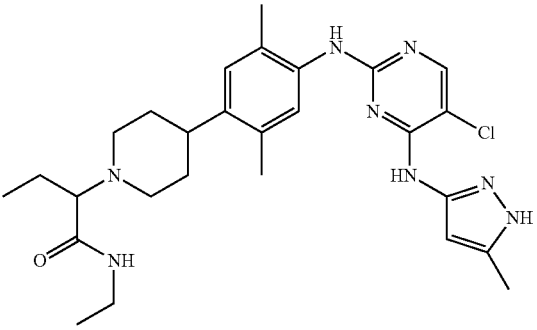 [SMILES: CCNC(=O)C(CC)N1CCC(c2cc(C)c(Nc3ncc(Cl)c(Nc4cc(C)[nH]n4)n3)cc2C)CC1]<br>2-(4-(4-(5-chloro-4-(5-methyl-1H-pyrazol-3-ylamino)pyrimidin-2-ylamino)-2,5-dimethylphenyl)piperidin-1-yl)-N-ethylbutanamide | ESMS m/z 525.3 (M + H$^+$) | 0.007 |
| 191 | 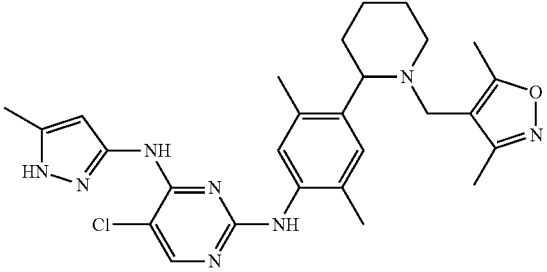 [SMILES: Cc1cc(Nc2nc(Nc3cc(C)c(C4CCCCN4Cc4c(C)noc4C)cc3C)ncc2Cl)n[nH]1]<br>5-chloro-N2-(4-(1-((3,5-dimethylisoxazol-4-yl)methyl)piperidin-2-yl)-2,5-dimethylphenyl)-N4-(5-methyl-1H-pyrazol-3-yl)pyrimidine-2,4-diamine | ESMS m/z 521.2 (M + H$^+$) | 0.113 |
| 192 | 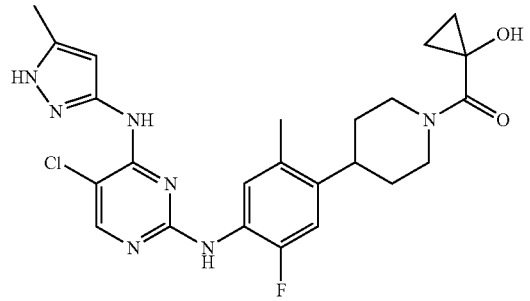 [SMILES: Cc1cc(Nc2nc(Nc3cc(C)c(C4CCN(C(=O)C5(O)CC5)CC4)cc3F)ncc2Cl)n[nH]1]<br>(4-(4-(5-chloro-4-(5-methyl-1H-pyrazol-3-ylamino)pyrimidin-2-ylamino)-5-fluoro-2-methylphenyl)piperidin-1-yl)(1-hydroxycyclopropyl)methanone | ESMS m/z 500.2 (M + H$^+$) | 0.021 |

TABLE 1-continued

| | STRUCTURE | NMR or ESMS | IGF-1R Ba/F3 IC50 (uM) |
|---|---|---|---|
| 193 | 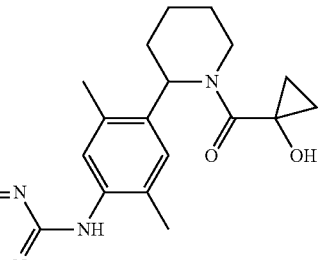<br>(2-(4-(5-chloro-4-(5-methyl-1H-pyrazol-3-ylamino)pyrimidin-2-ylamino)-2,5-dimethylphenyl)piperidin-1-yl)(1-hydroxycyclopropyl)methanone | ESMS m/z 496.2 (M + H$^+$) | 0.076 |
| 194 | 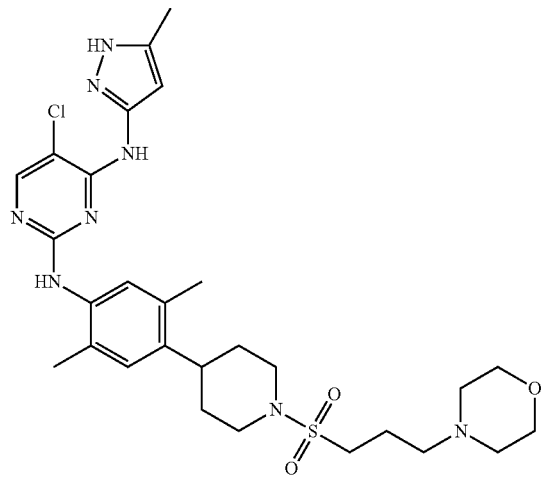 [SMILES: Cc1cc(Nc2nc(Nc3cc(C)c(C4CCN(S(=O)(=O)CCCN5CCOCC5)CC4)cc3C)ncc2Cl)n[nH]1]<br>5-chloro-N2-(2,5-dimethyl-4-(1-(3-morpholinopropylsulfonyl)piperidin-4-yl)phenyl)-N4-(5-methyl-1H-pyrazol-3-yl)pyrimidine-2,4-diamine | ESMS m/z 603.3 (M + H$^+$) | 0.013 |
| 195 | 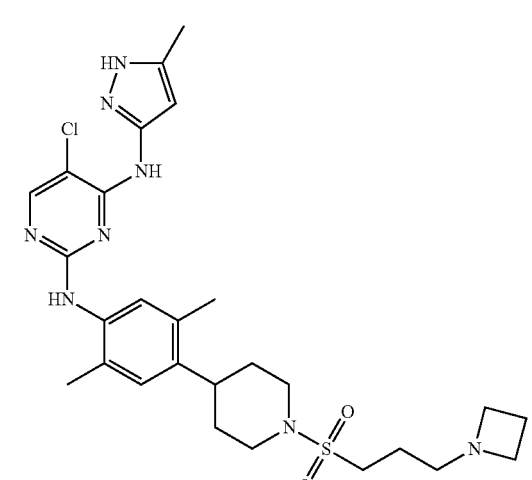<br>N2-(4-(1-(3-(azetidin-1-yl)propylsulfonyl)piperidin-4-yl)-2,5-dimethylphenyl)-5-chloro-N4-(5-methyl-1H-pyrazol-3-yl)pyrimidine-2,4-diamine | ESMS m/z 573.2 (M + H$^+$) | 0.027 |

| | STRUCTURE | NMR or ESMS | IGF-1R Ba/F3 IC50 (uM) |
|---|---|---|---|
| 196 | (3R,4R)-1-(3-(4-(4-(5-chloro-4-(5-methyl-1H-pyrazol-3-ylamino)pyrimidin-2-ylamino)-2,5-dimethylphenyl)piperidin-1-ylsulfonyl)propyl)pyrrolidine-3,4-diol | ESMS m/z 619.3 (M + H⁺) | 0.37 |
| 197 | (2S)-3-(2-(4-(5-chloro-4-(5-methyl-1H-pyrazol-3-ylamino)pyrimidin-2-ylamino)-2,5-dimethylphenyl)piperidin-1-yl)-1,1,1-trifluoropropan-2-ol | ESMS m/z 524.2 (M + H⁺) | 0.21 |
| 198 | 1-((4-(4-(5-chloro-4-(5-methyl-1H-pyrazol-3-ylamino)pyrimidin-2-ylamino)-2,5-dimethylphenyl)piperidin-1-yl)methyl)cyclopropanecarbonitrile | ESMS m/z 491.2 (M + H⁺) | 0.022 |

| | STRUCTURE | NMR or ESMS | IGF-1R Ba/F3 IC50 (uM) |
|---|---|---|---|
| 199 | 2-(4-(4-(5-chloro-4-(5-methyl-1H-pyrazol-3-ylamino)pyrimidin-2-ylamino)-5-fluoro-2-methylphenyl)piperidin-1-yl)acetonitrile | ESMS m/z 455.2 (M + H⁺) | 0.077 |
| 200 | 3-(4-(4-(5-chloro-4-(5-methyl-1H-pyrazol-3-ylamino)pyrimidin-2-ylamino)-5-fluoro-2-methylphenyl)piperidin-1-yl)propanenitrile | ESMS m/z 469.2 (M + H⁺) | 0.036 |
| 201 | (2S)-3-(3-(4-(5-chloro-4-(5-methyl-1H-pyrazol-3-ylamino)pyrimidin-2-ylamino)-2,5-dimethylphenyl)piperidin-1-yl)-1,1,1-trifluoropropan-2-ol | ESMS m/z 524.2 (M + H⁺) | 0.046 |
| 202 | 2-(4-(2,5-dimethyl-4-(4-(5-methyl-1H-pyrazol-3-ylamino)-5-(trifluoromethyl)pyrimidin-2-ylamino)phenyl)piperidin-1-yl)acetamide | ESMS m/z 503.2 (M + H⁺); ¹HNMR (MeOD-d₄) δ 8.23 (s, 1H), 7.26 (s, 1H), 7.20 (s, 1H), 6.20(s, 1H), 4.00 (s, 2H), 3.75 (d, 2H), 3.55 (m, 2H), 3.14 (m, 1H), 2.36 (s, 3H), 2.26 (s, 3H), 2.24 (s, 3H), 2.08(m, 4H). | 0.02 |

TABLE 1-continued

| | STRUCTURE | NMR or ESMS | IGF-1R Ba/F3 IC50 (uM) |
|---|---|---|---|
| 203 | 2-(4-(2,5-dimethyl-4-(4-(5-methyl-1H-pyrazol-3-ylamino)-5-(trifluoromethyl)pyrimidin-2-ylamino)phenyl)piperidin-1-yl)-N-methylacetamide | ESMS m/z 517.3 (M + H+) | 0.015 |
| 204 | 2-(4-(4-(5-chloro-4-(5-cyclopropyl-1H-pyrazol-3-ylamino)pyrimidin-2-ylamino)-2,5-dimethylphenyl)piperidin-1-yl)ethanol | ESMS m/z 482.2 (M + H+) | 0.016 |
| 205 | 5-chloro-N4-(5-cyclopropyl-1H-pyrazol-3-yl)-N2-(4-(1-ethylpiperidin-4-yl)-2,5-dimethylphenyl)pyrimidine-2,4-diamine | ESMS m/z 466.2 (M + H+) | 0.019 |
| 206 | 4-(4-(5-chloro-4-(5-methyl-1H-pyrazol-3-ylamino)pyrimidin-2-ylamino)-5-fluoro-2-methylphenyl)piperidine-1-carbaldehyde | ESMS m/z 444.2 (M + H+) | 0.03 |

TABLE 1-continued

| | STRUCTURE | NMR or ESMS | IGF-1R Ba/F3 IC50 (uM) |
|---|---|---|---|
| 207 | (R)-2-(3-(4-(5-chloro-4-(5-methyl-1H-pyrazol-3-ylamino)pyrimidin-2-ylamino)-2,5-dimethylphenyl)piperidin-1-yl)-N-methylacetamide | ESMS m/z 483.2 (M + H+) | 0.026 |
| 208 | (S)-2-(3-(4-(5-chloro-4-(5-methyl-1H-pyrazol-3-ylamino)pyrimidin-2-ylamino)-2,5-dimethylphenyl)piperidin-1-yl)-N-methylacetamide | ESMS m/z 483.2 (M + H+) | 0.01 |
| 209 | 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine | ESMS m/z 500.2 (M + H+); $^1$H NMR (DMSO-d$_6$, 400 MHz) δ 12.08 (br, 1H), 9.58 (br, 1H), 8.65 (d, J = 28.4 Hz, 1H), 8.02 (s, 1H), 7.36 (d, J = 8.4 Hz, 1H), 7.03 (d, J = 12.4 Hz, 1H), 6.08 (br, 1H), 3.89 (dd, J = 10.8, 3.6 Hz, 2H), 3.28 (t, J = 10.4 Hz, 2H), 2.99 (d, J = 10.8 Hz, 2H), 2.64-2.43 (m, 2H), 2.24-2.15 (m, 8H), 1.71-1.40(m, 8H) | 0.027 |
| 210 | 5-chloro-N2-(4-(1-cyclopropylpiperidin-4-yl)-2-fluoro-5-methylphenyl)-N4-(5-methyl-1H-pyrazol-3-yl)pyrimidine-2,4-diamine | ESMS m/z 456.2 (M + H+) | 0.032 |

TABLE 1-continued

| | STRUCTURE | NMR or ESMS | IGF-1R Ba/F3 IC50 (uM) |
|---|---|---|---|
| 211 | 5-chloro-N2-(4-(1-ethylpiperidin-4-yl)-2,5-dimethylphenyl)-N4-(5-methyl-1H-pyrazol-3-yl)pyrimidine-2,4-diamine | ESMS m/z 440.2 (M + H⁺) | 0.009 |
| 212 | 5-chloro-N2-(4-(1-(2-methoxyethyl)piperidin-4-yl)-2,5-dimethylphenyl)-N4-(5-methyl-1H-pyrazol-3-yl)pyrimidine-2,4-diamine | ESMS m/z 470.2 (M + H⁺) | 0.013 |
| 213 | (S)-3-(4-(4-(5-chloro-4-(5-methyl-1H-pyrazol-3-ylamino)pyrimidin-2-ylamino)-2-methoxy-5-methylphenyl)piperidin-1-yl)-1,1,1-trifluoropropan-2-ol | ESMS m/z 540.2 (M + H⁺) | 0.012 |

TABLE 1-continued

| | STRUCTURE | NMR or ESMS | IGF-1R Ba/F3 IC50 (uM) |
|---|---|---|---|
| 214 | N2-(4-(1-(3-(azetidin-1-ylsulfonyl)propyl)piperidin-4-yl)-2,5-dimethylphenyl)-5-chloro-N4-(5-methyl-1H-pyrazol-3-yl)pyrimidine-2,4-diamine | ESMS m/z 573.2 (M + H$^+$) | 0.04 |
| 215 | 5-chloro-N2-(2,5-dimethyl-4-(piperidin-4-yl)phenyl)-N4-(5-(trifluoromethyl)-1H-pyrazol-3-yl)pyrimidine-2,4-diamine | ESMS m/z 466.2 (M + H$^+$) | 0.047 |
| 216 | 5-chloro-N2-(2-fluoro-4-(1-methylpiperidin-4-yl)-5-(trifluoromethyl)phenyl)-N4-(5-methyl-1H-pyrazol-3-yl)pyrimidine-2,4-diamine | ESMS m/z 484.2 (M + H$^+$) | 0.047 |
| 217 | 2-(4-(4-(5-chloro-4-(5-(trifluoromethyl)-1H-pyrazol-3-ylamino)pyrimidin-2-ylamino)-2,5-dimethylphenyl)piperidin-1-yl)acetamide | ESMS m/z 523.2 (M + H$^+$) | 0.034 |

TABLE 1-continued

| | STRUCTURE | NMR or ESMS | IGF-1R Ba/F3 IC50 (uM) |
|---|---|---|---|
| 218 | 5-chloro-N4-(5-methyl-1H-pyrazol-3-yl)-N2-(2-methyl-4-(1-methylpiperidin-4-yl)-5-(trifluoromethyl)phenyl)pyrimidine-2,4-diamine | ESMS m/z 480.2 (M + H$^+$) | 0.026 |
| 219 | 5-chloro-N2-(5-methoxy-2-methyl-4-(1-methylpiperidin-4-yl)phenyl)-N4-(5-methyl-1H-pyrazol-3-yl)pyrimidine-2,4-diamine | ESMS m/z 442.2 (M + H$^+$) | 0.009 |
| 220 | 2-(4-(4-(5-chloro-4-(5-(trifluoromethyl)-1H-pyrazol-3-ylamino)pyrimidin-2-ylamino)-2,5-dimethylphenyl)piperidin-1-yl)-N-methylacetamide | ESMS m/z 537.2 (M + H$^+$) | 0.037 |
| 221 | N2-(4-(1-ethylpiperidin-4-yl)-2,5-dimethylphenyl)-N4-(5-methyl-1H-pyrazol-3-yl)-5-(trifluoromethyl)pyrimidine-2,4-diamine | ESMS m/z 474.3 (M + H$^+$) | 0.034 |

| | | IGF-1R Ba/F3 |
|---|---|---|
| STRUCTURE | NMR or ESMS | IC50 (uM) |

222

ESMS m/z 490.2 (M + H+)   0.038

2-(4-(2,5-dimethyl-4-(4-(5-methyl-1H-pyrazol-
3-ylamino)-5-(trifluoromethyl)pyrimidin-2-
ylamino)phenyl)piperidin-1-yl)ethanol

223

ESMS m/z 551.2 (M + H+)   0.036

1-(4-(4-(5-chloro-4-(5-(trifluoromethyl)-1H-
pyrazol-3-ylamino)pyrimidin-2-ylamino)-2,5-
dimethylphenyl)piperidin-1-yl)-2-
(dimethylamino)ethanone

224

ESMS m/z 567.3 (M + H+)   0.02

1-(4-(4-(5-chloro-4-(5-methyl-1H-pyrazol-3-
ylamino)pyrimidin-2-ylamino)-2,5-
dimethylphenyl)piperidin-1-yl)-4-
morpholinobutan-1-one TABLE 1-continued
| | STRUCTURE | NMR or ESMS | IGF-1R Ba/F3 IC50 (uM) |
|---|---|---|---|
| 225 | 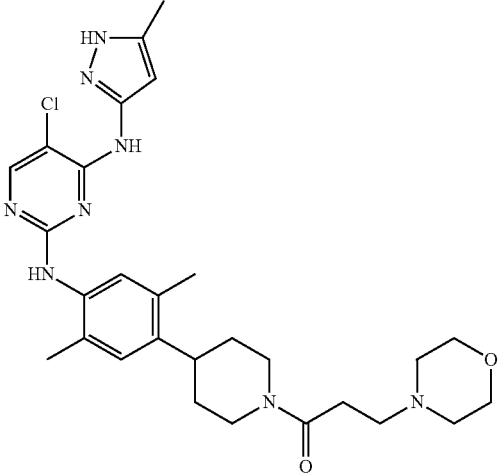 [SMILES: Cc1cc(Nc2nc(Nc3cc(C)c(C4CCN(C(=O)CCN5CCOCC5)CC4)cc3C)ncc2Cl)n[nH]1] 1-(4-(4-(5-chloro-4-(5-methyl-1H-pyrazol-3-ylamino)pyrimidin-2-ylamino)-2,5-dimethylphenyl)piperidin-1-yl)-3-morpholinopropan-1-one | ESMS m/z 553.3 (M + H+) | 0.017 |
| 226 | 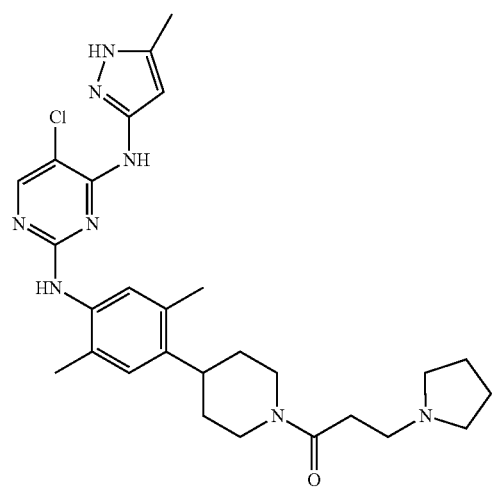 [SMILES: Cc1cc(Nc2nc(Nc3cc(C)c(C4CCN(C(=O)CCN5CCCC5)CC4)cc3C)ncc2Cl)n[nH]1] 1-(4-(4-(5-chloro-4-(5-methyl-1H-pyrazol-3-ylamino)pyrimidin-2-ylamino)-2,5-dimethylphenyl)piperidin-1-yl)-3-(pyrrolidin-1-yl)propan-1-one | ESMS m/z 537.3 (M + H+) | 0.061 |

| | STRUCTURE | NMR or ESMS | IGF-1R Ba/F3 IC50 (uM) |
|---|---|---|---|
| 227 | 1-(4-(4-(5-chloro-4-(5-methyl-1H-pyrazol-3-ylamino)pyrimidin-2-ylamino)-2,5-dimethylphenyl)piperidin-1-yl)-4-(pyrrolidin-1-yl)butan-1-one | ESMS m/z 551.3 (M + H$^+$) | 0.123 |
| 228 | (R)-3-(4-(4-(5-chloro-4-(5-methyl-1H-pyrazol-3-ylamino)pyrimidin-2-ylamino)-2-methoxy-5-methylphenyl)piperidin-1-yl)-1,1,1-trifluoropropan-2-ol | ESMS m/z 540.2 (M + H$^+$) | 0.023 |
| 229 | (2R)-3-(2-(4-(5-chloro-4-(5-methyl-1H-pyrazol-3-ylamino)pyrimidin-2-ylamino)-2,5-dimethylphenyl)piperidin-1-yl)-1,1,1-trifluoropropan-2-ol | ESMS m/z 524.2 (M + H$^+$) | 0.211 |

TABLE 1-continued

| | STRUCTURE | NMR or ESMS | IGF-1R Ba/F3 IC50 (uM) |
|---|---|---|---|
| 230 | 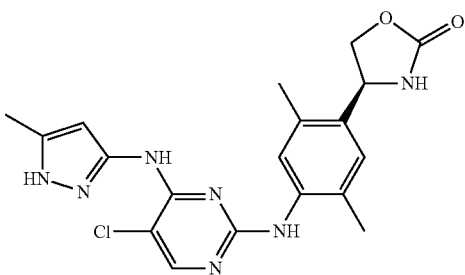<br>(S)-4-(4-(5-chloro-4-(5-methyl-1H-pyrazol-3-ylamino)pyrimidin-2-ylamino)-2,5-dimethylphenyl)oxazolidin-2-one | ESMS m/z 414.1 (M + H$^+$) | 0.04 |
| 231 | 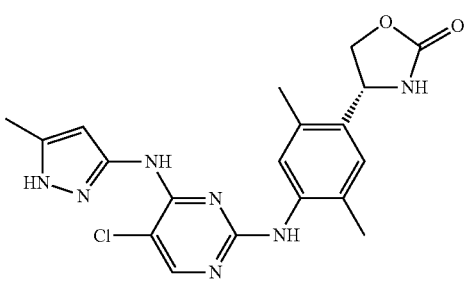 [SMILES: Cc1cc(Nc2nc(Nc3cc(C)c([C@@H]4COC(=O)N4)cc3C)ncc2Cl)n[nH]1]<br>(R)-4-(4-(5-chloro-4-(5-methyl-1H-pyrazol-3-ylamino)pyrimidin-2-ylamino)-2,5-dimethylphenyl)oxazolidin-2-one | ESMS m/z 414.1 (M + H$^+$) | 0.05 |
| 232 | 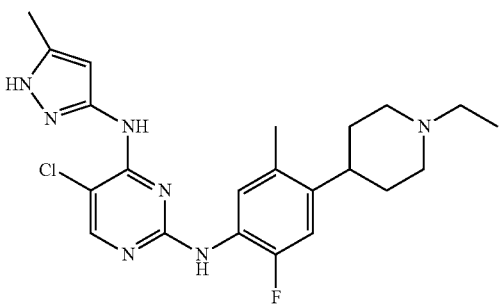 [SMILES: CCN1CCC(c2cc(F)c(Nc3ncc(Cl)c(Nc4cc(C)[nH]n4)n3)cc2C)CC1]<br>5-chloro-N2-(4-(1-ethylpiperidin-4-yl)-2-fluoro-5-methylphenyl)-N4-(5-methyl-1H-pyrazol-3-yl)pyrimidine-2,4-diamine | ESMS m/z 444.2 (M + H$^+$); $^1$HNMR (DMSO-d$_6$) δ 8.01 (s, 1H), 7.35 (m, 1H), 7.02 (d, 1H), 6.22 (s, 1H), 2.97 (d, 2H), 2.62 (m, 1H), 2.34 (q, 2H), 2.21 (s, 3H), 2.13 (s, 3H), 1.98 (t, 2H), 1.64 (m, 4H), 1.01 (t, 3H). | 0.020 |

TABLE 1-continued

| | STRUCTURE | NMR or ESMS | IGF-1R Ba/F3 IC50 (uM) |
|---|---|---|---|
| 233 | 5-chloro-N2-(2,5-dimethyl-4-(1-(3-(pyrrolidin-1-yl)propylsulfonyl)piperidin-4-yl)phenyl)-N4-(5-methyl-1H-pyrazol-3-yl)pyrimidine-2,4-diamine | ESMS m/z 587.3 (M + H$^+$) | 0.054 |
| 234 | (R)-1-(3-(4-(4-(5-chloro-4-(5-methyl-1H-pyrazol-3-ylamino)pyrimidin-2-ylamino)-2,5-dimethylphenyl)piperidin-1-ylsulfonyl)propyl)pyrrolidin-3-ol | ESMS m/z 603.3 (M + H$^+$) | 0.073 |
| 235 | 5-chloro-N2-(4-(1-((2,2-difluorocyclopropyl)methyl)piperidin-4-yl)-2-fluoro-5-methylphenyl)-N4-(5-methyl-1H-pyrazol-3-yl)pyrimidine-2,4-diamine | ESMS m/z 506.2 (M + H$^+$) | 0.063 |

TABLE 1-continued

| | STRUCTURE | NMR or ESMS | IGF-1R Ba/F3 IC50 (uM) |
|---|---|---|---|
| 236 | 3-(4-(4-(5-chloro-4-(5-methyl-1H-pyrazol-3-ylamino)pyrimidin-2-ylamino)-2,5-dimethylphenyl)piperidin-1-yl)propanamide | ESMS m/z 483.2 (M + H$^+$) | 0.059 |
| 237 | N2-(4-(azetidin-3-yl)-2,5-dimethylphenyl)-5-chloro-N4-(5-methyl-1H-pyrazol-3-yl)pyrimidine-2,4-diamine | ESMS m/z 384.2 (M + H$^+$) | 0.41 |
| 238 | 3-(4-(4-(5-chloro-4-(5-methyl-1H-pyrazol-3-ylamino)pyrimidin-2-ylamino)-2,5-dimethylphenyl)piperidin-1-yl)-1-(pyrrolidin-1-yl)propan-1-one | ESMS m/z 537.3 (M + H$^+$) | 0.039 |

TABLE 1-continued

| | STRUCTURE | NMR or ESMS | IGF-1R Ba/F3 IC50 (uM) |
|---|---|---|---|
| 239 | 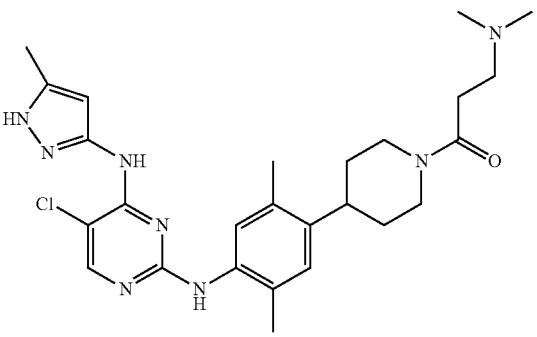 [SMILES: Cc1cc(Nc2nc(Nc3cc(C)c(C4CCN(C(=O)CCN(C)C)CC4)cc3C)ncc2Cl)n[nH]1]<br>1-(4-(4-(5-chloro-4-(5-methyl-1H-pyrazol-3-ylamino)pyrimidin-2-ylamino)-2,5-dimethylphenyl)piperidin-1-yl)-3-(dimethylamino)propan-1-one | ESMS m/z 511.3 (M + H$^+$) | 0.073 |
| 240 | 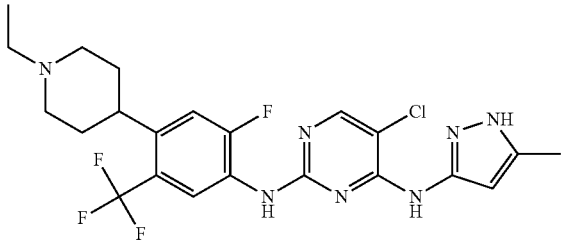 [SMILES: CCN1CCC(c2cc(F)c(Nc3ncc(Cl)c(Nc4cc(C)[nH]n4)n3)cc2C(F)(F)F)CC1]<br>5-chloro-N2-(4-(1-ethylpiperidin-4-yl)-2-fluoro-5-(trifluoromethyl)phenyl)-N4-(5-methyl-1H-pyrazol-3-yl)pyrimidine-2,4-diamine | ESMS m/z 498.2 (M + H$^+$) | 0.102 |
| 241 | 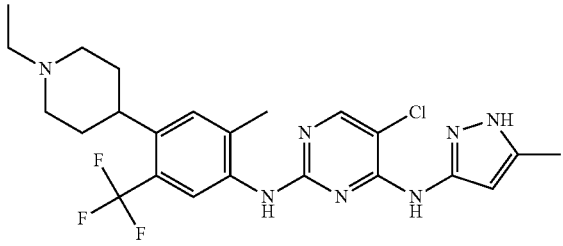 [SMILES: CCN1CCC(c2cc(C)c(Nc3ncc(Cl)c(Nc4cc(C)[nH]n4)n3)cc2C(F)(F)F)CC1]<br>5-chloro-N2-(4-(1-ethylpiperidin-4-yl)-2-methyl-5-(trifluoromethyl)phenyl)-N4-(5-methyl-1H-pyrazol-3-yl)pyrimidine-2,4-diamine | ESMS m/z 494.2 (M + H$^+$) | 0.068 |
| 242 | 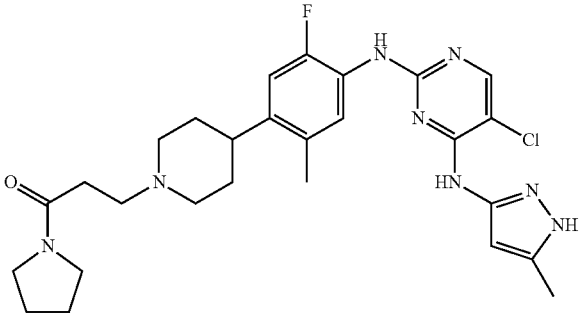 [SMILES: Cc1cc(Nc2nc(Nc3cc(C)c(C4CCN(CCC(=O)N5CCCC5)CC4)cc3F)ncc2Cl)n[nH]1]<br>3-(4-(4-(5-chloro-4-(5-methyl-1H-pyrazol-3-ylamino)pyrimidin-2-ylamino)-5-fluoro-2-methylphenyl)piperidin-1-yl)-1-(pyrrolidin-1-yl)propan-1-one | ESMS m/z 541.3 (M + H$^+$) | 0.06 |

TABLE 1-continued

| | STRUCTURE | NMR or ESMS | IGF-1R Ba/F3 IC50 (uM) |
|---|---|---|---|
| 243 | N2-(4-(1-(3-(azetidin-1-ylsulfonyl)propyl)piperidin-4-yl)-2-fluoro-5-methylphenyl)-5-chloro-N4-(5-methyl-1H-pyrazol-3-yl)pyrimidine-2,4-diamine | ESMS m/z 577.2 (M + H$^+$) | 0.076 |
| 244 | 5-chloro-N2-(2-fluoro-5-methyl-4-(1-(3-(pyrrolidin-1-ylsulfonyl)propyl)piperidin-4-yl)phenyl)-N4-(5-methyl-1H-pyrazol-3-yl)pyrimidine-2,4-diamine | ESMS m/z 591.2 (M + H$^+$) | 0.084 |
| 245 | 5-chloro-N2-(2-fluoro-5-methyl-4-(1-(3-(morpholinosulfonyl)propyl)piperidin-4-yl)phenyl)-N4-(5-methyl-1H-pyrazol-3-yl)pyrimidine-2,4-diamine | ESMS m/z 607.2 (M + H$^+$) | 0.077 |

TABLE 1-continued

| | STRUCTURE | NMR or ESMS | IGF-1R Ba/F3 IC50 (uM) |
|---|---|---|---|
| 246 | 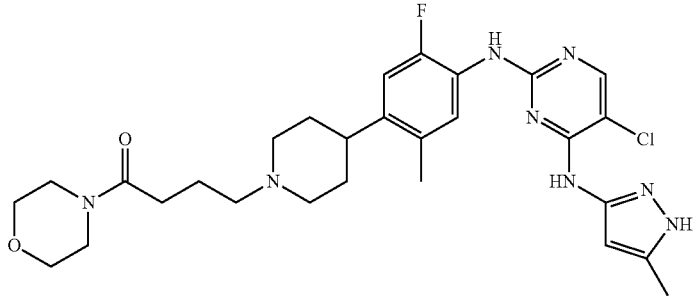 [SMILES: Cc1cc(Nc2nc(Nc3cc(C)c(C4CCN(CCCC(=O)N5CCOCC5)CC4)cc3F)ncc2Cl)n[nH]1]<br>4-(4-(4-(5-chloro-4-(5-methyl-1H-pyrazol-3-ylamino)pyrimidin-2-ylamino)-5-fluoro-2-methylphenyl)piperidin-1-yl)-1-morpholinobutan-1-one | ESMS m/z 571.3 (M + H$^+$) | 0.058 |
| 247 | 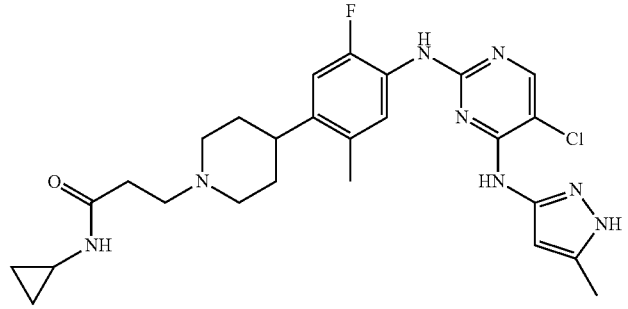 [SMILES: Cc1cc(Nc2nc(Nc3cc(C)c(C4CCN(CCC(=O)NC5CC5)CC4)cc3F)ncc2Cl)n[nH]1]<br>3-(4-(4-(5-chloro-4-(5-methyl-1H-pyrazol-3-ylamino)pyrimidin-2-ylamino)-5-fluoro-2-methylphenyl)piperidin-1-yl)-N-cyclopropylpropanamide | ESMS m/z 527.2 (M + H$^+$) | 0.062 |
| 248 | 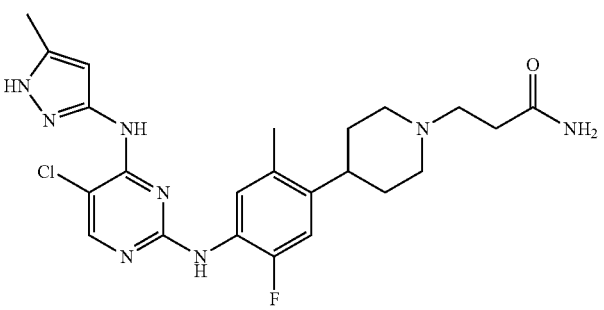 [SMILES: Cc1cc(Nc2nc(Nc3cc(C)c(C4CCN(CCC(N)=O)CC4)cc3F)ncc2Cl)n[nH]1]<br>3-(4-(4-(5-chloro-4-(5-methyl-1H-pyrazol-3-ylamino)pyrimidin-2-ylamino)-5-fluoro-2-methylphenyl)piperidin-1-yl)propanamide | ESMS m/z 487.2 (M + H$^+$) | 0.14 |

TABLE 1-continued

| | STRUCTURE | NMR or ESMS | IGF-1R Ba/F3 IC50 (uM) |
|---|---|---|---|
| 249 | 5-chloro-N2-(4-(1-((2,2-difluorocyclopropyl)methyl)piperidin-4-yl)-2,5-dimethylphenyl)-N4-(5-methyl-1H-pyrazol-3-yl)pyrimidine-2,4-diamine | ESMS m/z 502.2 (M + H⁺) | 0.032 |
| 250 | 5-chloro-N2-(4-(1-cyclopropylpiperidin-4-yl)-2,5-dimethylphenyl)-N4-(5-methyl-1H-pyrazol-3-yl)pyrimidine-2,4-diamine | ESMS m/z 452.2 (M + H⁺) | 0.025 |
| 251 | N2-(4-(1-((2,2-difluorocyclopropyl)methyl)piperidin-4-yl)-2-fluoro-5-methylphenyl)-N4-(5-methyl-1H-pyrazol-3-yl)-5-(trifluoromethyl)pyrimidine-2,4-diamine | ESMS m/z 540.2 (M + H⁺) | 0.052 |

TABLE 1-continued

| | STRUCTURE | NMR or ESMS | IGF-1R Ba/F3 IC50 (uM) |
|---|---|---|---|
| 252 | 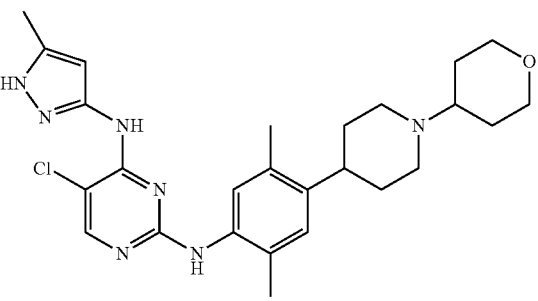 [SMILES: Cc1cc(Nc2nc(Nc3cc(C)c(C4CCN(C5CCOCC5)CC4)cc3C)ncc2Cl)n[nH]1]<br>5-chloro-N2-(2,5-dimethyl-4-(1-(tetrahydro-2H-pyran-4-yl)piperidin-4-yl)phenyl)-N4-(5-methyl-1H-pyrazol-3-yl)pyrimidine-2,4-diamine | ESMS m/z 496.3 (M + H⁺) | 0.014 |
| 253 | 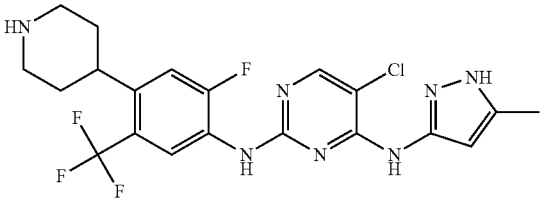<br>5-chloro-N2-(2-fluoro-4-(piperidin-4-yl)-5-(trifluoromethyl)phenyl)-N4-(5-methyl-1H-pyrazol-3-yl)pyrimidine-2,4-diamine | ESMS m/z 470.1 (M + H⁺) | 0.075 |
| 254 | 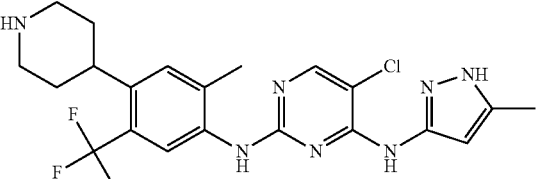<br>5-chloro-N4-(5-methyl-1H-pyrazol-3-yl)-N2-(2-methyl-4-(piperidin-4-yl)-5-(trifluoromethyl)phenyl)pyrimidine-2,4-diamine | ESMS m/z 466.2 (M + H⁺) | 0.07 |
| 255 | 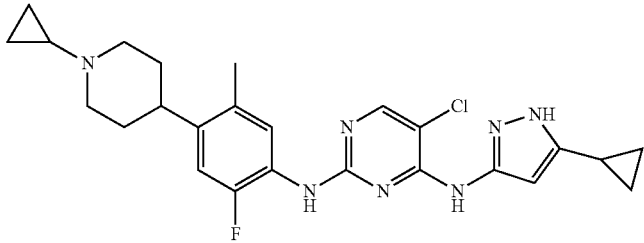 [SMILES: Cc1cc(Nc2ncc(Cl)c(Nc3cc(C4CC4)[nH]n3)n2)c(F)cc1C1CCN(C2CC2)CC1]<br>5-chloro-N4-(5-cyclopropyl-1H-pyrazol-3-yl)-N2-(4-(1-cyclopropylpiperidin-4-yl)-2-fluoro-5-methylphenyl)pyrimidine-2,4-diamine | ESMS m/z 482.2 (M + H⁺) | 0.228 |

TABLE 1-continued

| | STRUCTURE | NMR or ESMS | IGF-1R Ba/F3 IC50 (uM) |
|---|---|---|---|
| 256 | 5-chloro-N2-(2,5-dimethyl-4-(piperidin-4-yl)phenyl)-N4-(5-methyl-1H-pyrazol-3-yl)pyrimidine-2,4-diamine | ESMS m/z 412.2 (M + H$^+$) | 0.044 |
| 257 | N2-(2,5-dimethyl-4-(piperidin-4-yl)phenyl)-N4-(5-methyl-1H-pyrazol-3-yl)-5-(trifluoromethyl)pyrimidine-2,4-diamine | ESMS m/z 446.2 (M + H$^+$) | 0.064 |
| 258 | 5-chloro-N4-(5-cyclopropyl-1H-pyrazol-3-yl)-N2-(4-(1-cyclopropylpiperidin-4-yl)-2,5-dimethylphenyl)pyrimidine-2,4-diamine | ESMS m/z 478.2 (M + H$^+$) | 0.026 |
| 259 | 5-chloro-N2-(2-fluoro-4-(1-((3-isopropyl-1,2,4-oxadiazol-5-yl)methyl)piperidin-4-yl)-5-methylphenyl)-N4-(5-methyl-1H-pyrazol-3-yl)pyrimidine-2,4-diamine | ESMS m/z 540.2 (M + H$^+$) | 0.064 |

| | STRUCTURE | NMR or ESMS | IGF-1R Ba/F3 IC50 (uM) |
|---|---|---|---|
| 260 | 5-chloro-N2-(4-(1-((3-isopropyl-1,2,4-oxadiazol-5-yl)methyl)piperidin-4-yl)-2,5-dimethylphenyl)-N4-(5-methyl-1H-pyrazol-3-yl)pyrimidine-2,4-diamine | ESMS m/z 536.3 (M + H⁺) | 0.018 |
| 261 | 2-(4-(4-(5-chloro-4-(5-methyl-1H-pyrazol-3-ylamino)pyrimidin-2-ylamino)-2-ethyl-5-methylphenyl)piperidin-1-yl)acetamide | ESMS m/z 483.2 (M + H⁺) | 0.027 |
| 262 | 2-(4-(4-(5-chloro-4-(5-methyl-1H-pyrazol-3-ylamino)pyrimidin-2-ylamino)-2-methoxy-5-methylphenyl)piperidin-1-yl)acetamide | ESMS m/z 485.2 (M + H⁺) | 0.019 |

TABLE 1-continued

| | STRUCTURE | NMR or ESMS | IGF-1R Ba/F3 IC50 (uM) |
|---|---|---|---|
| 263 | 2-(4-(4-(5-chloro-4-(5-ethyl-1H-pyrazol-3-ylamino)pyrimidin-2-ylamino)-5-fluoro-2-methylphenyl)piperidin-1-yl)acetamide | ESMS m/z 487.2 (M + H$^+$) | 0.033 |
| 264 | 5-Chloro-N2-{4-[1-(1,1-dioxo-1λ6-thietan-3-yl)-piperidin-4-yl]-2-fluoro-5-methyl-phenyl}-N4-(5-ethyl-1H-pyrazol-3-yl)-pyrimidine-2,4-diamine | ESMS m/z 534.2 (M + H$^+$) | 0.021 |
| 265 | (4-(4-(5-chloro-4-(5-methyl-1H-pyrazol-3-ylamino)pyrimidin-2-ylamino)-5-fluoro-2-methylphenyl)piperidin-1-yl)(3-isopropyl-1,2,4-oxadiazol-5-yl)methanone | ESMS m/z 554.2 (M + H$^+$); $^1$H NMR (400 MHz, CDCl$_3$) δ 9.67 (br s, 2H), 8.50 (s, 1H), 8.07 (s, 1H), 7.57 (d, J = 8.4 Hz, 1H), 7.05 (d, J = 12.4 Hz, 1H), 6.16 (s, 1H), 5.53 (s, 1H), 3.98 (d, J = 13.2 Hz, 1H), 3.34 (dt, J = 2.0, 2.8 Hz, 1H), 3.15 (m, 1H), 2.82 (m, 2H), 2.62 (t, J = 4.8 Hz, 2H), 2.34 (s, 3H), 2.25 9s, 3H), 1.90 (m, 2H, 1.76 (2H) | 0.091 |

TABLE 1-continued

| | STRUCTURE | NMR or ESMS | IGF-1R Ba/F3 IC50 (uM) |
|---|---|---|---|
| 266 | N2-(4-(1-((5-tert-butyl-1,2,4-oxadiazol-3-yl)methyl)piperidin-4-yl)-2,5-dimethylphenyl)-5-chloro-N4-(5-methyl-1H-pyrazol-3-yl)pyrimidine-2,4-diamine | ESMS m/z 550.3 (M + H$^+$) | 0.025 |
| 267 | N2-(4-(1-((5-tert-butyl-1,2,4-oxadiazol-3-yl)methyl)piperidin-4-yl)-2-fluoro-5-methylphenyl)-5-chloro-N4-(5-methyl-1H-pyrazol-3-yl)pyrimidine-2,4-diamine | ESMS m/z 554.3 (M + H$^+$) | 0.077 |
| 268 | 5-chloro-N4-(5-ethyl-1H-pyrazol-3-yl)-N2-(4-(1-ethylpiperidin-4-yl)-2-fluoro-5-methylphenyl)pyrimidine-2,4-diamine | ESMS m/z 458.2 (M + H$^+$) | 0.022 |

TABLE 1-continued

| | STRUCTURE | NMR or ESMS | IGF-1R Ba/F3 IC50 (uM) |
|---|---|---|---|
| 269 | 5-chloro-N2-(4-(1-(2-(3-isopropyl-1,2,4-oxadiazol-5-yl)ethyl)piperidin-4-yl)-2,5-dimethylphenyl)-N4-(5-methyl-1H-pyrazol-3-yl)pyrimidine-2,4-diamine | ESMS m/z 550.3 (M + H+) | 0.039 |
| 270 | (4-(4-(5-chloro-4-(5-methyl-1H-pyrazol-3-ylamino)pyrimidin-2-ylamino)-2,5-dimethylphenyl)piperidin-1-yl)(3-isopropyl-1,2,4-oxadiazol-5-yl)methanone | ESMS m/z 550.2 (M + H+) | 0.018 |
| 271 | 5-chloro-N4-(5-ethyl-1H-pyrazol-3-yl)-N2-(2-fluoro-5-methyl-4-(1-methylpiperidin-4-yl)phenyl)pyrimidine-2,4-diamine | ESMS m/z 444.2 (M + H+) | 0.013 |

TABLE 1-continued

| | STRUCTURE | NMR or ESMS | IGF-1R Ba/F3 IC50 (uM) |
|---|---|---|---|
| 272 | 5-chloro-N2-(4-(1-cyclobutylpiperidin-4-yl)-2-fluoro-5-methylphenyl)-N4-(5-methyl-1H-pyrazol-3-yl)pyrimidine-2,4-diamine | ESMS m/z 470.2 (M + H$^+$) | 0.050 |
| 273 | 5-chloro-N2-(2-fluoro-5-methyl-4-(2-methylpiperidin-4-yl)phenyl)-N4-(5-methyl-1H-pyrazol-3-yl)pyrimidine-2,4-diamine | ESMS m/z 430.2 (M + H$^+$) | 0.018 |
| 274 | 2-(4-(4-(5-chloro-4-(5-methyl-1H-pyrazol-3-ylamino)pyrimidin-2-ylamino)-5-fluoro-2-methylphenyl)-2-methylpiperidin-1-yl)acetamide | ESMS m/z 487.2 (M + H$^+$) | 0.006 |
| 275 | 5-chloro-N2-(4-(1,2-dimethylpiperidin-4-yl)-2-fluoro-5-methylphenyl)-N4-(5-methyl-1H-pyrazol-3-yl)pyrimidine-2,4-diamine | ESMS m/z 444.2 (M + H$^+$) | 0.009 |

//

TABLE 1-continued

| | STRUCTURE | NMR or ESMS | IGF-1R Ba/F3 IC50 (uM) |
|---|---|---|---|
| 276 | 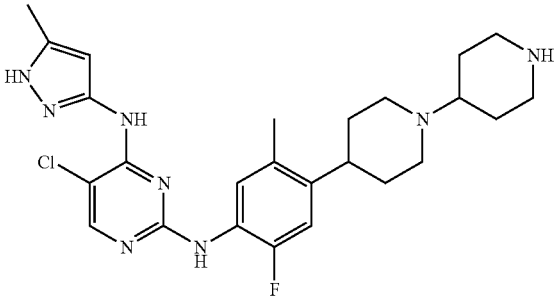 [SMILES: Cc1cc(Nc2nc(Nc3cc(C)c(C4CCN(C5CCNCC5)CC4)cc3F)ncc2Cl)n[nH]1]<br>N2-(4-(1,4'-bipiperidin-4-yl)-2-fluoro-5-methylphenyl)-5-chloro-N4-(5-methyl-1H-pyrazol-3-yl)pyrimidine-2,4-diamine | ESMS m/z 499.2 (M + H⁺) | 0.437 |
| 277 | 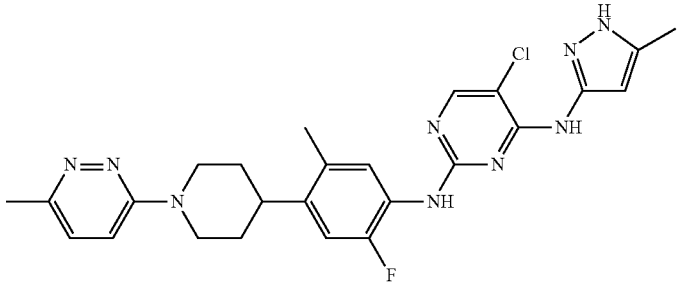<br>5-chloro-N2-(2-fluoro-5-methyl-4-(1-(6-methylpyridazin-3-yl)piperidin-4-yl)phenyl)-N4-(5-methyl-1H-pyrazol-3-yl)pyrimidine-2,4-diamine | ESMS m/z 508.2 (M + H⁺) | 0.097 |
| 278 | 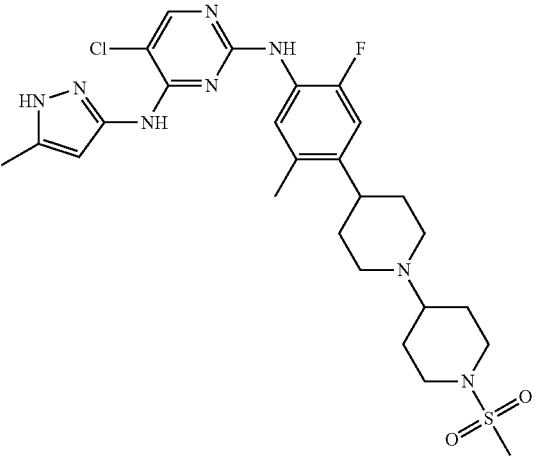 [SMILES: Cc1cc(Nc2nc(Nc3cc(C)c(C4CCN(C5CCN(S(C)(=O)=O)CC5)CC4)cc3F)ncc2Cl)n[nH]1]<br>5-chloro-N2-(2-fluoro-5-methyl-4-(1'-(methylsulfonyl)-1,4'-bipiperidin-4-yl)phenyl)-N4-(5-methyl-1H-pyrazol-3-yl)pyrimidine-2,4-diamine | ESMS m/z 577.2 (M + H⁺) | 0.009 |

TABLE 1-continued

| | STRUCTURE | NMR or ESMS | IGF-1R Ba/F3 IC50 (uM) |
|---|---|---|---|
| 279 | 5-chloro-N2-(2-fluoro-5-methyl-4-((trans)-2-methylpiperidin-4-yl)phenyl)-N4-(5-methyl-1H-pyrazol-3-yl)pyrimidine-2,4-diamine | ESMS m/z 430.2 (M + H+) | 0.064 |
| 280 | 5-chloro-N2-(2-fluoro-5-methyl-4-((cis)-2-methylpiperidin-4-yl)phenyl)-N4-(5-methyl-1H-pyrazol-3-yl)pyrimidine-2,4-diamine | ESMS m/z 430.2 (M + H+) | 0.163 |
| 281 | 5-chloro-N2-(2-fluoro-5-methyl-4-(1-(pyridin-2-ylmethyl)piperidin-4-yl)phenyl)-N4-(5-methyl-1H-pyrazol-3-yl)pyrimidine-2,4-diamine | ESMS m/z 507.2 (M + H+) | 0.087 |
| 282 | 3-(4-(4-(5-chloro-4-(5-methyl-1H-pyrazol-3-ylamino)pyrimidin-2-ylamino)-5-fluoro-2-methylphenyl)piperidin-1-yl)cyclopent-2-enone | ESMS m/z 496.2 (M + H+); $^1$H NMR (400 MHz, DMSO-d$_6$) δ 9.97 (br s, 1H), 9.83 (br s, 1H), 8.90 (s, 1H), 8.32 (d, J = 6.8 Hz, 1H), 7.88 (d, J = 12.8 Hz, 1H, 6.97 (s, 1H), 6.04 (s, 1H), 5.30 (br s, 1H), 4.71 (d, J= 12.0 Hz, 2H), 4.04 (t, J = 12.4 Hz, 2H), 3.84 (m, 1H), 3.53 (m, 2H), 3.13 (m, 2H), 3.08 (s, 3H), 2.96 (s, 3H), 2.59-2.40 (m, 4H) | 0.048 |

TABLE 1-continued

| | STRUCTURE | NMR or ESMS | IGF-1R Ba/F3 IC50 (uM) |
|---|---|---|---|
| 283 | 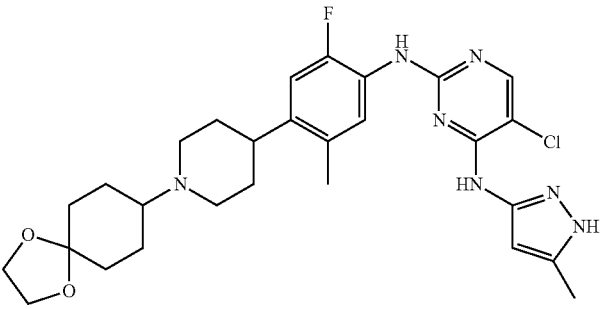 [SMILES: Cc1cc(Nc2nc(Nc3cc(C)c(C4CCN(C5CCC6(CC5)OCCO6)CC4)cc3F)ncc2Cl)n[nH]1]<br>N2-(4-(1-(1,4-dioxaspiro[4.5]decan-8-yl)piperidin-4-yl)-2-fluoro-5-methylphenyl)-5-chloro-N4-(5-methyl-1H-pyrazol-3-yl)pyrimidine-2,4-diamine | ESMS m/z 556.3 (M + H⁺) | 0.016 |
| 284 | 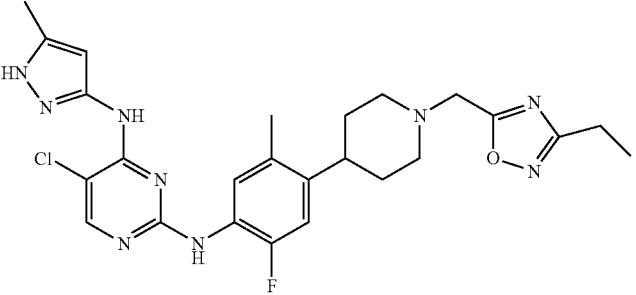 [SMILES: CCc1noc(CN2CCC(c3cc(F)c(Nc4ncc(Cl)c(Nc5cc(C)[nH]n5)n4)cc3C)CC2)n1]<br>5-chloro-N2-(4-(1-((3-ethyl-1,2,4-oxadiazol-5-yl)methyl)piperidin-4-yl)-2-fluoro-5-methylphenyl)-N4-(5-methyl-1H-pyrazol-3-yl)pyrimidine-2,4-diamine | ESMS m/z 526.2 (M + H⁺) | 0.033 |
| 285 | 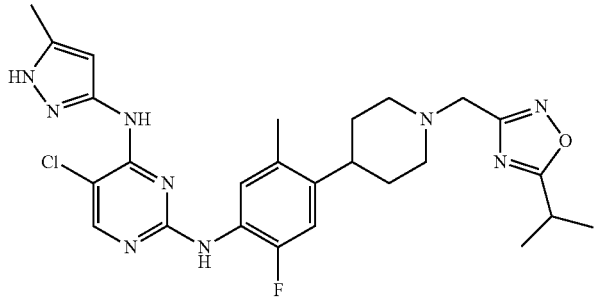 [SMILES: Cc1cc(Nc2nc(Nc3cc(C)c(C4CCN(Cc5noc(C(C)C)n5)CC4)cc3F)ncc2Cl)n[nH]1]<br>5-chloro-N2-(2-fluoro-4-(1-((5-isopropyl-1,2,4-oxadiazol-3-yl)methyl)piperidin-4-yl)-5-methylphenyl)-N4-(5-methyl-1H-pyrazol-3-yl)pyrimidine-2,4-diamine | ESMS m/z 540.2 (M + H⁺) | 0.068 |
| 286 | 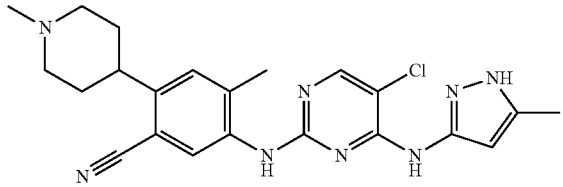<br>5-(5-chloro-4-(5-methyl-1H-pyrazol-3-ylamino)pyrimidin-2-ylamino)-4-methyl-2-(1-methylpiperidin-4-yl)benzonitrile | ESMS m/z 437.2 (M + H⁺) | 0.037 |

TABLE 1-continued

| | STRUCTURE | NMR or ESMS | IGF-1R Ba/F3 IC50 (uM) |
|---|---|---|---|
| 287 | methyl 5-(5-chloro-4-(5-methyl-1H-pyrazol-3-ylamino)pyrimidin-2-ylamino)-4-methyl-2-(1-methylpiperidin-4-yl)benzoate | ESMS m/z 470.2 (M + H$^+$) | 0.027 |
| 288 | 5-chloro-N2-(2-fluoro-5-methyl-4-(1-(pyridin-4-ylmethyl)piperidin-4-yl)phenyl)-N4-(5-methyl-1H-pyrazol-3-yl)pyrimidine-2,4-diamine | ESMS m/z 507.2 (M + H$^+$) | 0.093 |
| 289 | 4-(4-(5-chloro-4-(5-methyl-1H-pyrazol-3-ylamino)pyrimidin-2-ylamino)-5-fluoro-2-methylphenyl)-1-ethylpiperidine 1-oxide | ESMS m/z 460.2 (M + H$^+$); $^1$HNMR (MeOD-d$_4$) δ 7.91 (s, 1H), 7.69 (d, 1H), 7.00 (d, 1H), 6.15 (s, 1H), 3.28 (m, 4H), 2.91 (m, 1H), 2.32 (m, 2H), 2.20 (s, 3H), 2.16 (s, 3H), 1.83 (s, 2H), 1.64 (d, 2H), 1.31 (t, 3H). | 0.37 |

| | STRUCTURE | NMR or ESMS | IGF-1R Ba/F3 IC50 (uM) |
|---|---|---|---|
| 290 | 4-(4-(4-(5-chloro-4-(5-methyl-1H-pyrazol-3-ylamino)pyrimidin-2-ylamino)-5-fluoro-2-methylphenyl)piperidin-1-yl)cyclohexanone | ESMS m/z 512.2 (M + H$^+$) | 0.023 |
| 291 | tert-butyl 3-(4-(4-(5-chloro-4-(5-methyl-1H-pyrazol-3-ylamino)pyrimidin-2-ylamino)-5-fluoro-2-methylphenyl)piperidin-1-yl)pyrrolidine-1-carboxylate | ESMS m/z 585.3 (M + H$^+$) | 0.067 |
| 292 | 5-chloro-N2-(2-fluoro-5-methyl-4-(1-((5-methyl-1,2,4-oxadiazol-3-yl)methyl)piperidin-4-yl)phenyl)-N4-(5-methyl-1H-pyrazol-3-yl)pyrimidine-2,4-diamine | ESMS m/z 512.2 (M + H$^+$) | 0.023 |

TABLE 1-continued

| | STRUCTURE | NMR or ESMS | IGF-1R Ba/F3 IC50 (uM) |
|---|---|---|---|
| 293 | 5-chloro-N2-(2-fluoro-5-methyl-4-(1-((3-methyl-1,2,4-oxadiazol-5-yl)methyl)piperidin-4-yl)phenyl)-N4-(5-methyl-1H-pyrazol-3-yl)pyrimidine-2,4-diamine | ESMS m/z 512.2 (M + H$^+$) | 0.026 |
| 294 | 4-(4-(5-chloro-4-(5-methyl-1H-pyrazol-3-ylamino)pyrimidin-2-ylamino)-5-fluoro-2-methylphenyl)-1-(tetrahydro-2H-pyran-4-yl)piperidine 1-oxide | ESMS m/z 516.2 (M + H$^+$) | 0.064 |
| 295 | 5-Chloro-N2-{4-[1-(1,1-dioxo-1λ6-thietan-3-yl)-1-oxide-piperidin-4-yl]-2-fluoro-5-methyl-phenyl}-N4-(5-ethyl-1H-pyrazol-3-yl)-pyrimidine-2,4-diamine | ESMS m/z 536.2 (M + H$^+$) | 0.039 |

TABLE 1-continued

| | STRUCTURE | NMR or ESMS | IGF-1R Ba/F3 IC50 (uM) |
|---|---|---|---|
| 296 | 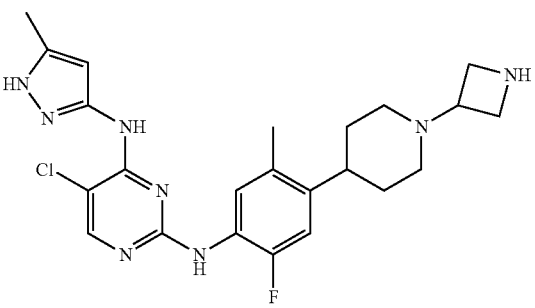 [SMILES: Cc1cc(Nc2nc(Nc3cc(C)c(C4CCN(C5CNC5)CC4)cc3F)ncc2Cl)n[nH]1] N2-(4-(1-(azetidin-3-yl)piperidin-4-yl)-2-fluoro-5-methylphenyl)-5-chloro-N4-(5-methyl-1H-pyrazol-3-yl)pyrimidine-2,4-diamine | ESMS m/z 471.2 (M + H⁺) | 0.101 |
| 297 | 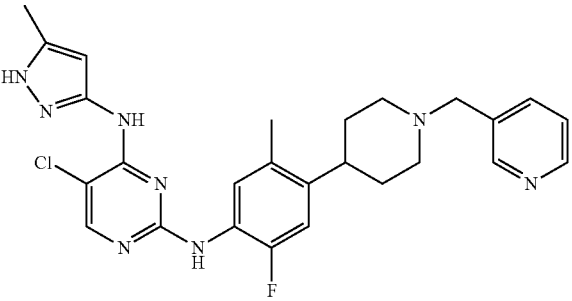 [SMILES: Cc1cc(Nc2nc(Nc3cc(C)c(C4CCN(Cc5cccnc5)CC4)cc3F)ncc2Cl)n[nH]1] 5-chloro-N2-(2-fluoro-5-methyl-4-(1-(pyridin-3-ylmethyl)piperidin-4-yl)phenyl)-N4-(5-methyl-1H-pyrazol-3-yl)pyrimidine-2,4-diamine | ESMS m/z 507.2 (M + H⁺) | 0.079 |
| 298 | 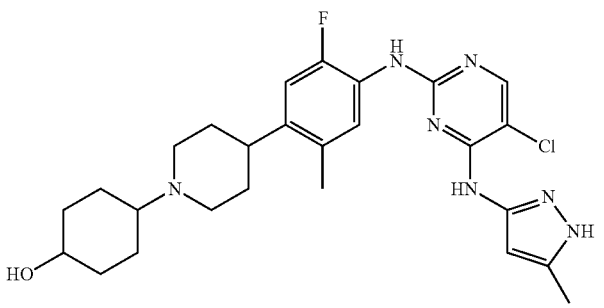 [SMILES: Cc1cc(Nc2nc(Nc3cc(C)c(C4CCN(C5CCC(O)CC5)CC4)cc3F)ncc2Cl)n[nH]1] 4-(4-(4-(5-chloro-4-(5-methyl-1H-pyrazol-3-ylamino)pyrimidin-2-ylamino)-5-fluoro-2-methylphenyl)piperidin-1-yl)cyclohexanol | ESMS m/z 514.2 (M + H⁺) | 0.026 |

TABLE 1-continued
| | STRUCTURE | NMR or ESMS | IGF-1R Ba/F3 IC50 (uM) |
|---|---|---|---|
| 299 | 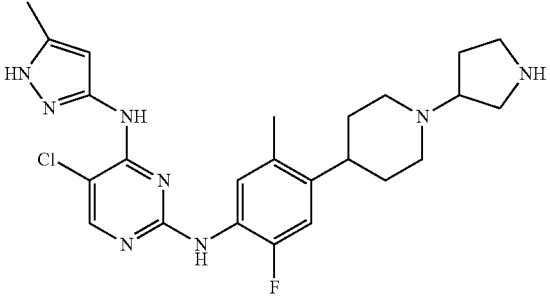 [SMILES: Cc1cc(Nc2nc(Nc3cc(C)c(C4CCN(C5CCNC5)CC4)cc3F)ncc2Cl)n[nH]1]<br>5-chloro-N2-(2-fluoro-5-methyl-4-(1-(pyrrolidin-3-yl)piperidin-4-yl)phenyl)-N4-(5-methyl-1H-pyrazol-3-yl)pyrimidine-2,4-diamine | ESMS m/z 485.2 (M + H$^+$) | 0.101 |
| 300 | 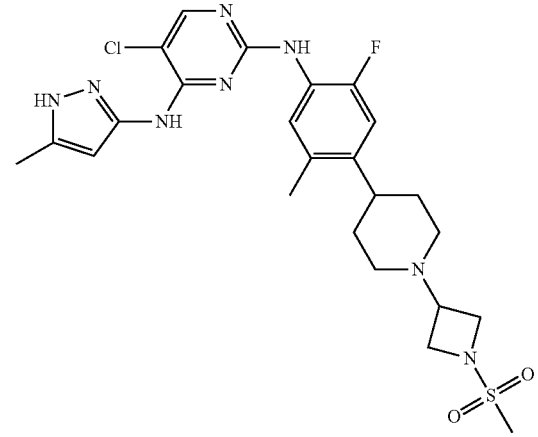<br>5-chloro-N2-(2-fluoro-5-methyl-4-(1-(1-(methylsulfonyl)azetidin-3-yl)piperidin-4-yl)phenyl)-N4-(5-methyl-1H-pyrazol-3-yl)pyrimidine-2,4-diamine | ESMS m/z 549.2 (M + H$^+$) | 0.032 |

TABLE 1-continued

| | STRUCTURE | NMR or ESMS | IGF-1R Ba/F3 IC50 (uM) |
|---|---|---|---|
| 301 | 5-chloro-N2-(2-fluoro-5-methyl-4-(1-(1-(methylsulfonyl)pyrrolidin-3-yl)piperidin-4-yl)phenyl)-N4-(5-methyl-1H-pyrazol-3-yl)pyrimidine-2,4-diamine | ESMS m/z 563.2 (M + H$^+$) | 0.038 |
| 302 | 5-chloro-N2-(2,5-dimethyl-4-(1-((3-methyl-1,2,4-oxadiazol-5-yl)methyl)piperidin-4-yl)phenyl)-N4-(5-methyl-1H-pyrazol-3-yl)pyrimidine-2,4-diamine | ESMS m/z 508.2 (M + H$^+$) | 0.006 |
| 303 | 5-chloro-N2-(4-(1-((3-ethyl-1,2,4-oxadiazol-5-yl)methyl)piperidin-4-yl)-2,5-dimethylphenyl)-N4-(5-methyl-1H-pyrazol-3-yl)pyrimidine-2,4-diamine | ESMS m/z 522.2 (M + H$^+$) | 0.006 |

TABLE 1-continued

| | STRUCTURE | NMR or ESMS | IGF-1R Ba/F3 IC50 (uM) |
|---|---|---|---|
| 304 | 5-chloro-N2-(2,5-dimethyl-4-(1-((5-methyl-1,2,4-oxadiazol-3-yl)methyl)piperidin-4-yl)phenyl)-N4-(5-methyl-1H-pyrazol-3-yl)pyrimidine-2,4-diamine | ESMS m/z 508.2 (M + H+) | 0.005 |
| 305 | 5-chloro-N2-(4-(1-((5-isopropyl-1,2,4-oxadiazol-3-yl)methyl)piperidin-4-yl)-2,5-dimethylphenyl)-N4-(5-methyl-1H-pyrazol-3-yl)pyrimidine-2,4-diamine | ESMS m/z 536.3 (M + H+) | 0.025 |
| 306 | 5-chloro-N2-(2-fluoro-5-methyl-4-(1-(oxetan-3-yl)piperidin-4-yl)phenyl)-N4-(5-methyl-1H-pyrazol-3-yl)pyrimidine-2,4-diamine | ESMS m/z 472.2 (M + H+) | 0.015 |

TABLE 1-continued

| | STRUCTURE | NMR or ESMS | IGF-1R Ba/F3 IC50 (uM) |
|---|---|---|---|
| 307 | 5-chloro-N2-(2,5-dimethyl-4-(1-(pyridin-2-ylmethyl)piperidin-4-yl)phenyl)-N4-(5-methyl-1H-pyrazol-3-yl)pyrimidine-2,4-diamine | ESMS m/z 503.2 (M + H+) | 0.007 |
| 308 | 5-chloro-N2-(2,5-dimethyl-4-(1-(pyridin-3-ylmethyl)piperidin-4-yl)phenyl)-N4-(5-methyl-1H-pyrazol-3-yl)pyrimidine-2,4-diamine | ESMS m/z 503.2 (M + H+) | 0.006 |
| 309 | 5-chloro-N2-(2,5-dimethyl-4-(1-(pyridin-4-ylmethyl)piperidin-4-yl)phenyl)-N4-(5-methyl-1H-pyrazol-3-yl)pyrimidine-2,4-diamine | ESMS m/z 503.2 (M + H+) | 0.008 |
| 310 | Trans-4-(4-(4-(5-chloro-4-(5-methyl-1H-pyrazol-3-ylamino)pyrimidin-2-ylamino)-5-fluoro-2-methylphenyl)piperidin-1-yl)cyclohexanol | ESMS m/z 514.2 (M + H+) | 0.027 |

TABLE 1-continued

| | STRUCTURE | NMR or ESMS | IGF-1R Ba/F3 IC50 (uM) |
|---|---|---|---|
| 311 | Cis-4-(4-(4-(5-chloro-4-(5-methyl-1H-pyrazol-3-ylamino)pyrimidin-2-ylamino)-5-fluoro-2-methylphenyl)piperidin-1-yl)cyclohexanol | ESMS m/z 514.2 (M + H$^+$) | 0.021 |
| 312 | (R)-5-chloro-N2-(2-fluoro-5-methyl-4-(1-(1-(methylsulfonyl)pyrrolidin-3-yl)piperidin-4-yl)phenyl)-N4-(5-methyl-1H-pyrazol-3-yl)pyrimidine-2,4-diamine | ESMS m/z 563.2 (M + H+) | 0.025 |
| 313 | (S)-5-chloro-N2-(2-fluoro-5-methyl-4-(1-(1-(methylsulfonyl)pyrrolidin-3-yl)piperidin-4-yl)phenyl)-N4-(5-methyl-1H-pyrazol-3-yl)pyrimidine-2,4-diamine | ESMS m/z 563.2 (M + H$^+$) | 0.030 |
| 314 | 5-chloro-N2-(2-fluoro-5-methyl-4-(1-(pyrimidin-5-ylmethyl)piperidin-4-yl)phenyl)-N4-(5-methyl-1H-pyrazol-3-yl)pyrimidine-2,4-diamine | ESMS m/z 508.2 (M + H$^+$); $^1$H NMR (400 MHz, CD$_3$OD) δ 9.09 (s, 1H), 8.81 (s, 2H), 8.00 (s, 1H), 7.73 (d, J = 8.4 Hz, 1H), 6.99 (d, J = 13.2 Hz, 1H), 6.23 (br s, 1H), 3.65 (s, 2H), 3.03 (m, 2H), 2.76 (m, 1H), 2.27 (s, 3H), 2.25 (s, 3H), 2.25 (m, 2H), 1.80-1.68 (m, 4H) | 0.037 |

TABLE 1-continued

| | STRUCTURE | NMR or ESMS | IGF-1R Ba/F3 IC50 (uM) |
|---|---|---|---|
| 315 | 5-chloro-N2-(2-fluoro-5-methyl-4-(1-(pyrazin-2-ylmethyl)piperidin-4-yl)phenyl)-N4-(5-methyl-1H-pyrazol-3-yl)pyrimidine-2,4-diamine | ESMS m/z 508.2 (M + H$^+$) | 0.036 |
| 316 | 5-chloro-N2-(2-fluoro-5-methyl-4-(1-(pyridazin-4-ylmethyl)piperidin-4-yl)phenyl)-N4-(5-methyl-1H-pyrazol-3-yl)pyrimidine-2,4-diamine | ESMS m/z 508.2 (M + H$^+$) | 0.027 |
| 317 | 5-chloro-N2-(2,5-dimethyl-4-(1-(pyrimidin-5-ylmethyl)piperidin-4-yl)phenyl)-N4-(5-methyl-1H-pyrazol-3-yl)pyrimidine-2,4-diamine | ESMS m/z 504.2 (M + H$^+$) | 0.004 |

TABLE 1-continued

| | STRUCTURE | NMR or ESMS | IGF-1R Ba/F3 IC50 (uM) |
|---|---|---|---|
| 318 | 5-chloro-N2-(2,5-dimethyl-4-(1-(pyrazin-2-ylmethyl)piperidin-4-yl)phenyl)-N4-(5-methyl-1H-pyrazol-3-yl)pyrimidine-2,4-diamine | ESMS m/z 504.2 (M + H⁺) | 0.010 |

Assays

The $IC_{50}$ of a drug may be determined constructing a dose-response curve and examining the effect of different concentrations of antagonist on reversing agonist activity. $IC_{50}$ values may be calculated for a given antagonist by determining the concentration needed to inhibit half of the maximum biological response of the agonist. To calculate $IC_{50}$ values, a series of dose-response data (e.g., drug concentrations x1, x2, ..., xn and growth inhibition y1, y2, ..., yn, the values of y are in the range of 0-1) is generated. $IC_{50}$ values may be determined by a computer-aided system using the formula:

$$y = D + ((A-D)/(1+10^{(x-\log(IC50)B)}))$$

where A is the ratio of growth inhibition between lowest drug concentration and control; B is the slope of sigmoidal curvel; and D is the ratio of growth inhibition between highest drug concentration and control.

The $IC_{50}$ value is given as that concentration of the test compound that results in growth inhibition that is 50% lower than that obtained using the control without inhibitor. The compounds of the invention in free form or in pharmaceutically acceptable salt form may exhibit valuable pharmacological properties, for example, as indicated by the in vitro tests described in this application. In general, compounds of the invention have $IC_{50}$ values from 1 nM to 10 µM. In some examples, compounds of the invention have $IC_{50}$ values from 0.01 µM to 5 µM. In other examples, compounds of the invention have $IC_{50}$ values from 0.01 µM to 1 µM, or more particularly from 1 nM to 1 µM. In yet other examples, compounds of the invention have $IC_{50}$ values of less than 1 nM or more than 10 µM. The compounds of the invention may exhibit a percentage inhibition of greater than 50%, or in other embodiments, may exhibit a percentage inhibition greater than about 70%, against IGF-1R at 10 µM.

Ba/F3 Cell Line Panel and Reagents

Ba/F3 is a murine IL-3-dependent pro-B lymphoma cell line. Parental Ba/F3 cells are used to generate a panel of sublines whose proliferation and survival is rendered IL-3-independent by stable transduction with individual tyrosine kinases activated by fusion with the amino-terminal portion of TEL (amino acid 1-375) or BCR. In order to generate Ba/F3 cell lines transformed by Tel-Tyrosine Kinase (TK) fusions, parental Ba/F3 cells are infected with a retrovirus harboring each TEL-fusion kinase and subjected to puromycin selection and IL-3 withdrawal to obtain IL-3-independent, transformed Ba/F3 cells.

Each transformed Ba/F3 cells are cultured in RPMI-1640 media (Gibco Cat #11875093, Carlsbad, Calif.) supplemented with 10% FBS (Hyclone Cat #SV30014.03, Logan, Utah), 4.5 g/L glucose (Sigma #G5400, St. Louis, Mo.), 1.5 g/L sodium bicarbonate (Biowhittaker #17-613E, Walkersville, Md.) and Pen/Strep (Gibco #10378-016, Carlsbad, Calif.). Cells are splitted twice weekly.

Ba/F3 Cell Viability Inhibition Assay

The potency of test compounds against various Tel-TK transformed Ba/F3 lines is determined as follows. Exponentially growing BaF3 Tel-TK cells are diluted in fresh medium to 75,000 cells/mL and seeded into 384-well plates (3750 cells/well) at 50 µL/well using a µFill liquid dispenser (BioTek, Winooski, Vt., USA). Duplicate plates are run for each cell line. Test and control compounds are serially diluted with DMSO and arrayed in a polypropylene 384-well plate. 50 mL of compound is transferred into the assay plates using a pin-transfer device, and the plates are incubated at 37° C. (5% $CO_2$) for 48 hours. 25 µL Britelite (Perkin Elmer) is added and luminescence is quantified using Analyst GT (Molecular Devices). Custom curve-fitting software is used to produce a logistic fit of percent cell viability as a function of the logarithm of inhibitor concentration. The $IC_{50}$ is interpolated as the concentration of compound needed to reduce cell viability to 50% of a DMSO control. Parental Ba/F3 cells that are maintained and cultured in presence of IL-3 (1 ng/ml in final) are diluted in fresh medium containing IL-3 (1 ng/ml in final) to 75,000 cells/mL following the same procedure as described above.

Enzymatic HTRF Assay

IGF-1R and INSR (insulin receptor) are purchased from Upstate. Following reagents are prepared in-house; 10× kinase buffer (KB) (200 mM Tris (pH 7.0), 100 mM $MgCl_2$, 30 mM $MnCl_2$, 50 nM $NaVO_4$), 10 mM ATP, 100 mg/ml BSA, 0.5 M EDTA, 4 M KF. Proxiplate-384 from Perkin-Elmer is used for set up assay. All the HTRF reagents including substrate (Biotin-poly-GT (61GT0BLB), Mab PT66-K, (61T66KLB), Streptavidin-XL$^{ent}$ (611SAXLB)) are purchased from CIS-US, Inc.

The substrate/ATP mix is prepared by adding ATP (final concentration, 3 µM) and biotinylated poly-GT (final concentration, 10 ng/µl) into 1×KB, and dispensed into Proxiplate- 384 at 5 µl/well using µFill (Bio-TEK). Serially diluted compounds (in DMSO) are transferred into plate using 50 mL pinhead. 5 µL of prepared Enzyme mix (enzyme (final concentration, 5 ng/µl), mixed with BSA and DTT in 1×KB) is added to initiate kinase reaction using µFill (Bio-TEK). Assay plate is incubated at room temperature for 2 hours. Detection mix is prepared by adding both Mab PT66-K and Streptavidin-XL$^{ent}$ into 0.5×KB solution containing KF (final concentration, 125 mM), EDTA (final concentration, 50 mM) and BSA (final concentration, 100 µg/ml) in. At the end of reaction, 10 µL of detection mix is added and incubated for 30 minutes at room temperature before measurement. HTRF signal is detected using Analyst-GT (molecular Devices).

Cancer Cell Proliferation Inhibition Assay

For luciferizing cancer cell line, each cell line is transduced by ampholytic retrovirus carrying both luciferase gene and puromycin-resistant gene whose expression is driven by LTR. Briefly, the retroviral vector pMSCV-Puro-Luc is transfected into Phoenix cell line using Fugene6 (Roche) according to manufacturer's instruction. Two days after transfection, supernatant containing virus is harvested and filtered with 0.2 µm filter. Harvested virus is used immediately or stored at −80°C. For infection, cultured cancer cells are harvested and plated ($5\times10^5$ cells/well in 1 ml medium) on 6-well tissue culture plate. For each well, 3 ml virus supernatant is added together with 400 µl FBS, 40 µl 1 M HEPES (pH8.0) and 4 µl of polybrene (10 g/ml, Specialty media). The plate is centrifuged down for 90 minutes at 2500 rpm for spin-infection and is transferred into an incubator for overnight infection. Next day, infected cell line is transferred into T-75 flask containing fresh medium and incubated for one day. Two days after infection, puromycin is added at the final concentration of 1 µg/ml to begin selection. Within 1-2 weeks, puromycin-resistant cell line is established after at least two subsequent splits and is preserved as luciferized stock.

Each cell line is harvested while in log phase growth by trypsinization and diluted in respective media to appropriate density prior to plating. Cells are dispensed using µFill (BioTeK) at 50 µl/well into white walled clear bottom plates (Greiner—custom for GNF). Cells are then placed in 37° C. incubator supplying 5% CO2 overnight. Compounds are transferred using 50 mL/well Pintool technology via Platemate (Matrix). Assay plates are then placed back into the incubator for 3 days. On the third day following compound transfer, BRITELITE® (Perkin Elmer, diluted according to manufacturer's suggestion) is added to assay plates and read on Analyst GT (Molecular Devices) or Envision (Perkin Elmer). Raw data is generated in RLU.

Tumor Activity of Exemplary Compounds

Three to $4\times10^6$ human neuroblastoma SK-N-MC cells resuspended in HBSS and mixed in 50% matrigel were injected subcutaneously (0.05 ml/mouse) into female nude (HsdNpa:athymic/nu) mice 10-12 weeks of age. Treatments were initiated when the mean tumor volumes were approximately 150-200 mm³. Body weights and tumor volumes were recorded three times a week. Tumor volumes were measured with calipers and determined according to the formula length×diameter²×π/6. In addition to presenting fractional changes of tumor volumes over the course of treatments, antitumor activity is expressed as T/C % (mean change of tumor volume of treated animals/mean change of tumor volume of control animals)×100. Efficacy of test compounds was determined by initiating oral dosing on day 19 post-cell injection following randomization of the mice so that each group has similar mean tumor size. Dosing with an appropriate schedule continued for 7 days based on the general health condition of the animals. All test compounds were formulated in NMP/PEG300 (10:90) and applied daily by gavage. Vehicle consisted of NMP/PEG300 (10:90). All application volumes were 5 ml/kg. The activity of exemplary compounds of the invention on tumor growth is shown in Tables 2-4.

TABLE 2

| Treatment | Tumor response | | | |
|---|---|---|---|---|
| | T/C (%) | Regr. (%) | Δ tumor volume (mean mm³ ± SEM) | Mean fold change in tumor growth |
| NMP/PEG300 (10/90) 5 ml/kg po q8/16 h | 100 | 0 | 334 ± 59 | 3.1 ± 0.3 |
| Test Compound 1 20 mg/kg, q8/16 h, po | 53 | — | 231 ± 145 | 2.1 ± 0.4 |
| Test Compound 1 40 mg/kg, q8/16 h, po | 35 | — | 107 ± 48* | 1.7 ± 0.2* |

TABLE 3

| Treatment | Tumor response | | | |
|---|---|---|---|---|
| | T/C (%) | Regr. (%) | Δ tumor volume mean mm³ ± SEM | Mean fold change in tumor growth |
| NMP/PEG300 (10/90) 5 ml/kg po q8/16 h | 100 | 0 | 334 ± 59 | 3.1 ± 0.3 |
| Test Compound 2 12.5 mg/kg, q8/16 h, po | 69 | — | 232 ± 103 | 2.5 ± 0.4 |
| Test Compound 2 25 mg/kg, q8/16 h, po | 22 | — | 42 ± 10* | 1.5 ± 0.2* |

TABLE 4

| Treatment | Tumor response | | | |
|---|---|---|---|---|
| | T/C (%) | Regr. (%) | Δ tumor volume (mean mm³ ± SEM) | Mean fold change in tumor growth |
| NMP/PEG300 (10/90) 5 ml/kg po q8/16 h | 100 | 0 | 334 ± 59 | 3.1 ± 0.3 |
| Test Compound 3 12.5 mg/kg, q8/16 h, po | 58 | — | 220 ± 67 | 2.2 ± 0.3 |
| Test Compound 3 25 mg/kg, q8/16 h, po | 26 | — | 102 ± 40* | 1.6 ± 0.3* |

*p < 0.05 vs. Vehicle controls - ANOVA on ranks and post hoc Dunnett's test.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A method for treating an IGF-1R-mediated condition in a mammal suffering therefrom, comprising administering to the mammal a therapeutically effective amount of a compound of Formula (3) or a pharmaceutically acceptable salt thereof, and optionally in combination with a second therapeutic agent;

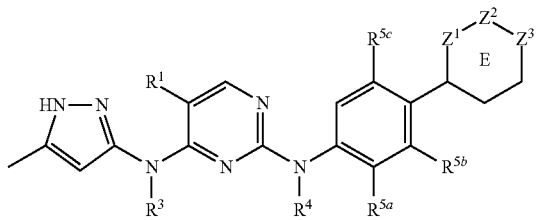

(3)

a pharmaceutically acceptable salt thereof, or a tautomer thereof;
wherein ring E may optionally contain a double bond;
wherein $R^{5b}$ is H; and $R^{5a}$ and $R^{5c}$ are independently halo, $C_{1-6}$ alkyl, $C_{1-6}$ alkoxy, halo-substituted $C_{1-6}$ alkyl, cyano or $C(O)O_{0-1}R^8$;
$Z^1$ and $Z^2$ are $CH_2$;
$Z^3$ is $NR^6$ or $N(R^6)^+$—$O^-$;
$R^1$ is halo or an optionally halogenated $C_{1-6}$ alkyl;
$R^3$ and $R^4$ are each H;
$R^6$ is a radical selected from formula (a), (b), (c) or (d):

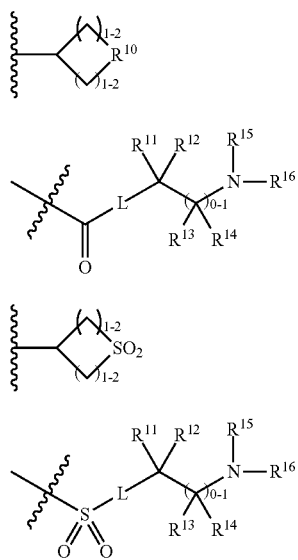

L is $(CR_2)_{1-4}$ or a bond; wherein R is independently H or $C_{1-6}$ alkyl;
$R^{10}$ is O, S, $NR^{17}$ wherein $R^{17}$ is H, $C_{1-6}$ alkyl, $SO_2R^{8a}$ or $CO_2R^{8a}$ and $R^{8a}$ is $C_{1-6}$ alkyl;
$R^{11}$, $R^{12}$, $R^{13}$, $R^{14}$, $R^{15}$ and $R^{16}$ are independently selected from H; $C_{1-6}$ alkoxy; $C_{1-6}$ alkyl, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the atoms to which they are attached may form a 3-7 membered saturated, unsaturated or partially unsaturated ring containing 1-3 heteroatoms selected from N, O and S, and optionally substituted with oxo and 1-3 $R^5$ groups;
wherein $R^5$ is halo, hydroxyl, $C_{1-6}$ alkyl, $C_{1-6}$ alkoxy, halo-substituted $C_{1-6}$ alkyl, halo-substituted $C_{1-6}$ alkoxy, cyano or $C(O)O_{0-1}R^8$; and
$R^8$ is $C_{1-6}$ alkyl;
wherein said condition is breast cancer or neuroblastoma.

2. The method of claim 1, wherein $R^{5a}$ is halo and $R^{5c}$ is $C_{1-6}$ alkyl.

3. The method of claim 1, wherein $R^6$ is a radical of formula (a) or (c); and $R^{10}$ is O.

4. The method of claim 1, wherein $R^1$ is halo.

5. The method of claim 1, wherein said compound is selected from the group

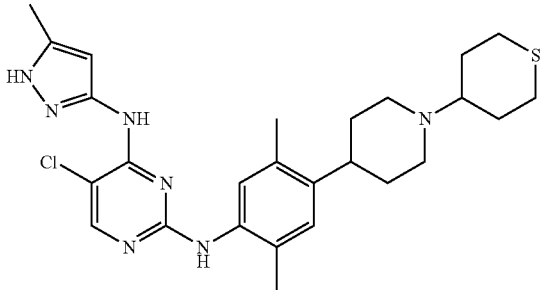

5-chloro-N2-(2,5-dimethyl-4-(1-(tetrahydro-2H-thiopyran-4-yl)piperidin-4-yl)phenyl)-N4-(5-methyl-1H-pyrazol-3-yl)pyrimidine-2,4-diamine

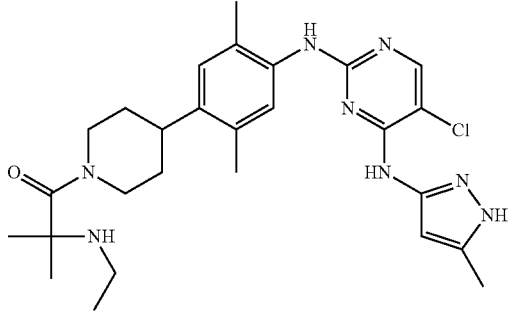

1-(4-(4-(5-chloro-4-(5-methyl-1H-pyrazol-3-ylamino)pyrimidin-2-ylamino)-2,5-dimethylphenyl)piperidin-1-yl)-2-(ethylamino)-2-methylpropan-1-one

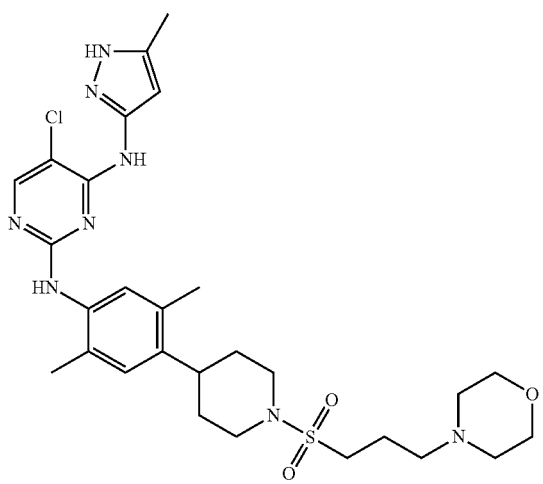

5-chloro-N2-(2,5-dimethyl-4-(1-(3-morpholinopropylsulfonyl)piperidin-4-yl)phenyl)-N4-(5-methyl-1H-pyrazol-3-yl)pyrimidine-2,4-diamine 267
-continued

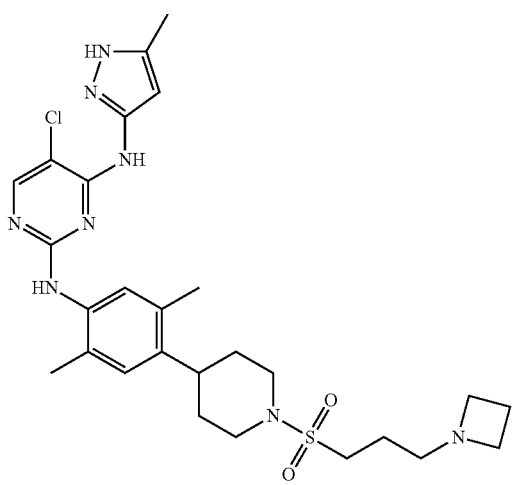

N2-(4-(1-(3-(azetidin-1-yl)propylsulfonyl)piperidin-4-yl)-2,5-dimethylphenyl)-5-chloro-N4-(5-methyl-1H-pyrazol-3-yl)pyrimidine-2,4-diamine

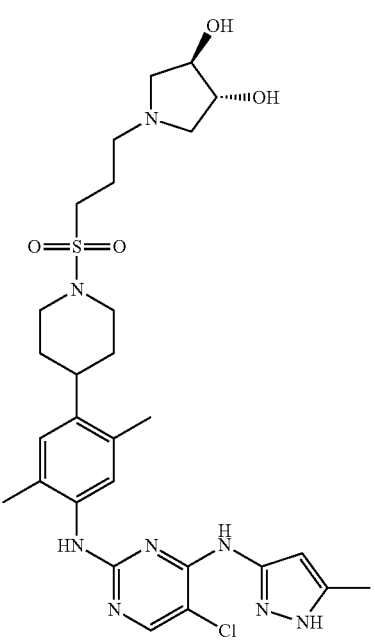

(3R,4R)-1-(3-(4-(4-(5-chloro-4-(5-methyl-1H-pyrazol-3-ylamino)pyrimidin-2-ylamino)-2,5-dimethylphenyl)piperidin-1-ylsulfonyl)propyl)pyrrolidine-3,4-diol 268
-continued

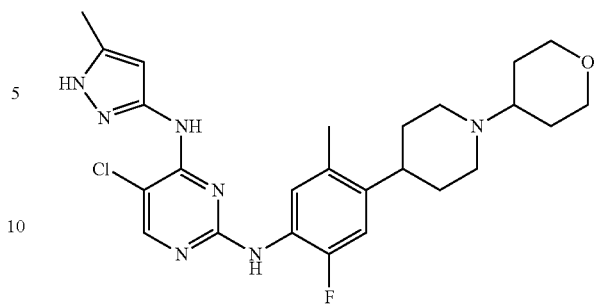

5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine

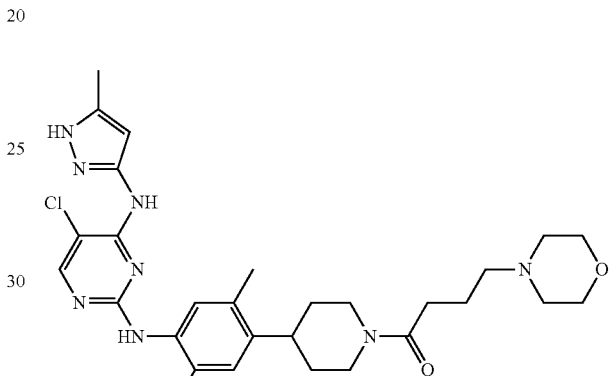

1-(4-(4-(5-chloro-4-(5-methyl-1H-pyrazol-3-ylamino)pyrimidin-2-ylamino)-2,5-dimethylphenyl)piperidin-1-yl)-4-morpholinobutan-1-one

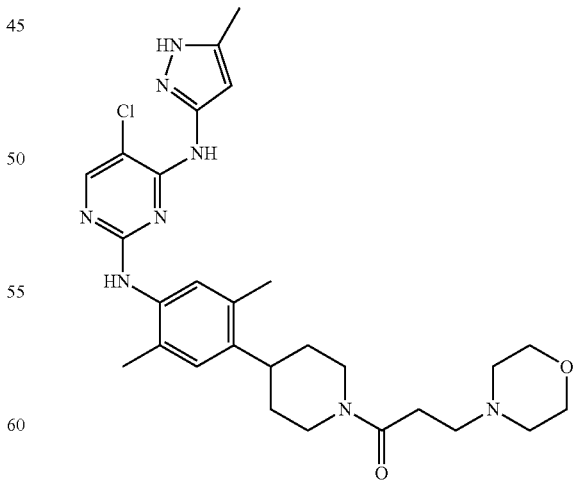

1-(4-(4-(5-chloro-4-(5-methyl-1H-pyrazol-3-ylamino)pyrimidin-2-ylamino)-2,5-dimethylphenyl)piperidin-1-yl)-3-morpholinopropan-1-one

269
-continued

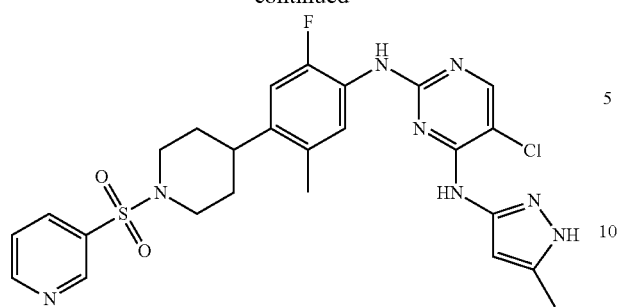

5-chloro-N2-(2-fluoro-5-methyl-4-(1-(pyridin-3-ylsulfonyl)piperidin-4-yl)phenyl)-N4-(5-methyl-1H-pyrazol-3-yl)pyrimidine-2,4-diamine

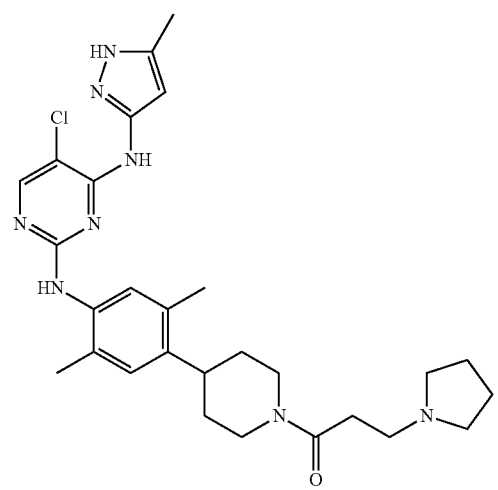

1-(4-(4-(5-chloro-4-(5-methyl-1H-pyrazol-3-ylamino)pyrimidin-2-ylamino)-2,5-dimethylphenyl)piperidin-1-yl)-3-(pyrrolidin-1-yl)propan-1-one

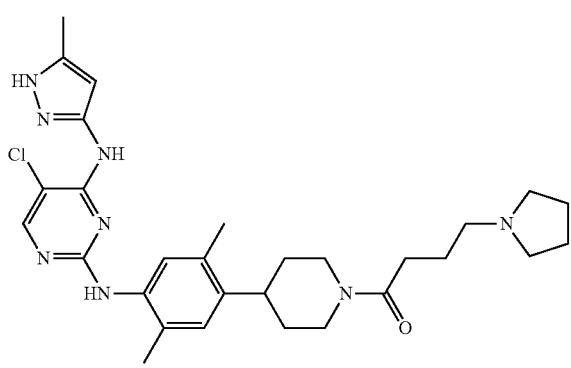

1-(4-(4-(5-chloro-4-(5-methyl-1H-pyrazol-3-ylamino)pyrimidin-2-ylamino)-2,5-dimethylphenyl)piperidin-1-yl)-4-(pyrrolidin-1-yl)butane-1-one

270
-continued

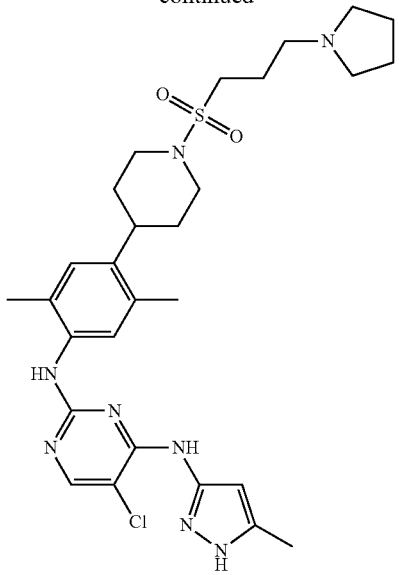

5-chloro-N2-(2,5-dimethyl-4-(1-(3-(pyrrolidin-1-yl)propylsulfonyl)piperidin-4-yl)phenyl)-N4-(5-methyl-1H-pyrazol-3-yl)pyrimidine-2,4-diamine

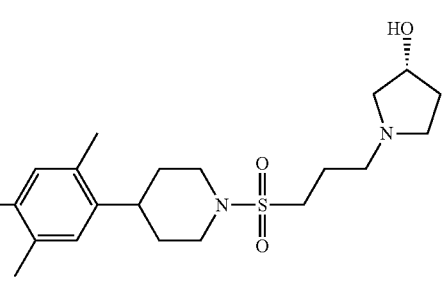

(R)-1-(3-(4-(4-(5-chloro-4-(5-methyl-1H-pyrazol-3-ylamino)pyrimidin-2-ylamino)-2,5-dimethylphenyl)piperidin-1-ylsulfonyl)propyl)pyrrolidin-3-ol

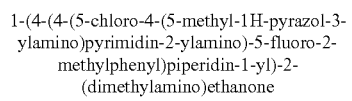

1-(4-(4-(5-chloro-4-(5-methyl-1H-pyrazol-3-ylamino)pyrimidin-2-ylamino)-5-fluoro-2-methylphenyl)piperidin-1-yl)-2-(dimethylamino)ethanone

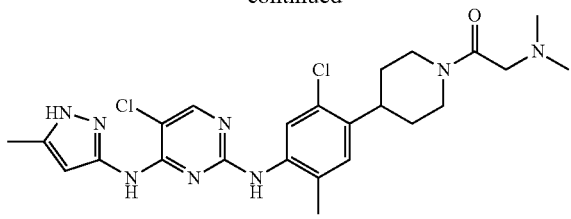

1-(4-(2-chloro-4-(5-chloro-4-(5-methyl-1H-pyrazol-3-ylamino)pyrimidin-2-ylamino)-5-methylphenyl)piperidin-1-yl)-2-

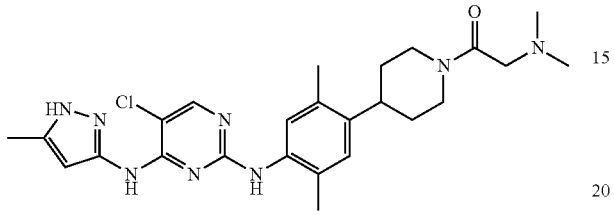

1-(4-(4-(5-chloro-4-(5-methyl-1H-pyrazol-3-ylamino)pyrimidin-2-ylamino)-2,5-dimethylphenyl)piperidin-1-yl)-2-(dimethylamino)ethanone

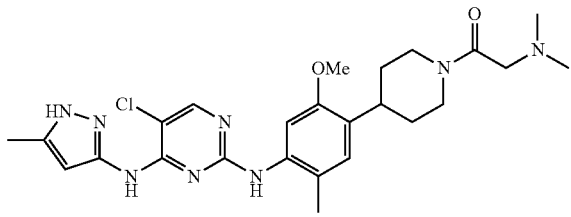

1-(4-(4-(5-chloro-4-(5-methyl-1H-pyrazol-3-ylamino)pyrimidin-2-ylamino)-2-methoxy-5-methylphenyl)piperidin-1-yl)-2-(dimethylamino)ethanone

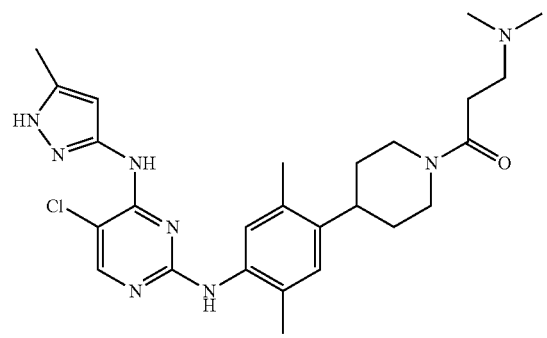

1-(4-(4-(5-chloro-4-(5-methyl-1H-pyrazol-3-ylamino)pyrimidin-2-ylamino)-2,5-dimethylphenyl)piperidin-1-yl)-3-(dimethylamino)propan-1-one

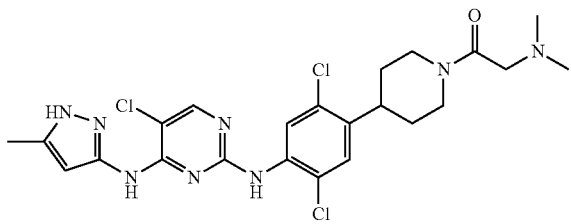

1-(4-(2,5-dichloro-4-(5-chloro-4-(5-methyl-1H-pyrazol-3-ylamino)pyrimidin-2-ylamino)phenyl)piperidin-1-yl)-2-(dimethylamino)ethanone

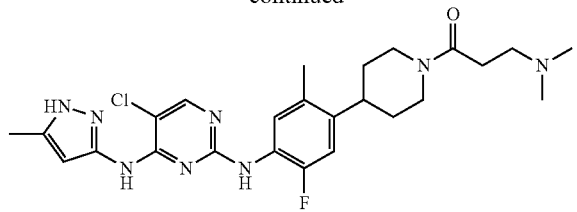

1-(4-(4-(5-chloro-4-(5-methyl-1H-pyrazol-3-ylamino)pyrimidin-2-ylamino)-5-fluoro-2-methylphenyl)piperidin-1-yl)-3-(dimethylamino)propan-1-one

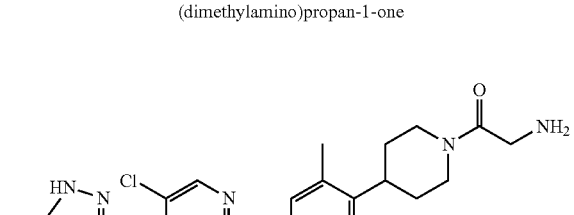

2-amino-1-(4-(4-(5-chloro-4-(5-methyl-1H-pyrazol-3-ylamino)pyrimidin-2-ylamino)5-fluoro-2-methylphenyl)piperidin-1-yl)ethanone

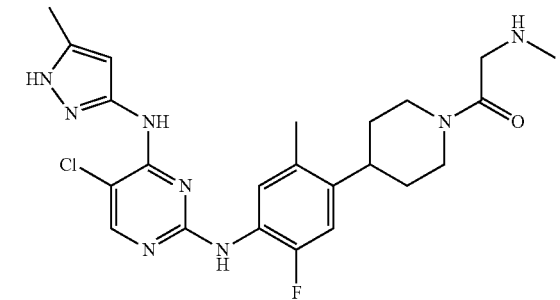

1-(4-(4-(5-chloro-4-(5-methyl-1H-pyrazol-3-ylamino)pyrimidin-2-ylamino)-5-fluoro-2-methylphenyl)piperidin-1-yl)-2-(methylamino)ethanone

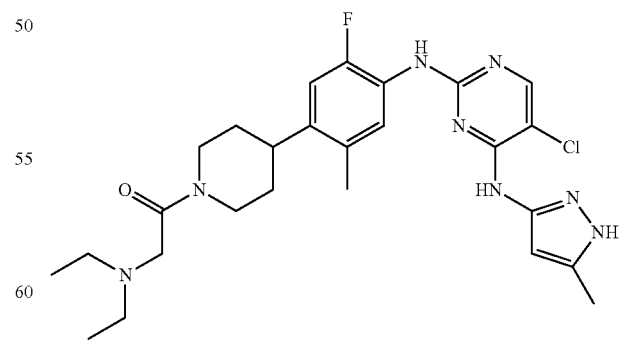

1-(4-(4-(5-chloro-4-(5-methyl-1H-pyrazol-3-ylamino)pyrimidin-2-ylamino)-5-fluoro-2-methylphenyl)piperidin-1-yl)-2-(diethylamino)ethanone

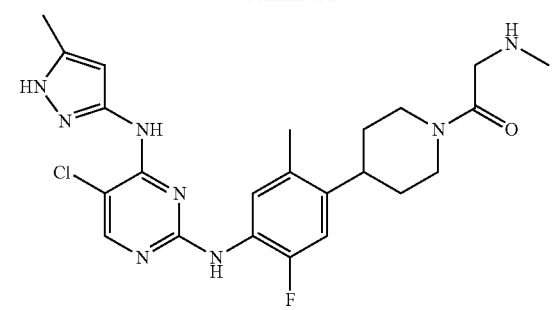

1-(4-(4-(5-chloro-4-(5-methyl-1H-pyrazol-3-
ylamino)pyrimidin-2-ylamino)-5-fluoro-2-
methylphenyl)piperidin-1-yl)-2-
(methylamino)ethanone

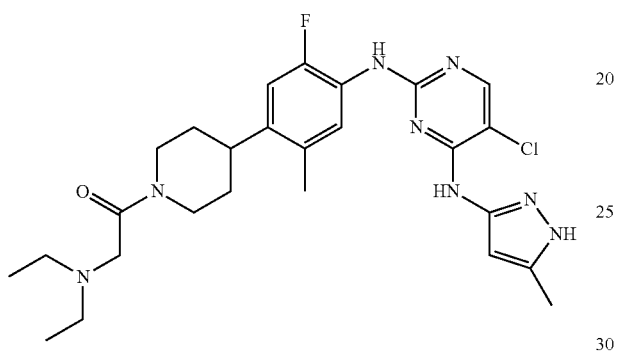

1-(4-(4-(5-chloro-4-(5-methyl-1H-pyrazol-3-
ylamino)pyrimidin-2-ylamino)-5-fluoro-2-
methylphenyl)piperidin-1-yl)-2-
(diethylamino)ethanone

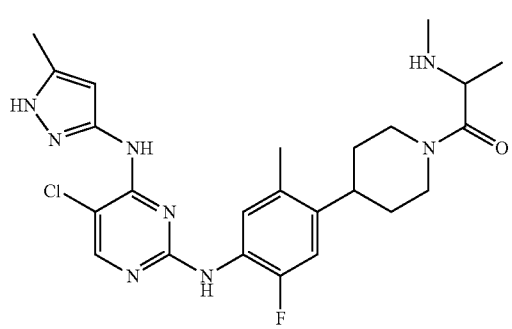

1-(4-(4-(5-chloro-4-(5-methyl-1H-pyrazol-3-
ylamino)pyrimidin-2-ylamino)-5-fluoro-2-
methylphenyl)piperidin-1-yl)-2-
(methylamino)propan-1-one

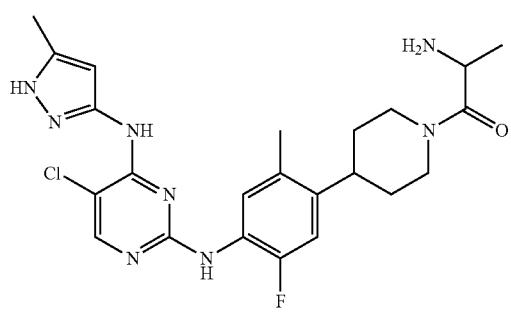

2-amino-1-(4-(4-(5-chloro-4-(5-methyl-1H-
pyrazol-3-ylamino)pyrimidin-2-ylamino)-5-fluoro-
2-methylphenyl)piperidin-1-yl)propan-1-one

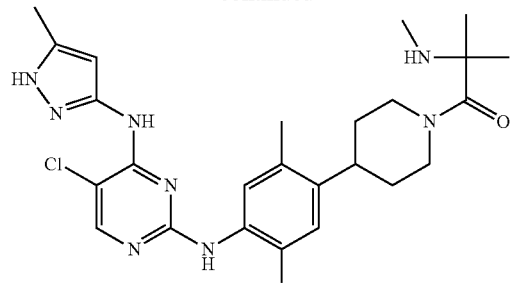

1-(4-(4-(5-chloro-4-(5-methyl-1H-pyrazol-3-
ylamino)pyrimidin-2-ylamino)-5-fluoro-2-
methylphenyl)piperidin-1-yl)-2-methyl-2-
(methylamino)propan-1-one

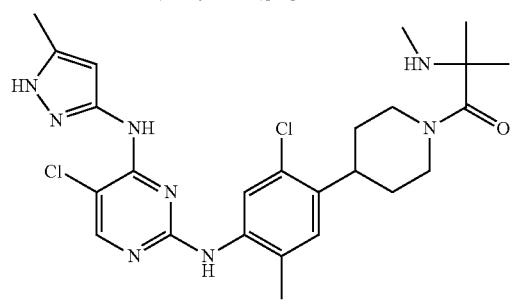

1-(4-(2-chloro-4-(5-chloro-4-(5-methyl-1H-
pyrazol-3-ylamino)pyrimidin-2-ylamino)-5-
methylphenyl)piperidin-1-yl)-2-methyl-2-
(methylamino)propan-1-one

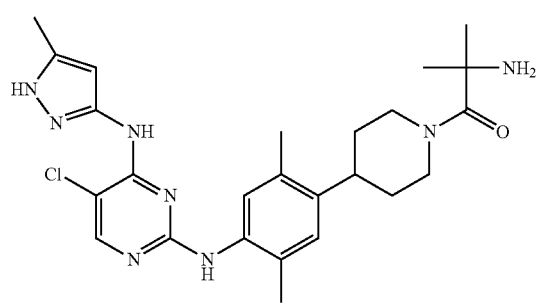

2-amino-1-(4-(4-(5-chloro-4-(5-methyl-1H-
pyrazol-3-ylamino)pyrimidin-2-ylamino)-2,5-
dimethylphenyl)piperidin-1-yl)-2-methylpropan-1-
one

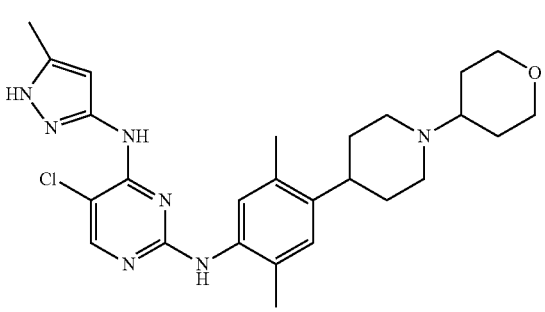

5-chloro-N2-(2,5-dimethyl-4-(1-
(tetrahydro-2H-pyran-4-yl)piperidin-4-
yl)phenyl)-N4-(5-methyl-1H-pyrazol-3-
yl)pyrimidine-2,4-diamine

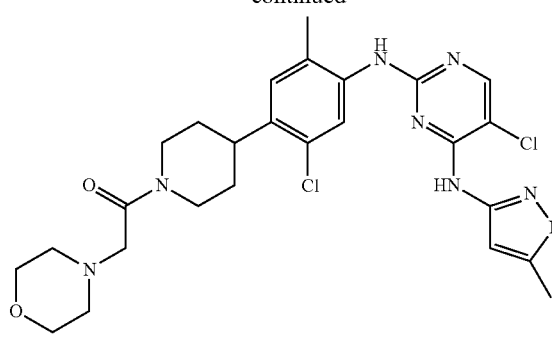

1-(4-(2-chloro-4-(5-chloro-4-(5-methyl-1H-pyrazol-3-ylamino)pyrimidine-2-ylamino)-5-methylphenyl)piperidin-1-yl)-2-morpholinoethanone

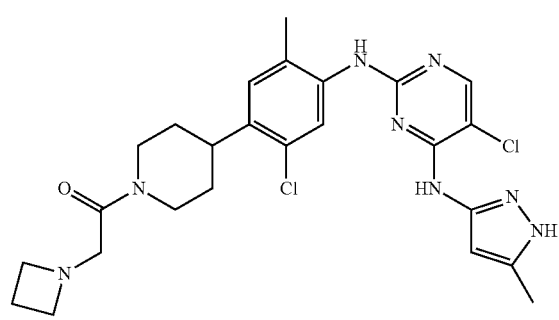

2-(azetidin-1-yl)-1-(4-(2-chloro-4-(5-chloro-4-(5-methyl-1H-pyrazol-3-ylamino)pyrimidin-2-ylamino)-5-methylphenyl)piperidin-1-yl)ethanone

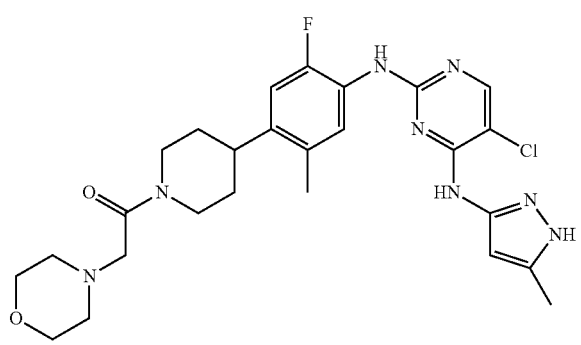

1-(4-(4-(5-chloro-4-(5-methyl-1H-pyrazol-3-ylamino)pyrimidin-2-ylamino)-5-fluoro-2-methylphenyl)piperidin-1-yl)-2-morpholinoethanone

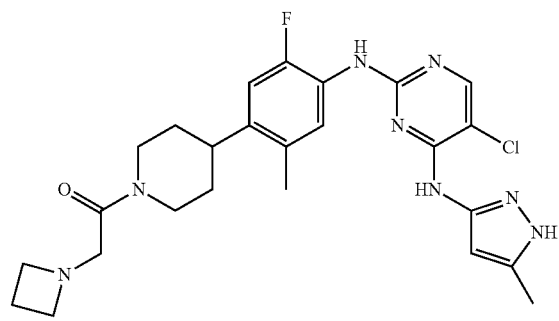

2-(azetidin-1-yl)-1-(4-(4-(5-chloro-4-(5-methyl-1H-pyrazol-3-ylamino)pyrimidin-2-ylamino)-5-fluoro-2-methylphenyl)piperidin-1-yl)ethanone

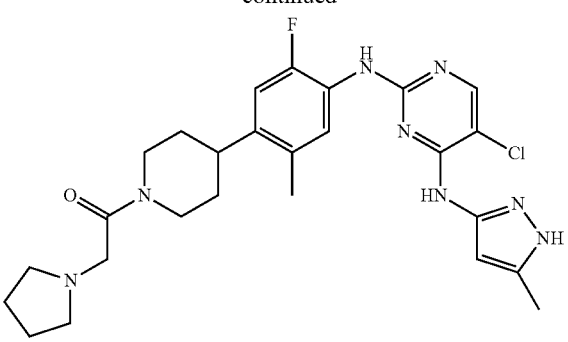

1-(4-(4-(5-chloro-4-(5-methyl-1H-pyrazol-3-ylamino)pyrimidin-2-ylamino)-5-fluoro-2-methylphenyl)piperidin-1-yl)-2-(pyrrolidin-1-yl)ethanone

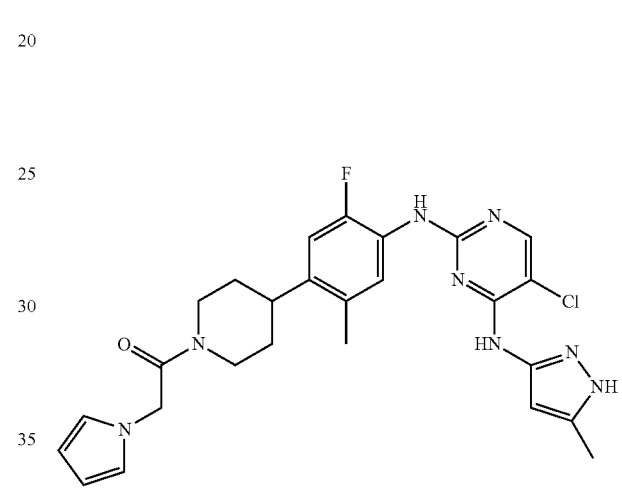

1-(4-(4-(5-chloro-4-(5-methyl-1H-pyrazol-3-ylamino)pyrimidin-2-ylamino)-5-fluoro-2-methylphenyl)piperidin-1-yl)-2-(1H-pyrrol-1-yl)ethanone

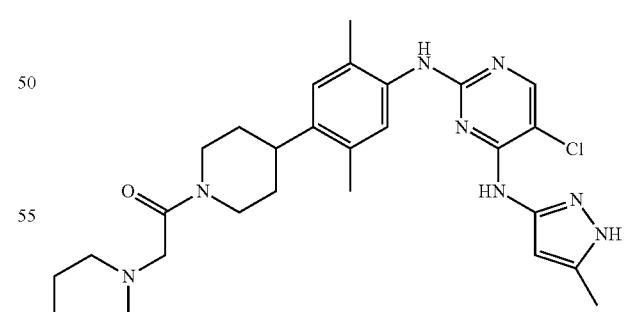

1-(4-(4-(5-chloro-4-(5-methyl-1H-pyrazol-3-ylamino)pyrimidin-2-ylamino)-2,5-dimethylphenyl)piperidin-1-yl)-2-(piperidin-1-yl)ethanone

277

-continued

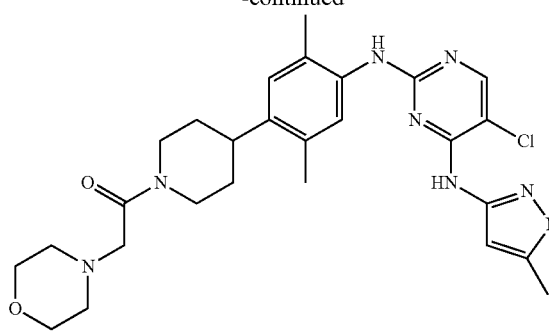

1-(4-(4-(5-chloro-4-(5-methyl-1H-pyrazol-3-ylamino)pyrimidin-2-ylamino)-2,5-dimethylphenyl)piperidin-1-yl)-2-morpholinoethanone

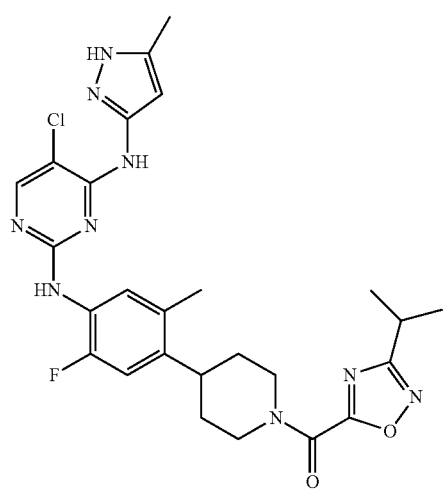

(4-(4-(5-chloro-4-(5-methyl-1H-pyrazol-3-ylamino)pyrimidin-2-ylamino)5-fluoro-2-methylphenyl)piperidin-1-yl)(3-isopropyl-1,2,4-oxadiazol-5-yl)methanone

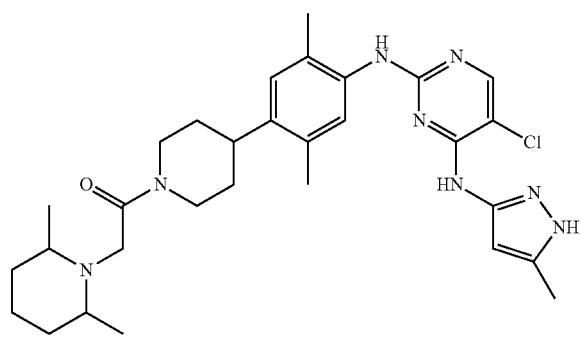

1-(4-(4-(5-chloro-4-(5-methyl-1H-pyrazol-3-ylamino)pyrimidin-2-ylamino)-2,5-dimethylphenyl)piperidin-1-yl)-2-(2,6-dimethylpiperidin-1-yl)ethanone

278

-continued

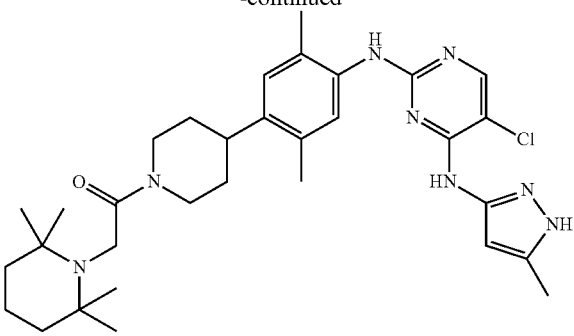

1-(4-(4-(5-chloro-4-(5-methyl-1H-pyrazol-3-ylamino)pyrimidin-2-ylamino)-2,5-dimethylphenyl)piperidin-1-yl)-2-(2,2,6,6-tetramethylpiperidin-1-yl)ethanone

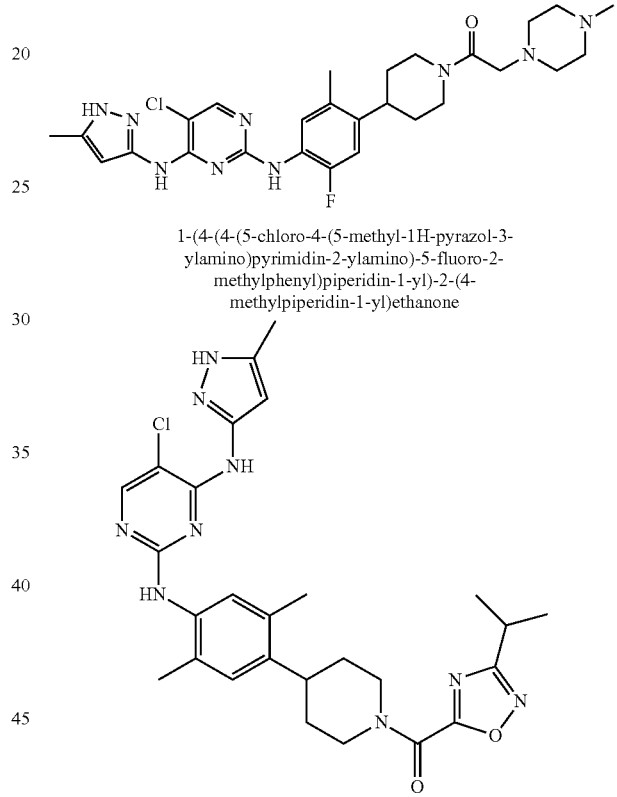

1-(4-(4-(5-chloro-4-(5-methyl-1H-pyrazol-3-ylamino)pyrimidin-2-ylamino)-5-fluoro-2-methylphenyl)piperidin-1-yl)-2-(4-methylpiperidin-1-yl)ethanone (4-(4-(5-chloro-4-(5-methyl-1H-pyrazol-3-ylamino)pyrimidin-2-ylamino)-2,5-dimethylphenyl)piperidin-1-yl)(3-isopropyl-1,2,4-oxadiazol-5-yl)methanone

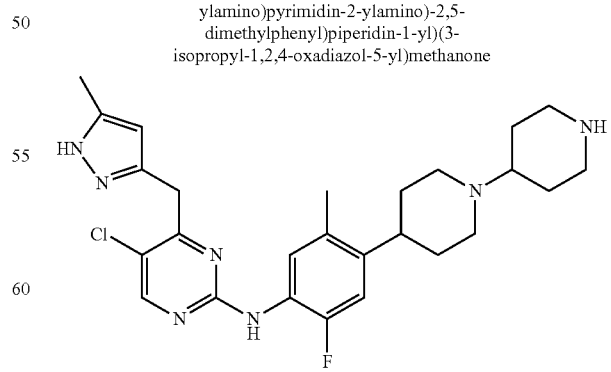

N2-(4-(1,4'-bipiperidin-4-yl)-2-fluoro-5-methylphenyl)-5-chloro-N4-(5-methyl-1H-pyrazol-3-yl)pyrimidine-2,4-diamine

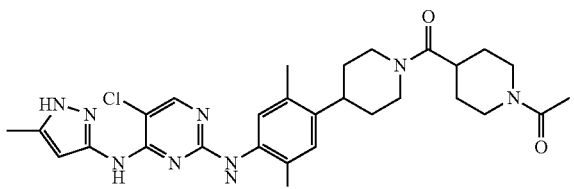

1-(4-(4-(5-chloro-4-(5-methyl-1H-pyrazol-3-ylamino)pyrimidin-2-ylamino)-2,5-dimethylphenyl)piperidin-1-yl)-2-methoxyethanone

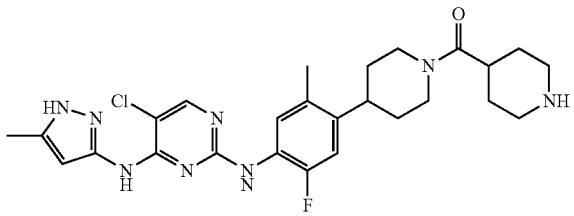

(4-(4-(5-chloro-4-(5-methyl-1H-pyrazol-3-ylamino)pyrimidin-2-ylamino)-5-fluoro-2-methylphenyl)piperidin-1-yl)(piperidin-4-yl)methanone

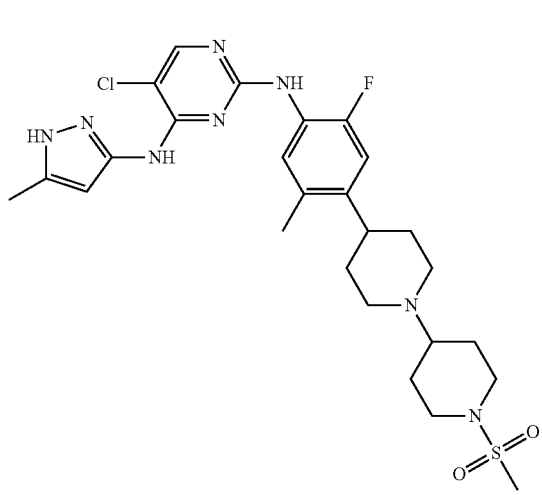

5-chloro-N2-(2-fluoro-5-methyl-4-(1'-(methylsulfonyl)-1,4'-bipiperidin-4-yl)phenyl)-N4-(5-methyl-1H-pyrazol-3-yl)pyrimidine-2,4-diamine

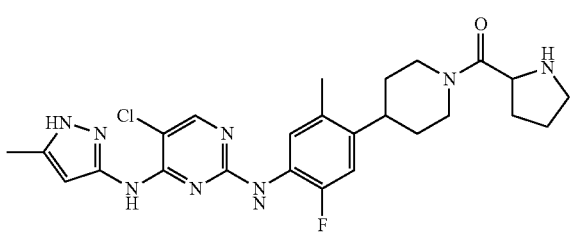

(S)-(4-(4-(5-chloro-4-(5-methyl-1H-pyrazol-3-ylamino)pyrimidin-2-ylamino)-5-fluoro-2-methylphenyl)piperidin-1-yl)(piperidin-4-yl)methanone

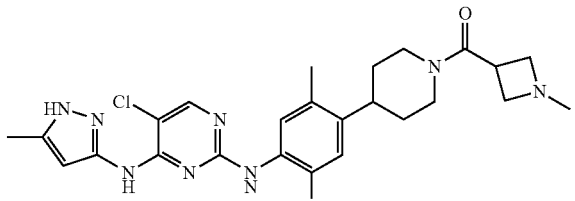

(4-(4-(5-chloro-4-(5-methyl-1H-pyrazol-3-ylamino)pyrimidin-2-ylamino)-5-fluoro-2-methylphenyl)piperidin-1-yl)(1-methylazetidin-3-yl)methanone

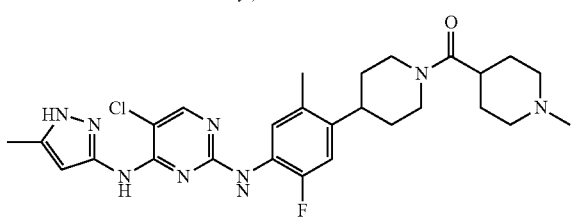

(4-(4-(5-chloro-4-(5-methyl-1H-pyrazol-3-ylamino)pyrimidin-2-ylamino)-5-fluoro-2-methylphenyl)piperidin-1-yl)(1-methylpiperidin-4-yl)methanone

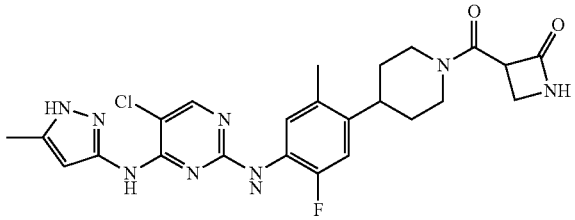

3-(4-(4-(5-chloro-4-(5-methyl-1H-pyrazol-3-ylamino)pyrimidin-2-ylamino)-5-fluoro-2-methylphenyl)piperidin-1-carbonyl)azetidin-2-one

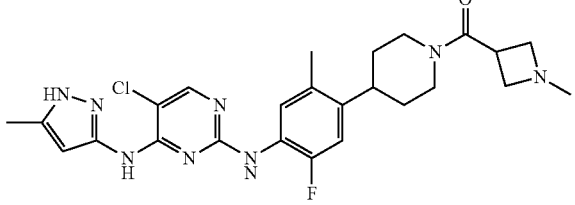

(4-(4-(5-chloro-4-(5-methyl-1H-pyrazol-3-ylamino)pyrimidin-2-ylamino)-2,5-dimethylphenyl)piperidin-1-yl)(1-methylazetidin-3-yl)methanone

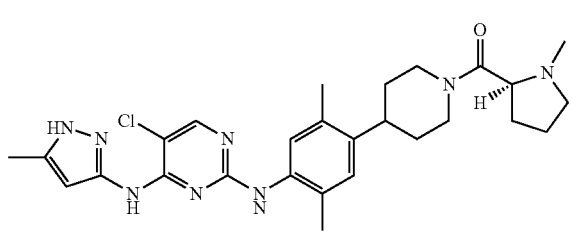

(S)-(4-(4-(5-chloro-4-(5-methyl-1H-pyrazol-3-ylamino)pyrimidin-2-ylamino)-2,5-dimethylphenyl)piperidin-1-yl)(1-methylpyrrolidin-2-yl)methanone

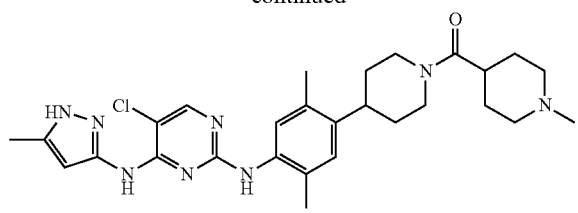

(4-(4-(5-chloro-4-(5-methyl-1H-pyrazol-3-
ylamino)pyrimidin-2-ylamino)-2,5-
dimethylphenyl)piperidin-1-yl)(1-methylpiperidin-
4-yl)methanone

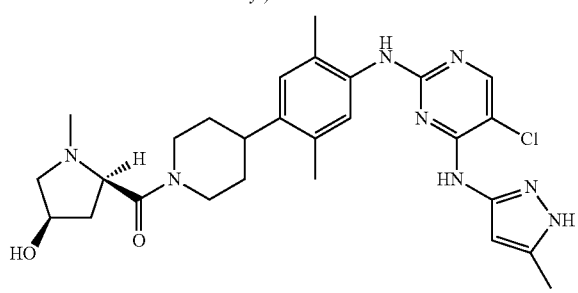

(4-(4-(5-chloro-4-(5-methyl-1H-pyrazol-3-
ylamino)pyrimidin-2-ylamino)-2,5-
dimethylphenyl)piperidin-1-yl)((2R,4R)-4-
hydroxy-1-methylpyrrolidin-2-yl)methanone

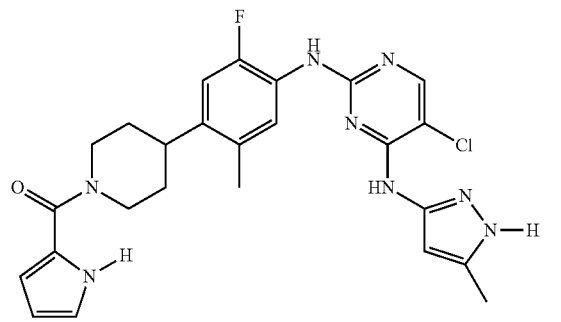

(4-(4-(5-chloro-4-(5-methyl-1H-pyrazol-3-
ylamino)pyrimidin-2-ylamino)-5-fluoro-2-
methylphenyl)piperidin-1-yl)(1H-pyrrol-2-
yl)methanone

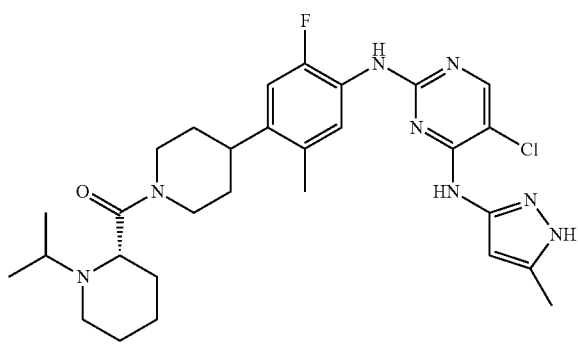

(S)-(4-(4-(5-chloro-4-(5-methyl-1H-pyrazol-3-
ylamino)pyrimidin-2-ylamino)-5-fluoro-2-
methylphenyl)piperidin-1-yl)(1-isopropylpiperidin-
2-yl)methanone

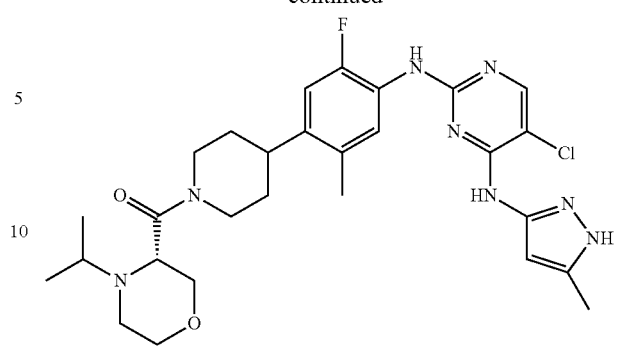

(S)-(4-(4-(5-chloro-4-(5-methyl-1H-pyrazol-3-
ylamino)pyrimidin-2-ylamino)-5-fluoro-2-
methylphenyl)piperidin-1-yl)(4-
isopropylmorpholin-3-yl)methanone

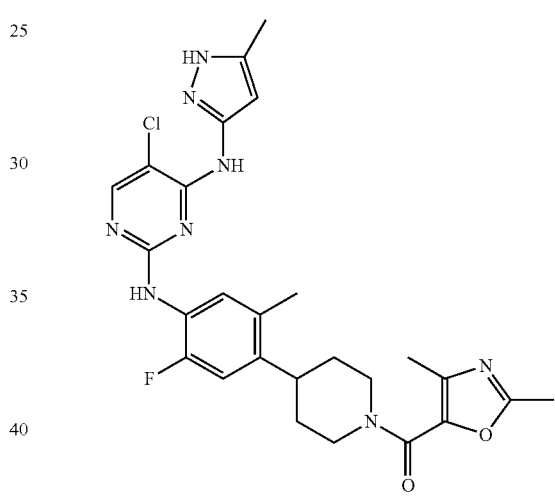

(4-(4-(5-chloro-4-(5-methyl-1H-pyrazol-3-
ylamino)pyrimidin-2-ylamino)-5-fluoro-2-
methylphenyl)piperidin-1-yl)(2,4-dimethyloxazol-
5-yl)methanone

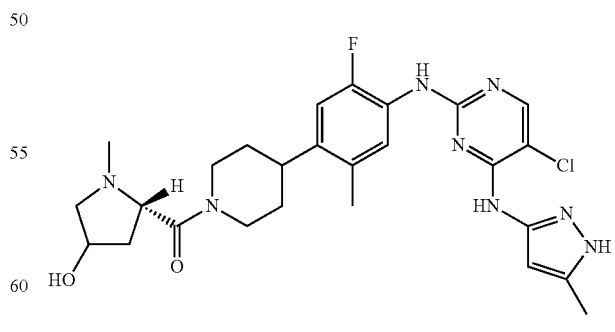

(4-(4-(5-chloro-4-(5-methyl-1H-pyrazol-3-
ylamino)pyrimidin-2-ylamino)-5-fluoro-2-
methylphenyl)piperidin-1-yl)((2S)-4-hydroxy-1-
methylpyrrolidin-2-yl)methanone

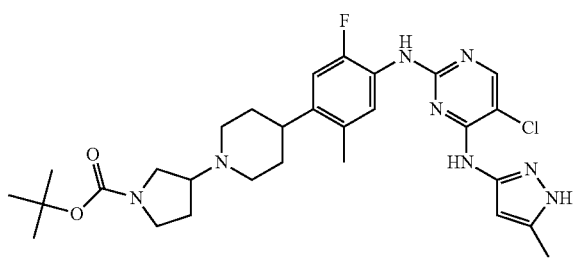

tert-butyl 3-(4-(4-(5-chloro-4-(5-methyl-
1H-pyrazol-3-ylamino)pyrimidin-2-
ylamino)-5-fluoro-2-
methylphenyl)piperidin-1-yl)pyrrolidine-1-
carboxylate

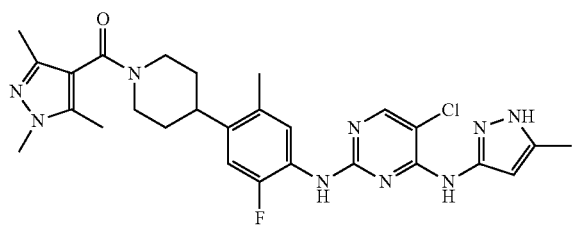

(4-(4-(5-chloro-4-(5-methyl-1H-pyrazol-3-
ylamino)pyrimidin-2-ylamino)-5-fluoro-2-
methylphenyl)piperidin-1-yl)(1,3,5-trimethyl-1H-
pyrazol-4-yl)methanone

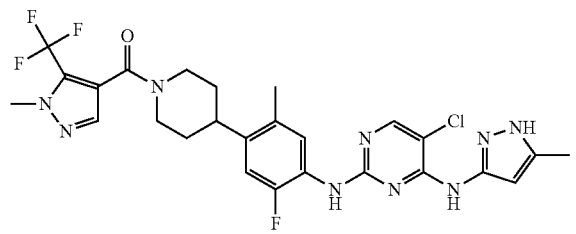

(4-(4-(5-chloro-4-(5-methyl-1H-pyrazol-3-
ylamino)pyrimidin-2-ylamino)-5-fluoro-2-
methylphenyl)piperidin-1-yl)(1-methyl-5-
(trifluoromethyl)-1H-pyrazol-4-yl)methanone

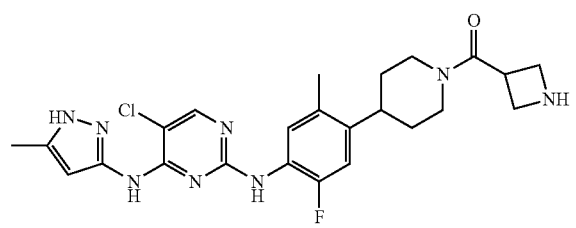

azetidin-3-yl(4-(4-(5-chloro-4-(5-methyl-1H-
pyrazol-3-ylamino)pyrimidin-2-ylamino)-5-fluoro-
2-methylphenyl)piperidin-1-yl)methanone

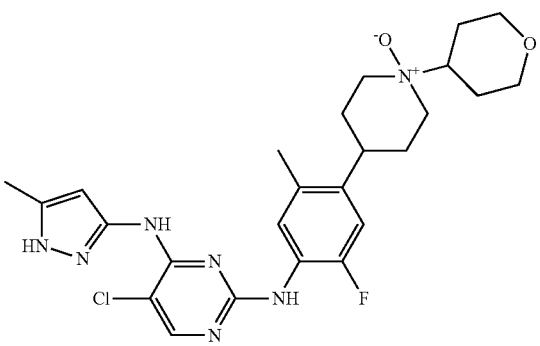

4-(4-(5-chloro-4-(5-methyl-1H-pyrazol-3-
ylamino)pyrimidin-2-ylamino)-5-fluoro-2-
methylphenyl)-1-(tetrahydro-2H-pyran-4-
yl)piperidin 1-oxide

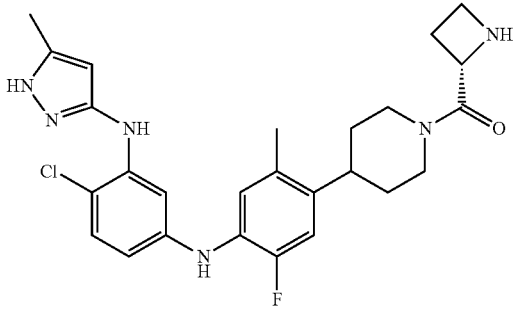

(S)-azetidin-2-yl(4-(4-(5-chloro-4-(5-methyl-1H-
pyrazol-3-ylamino)pyrimidin-2-ylamino)-5-fluoro-
2-methylphenyl)piperidin-1-yl)methanone

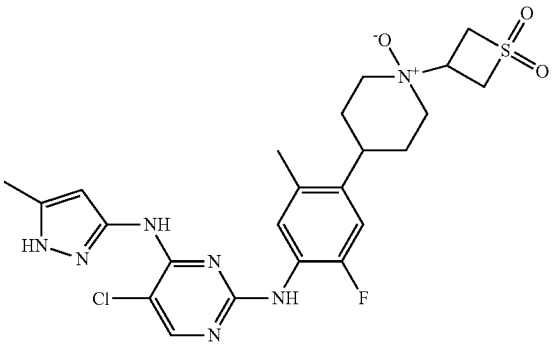

5-Chloro-N2-{4-[1-(1,1-dioxo-1λ6-thietan-
3-yl)-1-oxide-piperidin-4-yl]-2-fluoro-5-
methyl-phenyl}-N4-(5-ethyl-1H-pyrazol-3-
yl)-pyrimidine-2,4-diamine

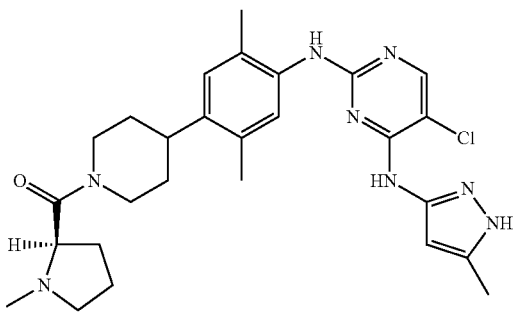

(R)-(4-(4-(5-chloro-4-(5-methyl-1H-pyrazol-3-
ylamino)pyrimidin-2-ylamino)-2,5-
dimethylphenyl) piperidin-1-yl)1-
methylpyrrolidin-2-yl)methanone

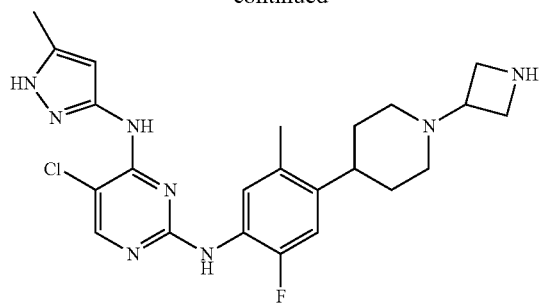

N2-(4-(1-(azetidin-3-yl)piperidin-4-yl)-2-fluoro-5-methylphenyl)-5-chloro-N4-(5-methyl-1H-pyrazol-3-yl)pyrimidine-2,4-diamine

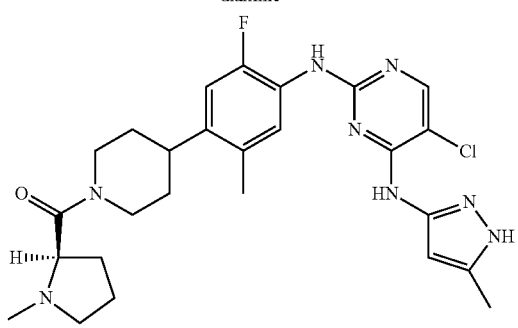

(R)-(4-(4-(5-chloro-4-(5-methyl-1H-pyrazol-3-ylamino)pyrimidin-2-ylamino)-5-fluoro-2-methylphenyl) piperidin-1-yl)1-methylpyrrolidin-2-yl)methanone

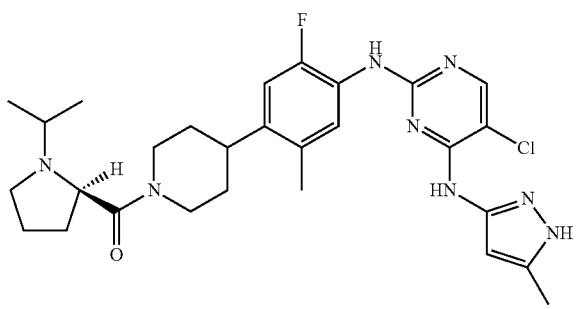

(R)-(4-(4-(5-chloro-4-(5-methyl-1H-pyrazol-3-ylamino)pyrimidin-2-ylamino)-5-fluoro-2-methylphenyl)piperidin-1-yl)(1-isopropylpyrrolidin-2-yl)methanone

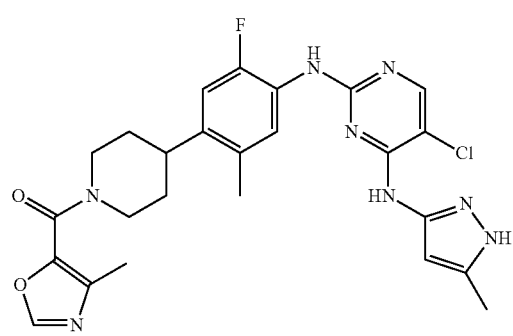

(4-(4-(5-chloro-4-(5-methyl-1H-pyrazol-3-ylamino)pyrimidin-2-ylamino)-5-fluoro-2-methylphenyl)piperidin-1-yl)(1-methyloxazol-5-yl)methanone

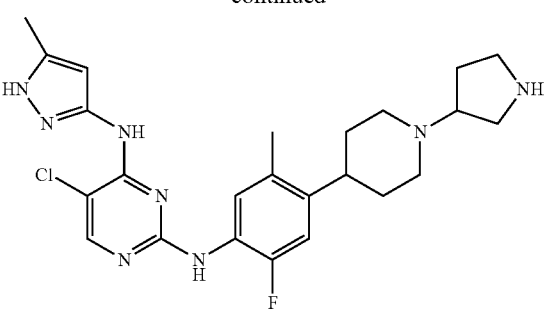

5-chloro-N2-(2-fluoro-5-methyl-4-(1-(pyrrolidin-3-yl)piperidin-4-yl)phenyl)-N4-(5-methyl-1H-pyrazol-3-yl)pyrimidine-2,4-diamine

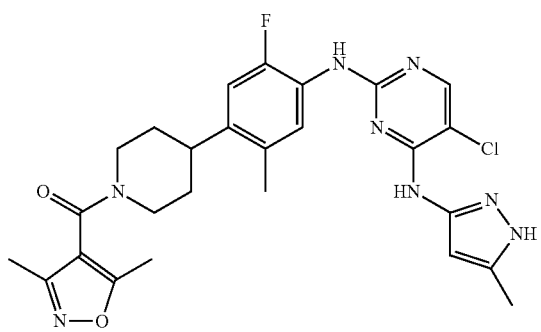

(4-(4-(5-chloro-4-(5-methyl-1H-pyrazol-3-ylamino)pyrimidin-2-ylamino)-5-fluoro-2-methylphenyl)piperidin-1-yl)(3,5-dimethylisoxazol-4-yl)methanone

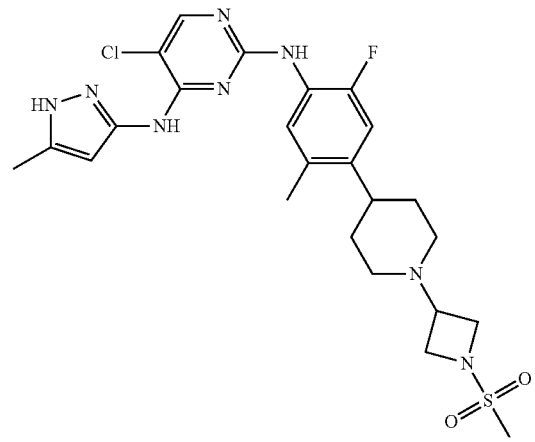 [SMILES: Cc1cc(Nc2nc(Nc3cc(C)c(C4CCN(C5CN(S(C)(=O)=O)C5)CC4)cc3F)ncc2Cl)n[nH]1]

5-chloro-N2-(2-fluoro-5-methyl-4-(1-(1-(methylsulfonyl)azetidin-3-yl)piperidin-4-yl)phenyl)-N4-(5-methyl-1H-pyrazol-3-yl)pyrimidine-2,4-diamine

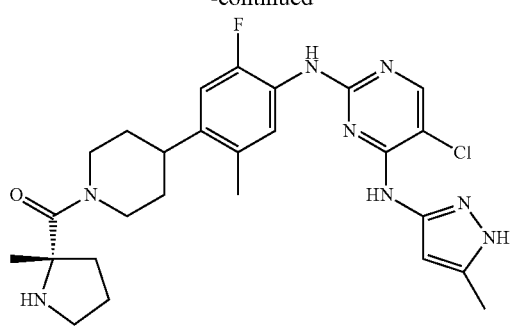

(S)-(4-(4-(5-chloro-4-(5-methyl-1H-pyrazol-3-
ylamino)pyrimidin-2-ylamino)-5-fluoro-2-
methylphenyl)piperidin-1-yl)(2-methylpyrrolidin-
2-yl)methanone

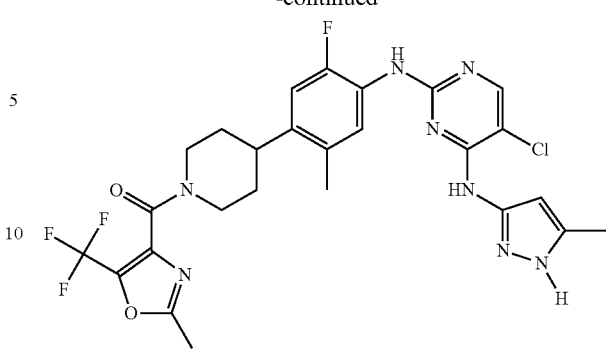

(4-(4-(5-chloro-4-(5-methyl-1H-pyrazol-3-
ylamino)pyrimidin-2-ylamino)-5-fluoro-2-
methylphenyl)piperidin-1-yl)(2-methyl-5-
(trifluoromethyl)oxazol-4-yl)methanone

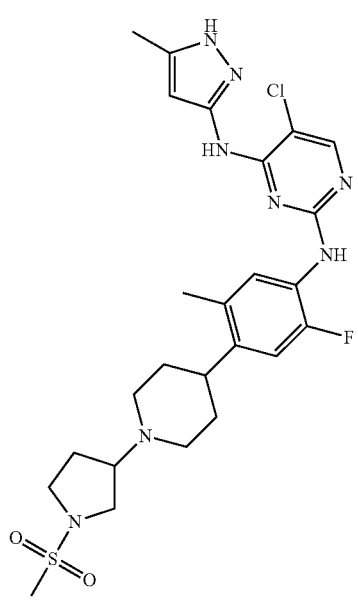

5-chloro-N2-(2-fluoro-5-methyl-4-(1-(1-
(methylsulfonyl)pyrrolidin-3-yl)piperidin-
4-yl)phenyl)-N4-(5-methyl-1H-pyrazol-3-
yl)pyrimidine-2,4-diamine

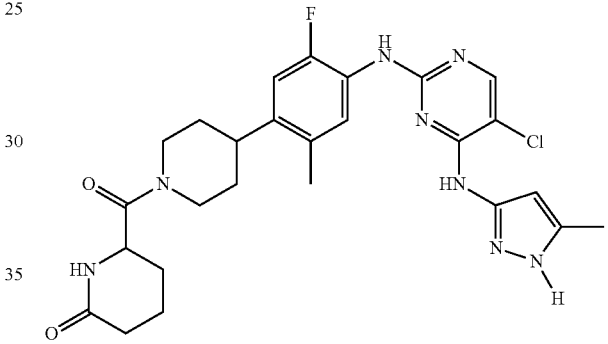

6-(4-(4-(5-chloro-4-(5-methyl-1H-pyrazol-3-
ylamino)pyrimidin-2-ylamino)-5-fluoro-2-
methylphenyl)piperidin-1-carbonyl)piperidin-2-
one

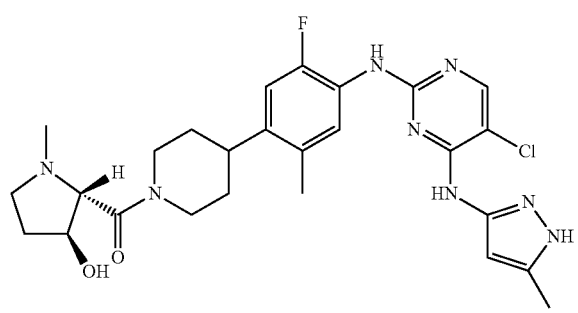

(4-(4-(5-chloro-4-(5-methyl-1H-pyrazol-3-
ylamino)pyrimidin-2-ylamino)-5-fluoro-2-
methylphenyl)piperidin-1-yl)((2S,3R)-3-hydroxy-
1-methylpyrrolidin-2-yl)methanone

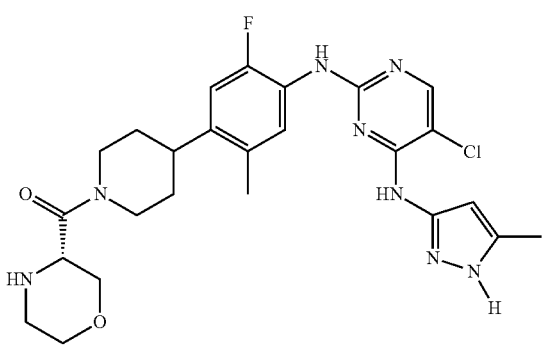

(S)-(4-(4-(5-chloro-4-(5-methyl-1H-pyrazol-3-
ylamino)pyrimidin-2-ylamino)-5-fluoro-2-
methylphenyl)piperidin-1-yl)(morpholin-3-
yl)methanone 289
-continued

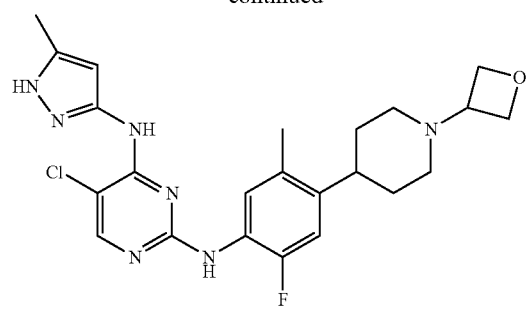

5-chloro-N2-(2-fluoro-5-methyl-4-(1-
(oxetan-3-yl)piperidin-4-yl)phenyl)-N4-(5-
methyl-1H-pyrazol-3-yl)pyrimidine-2,4-
diamine

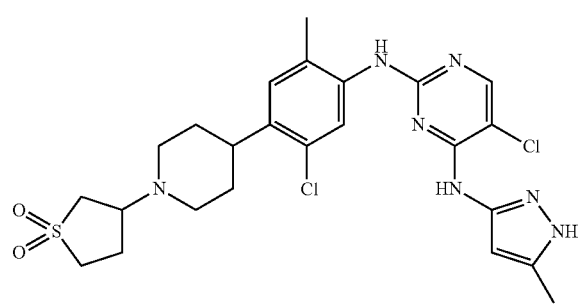

5-chloro-N$^2$-(2-methyl-5-chloro-4-(1-(tetraydro-
1,1-dioxido-3-thienyl)piperidin-4-yl)phenyl)-N$^4$-
(5-methyl-1H-pyrazol-3-yl)pyrimidine-2,4-diamine

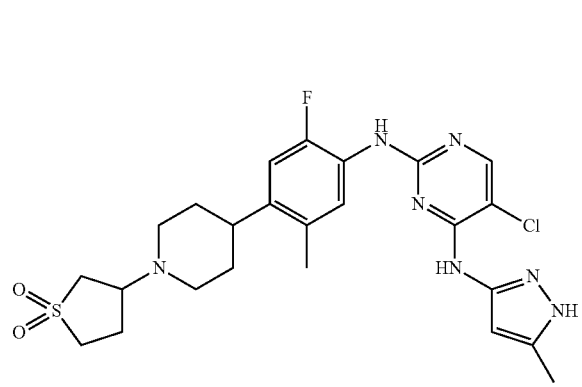

5-chloro-N$^2$-(2-fluoro-5-methyl-4-(1-(tetrahydro-
1,1-dioxido-3-thienyl)piperidin-4-yl)phenyl)-N$^4$-
(5-methyl-1H-pyrazol-3-yl)pyrimidine-2,4-diamine

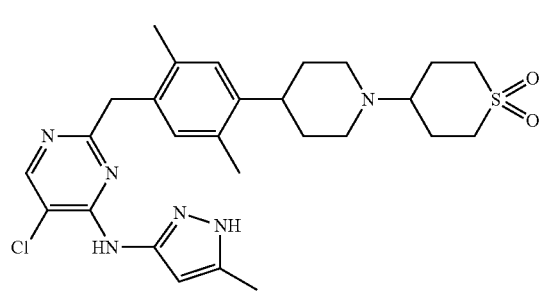

5-chloro-N2-(2,5-dimethyl-4-(1-(tetrahydro-1,1-
dioxido-2H-thiopyran-4-yl)piperidin-4-yl)phenyl)-
N4-(5-methyl-1H-pyrazol-3-yl)pyrimidine-2,4-
diamine 290
-continued

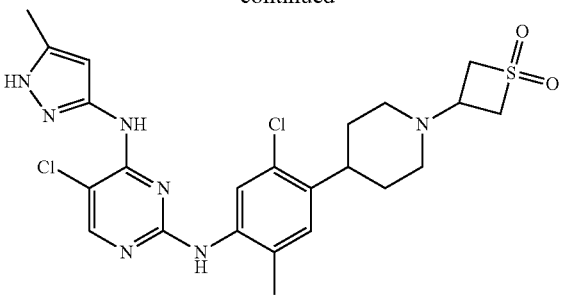

5-chloro-N2-(2-chloro-5-methyl-4-(1-(1,1-dioxido-
3-thietanyl)piperidin-4-yl)phenyl)-N4-(5-methyl-
1H-pyrazol-3-yl)pyrimidine-2,4-diamine

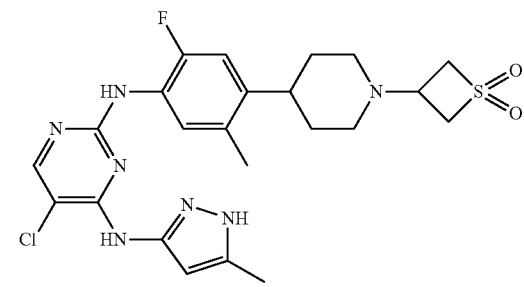

5-chloro-N2-(2-fluoro-5-methyl-4-(1-(1,1-dioxido-
3-thietanyl)-piperidin-4-yl)phenyl)-N4-(5-methyl-
1H-pyrazol-3-yl)pyrimidine-2,4-diamine

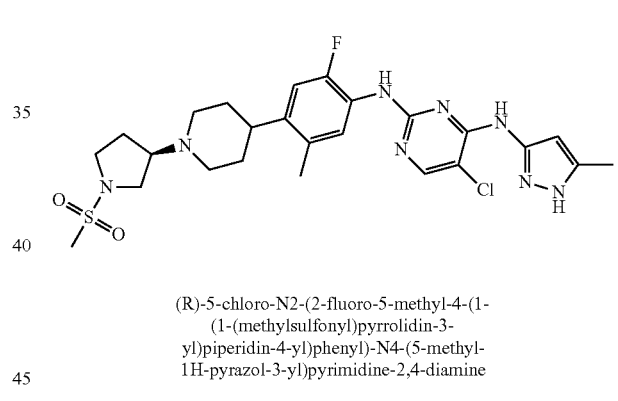

(R)-5-chloro-N2-(2-fluoro-5-methyl-4-(1-
(1-(methylsulfonyl)pyrrolidin-3-
yl)piperidin-4-yl)phenyl)-N4-(5-methyl-
1H-pyrazol-3-yl)pyrimidine-2,4-diamine

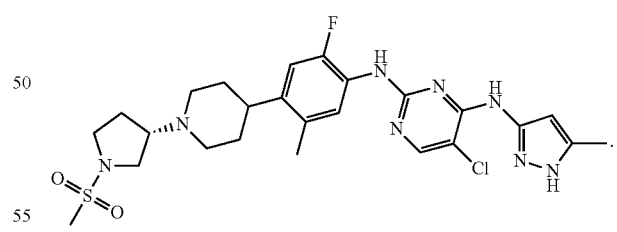

(S)-5-chloro-N2-(2-fluoro-5-methyl-4-(1-
(1-(methylsulfonyl)pyrrolidin-3-
yl)piperidin-4-yl)phenyl)-N4-(5-methyl-
1H-pyrazol-3-yl)pyrimidine-2,4-diamine 6. The method of claim 1, wherein said compound is 5-chloro-N2-(2-fluoro-5-methyl-4-(1-(1,1-dioxido-3-thietanyl)piperidin-4-yl)phenyl)-N4-(5-methyl-1H-pyrazol-3-yl)pyrimidine-2,4-diamine, or a pharmaceutically acceptable salt thereof.

7. The method of claim 1, wherein said compound is 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine, or a pharmaceutically acceptable salt thereof.

8. The method of claim 1, wherein said second therapeutic agent is a chemotherapeutic agent.

* * * * *